US009631191B2

(12) United States Patent
Zdanovsky

(10) Patent No.: US 9,631,191 B2
(45) Date of Patent: Apr. 25, 2017

(54) SYSTEM FOR PRODUCTION OF ANTIBODIES AND THEIR DERIVATIVES

(71) Applicant: Alexey Gennadievich Zdanovsky, Madison, WI (US)

(72) Inventor: Alexey Gennadievich Zdanovsky, Madison, WI (US)

(73) Assignee: Alexey Gennadievich Zdanovsky, Madison, WI (US)

( * ) Notice: Subject to any disclaimer, the term of this patent is extended or adjusted under 35 U.S.C. 154(b) by 30 days.

(21) Appl. No.: 14/094,109

(22) Filed: Dec. 2, 2013

(65) Prior Publication Data

US 2014/0206558 A1 Jul. 24, 2014

Related U.S. Application Data

(60) Provisional application No. 61/733,358, filed on Dec. 4, 2012.

(51) Int. Cl.

| | |
|---|---|
| ***C12N 5/10*** | (2006.01) |
| ***C12N 15/13*** | (2006.01) |
| ***C12N 15/85*** | (2006.01) |
| ***C12P 21/04*** | (2006.01) |
| ***C12P 21/08*** | (2006.01) |
| ***C12N 15/10*** | (2006.01) |
| ***C12Q 1/66*** | (2006.01) |
| ***G01N 33/68*** | (2006.01) |
| ***C07K 16/12*** | (2006.01) |

(52) U.S. Cl.

CPC ...... *C12N 15/1037* (2013.01); *C07K 16/1282* (2013.01); *C12Q 1/66* (2013.01); *G01N 33/6845* (2013.01); *G01N 33/6854* (2013.01); *G01N 2333/33* (2013.01)

(58) Field of Classification Search

CPC ........ C12N 15/64; C12N 15/66; C12N 15/79; C12N 15/85; C12P 21/00

USPC ............ 435/320.1, 326, 455, 465, 340, 69.6

See application file for complete search history.

(56) References Cited

PUBLICATIONS

Smith et al. (2009) Nature Protocols, vol. 4(3), 372-384, including Supplemental Figure 1.*
Adekar et al. (2008) PLoS ONE, vol. 3(8), e3023, pp. 1-7.*
Iwamoto et al. (1993) Biochem. Biophys. ACTA, 1153(1), 89-96, abstract.*
Kunes et al. (2009) Amer. Instit. Chem. Engineers, vol. 25(3), 735-744.*
Adekar, Sharad P. et al., "Neutralization of Botulinum Neurotoxin by a Human Monoclonal Antibody Specific for the Catalytic Light Chain," PLoS One, (Aug. 2008), vol. 3, Issue 8, e3023 (7 pages).
Arnon, Stephen S. et al., "Botulinum Toxin as a Biological Weapon. Medical and Public Health Management," Jama, (2001), vol. 285, No. 8, pp. 1059-1070.
Beidler, C.B. et al., "Cloning and high level expression of a chimeric antibody with specificity for human carcinoembryonic antigen," J Immunol, (Dec. 1, 1988), vol. 141, No. 11, pp. 4053-4060.
Black, Robert E. et al., "Hypersensitivity reactions associated with botulinal antitoxin," Am Jrnl of Medicine, (Oct. 1980), vol. 69, Issue 4, pp. 567-570.
Cao, Yu et al., "Preparation of novel immunomagnetic cellulose microspheres via cellulose binding domain-protein A linkage and its use for the isolation of interferon α-2b," J Chromatogr A, (May 18, 2007), vol. 1149, No. 2, pp. 228-235.
Centers for Disease Control and Prevention, "Notice of CDC's Discontinuation of Investigational Pentavalent (ABCDE) Botulinum Toxoid Vaccine for Workers at Risk for Occupational Exposure to Botulinum Toxins," MMWR, (Oct. 28, 2011), 60(42), pp. 1454-1455.
Clayton, Michael A. et al., "Protective Vaccination with a Recombinant Fragment of Clostridium botulinum Neurotoxin Serotype A Expressed from a Synthetic Gene in *Escherichia coli*," Infect Immun., (Jul. 1995), vol. 63, No. 7, pp. 2738-2742.
Florin, Lore et al., "Heterologous expression of the lipid transfer protein CERT increases therapeutic protein productivity of mammalian cells," J Biotechnol, (Apr. 20, 2009), vol. 141, Issues 1-2, pp. 84-90.
Gillies, Stephen D. et al., "High-level expression of chimeric antibodies using adapted cDNA variable region cassettes", J. Immunol. Methods, (Dec. 20, 1989), vol. 125, Issues 1-2, pp. 191-202.
Hansen, Arne et al., "Cryopreserved human B cells as an alternative source for single cell mRNA analysis," Cell Tissue Bank, (2005), vol. 6, No. 4, pp. 299-308.
Liu, Alvin Y. et al., "Expression of mouse::human immunoglobulin heavy-chain cDNA in lymphoid cells," Gene, (1987), vol. 54, Issue 1, pp. 33-40.
Markova, Svetlana V. et al., "Cloning and Expression of cDNA for a Luciferase from the Marine Copepod Metridia longa a Novel Secreted Bioluminescent Reporter Enzyme*," J Biol Chem, (Jan. 30, 2004), vol. 279, No. 5, pp. 3212-3217.
Markova, Svetlana V. et al., "High-active truncated luciferase of copepod Metridia longa," Biochem Biophys Res Commun, (Jan. 6, 2012), vol. 417, Issue 1, pp. 98-103.
Norderhaug, Lars et al., "Versatile vectors for transient and stable expression of recombinant antibody molecules in mammalian cells," J of Immunological Methods, (May 12, 1997), vol. 204, Issue 1, pp. 77-87.
Nowakowski, A. et al., "Potent neutralization of botulinum neurotoxin by recombinant oligoclonal antibody", Proc Natl Aced Sci USA, (Aug. 20, 2002), vol. 99, No. 17, pp. 11346-11350.
O'Callaghan, Peter M. et al., "Cell line-specific control of recombinant monoclonal antibody production by CHO cells," Biotechnol Bioeng, (Aug. 15, 2010), vol. 106, No. 6, pp. 938-951.
Orlandi, Rosaria et al., "Cloning immunoglobulin variable domains for expression by the polymerase chain reaction," Prox. Natl. Acad. Sci. USA, (May 1989), vol. 86, pp. 3833-3837.
Peng, Ren-Wang et al., "Differential effect of exocytic SNAREs on the production of recombinant proteins in mammalian cells," Biotech Bioeng, (Mar. 2011), vol. 108, Issue 3, pp. 611-620.
(Continued)

*Primary Examiner* — Anne Marie S Wehbe
(74) *Attorney, Agent, or Firm* — Foley & Lardner LLP

(57) ABSTRACT

The present disclosure provides methods and compositions for the production of chimeric antibodies that specifically bind an antigen of interest.

20 Claims, 7 Drawing Sheets

(56) References Cited

PUBLICATIONS

Peng, Ren-Wang et al., "Molecular engineering of exocytic vesicle traffic enhances the productivity of Chinese hamster ovary cells," Biotechnol Bioeng, (Mar. 1, 2009), vol. 102, Issue 4, pp. 1170-1181.
Schmitt, Clare K. et al., "Expression of Gene 1.2 and Gene 10 of Bacteriophage T7 is Lethal to F Plasmid-Containing *Escherichia coli*," J Bacteriol., (Feb. 1991), vol. 173, No. 4, pp. 1536-1543.
Shpigel, Etai et al., "Immobilization of recombinant heparinase I fused to cellulose-binding domain," Biotechnol Bioeng, (Oct. 5, 1990), vol. 65, Issue 1, pp. 17-23.
Smith, Kenneth et al., "Rapid Generation of Fully Human Monoclonal Antibodies Specific to a Vaccinating Antigen," Nature Protocols, (2009), vol. 4, pp. 372-384.
Smith, Leonard A. et al., "Botulinum Neurotoxin Vaccines: Past, Present, and Future," Critical Reviews in Immunology, (2007), vol. 27, No. 4, pp. 303-318.
St. John, Ronald et al., "Bioterrorism in Canada: An economic assessment of prevention and postattack response," Can J Infect Dis., (Sep.-Oct. 2001), vol. 12, No. 5, pp. 275-284.
Wang, Xiaowei et al., "Human immunoglbulin variable region gene analysis by single cell RT-PCR," Jrnl of Immunological Methods, (Oct. 20, 2000), vol. 244, Issues 1-2, pp. 217-225.
Zdanovsky, Alexey et al., "Epitope mapping of botulinum neurotoxins light chains," Toxicon, (Dec. 1, 2012), vol. 60, No. 7, pp. 1277-1286.
Zhao, Yaofeng et al., "Cloning of the complete rat immunoglobulin δ gene: evolutionary implications," Immunology, (2003), vol. 108, pp. 288-295.
Zhou, Chen et al., "Development of a novel mammalian cell surface antibody display platform," MAbs, (Sep.-Oct. 2010), vol. 2, Issue 5, pp. 508-518.

* cited by examiner

SEQUENCE LISTING

<160> NUMBER OF SEQ ID NOS: 97

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 1

His His His His His His
1 5

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2
ggggaagagg aagactgacg gtc 23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 3
cagtactgcg atgagtggca 20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
tgtggccttg ttggcttg 18

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
gagtcagdyy cdrycaggac acagcatg 28

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6

-continued agaccctgtc aggacacagc atagacatg 29

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
ggactcctca gttcaccttc tcacaatg 28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
tgctcagtta ggacccagag gaaccatg 28

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
taatggccta acactctccc ctgttgaagc tctt 34

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
tgagvdmmgy wchtcaccat ggactg 26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
actgaacaca gaggactcac catgga 26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
cagtgactcc tgtgccccac catggaca 28

-continued

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttctgtcct ccaccatcat ggggtc 26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcactgaaca cagaccacca atcatgg 27

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggggaagagg aagactgacg gtc 23

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctgggagca cagctcatca ccatgga 27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cactgaacac agaggactca ccatgga 27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catggacctc ctgcacaaga acatgaa 27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
actgaacaga gagaactcac catgga 26

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cagtactgcg atgagtggca 20

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
tttaggccat ggcctggacc cctctcctgc tc 32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
tttaggccat ggcctggacc kttctcctcc tc 32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tttaggccat ggcctggdct cykctcctyc tc 32

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tttaggccat ggcatggcca gcttccctct cctcctc 37

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
tttaggccat gacctgctcc cctctcctcc tc 32

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
cctgcagctc tagtctcccg tgg 23

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
tttaggcatg gacatgaggg tccccgctca gctcctgg 38

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
tttaggcatg gaaaccccag cgcagcttct 30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
tttaggcatg gtgttgcaga cccaggtctt 30

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
taatggccta acactctccc ctgttgaagc tctt 34

<210> SEQ ID NO 31

<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
tattggcgag ctggcctctc accaactgtc ttgtccacct tggtgttg 48

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
cactggagac ggtgaccagb gtbccytgkc ccca 34

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
tattggcact cacggaagag acggtgacca gbgtbccytg 40

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
tatagccatg gactggacct gga 23

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
tatagccatg gacatacttt gttccac 27

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
tatagccatg gagtttgggc tgagc 25

<210> SEQ ID NO 37
<211> LENGTH: 27

<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
tatagccatg aaacacctgt ggttctt 27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
tatagccatg gggtcaaccg ccatcct 27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
tatagccatg tctgtctcct tcctcat 27

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
tatagccatg gaatttgggc ttagct 26

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
tatagccatg gaattggggc tgag 24

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
tattggcact cacggaagag acggtgacca gbgtbccytg 40

<210> SEQ ID NO 43
<211> LENGTH: 31
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 43
tatagaccat ggactggacc tggaggttcc t 31

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
tatagaccat ggagtttggg ctgagctggg t 31

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
tatagaacat gaaacacctg tggttcttcc t 31

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
tattggcact cacggaagag acggtgacca gbgtbccytg 40

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
tttaggccat ggcctggacc cctctcctgc tc 32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
tttaggccat ggcctggacc kttctcctcc tc 32

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
tttaggccat ggcctggdct cykctcctyc tc 32

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
tttaggccat ggcatggcca gcttccctct cctcctc 37

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
tttaggccat gacctgctcc cctctcctcc tc 32

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
taatggccta tgaacattct gtaggggcca c 31

<210> SEQ ID NO 53
<211> LENGTH: 13968
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
tggcccgcct ggctgaccgc ccaacgaccc ccgcccattg acgtcaataa tgacgtatgt 60
tcccatagta acgccaatag ggactttcca ttgacgtcaa accgggcgga ccgactggcg 120
ggttgctggg ggcgggtaac tgcagttatt actgcataca agggtatcat tgcggttatc 180
cctgaaaggt aactgcagtt tgggtggagt atttacggta aactgcccac ttggcagtac 240
atcaagtgta tcatatgcca agtacgcccc ctattgacgt caatgacggt aaatggcccg 300
acccacctca taaatgccat ttgacgggtg aaccgtcatg tagttcacat agtatacggt 360
tcatgcgggg gataactgca gttactgcca tttaccgggc cctggcatta tgcccagtac 420
atgaccttat gggactttcc tacttggcag tacatctacg tattagtcat cgctattacc 480
atggtgatgc ggttttggca ggaccgtaat acgggtcatg tactggaata ccctgaaagg 540
atgaaccgtc atgtagatgc ataatcagta gcgataatgg taccactacg ccaaaaccgt 600
gtacatcaat gggcgtggat agcggtttga ctcacgggga tttccaagtc tccaccccat 660

-continued

```
tgacgtcaat gggagtttgt tttggcacca aaatcaacgg catgtagtta cccgcaccta    720
tcgccaaact gagtgcccct aaaggttcag aggtggggta actgcagtta ccctcaaaca    780
aaaccgtggt tttagttgcc gactttccaa aatgtcgtaa caactccgcc ccattgacgc    840
aaatgggcgg taggcgtgta cggtgggagg tctatataag cagagctggt ttagtgaacc    900
ctgaaaggtt ttacagcatt gttgaggcgg ggtaactgcg tttacccgcc atccgcacat    960
gccaccctcc agatatattc gtctcgacca aatcacttgg gtcagatccg ctagacgtct   1020
catttaactt taagaaggag atatacatat ggctagcatg actggtggac agcaaatggg   1080
tactaaccaa ggtaaaggtg cagtctaggc gatctgcaga gtaaattgaa attcttcctc   1140
tatatgtata ccgatcgtac tgaccacctg tcgtttaccc atgattggtt ccatttccac   1200
tagttgctgc tggagataaa ctggcgttgt tcttgaaggt atttggcggt gaagtcctga   1260
ctgcgttcgc tcgtacctcc gtgaccactt ctcgccacat atcaacgacg acctctattt   1320
gaccgcaaca agaacttcca taaaccgcca cttcaggact gacgcaagcg agcatggagg   1380
cactggtgaa gagcggtgta ggtacgttcc atctccagcg gtaaatccgc tcagttccct   1440
gttctgggtc gcactcaggc agcgtatctg gctccgggcg agaacctcga cgataaacgt   1500
ccatgcaagg tagaggtcgc catttaggcg agtcaaggga caagacccag cgtgagtccg   1560
tcgcatagac cgaggcccgc tcttggagct gctatttgca aaggacatca aacacaccga   1620
gaaggtaatc accattgacg gtctcctgac ggctgacgtt ctgatttatg atattgagga   1680
cgcgatgaac cactacgacg ttcctgtagt ttgtgtggct cttccattag tggtaactgc   1740
cagaggactg ccgactgcaa gactaaatac tataactcct gcgctacttg gtgatgctgc   1800
ttcgctctga gtatacctct cagttgggtg aatctctggc gatggctgcg gatggtgcgg   1860
ttctggctga gattgccggt ctgtgtaacg tggaaagcaa aagcgagact catatggaga   1920
gtcaacccac ttagagaccg ctaccgacgc ctaccacgcc aagaccgact ctaacggcca   1980
gacacattgc acctttcgtt atataatgag aacatcgagg gcttaggtac tgctaccgta   2040
attgagacca ctcagaacaa ggccgcactt accgaccaag ttgcgctggg taaggagatt   2100
tatattactc ttgtagctcc cgaatccatg acgatggcat taactctggt gagtcttgtt   2160
ccggcgtgaa tggctggttc aacgcgaccc attcctctaa attgcggctc tgactaaggc   2220
tcgtgcggct ctgaccaaga actatgttcc ggctgctgac cgtgtgttct actgtgaccc   2280
agatagctac tctgcgattc taacgccgag actgattccg agcacgccga gactggttct   2340
tgatacaagg ccgacgactg gcacacaaga tgacactggg tctatcgatg agacgctaag   2400
tggcagcact gatgccgaac gcagcaaact acgctgctct gattgaccct gagaagggtt   2460
ctatccgcaa cgttatgggc tttgaggttg tagaagttcc accgtcgtga ctacggcttg   2520
cgtcgtttga tgcgacgaga ctaactggga ctcttcccaa gataggcgtt gcaatacccg   2580
aaactccaac atcttcaagg gcacctcacc gctggtggtg ctggtaccgc tcgtgagggc   2640
actactggtc agaagcacgt cttccctgcc aataaaggtg agggtaatgt caaggttgct   2700
cgtggagtgg cgaccaccac gaccatggcg agcactcccg tgatgaccag tcttcgtgca   2760
gaagggacgg ttatttccac tcccattaca gttccaacga aaggacaacg ttatcggcct   2820
gttcatgcac cgctctgcgg taggtactgt taagctgcgt gacttggctc tggagcgcgc   2880
tcgccgtgct aacttccaag ttcctgttgc aatagccgga caagtacgtg gcgagacgcc   2940
atccatgaca attcgacgca ctgaaccgag acctcgcgcg agcggcacga ttgaaggttc   3000
```

-continued

```
cggaccagat tatcgctaag tacgcaatgg gccacggtgg tcttcgccca gaagctgcag   3060
gagctgtcgt attccagtca ggttaattac gagacgctcg gcctggtcta atagcgattc   3120
atgcgttacc cggtgccacc agaagcgggt cttcgacgtc ctcgacagca taaggtcagt   3180
ccaattaatg ctctgcgagc agccgatccg catcaaagca tgctgttttc tgtctgtccc   3240
taacatgccc tgtgattatc cgcaaacaac acacccaagg gcagaacttt gttacttaaa   3300
tcggctaggc gtagtttcgt acgacaaaag acagacaggg attgtacggg acactaatag   3360
gcgtttgttg tgtgggttcc cgtcttgaaa caatgaattt caccatcctg tttgcttctt   3420
tcctcaggaa ctgtggctgc accatctgtc ttcatcttcc cgccatctga tgagcagttg   3480
aaatctggaa ctgcctctgt gtggtaggac aaacgaagaa aggagtcctt gacaccgacg   3540
tggtagacag aagtagaagg gcggtagact actcgtcaac tttagacctt gacggagaca   3600
tgtgtgcctg ctgaataact tctatcccag agaggccaaa gtacagtgga aggtggataa   3660
cgccctccaa tcgggtaact cccaggagag tgtcacagag acacacggac gacttattga   3720
agatagggtc tctccggttt catgtcacct tccacctatt gcgggaggtt agcccattga   3780
gggtcctctc acagtgtctc caggacagca aggacagcac ctacagcctc agcagcaccc   3840
tgacgctgag caaagcagac tacgagaaac acaaagtcta cgcctgcgaa gtcacccatc   3900
gtcctgtcgt tcctgtcgtg gatgtcggag tcgtcgtggg actgcgactc gtttcgtctg   3960
atgctctttg tgtttcagat gcggacgctt cagtgggtag agggcctgag ctcgcccgtc   4020
acaaagagct tcaacagggg agagtgttag cggccaattg gcggccgcaa tttaattccg   4080
gttattttcc accatattgc tcccggactc gagcgggcag tgtttctcga agttgtcccc   4140
tctcacaatc gccggttaac cgccggcgtt aaattaaggc caataaaagg tggtataacg   4200
cgtcttttgg caatgtgagg gcccggaaac ctggccctgt cttcttgacg agcattccta   4260
ggggtctttc ccctctcgcc aaaggaatgc aaggtctgtt gcagaaaacc gttacactcc   4320
cgggcctttg gaccgggaca gaagaactgc tcgtaaggat ccccagaaag gggagagcgg   4380
tttccttacg ttccagacaa gaatgtcgtg aaggaagcag ttcctctgga agcttcttga   4440
agacaaacaa cgtctgtagc gaccctttgc aggcagcgga accccccacc tggcgacagg   4500
cttacagcac ttccttcgtc aaggagacct tcgaagaact tctgtttgtt gcagacatcg   4560
ctgggaaacg tccgtcgcct tggggggtgg accgctgtcc tgcctctgcg gccaaaagcc   4620
acgtgtataa gatacacctg caaaggcggc acaaccccag tgccacgttg tgagttggat   4680
agttgtggaa agagtcaaat acggagacgc cggttttcgg tgcacatatt ctatgtggac   4740
gtttccgccg tgttggggtc acggtgcaac actcaaccta tcaacacctt tctcagttta   4800
ggctcacctc aagcgtattc aacaaggggc tgaaggatgc ccagaaggta ccccattgta   4860
tgggatctga tctggggcct cggtgcacat gctttacatg ccgagtggag ttcgcataag   4920
ttgttccccg acttcctacg ggtcttccat ggggtaacat accctagact agaccccgga   4980
gccacgtgta cgaaatgtac tgtttagtcg aggttaaaaa acgtctaggc cccccgaacc   5040
acggggacgt ggttttcctt tgaaaaacac gatgataata tggccaccac ccatacctag   5100
acaaatcagc tccaattttt tgcagatccg gggggcttgg tgcccctgca ccaaaaggaa   5160
actttttgtg ctactattat accggtggtg ggtatggatc gcttttgcaa agatcgatca   5220
gatcccgggg ggcaatgaga tatgaaaaag cctgaactca ccgcgacgtc tgtcgagaag   5280
tttctgatcg aaaagttcga cgaaaacgtt tctagctagt ctagggcccc ccgttactct   5340
atactttttc ggacttgagt ggcgctgcag acagctcttc aaagactagc ttttcaagct   5400
```

-continued

```
cagcgtatcc gacctgatgc agctctcgga gggcgaagaa tctcgtgctt tcagcttcga   5460
tgtaggaggg cgtggatatg tcctgcgggt aaatagctgc gtcgcatagg ctggactacg   5520
tcgagagcct cccgcttctt agagcacgaa agtcgaagct acatcctccc gcacctatac   5580
aggacgccca tttatcgacg gccgatggtt tctacaaaga tcgttatgtt tatcggcact   5640
ttgcatcggc cgcgctcccg attccggaag tgcttgacat tggggaattc agcgagagcc   5700
cggctaccaa agatgtttct agcaatacaa atagccgtga aacgtagccg gcgcgagggc   5760
taaggccttc acgaactgta accccttaag tcgctctcgg tgacctattg catctcccgc   5820
cgtgcacagg gtgtcacgtt gcaagacctg cctgaaaccg aactgcccgc tgttctgcag   5880
ccggtcgcgg aggccatgga actggataac gtagagggcg gcacgtgtcc cacagtgcaa   5940
cgttctggac ggactttggc ttgacgggcg acaagacgtc ggccagcgcc tccggtacct   6000
tgcgatcgct gcggccgatc ttagccagac gagcgggttc ggcccattcg gaccgcaagg   6060
aatcggtcaa tacactacat ggcgtgattt catatgcgcg acgctagcga cgccggctag   6120
aatcggtctg ctcgcccaag ccgggtaagc ctggcgttcc ttagccagtt atgtgatgta   6180
ccgcactaaa gtatacgcgc attgctgatc cccatgtgta tcactggcaa actgtgatgg   6240
acgacaccgt cagtgcgtcc gtcgcgcagg ctctcgatga gctgatgctt tgggccgagg   6300
taacgactag ggtacacat agtgaccgtt tgacactacc tgctgtggca gtcacgcagg   6360
cagcgcgtcc gagagctact cgactacgaa acccggctcc actgccccga agtccggcac   6420
ctcgtgcacg cggatttcgg ctccaacaat gtcctgacgg acaatggccg cataacagcg   6480
gtcattgact ggagcgaggc tgacggggct tcaggccgtg gagcacgtgc gcctaaagcc   6540
gaggttgtta caggactgcc tgttaccggc gtattgtcgc cagtaactga cctcgctccg   6600
gatgttcggg gattcccaat acgaggtcgc caacatcttc ttctggaggc cgtggttggc   6660
ttgtatggag cagcagacgc gctacttcga gcggaggcat ctacaagccc ctaagggtta   6720
tgctccagcg gttgtagaag aagacctccg gcaccaaccg aacatacctc gtcgtctgcg   6780
cgatgaagct cgcctccgta ccggagcttg caggatcgcc gcggctccgg gcgtatatgc   6840
tccgcattgg tcttgaccaa ctctatcaga gcttggttga cggcaatttc gatgatgcag   6900
ggcctcgaac gtcctagcgg cgccgaggcc cgcatatacg aggcgtaacc agaactggtt   6960
gagatagtct cgaaccaact gccgttaaag ctactacgtc cttgggcgca gggtcgatgc   7020
gacgcaatcg tccgatccgg agccgggact gtcgggcgta cacaaatcgc ccgcagaagc   7080
gcggccgtct ggaccgatgg gaacccgcgt cccagctacg ctgcgttagc aggctaggcc   7140
tcggccctga cagcccgcat gtgtttagcg ggcgtcttcg cgccggcaga cctggctacc   7200
ctgtgtagaa gtactcgccg atagtggaaa ccgacgcccc agcactcgtc cggatcggga   7260
gatgggggag gctaactgaa acacggaagg agacaatacc gacacatctt catgagcggc   7320
tatcaccttt ggctgcgggg tcgtgagcag gcctagccct ctaccccctc cgattgactt   7380
tgtgccttcc tctgttatgg ggaaggaacc tcgacgttaa cttgtttatt gcagcttata   7440
atggttacaa ataaagcaat agcatcacaa atttcacaaa taaagcattt attaccctgt   7500
ccttccttgg agctgcaatt gaacaaataa cgtcgaatat taccaatgtt tatttcgtta   7560
tcgtagtgtt taaagtgttt atttcgtaaa taatgggaca tatccctaga attcactggc   7620
cgtcgtttta caacgtcgtg actgggaaaa ccctggcgtt acccaactta atcgccttgc   7680
agcacatccc cctttcgcca atagggatct taagtgaccg gcagcaaaat gttgcagcac   7740
```

-continued

```
tgacccttt gggaccgcaa tgggttgaat tagcggaacg tcgtgtaggg ggaaagcggt   7800
gctggcgtaa tagcgaagag gcccgcaccg atcgcccttc ccaacagttg cgcagcctga   7860
atggcgaatg gcgcctgatg cggtattttc tccttacgca cgaccgcatt atcgcttctc   7920
cgggcgtggc tagcgggaag ggttgtcaac gcgtcggact taccgcttac cgcggactac   7980
gccataaaag aggaatgcgt tctgtgcggt atttcacacc gcatacgtca aagcaaccat   8040
agtacgcgcc ctgtagcggc gcattaagcg cggcgggtgt ggtggttacg cgcagcgtga   8100
agacacgcca taaagtgtgg cgtatgcagt ttcgttggta tcatgcgcgg gacatcgccg   8160
cgtaattcgc gccgcccaca ccaccaatgc gcgtcgcact ccgctacact tgccagcgcc   8220
ctagcgcccg ctcctttcgc tttcttccct tcctttctcg ccacgttcgc cggctttccc   8280
cgtcaagctc taaatcgggg ggcgatgtga acggtcgcgg gatcgcgggc gaggaaagcg   8340
aaagaaggga aggaaagagc ggtgcaagcg gccgaaaggg gcagttcgag atttagcccc   8400
gctcccttta gggttccgat ttagtgcttt acggcacctc gaccccaaaa aacttgattt   8460
gggtgatggt tcacgtagtg ggccatcgcc ctgatagacg cgagggaaat cccaaggcta   8520
aatcacgaaa tgccgtggag ctggggtttt ttgaactaaa cccactacca agtgcatcac   8580
ccggtagcgg gactatctgc gtttttcgcc ctttgacgtt ggagtccacg ttctttaata   8640
gtggactctt gttccaaact ggaacaacac tcaaccctat ctcgggctat tcttttgatt   8700
caaaaagcgg gaaactgcaa cctcaggtgc aagaaattat cacctgagaa caaggtttga   8760
ccttgttgtg agttgggata gagcccgata agaaaactaa tataagggat tttgccgatt   8820
tcggcctatt ggttaaaaaa tgagctgatt taacaaaaat ttaacgcgaa ttttaacaaa   8880
atattaacgt ttacaatttt atattcccta aaacggctaa agccggataa ccaatttttt   8940
actcgactaa attgttttta aattgcgctt aaaattgttt tataattgca aatgttaaaa   9000
atggtgcact ctcagtacaa tctgctctga tgccgcatag ttaagccagc cccgacaccc   9060
gccaacaccc gctgacgcgc cctgacgggc ttgtctgctc taccacgtga gagtcatgtt   9120
agacgagact acggcgtatc aattcggtcg gggctgtggg cggttgtggg cgactgcgcg   9180
ggactgcccg aacagacgag ccggcatccg cttacagaca agctgtgacc gtctagacga   9240
aagggcctcg tgatacgcct atttttatag gttaatgtca tgataataat ggtttcttag   9300
ggccgtaggc gaatgtctgt tcgacactgg cagatctgct ttcccggagc actatgcgga   9360
taaaaatatc caattacagt actattatta ccaaagaatc acgtcaggtg gcacttttcg   9420
gggaaatgtg cgcggaaccc ctatttgttt atttttctaa atacattcaa atatgtatcc   9480
gctcatgaga caataaccct tgcagtccac cgtgaaaagc ccctttacac gcgccttggg   9540
gataaacaaa taaaaagatt tatgtaagtt tatacatagg cgagtactct gttattggga   9600
gataaatgct tcaataatat tgaaaaagga agagtatgag tattcaacat ttccgtgtcg   9660
cccttattcc ctttttttgcg gcattttgcc ttcctgtttt ctatttacga agttattata   9720
actttttcct tctcatactc ataagttgta aaggcacagc gggaataagg gaaaaaacgc   9780
cgtaaaacgg aaggacaaaa tgctcaccca gaaacgctgg tgaaagtaaa agatgctgaa   9840
gatcagttgg gtgcacgagt gggttacatc gaactggatc tcaacagcgg taagatcctt   9900
acgagtgggt ctttgcgacc actttcattt tctacgactt ctagtcaacc cacgtgctca   9960
cccaatgtag cttgacctag agttgtcgcc attctaggaa gagagttttc gccccgaaga  10020
acgttttcca atgatgagca cttttaaagt tctgctatgt ggcgcggtat tatcccgtat  10080
tgacgccggg caagagcaac ctctcaaaag cggggcttct tgcaaaaggt tactactcgt  10140
```

-continued

```
gaaaatttca agacgataca ccgcgccata atagggcata actgcggccc gttctcgttg  10200
tcggtcgccg catacactat tctcagaatg acttggttga gtactcacca gtcacagaaa  10260
agcatcttac ggatggcatg acagtaagag aattatgcag agccagcggc gtatgtgata  10320
agagtcttac tgaaccaact catgagtggt cagtgtcttt tcgtagaatg cctaccgtac  10380
tgtcattctc ttaatacgtc tgctgccata accatgagtg ataacactgc ggccaactta  10440
cttctgacaa cgatcggagg accgaaggag ctaaccgctt ttttgcacaa catgggggat  10500
acgacggtat tggtactcac tattgtgacg ccggttgaat gaagactgtt gctagcctcc  10560
tggcttcctc gattggcgaa aaaacgtgtt gtacccccta catgtaactc gccttgatcg  10620
ttgggaaccg gagctgaatg aagccatacc aaacgacgag cgtgacacca cgatgcctgt  10680
agcaatggca acaacgttgc gtacattgag cggaactagc aacccttggc ctcgacttac  10740
ttcggtatgg tttgctgctc gcactgtggt gctacggaca tcgttaccgt tgttgcaacg  10800
gcaaactatt aactggcgaa ctacttactc tagcttcccg gcaacaatta atagactgga  10860
tggaggcgga taaagttgca ggaccacttc tgcgctcggc cgtttgataa ttgaccgctt  10920
gatgaatgag atcgaagggc cgttgttaat tatctgacct acctccgcct atttcaacgt  10980
cctggtgaag acgcgagccg ccttccggct ggctggttta ttgctgataa atctggagcc  11040
ggtgagcgtg ggtctcgcgg tatcattgca gcactggggc cagatggtaa gccctcccgt  11100
ggaaggccga ccgaccaaat aacgactatt tagacctcgg ccactcgcac ccagagcgcc  11160
atagtaacgt cgtgaccccg gtctaccatt cgggagggca atcgtagtta tctacacgac  11220
ggggagtcag gcaactatgg atgaacgaaa tagacagatc gctgagatag gtgcctcact  11280
gattaagcat tggtaactgt tagcatcaat agatgtgctg cccctcagtc cgttgatacc  11340
tacttgcttt atctgtctag cgactctatc cacggagtga ctaattcgta accattgaca  11400
cagaccaagt ttactcatat atactttaga ttgatttaaa acttcatttt taatttaaaa  11460
ggatctaggt gaagatcctt tttgataatc tcatgaccaa gtctggttca aatgagtata  11520
tatgaaatct aactaaattt tgaagtaaaa attaaatttt cctagatcca cttctaggaa  11580
aaactattag agtactggtt aatcccttaa cgtgagtttt cgttccactg agcgtcagac  11640
cccgtagaaa agatcaaagg atcttcttga gatccttttt ttctgcgcgt aatctgctgc  11700
ttagggaatt gcactcaaaa gcaaggtgac tcgcagtctg ggcatcttt tctagtttcc  11760
tagaagaact ctaggaaaaa aagacgcgca ttagacgacg ttgcaaacaa aaaaaccacc  11820
gctaccagcg gtggtttgtt tgccggatca agagctacca actctttttc cgaaggtaac  11880
tggcttcagc agagcgcaga aacgtttgtt tttttggtgg cgatggtcgc caccaaacaa  11940
acggcctagt tctcgatggt tgagaaaaag gcttccattg accgaagtcg tctcgcgtct  12000
taccaaatac tgtccttcta gtgtagccgt agttaggcca ccacttcaag aactctgtag  12060
caccgcctac atacctcgct ctgctaatcc tgttaccagt atggtttatg acaggaagat  12120
cacatcggca tcaatccggt ggtgaagttc ttgagacatc gtggcggatg tatggagcga  12180
gacgattagg acaatggtca ggctgctgcc agtggcgata agtcgtgtct taccgggttg  12240
gactcaagac gatagttacc ggataaggcg cagcggtcgg gctgaacggg gggttcgtgc  12300
ccgacgacgg tcaccgctat tcagcacaga atggcccaac ctgagttctg ctatcaatgg  12360
cctattccgc gtcgccagcc cgacttgccc cccaagcacg acacagccca gcttggagcg  12420
aacgacctac accgaactga gatacctaca gcgtgagcta tgagaaagcg ccacgcttcc  12480
```

-continued cgaagggaga aaggcggaca tgtgtcgggt cgaacctcgc ttgctggatg tggcttgact 12540
ctatggatgt cgcactcgat actctttcgc ggtgcgaagg gcttccctct ttccgcctgt 12600
ggtatccggt aagcggcagg gtcggaacag gagagcgcac gagggagctt ccagggggaa 12660
acgcctggta tctttatagt cctgtcgggt ttcgccacct ccataggcca ttcgccgtcc 12720
cagccttgtc ctctcgcgtg ctccctcgaa ggtccccctt tgcggaccat agaaatatca 12780
ggacagccca aagcggtgga ctgacttgag cgtcgatttt tgtgatgctc gtcagggggg 12840
cggagcctat ggaaaaacgc cagcaacgcg gcctttttac ggttcctggc cttttgctgg 12900
gactgaactc gcagctaaaa acactacgag cagtcccccc gcctcggata ccttttttgcg 12960 gtcgttgcgc cggaaaaatg ccaaggaccg gaaaacgacc ccttttgctc acatgttctt 13020
tcctgcgtta tcccctgatt ctgtggataa ccgtattacc gcctttgagt gagctgatac 13080
cgctcgccgc agccgaacga ggaaaacgag tgtacaagaa aggacgcaat aggggactaa 13140
gacacctatt ggcataatgg cggaaactca ctcgactatg gcgagcggcg tcggcttgct 13200
ccgagcgcag cgagtcagtg agcgaggaag cggaagagcg cccaatacgc aaaccgcctc 13260
tccccgcgcg ttggccgatt cattaatgca gctggcacga ggctcgcgtc gctcagtcac 13320
tcgctccttc gccttctcgc gggttatgcg tttggcggag aggggcgcgc aaccggctaa 13380
gtaattacgt cgaccgtgct caggtttccc gactggaaag cgggcagtga gcgcaacgca 13440
attaatgtga gttagctcac tcattaggca ccccaggctt tacactttat gcttccggct 13500
gtccaaaggg ctgacctttc gcccgtcact cgcgttgcgt taattacact caatcgagtg 13560
agtaatccgt ggggtccgaa atgtgaaata cgaaggccga cgtatgttgt gtggaattgt 13620
gagcggataa caatttcaca caggaaacag ctatgaccat gattacgcca agctttaggg 13680
ataacagggt aatcgccatg gcatacaaca caccttaaca ctcgcctatt gttaaagtgt 13740
gtcctttgtc gatactggta ctaatgcggt tcgaaatccc tattgtccca ttagcggtac 13800
cattagttat taatagtaat caattacggg gtcattagtt catagcccat atatggagtt 13860
ccgcgttaca taacttacgg taaagtaatc aataattatc attagttaat gccccagtaa 13920
tcaagtatcg ggtatatacc tcaaggcgca atgtattgaa tgccattt 13968

<210> SEQ ID NO 54
<211> LENGTH: 15356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54
ggtttagtga accgtcagat ccgctagacg tctcatatac ctgactggaa tacgacagct 60
cctgcagctt ctgggcgaag accaccgtgg cccattgcgt ccaaatcact tggcagtcta 120
ggcgatctgc agagtatatg gactgacctt atgctgtcga ggacgtcgaa gacccgcttc 180
tggtggcacc gggtaacgca acttagcgat aatctggtcc gcttggaagt tagcacggcg 240
agcgcgctcc agagccaagt cacgcagctt aacagtacct accgcagagc ggtgcatgaa 300
tgaatcgcta ttagaccagg cgaaccttca atcgtgccgc tcgcgcgagg tctcggttca 360
gtgcgtcgaa ttgtcatgga tggcgtctcg ccacgtactt caggccgata acgttgtcct 420
tagcaacctt gacattaccc tcacctttat tggcagggaa gacgtgcttc tgaccagtag 480
tgccctcacg agcggtacca gtccggctat tgcaacagga atcgttggaa ctgtaatggg 540

-continued

```
agtggaaata accgtccctt ctgcacgaag actggtcatc acgggagtgc tcgccatggt    600
gcaccaccag cggtgaggtg cggaacttct acaacctcaa agcccataac gttgcggata    660
gaacccttct cagggtcaat cagagcagcg tagtttgctg cgtggtggtc gccactccac    720
gccttgaaga tgttggagtt tcgggtattg caacgcctat cttgggaaga gtcccagtta    780
gtctcgtcgc atcaaacgac cgttcggcat cagtgctgcc agaatcgcag agtagctatc    840
tgggtcacag tagaacacac ggtcagcagc cggaacatag ttcttggtca gagccgcacg    900
gcaagccgta gtcacgacgg tcttagcgtc tcatcgatag acccagtgtc atcttgtgtg    960
ccagtcgtcg gccttgtatc aagaaccagt ctcggcgtgc agccttagtc agagccgcaa   1020
taatctcctt acccagcgca acttggtcgg taagtgcggc cttgttctga gtggtctcaa   1080
ttacggtagc agtacctaag tcggaatcag tctcggcgtt attagaggaa tgggtcgcgt   1140
tgaaccagcc attcacgccg gaacaagact caccagagtt aatgccatcg tcatggattc   1200
ccctcgatgt tctcattata tttgctttcc acgttacaca gaccggcaat ctcagccaga   1260
accgcaccat ccgcagccat cgccagagat tcacccaact gggagctaca agagtaatat   1320
aaacgaaagg tgcaatgtgt ctggccgtta gagtcggtct tggcgtggta ggcgtcggta   1380
gcggtctcta agtgggttga gagaggtata ctcagagcga acgtcgtagt ggttcatcgc   1440
gtcctcaata tcataaatca gaacgtcagc cgtcaggaga ccgtcaatgg tgattacctt   1500
ctctccatat gagtctcgct tgcagcatca ccaagtagcg caggagttat agtatttagt   1560
cttgcagtcg gcagtcctct ggcagttacc actaatggaa ctcggtgtgt ttgatgtcct   1620
tacgtttatc gtcgaggttc tcgcccggag ccagatacgc tgcctgagtg cgacccagaa   1680
cagggaactg agcggattta gagccacaca aactacagga atgcaaatag cagctccaag   1740
agcgggcctc ggtctatgcg acggactcac gctgggtctt gtcccttgac tcgcctaaat   1800
ccgctggaga tggaacgtac catgtggcga gaagtggtca cggaggtacg agcgaacgca   1860
gtcaggactt caccgccaaa taccttcaag aacaacgcca ggcgacctct accttgcatg   1920
gtacaccgct cttcaccagt gcctccatgc tcgcttgcgt cagtcctgaa gtggcggttt   1980
atggaagttc ttgttgcggt gtttatctcc agcagcaact acacctttac cttggttagt   2040
acccatttgc tgtccaccag tcatgctagc catatgtata tctccttctt aaagtcgtct   2100
caaatagagg tcgtcgttga tgtggaaatg gaaccaatca tgggtaaacg acaggtggtc   2160
agtacgatcg gtatacatat agaggaagaa tttcagcaga ccagtgcctc caccaagggc   2220
ccatcggtct tcccccctggc gccctgctcc aggagcacct ccgagagcac agcggccctg   2280
ggctgcctgg tcaaggacta ggtcacggag gtggttcccg ggtagccaga agggggaccg   2340
cgggacgagg tcctcgtgga ggctctcgtg tcgccgggac ccgacggacc agttcctgat   2400
cttccccgaa ccggtgacgg tgtcgtggaa ctcaggcgct ctgaccagcg gcgtgcacac   2460
cttcccagct gtcctacagt cctcaggact ctactccctc gaaggggctt ggccactgcc   2520
acagcacctt gagtccgcga gactggtcgc cgcacgtgtg gaagggtcga caggatgtca   2580
ggagtcctga gatgagggag agcagcgtgg tgaccgtgcc ctccagcagc ttgggcaccc   2640
agacctacat ctgcaacgtg aatcacaagc ccagcaacac caaggtggac aagaaagttg   2700
tcgtcgcacc actggcacgg gaggtcgtcg aacccgtggg tctggatgta gacgttgcac   2760
ttagtgttcg ggtcgttgtg gttccacctg ttctttcaac agcccaaatc ttgtgacaaa   2820
actcacacat gcccaccgtg cccagcacct gaactcctgg ggggaccgtc agtcttcctc   2880
ttccccccma aacccaagga tcgggtttag aacactgttt tgagtgtgta cgggtggcac   2940
```

gggtcgtgga cttgaggacc cccctggcag tcagaaggag aaggggggkt ttgggttcct 3000
caccctcatg atctcccgga cccctgaggt cacatgcgtg gtggtggacg tgagccacga 3060
agaccctgag gtcaagttca actggtacgt ggacggcgtg gtgggagtac tagagggcct 3120
ggggactcca gtgtacgcac caccacctgc actcggtgct tctgggactc cagttcaagt 3180
tgaccatgca cctgccgcac gaggtgcata atgccaagac aaagccgcgg gaggagcagt 3240
acaacagcac gtaccgtgtg gtcagcgtcc tcaccgtcct gcaccaggac tggctgaatg 3300
ctccacgtat tacggttctg tttcggcgcc ctcctcgtca tgttgtcgtg catggcacac 3360
cagtcgcagg agtggcagga cgtggtcctg accgacttac gcaaggagta caagtgcaag 3420
gtctccaaca aagccctccc agcccccatc gagaaaacca tctccaaagc caaagggcag 3480
ccccgagaac cacaggtgta cgttcctcat gttcacgttc cagaggttgt ttcgggaggg 3540
tcgggggtag ctcttttggt agaggtttcg gtttcccgtc ggggctcttg gtgtccacat 3600
caccctgccc ccatcccggg atgagctgac caagaaccag gtcagcctga cctgcctggt 3660
caaaggcttc tatcccagcg acatcgccgt ggagtgggag gtgggacggg ggtagggccc 3720
tactcgactg gttcttggtc cagtcggact ggacggacca gtttccgaag atagggtcgc 3780
tgtagcggca cctcaccctc agcaatgggc agccggagaa caactacaag accacgcctc 3840
ccgtgctgga ctccgacggc tccttcttcc tctacagcaa gctcaccgtg gacaagagca 3900
tcgttacccg tcggcctctt gttgatgttc tggtgcggag ggcacgacct gaggctgccg 3960
aggaagaagg agatgtcgtt cgagtggcac ctgttctcgt ggtggcagca ggggaacgtc 4020
ttctcatgct ccgtgatgca tgaggctctg cacaaccact acacgcagaa gagcctctcc 4080
ctgtctccgg gtaaatgagc ccaccgtcgt ccccttgcag aagagtacga ggcactacgt 4140
actccgagac gtgttggtga tgtgcgtctt ctcggagagg gacagaggcc catttactcg 4200
ggccgcaatt taattccggt tattttccac catattgccg tcttttggca atgtgagggc 4260
ccggaaacct ggccctgtct tcttgacgag cattcctagg ccggcgttaa attaaggcca 4320
ataaaaggtg gtataacggc agaaaaccgt tacactcccg ggcctttgga ccgggacaga 4380
agaactgctc gtaaggatcc ggtctttccc ctctcgccaa aggaatgcaa ggtctgttga 4440
atgtcgtgaa ggaagcagtt cctctggaag cttcttgaag acaaacaacg tctgtagcga 4500
ccagaaaggg gagagcggtt tccttacgtt ccagacaact tacagcactt ccttcgtcaa 4560
ggagaccttc gaagaacttc tgtttgttgc agacatcgct ccctttgcag gcagcggaac 4620
cccccacctg gcgacaggtg cctctgcggc caaaagccac gtgtataaga tacacctgca 4680
aaggcggcac aaccccagtg gggaaacgtc cgtcgccttg gggggtggac cgctgtccac 4740
ggagacgccg gttttcggtg cacatattct atgtggacgt ttccgccgtg ttggggtcac 4800
ccacgttgtg agttggatag ttgtggaaag agtcaaatgg ctcacctcaa gcgtattcaa 4860
caaggggctg aaggatgccc agaaggtacc ccattgtatg ggtgcaacac tcaacctatc 4920
aacacctttc tcagtttacc gagtggagtt cgcataagtt gttccccgac ttcctacggg 4980
tcttccatgg ggtaacatac ggatctgatc tggggcctcg gtgcacatgc tttacatgtg 5040
tttagtcgag gttaaaaaac gtctaggccc cccgaaccac ggggacgtgg ttttcctttg 5100
cctagactag accccggagc cacgtgtacg aaatgtacac aaatcagctc caatttttttg 5160 cagatccggg gggcttggtg cccctgcacc aaaaggaaac aaaaacacga tgataatatg 5220
gccaccaccc atacctaggc ttttgcaaag atcgatcaag agacaggatg aggatcgttt 5280

-continued

```
cgcatgattg aacaagatgg tttttgtgct actattatac cggtggtggg tatggatccg   5340
aaaacgtttc tagctagttc tctgtcctac tcctagcaaa gcgtactaac ttgttctacc   5400
attgcacgca ggttctccgg ccgcttgggt ggagaggcta ttcggctatg actgggcaca   5460
acagacaatc ggctgctctg atgccgccgt gttccggctg taacgtgcgt ccaagaggcc   5520
ggcgaaccca cctctccgat aagccgatac tgacccgtgt tgtctgttag ccgacgagac   5580
tacggcggca caaggccgac tcagcgcagg ggcgcccggt tctttttgtc aagaccgacc   5640
tgtccggtgc cctgaatgaa ctgcaagacg aggcagcgcg gctatcgtgg ctggccacga   5700
agtcgcgtcc ccgcgggcca agaaaaacag ttctggctgg acaggccacg ggacttactt   5760
gacgttctgc tccgtcgcgc cgatagcacc gaccggtgct cgggcgttcc ttgcgcagct   5820
gtgctcgacg ttgtcactga agcgggaagg gactggctgc tattgggcga agtgccgggg   5880
caggatctcc tgtcatctca gcccgcaagg aacgcgtcga cacgagctgc aacagtgact   5940
tcgcccttcc ctgaccgacg ataacccgct tcacggcccc gtcctagagg acagtagagt   6000
ccttgctcct gccgagaaag tatccatcat ggctgatgca atgcggcggc tgcatacgct   6060
tgatccggct acctgcccat tcgaccacca agcgaaacat ggaacgagga cggctctttc   6120
ataggtagta ccgactacgt tacgccgccg acgtatgcga actaggccga tggacgggta   6180
agctggtggt tcgctttgta cgcatcgagc gagcacgtac tcggatggaa gccggtcttg   6240
tcgatcagga tgatctggac gaagagcatc aggggctcgc gccagccgaa ctgttcgcca   6300
gcgtagctcg ctcgtgcatg agcctacctt cggccagaac agctagtcct actagacctg   6360
cttctcgtag tccccgagcg cggtcggctt gacaagcggt ggctcaaggc gagcatgccc   6420
gacggcgagg atctcgtcgt gacccatggc gatgcctgct tgccgaatat catggtggaa   6480
aatggccgct tttctggatt ccgagttccg ctcgtacggg ctgccgctcc tagagcagca   6540
ctgggtaccg ctacggacga acggcttata gtaccacctt ttaccggcga aaagacctaa   6600
catcgactgt ggccggctgg gtgtggcgga ccgctatcag gacatagcgt tggctacccg   6660
tgatattgct gaagagcttg gcggcgaatg ggctgaccgc gtagctgaca ccggccgacc   6720
cacaccgcct ggcgatagtc ctgtatcgca accgatgggc actataacga cttctcgaac   6780
cgccgcttac ccgactggcg ttcctcgtgc tttacggtat cgccgctccc gattcgcagc   6840
gcatcgcctt ctatcgcctt cttgacgagt tcttctgagc gggactctgg ggttcgggcc   6900
aaggagcacg aaatgccata gcggcgaggg ctaagcgtcg cgtagcggaa gatagcggaa   6960
gaactgctca agaagactcg ccctgagacc ccaagcccgg gcactcgagc ataaacttgt   7020
ttattgcagc ttataatggt tacaaataaa gcaatagcat cacaaatttc acaaataaag   7080
cattttttc actgcattct cgtgagctcg tatttgaaca aataacgtcg aatattacca   7140
atgtttattt cgttatcgta gtgtttaaag tgtttatttc gtaaaaaaag tgacgtaaga   7200
agttgtggtt tgtccaaact catcaatgta tcttaagtag ggataacagg gtaattttgt   7260
taaatcagct catttttaa ccaataggaa cgccatcaaa tcaacaccaa acaggtttga   7320
gtagttacat agaattcatc cctattgtcc cattaaaaca atttagtcga gtaaaaaatt   7380
ggttatcctt gcggtagttt aataattcgc gtctggcctt cctgtagcca gctttcatca   7440
acattaaatg tgagcgagta acaacccgtc ggattctccg tgggaacaaa cggcggattg   7500
ttattaagcg cagaccggaa ggacatcggt cgaaagtagt tgtaatttac actcgctcat   7560
tgttgggcag cctaagaggc acccttgttt gccgcctaac accgtaatgg gataggttac   7620
gttggtgtag atgggcgcat cgtaaccgtg catctgccag tttgagggga cgacgaccgt   7680
```

-continued

```
atcggcctca ggaagatcgc tggcattacc ctatccaatg caaccacatc tacccgcgta   7740
gcattggcac gtagacggtc aaactcccct gctgctggca tagccggagt ccttctagcg   7800
actccagcca gctttccggc accgcttctg gtgccggaaa ccaggcaaag cgccattcgc   7860
cattcaggct gcgcaactgt tgggaagggc gatcggtgcg tgaggtcggt cgaaaggccg   7920
tggcgaagac cacggccttt ggtccgtttc gcggtaagcg gtaagtccga cgcgttgaca   7980
acccttcccg ctagccacgc ggcctcttcg ctattacgcc agctggcgaa agggggatgt   8040
gctgcaaggc gattaagttg ggtaacgcca gggttttccc agtcacgacg ttgtaaaacg   8100
ccggagaagc gataatgcgg tcgaccgctt tccccctaca cgacgttccg ctaattcaac   8160
ccattgcggt cccaaaaggg tcagtgctgc aacattttgc acggccagtg aattgcaatt   8220
cgtaatcatg gtcatagctg tttcctgtgt gaaattgtta tccgctcaca attccacaca   8280
acatacgagc cggaagcata tgccggtcac ttaacgttaa gcattagtac cagtatcgac   8340
aaaggacaca ctttaacaat aggcgagtgt taaggtgtgt tgtatgctcg gccttcgtat   8400
aagtgtaaag cctggggtgc ctaatgagtg agctaactca cattaattgc gttgcgctca   8460
ctgccattac cctgttatcc ctagtgaacc atcaccctaa ttcacatttc ggaccccacg   8520
gattactcac tcgattgagt gtaattaacg caacgcgagt gacggtaatg ggacaatagg   8580
gatcacttgg tagtgggatt tcaagttttt tggggtcgag gtgccgtaaa gcactaaatc   8640
ggaaccctaa agggagcccc cgatttagag cttgacgggg aaagccggcg aacgtggcga   8700
agttcaaaaa accccagctc cacggcattt cgtgatttag ccttgggatt tccctcgggg   8760
gctaaatctc gaactgcccc tttcggccgc ttgcaccgct gaaaggaagg gaagaaagcg   8820
aaaggagcgg gcgctagggc gctggcaagt gtagcggtca cgctgcgcgt aaccaccaca   8880
cccgccgcgc ttaatgcgcc ctttccttcc cttctttcgc tttcctcgcc cgcgatcccg   8940
cgaccgttca catcgccagt gcgacgcgca ttggtggtgt gggcggcgcg aattacgcgg   9000
gctacagggc gcgtcaggtg gcacttttcg gggaaatgtg cgcggaaccc ctatttgttt   9060
atttttctaa atacattcaa atatgtatcc gctcatgaga cgatgtcccg cgcagtccac   9120
cgtgaaaagc ccctttacac gcgccttggg gataaacaaa taaaaagatt tatgtaagtt   9180
tatacatagg cgagtactct caataaccct gataaatgct tcaataataa cgaccggtaa   9240
tgaaaaagga agagtatgag tattcaacat ttccgtgtcg cccttattcc ctttttttgcg   9300
gttattggga ctatttacga agttattatt gctggccatt actttttcct tctcatactc   9360
ataagttgta aaggcacagc gggaataagg gaaaaaacgc gcattttgcc ttcctgtttt   9420
tgctcaccca gaaacgctgg tgaaagtaaa agatgctgaa gatcagttgg gtgcacgagt   9480
gggttacatc gaactggatc cgtaaaacgg aaggacaaaa acgagtgggt ctttgcgacc   9540
actttcattt tctacgactt ctagtcaacc cacgtgctca cccaatgtag cttgacctag   9600
tcaacagcgg taagatcctt gagagttttc gccccgaaga acgttttcca atgatgagca   9660
cttttaaagt tctgctatgt ggcgcggtat tatcccgtat agttgtcgcc attctaggaa   9720
ctctcaaaag cggggcttct tgcaaaaggt tactactcgt gaaaatttca agacgataca   9780
ccgcgccata atagggcata tgacgccggg caagagcaac tcggtcgccg catacactat   9840
tctcagaatg acttggttga gtctagcgtt gatcggcacg taagaggttc caactttcac   9900
actgcggccc gttctcgttg agccagcggc gtatgtgata agagtcttac tgaaccaact   9960
cagatcgcaa ctagccgtgc attctccaag gttgaaagtg cataatgaaa taagatcact  10020
```

-continued

```
accgggcgta ttttttgagt tatcgagatt ttcaggagct aaggaagcta aaatggagaa  10080
aaaaatcact ggatatacca gtattacttt attctagtga tggcccgcat aaaaaactca  10140
atagctctaa aagtcctcga ttccttcgat tttacctctt tttttagtga cctatatggt  10200
ccgttgatat atcccaatgg catcgtaaag aacattttga ggcatttcag tcagttgctc  10260
aatgtaccta taaccagacc gttcagctgg atattacggc ggcaactata tagggttacc  10320
gtagcatttc ttgtaaaact ccgtaaagtc agtcaacgag ttacatggat attggtctgg  10380
caagtcgacc tataatgccg ctttttaaag accgtaaaga aaaataagca caagttttat  10440
ccggccttta ttcacattct tgcccgcctg atgaatgctc atccggaatt ccgtatggca  10500
gaaaaatttc tggcatttct ttttattcgt gttcaaaata ggccggaaat aagtgtaaga  10560
acgggcggac tacttacgag taggccttaa ggcataccgt atgaaagacg gtgagctggt  10620
gatatgggat agtgttcacc cttgttacac cgttttccat gagcaaactg aaacgttttc  10680
atcgctctgg agtgaatacc tactttctgc cactcgacca ctataccta tcacaagtgg  10740
gaacaatgtg gcaaaaggta ctcgtttgac tttgcaaaag tagcgagacc tcacttatgg  10800
acgacgattt ccggcagttt ctacacatat attcgcaaga tgtggcgtgt tacggtgaaa  10860
acctggccta tttccctaaa gggtttattg agaatatgtt tgctgctaaa ggccgtcaaa  10920
gatgtgtata taagcgttct acaccgcaca atgccacttt tggaccggat aaagggattt  10980
cccaaataac tcttatacaa tttcgtatca gccaatccct gggtgagttt caccagtttt  11040
gatttaaacg tggccaatat ggacaacttc ttcgcccccg ttttcaccat gggcaaatat  11100
aaagcatagt cggttaggga cccactcaaa gtggtcaaaa ctaaatttgc accggttata  11160
cctgttgaag aagcgggggc aaaagtggta cccgtttata tatacgcaag gcgacaaggt  11220
gctgatgccg ctggcgattc aggttcatca tgccgtctgt gatggcttcc atgtcggcag  11280
aatgcttaat gaattacaac atatgcgttc cgctgttcca cgactacggc gaccgctaag  11340
tccaagtagt acggcagaca ctaccgaagg tacagccgtc ttacgaatta cttaatgttg  11400
agtactgcga tgagtggcag ggcggggcgt aattttttta aggcagttat tggtgccctt  11460
aaacgcctgg tgctacgcct gaataagtga taataagcgg tcatgacgct actcaccgtc  11520
ccgccccgca ttaaaaaaat tccgtcaata accacgggaa tttgcggacc acgatgcgga  11580
cttattcact attattcgcc atgaatggca gaaattcgaa atgaccgacc aagcgacgcc  11640
caacctgcca tcacgagatt tcgattccac cgccgccttc tatgaaaggt tgggcttcgg  11700
tacttaccgt ctttaagctt tactggctgg ttcgctgcgg gttggacggt agtgctctaa  11760
agctaaggtg gcggcggaag atactttcca acccgaagcc aatcgttttc cgggacgccg  11820
gctggatgat cctccagcgc ggggatctca tgctggagtt cttcgcccac cctaggggga  11880
ggctaactga aacacggaag ttagcaaaag gccctgcggc cgacctacta ggaggtcgcg  11940
cccctagagt acgacctcaa gaagcgggtg ggatcccct ccgattgact ttgtgccttc  12000
gagacaatac cggaaggaac ccgcgctatg acggcaataa aaagacagaa taaaacgcac  12060
ggtgttgggt cgtttgttca taaacgcggg gttcggtccc ctctgttatg gccttccttg  12120
ggcgcgatac tgccgttatt tttctgtctt attttgcgtg ccacaaccca gcaaacaagt  12180
atttgcgccc caagccaggg agggctggca ctctgtcgat accccaccga gaccccattg  12240
gggccaatac gcccgcgttt cttccttttc cccaccccac cccccaagtt cgggtgaagg  12300
tcccgaccgt gagacagcta tggggtggct ctggggtaac cccggttatg cgggcgcaaa  12360
gaaggaaaag gggtggggtg gggggttcaa gcccacttcc cccagggctc gcagccaacg  12420
```

-continued

```
tcggggcggc aggccctgcc atagcctcag gttactcata tatactttag attgatttaa  12480
aacttcattt ttaatttaaa gggtcccgag cgtcggttgc agccccgccg tccgggacgg  12540
tatcggagtc caatgagtat atatgaaatc taactaaatt ttgaagtaaa aattaaattt  12600
aggatctagg tgaagatcct ttttgataat ctcatgacca aaatccctta acgtgagttt  12660
tcgttccact gagcgtcaga ccccgtagaa aagatcaaag tcctagatcc acttctagga  12720
aaaactatta gagtactggt tttagggaat tgcactcaaa agcaaggtga ctcgcagtct  12780
ggggcatctt ttctagtttc gatcttcttg agatcctttt tttctgcgcg taatctgctg  12840
cttgcaaaca aaaaaaccac cgctaccagc ggtggtttgt ttgccggatc aagagctacc  12900
ctagaagaac tctaggaaaa aaagacgcgc attagacgac gaacgtttgt ttttttggtg  12960
gcgatggtcg ccaccaaaca aacggcctag ttctcgatgg aactcttttt ccgaaggtaa  13020
ctggcttcag cagagcgcag ataccaaata ctgtccttct agtgtagccg tagttaggcc  13080
accacttcaa gaactctgta ttgagaaaaa ggcttccatt gaccgaagtc gtctcgcgtc  13140
tatggtttat gacaggaaga tcacatcggc atcaatccgg tggtgaagtt cttgagacat  13200
gcaccgccta catacctcgc tctgctaatc ctgttaccag tggctgctgc cagtggcgat  13260
aagtcgtgtc ttaccgggtt ggactcaaga cgatagttac cgtggcggat gtatggagcg  13320
agacgattag gacaatggtc accgacgacg gtcaccgcta ttcagcacag aatggcccaa  13380
cctgagttct gctatcaatg cggataaggc gcagcggtcg ggctgaacgg ggggttcgtg  13440
cacacagccc agcttggagc gaacgaccta caccgaactg agatacctac agcgtgagct  13500
gcctattccg cgtcgccagc ccgacttgcc ccccaagcac gtgtgtcggg tcgaacctcg  13560
cttgctggat gtggcttgac tctatggatg tcgcactcga atgagaaagc gccacgcttc  13620
ccgaagggag aaaggcggac aggtatccgg taagcggcag ggtcggaaca ggagagcgca  13680
cgagggagct tccaggggga tactctttcg cggtgcgaag ggcttccctc tttccgcctg  13740
tccataggcc attcgccgtc ccagccttgt cctctcgcgt gctccctcga aggtccccct  13800
aacgcctggt atctttatag tcctgtcggg tttcgccacc tctgacttga gcgtcgattt  13860
ttgtgatgct cgtcaggggg gcggagccta tggaaaaacg ttgcggacca tagaaatatc  13920
aggacagccc aaagcggtgg agactgaact cgcagctaaa aacactacga gcagtccccc  13980
cgcctcggat acctttttgc ccagcaacgc ggcctttttta cggttcctgg ccttttgctg  14040
gccttttgct cacatgttct ttcctgcgtt atcccctgat tctgtggata accgtattac  14100
ggtcgttgcg ccggaaaaat gccaaggacc ggaaaacgac cggaaaacga gtgtacaaga  14160
aaggacgcaa taggggacta agacacctat tggcataatg cgccatgcat tagttattaa  14220
tagtaatcaa ttacggggtc attagttcat agcccatata tggagttccg cgttacataa  14280
cttacggtaa atggcccgcc gcggtacgta atcaataatt atcattagtt aatgccccag  14340
taatcaagta tcgggtatat acctcaaggc gcaatgtatt gaatgccatt taccgggcgg  14400
tggctgaccg cccaacgacc cccgcccatt gacgtcaata atgacgtatg ttcccatagt  14460
aacgccaata gggactttcc attgacgtca atgggtggag accgactggc gggttgctgg  14520
gggcgggtaa ctgcagttat tactgcatac aagggtatca ttgcggttat ccctgaaagg  14580
taactgcagt tacccacctc tatttacggt aaactgccca cttggcagta catcaagtgt  14640
atcatatgcc aagtacgccc cctattgacg tcaatgacgg taaatggccc gcctggcatt  14700
ataaatgcca tttgacgggt gaaccgtcat gtagttcaca tagtatacgg ttcatgcggg  14760
```

-continued

```
ggataactgc agttactgcc atttaccggg cggaccgtaa atgcccagta catgacctta  14820

tgggactttc ctacttggca gtacatctac gtattagtca tcgctattac catggtgatg  14880

cggttttggc agtacatcaa tacgggtcat gtactggaat accctgaaag gatgaaccgt  14940

catgtagatg cataatcagt agcgataatg gtaccactac gccaaaaccg tcatgtagtt  15000

tgggcgtgga tagcggtttg actcacgggg atttccaagt ctccacccca ttgacgtcaa  15060

tgggagtttg ttttggcacc aaaatcaacg ggactttcca acccgcacct atcgccaaac  15120

tgagtgcccc taaaggttca gaggtggggt aactgcagtt accctcaaac aaaaccgtgg  15180

ttttagttgc cctgaaaggt aaatgtcgta acaactccgc cccattgacg caaatgggcg  15240

gtaggcgtgt acggtgggag gtctatataa gcagagcttt tacagcattg ttgaggcggg  15300

gtaactgcgt ttacccgcca tccgcacatg ccaccctcca gatatattcg tctcga      15356
```

```
<210> SEQ ID NO 55
<211> LENGTH: 16876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

ggtttagtga accgtcagat ccgctagacg tctcatatac ctgactggaa tacgacagct     60

cctgcagctt ctgggcgaag accaccgtgg cccattgcgt ccaaatcact tggcagtcta    120

ggcgatctgc agagtatatg gactgacctt atgctgtcga ggacgtcgaa gacccgcttc    180

tggtggcacc gggtaacgca acttagcgat aatctggtcc gcttggaagt tagcacggcg    240

agcgcgctcc agagccaagt cacgcagctt aacagtacct accgcagagc ggtgcatgaa    300

tgaatcgcta ttagaccagg cgaaccttca atcgtgccgc tcgcgcgagg tctcggttca    360

gtgcgtcgaa ttgtcatgga tggcgtctcg ccacgtactt caggccgata acgttgtcct    420

tagcaacctt gacattaccc tcacctttat tggcagggaa gacgtgcttc tgaccagtag    480

tgccctcacg agcggtacca gtccggctat tgcaacagga atcgttggaa ctgtaatggg    540

agtggaaata accgtccctt ctgcacgaag actggtcatc acgggagtgc tcgccatggt    600

gcaccaccag cggtgaggtg cggaacttct acaacctcaa agcccataac gttgcggata    660

gaacccttct cagggtcaat cagagcagcg tagtttgctg cgtggtggtc gccactccac    720

gccttgaaga tgttggagtt tcgggtattg caacgcctat cttgggaaga gtcccagtta    780

gtctcgtcgc atcaaacgac cgttcggcat cagtgctgcc agaatcgcag agtagctatc    840

tgggtcacag tagaacacac ggtcagcagc cggaacatag ttcttggtca gagccgcacg    900

gcaagccgta gtcacgacgg tcttagcgtc tcatcgatag acccagtgtc atcttgtgtg    960

ccagtcgtcg gccttgtatc aagaaccagt ctcggcgtgc agccttagtc agagccgcaa   1020

taatctcctt acccagcgca acttggtcgg taagtgcggc cttgttctga gtggtctcaa   1080

ttacggtagc agtacctaag tcggaatcag tctcggcgtt attagaggaa tgggtcgcgt   1140

tgaaccagcc attcacgccg gaacaagact caccagagtt aatgccatcg tcatggattc   1200

ccctcgatgt tctcattata tttgctttcc acgttacaca gaccggcaat ctcagccaga   1260

accgcaccat ccgcagccat cgccagagat tcacccaact gggagctaca agagtaatat   1320

aaacgaaagg tgcaatgtgt ctggccgtta gagtcggtct tggcgtggta ggcgtcggta   1380

gcggtctcta agtgggttga gagaggtata ctcagagcga acgtcgtagt ggttcatcgc   1440
```

-continued

```
gtcctcaata tcataaatca gaacgtcagc cgtcaggaga ccgtcaatgg tgattacctt   1500
ctctccatat gagtctcgct tgcagcatca ccaagtagcg caggagttat agtatttagt   1560
cttgcagtcg gcagtcctct ggcagttacc actaatggaa ctcggtgtgt ttgatgtcct   1620
tacgtttatc gtcgaggttc tcgcccggag ccagatacgc tgcctgagtg cgacccagaa   1680
cagggaactg agcggattta gagccacaca aactacagga atgcaaatag cagctccaag   1740
agcgggcctc ggtctatgcg acggactcac gctgggtctt gtcccttgac tcgcctaaat   1800
ccgctggaga tggaacgtac catgtggcga gaagtggtca cggaggtacg agcgaacgca   1860
gtcaggactt caccgccaaa taccttcaag aacaacgcca ggcgacctct accttgcatg   1920
gtacaccgct cttcaccagt gcctccatgc tcgcttgcgt cagtcctgaa gtggcggttt   1980
atggaagttc ttgttgcggt gtttatctcc agcagcaact acacctttac cttggttagt   2040
acccatttgc tgtccaccag tcatgctagc catatgtata tctccttctt aaagtcgtct   2100
caaatagagg tcgtcgttga tgtggaaatg gaaccaatca tgggtaaacg acaggtggtc   2160
agtacgatcg gtatacatat agaggaagaa tttcagcaga ccagtgcctc caccaagggc   2220
ccatcggtct tccccctggc gccctgctcc aggagcacct ccgagagcac agcggccctg   2280
ggctgcctgg tcaaggacta ggtcacggag gtggttcccg ggtagccaga agggggaccg   2340
cgggacgagg tcctcgtgga ggctctcgtg tcgccgggac ccgacggacc agttcctgat   2400
cttccccgaa ccggtgacgg tgtcgtggaa ctcaggcgct ctgaccagcg gcgtgcacac   2460
cttcccagct gtcctacagt cctcaggact ctactccctc gaaggggctt ggccactgcc   2520
acagcacctt gagtccgcga gactggtcgc cgcacgtgtg gaagggtcga caggatgtca   2580
ggagtcctga gatgagggag agcagcgtgg tgaccgtgcc ctccagcagc ttgggcaccc   2640
agacctacat ctgcaacgtg aatcacaagc ccagcaacac caaggtggac aagaaagttg   2700
tcgtcgcacc actggcacgg gaggtcgtcg aacccgtggg tctggatgta gacgttgcac   2760
ttagtgttcg ggtcgttgtg gttccacctg ttctttcaac agcccaaatc ttgtgacaaa   2820
actcacacat gcccaccgtg cccagcacct gaactcctgg ggggaccgtc agtcttcctc   2880
ttccccccma aacccaagga tcgggtttag aacactgttt tgagtgtgta cgggtggcac   2940
gggtcgtgga cttgaggacc cccctggcag tcagaaggag aagggggkt ttgggttcct   3000
caccctcatg atctcccgga cccctgaggt cacatgcgtg gtggtggacg tgagccacga   3060
agaccctgag gtcaagttca actggtacgt ggacggcgtg gtgggagtac tagagggcct   3120
ggggactcca gtgtacgcac caccacctgc actcggtgct tctgggactc cagttcaagt   3180
tgaccatgca cctgccgcac gaggtgcata atgccaagac aaagccgcgg gaggagcagt   3240
acaacagcac gtaccgtgtg gtcagcgtcc tcaccgtcct gcaccaggac tggctgaatg   3300
ctccacgtat tacggttctg tttcggcgcc ctcctcgtca tgttgtcgtg catggcacac   3360
cagtcgcagg agtggcagga cgtggtcctg accgacttac gcaaggagta caagtgcaag   3420
gtctccaaca aagccctccc agcccccatc gagaaaacca tctccaaagc caaagggcag   3480
ccccgagaac cacaggtgta cgttcctcat gttcacgttc cagaggttgt ttcgggaggg   3540
tcgggggtag ctcttttggt agaggtttcg gtttcccgtc ggggctcttg gtgtccacat   3600
caccctgccc ccatcccggg atgagctgac caagaaccag gtcagcctga cctgcctggt   3660
caaaggcttc taccccagcg acatcgccgt ggagtgggag gtgggacggg ggtagggccc   3720
tactcgactg gttcttggtc cagtcggact ggacggacca gtttccgaag atggggtcgc   3780
tgtagcggca cctcaccctc agcaatgggc agccggagaa caactacaag accacgcctc   3840
```

-continued

```
ccatgctgga ctccgacggc tccttcttcc tctacagcaa gctcaccgtg gacaagagca   3900
tcgttacccg tcggcctctt gttgatgttc tggtgcggag ggtacgacct gaggctgccg   3960
aggaagaagg agatgtcgtt cgagtggcac ctgttctcgt ggtggcagca ggggaacgtc   4020
ttctcatgct ccgtgatgca tgaggctctg cacaaccact acacgcagaa gagcctctcc   4080
ctgtctccgg gtaaagggag ccaccgtcgt ccccttgcag aagagtacga ggcactacgt   4140
actccgagac gtgttggtga tgtgcgtctt ctcggagagg gacagaggcc catttccctc   4200
ctcgccagat aagtggtcag atccaccggt cgccaccatg gtgagcaagg gcgaggagct   4260
gttcaccggg gtggtgccca tcctggtcga gctggacggc gagcggtcta ttcaccagtc   4320
taggtggcca gcggtggtac cactcgttcc cgctcctcga caagtggccc caccacgggt   4380
aggaccagct cgacctgccg gacgtaaacg gccacaagtt cagcgtgtcc ggcgagggcg   4440
agggcgatgc cacctacggc aagctgaccc tgaagttcat ctgcaccacc ggcaagctgc   4500
ctgcatttgc cggtgttcaa gtcgcacagg ccgctcccgc tcccgctacg gtggatgccg   4560
ttcgactggg acttcaagta gacgtggtgg ccgttcgacg ccgtgccctg gcccaccctc   4620
gtgaccaccc tgacctacgg cgtgcagtgc ttcagccgct accccgacca catgaagcag   4680
cacgacttct tcaagtccgc ggcacgggac cgggtgggag cactggtggg actggatgcc   4740
gcacgtcacg aagtcggcga tggggctggt gtacttcgtc gtgctgaaga agttcaggcg   4800
catgcccgaa ggctacgtcc aggagcgcac catcttcttc aaggacgacg gcaactacaa   4860
gacccgcgcc gaggtgaagt tcgagggcga caccctggtg gtacgggctt ccgatgcagg   4920
tcctcgcgtg gtagaagaag ttcctgctgc cgttgatgtt ctgggcgcgg ctccacttca   4980
agctcccgct gtgggaccac aaccgcatcg agctgaaggg catcgacttc aaggaggacg   5040
gcaacatcct ggggcacaag ctggagtaca actacaacag ccacaacgtc tatatcatgg   5100
ttggcgtagc tcgacttccc gtagctgaag ttcctcctgc cgttgtagga ccccgtgttc   5160
gacctcatgt tgatgttgtc ggtgttgcag atatagtacc ccgacaagca gaagaacggc   5220
atcaaggtga acttcaagat ccgccacaac atcgaggacg gcagcgtgca gctcgccgac   5280
cactaccagc agaacacccc ggctgttcgt cttcttgccg tagttccact tgaagttcta   5340
ggcggtgttg tagctcctgc cgtcgcacgt cgagcggctg gtgatggtcg tcttgtgggg   5400
catcggcgac ggccccgtgc tgctgcccga caaccactac ctgagcaccc agtccgccct   5460
gagcaaagac cccaacgaga agcgcgatca catggtcctg gtagccgctg ccggggcacg   5520
acgacgggct gttggtgatg gactcgtggg tcaggcggga ctcgtttctg gggttgctct   5580
tcgcgctagt gtaccaggac ctggagttcg tgaccgccgc cgggatcact ctcggcatgg   5640
acgagctgta caagtaaagc ggccgcaatt taattccggt tattttccac catattgccg   5700
gacctcaagc actggcggcg gccctagtga gagccgtacc tgctcgacat gttcatttcg   5760
ccggcgttaa attaaggcca ataaaaggtg gtataacggc tcttttggca atgtgagggc   5820
ccggaaacct ggccctgtct tcttgacgag cattcctagg ggtctttccc ctctcgccaa   5880
aggaatgcaa ggtctgttga agaaaaccgt tacactcccg ggcctttgga ccgggacaga   5940
agaactgctc gtaaggatcc ccagaaaggg gagagcggtt tccttacgtt ccagacaact   6000
atgtcgtgaa ggaagcagtt cctctggaag cttcttgaag acaaacaacg tctgtagcga   6060
ccctttgcag gcagcggaac cccccacctg gcgacaggtg tacagcactt ccttcgtcaa   6120
ggagaccttc gaagaacttc tgtttgttgc agacatcgct gggaaacgtc cgtcgccttg   6180
```

-continued

```
gggggtggac cgctgtccac cctctgcggc caaaagccac gtgtataaga tacacctgca   6240
aaggcggcac aaccccagtg ccacgttgtg agttggatag ttgtggaaag agtcaaatgg   6300
ggagacgccg gttttcggtg cacatattct atgtggacgt ttccgccgtg ttggggtcac   6360
ggtgcaacac tcaacctatc aacacctttc tcagtttacc ctcacctcaa gcgtattcaa   6420
caaggggctg aaggatgccc agaaggtacc ccattgtatg ggatctgatc tggggcctcg   6480
gtgcacatgc tttacatgtg gagtggagtt cgcataagtt gttccccgac ttcctacggg   6540
tcttccatgg ggtaacatac cctagactag accccggagc cacgtgtacg aaatgtacac   6600
tttagtcgag gttaaaaaac gtctaggccc cccgaaccac ggggacgtgg ttttcctttg   6660
aaaaacacga tgataatatg gccaccaccc atacctaggc aaatcagctc caatttttg    6720
cagatccggg gggcttggtg cccctgcacc aaaaggaaac tttttgtgct actattatac   6780
cggtggtggg tatggatccg ttttgcaaag atcgatcaag agacaggatg aggatcgttt   6840
cgcatgattg aacaagatgg attgcacgca ggttctccgg ccgcttgggt ggagaggcta   6900
aaaacgtttc tagctagttc tctgtcctac tcctagcaaa gcgtactaac ttgttctacc   6960
taacgtgcgt ccaagaggcc ggcgaaccca cctctccgat ttcggctatg actgggcaca   7020
acagacaatc ggctgctctg atgccgccgt gttccggctg tcagcgcagg ggcgcccggt   7080
tctttttgtc aagaccgacc aagccgatac tgacccgtgt tgtctgttag ccgacgagac   7140
tacggcggca caaggccgac agtcgcgtcc ccgcgggcca agaaaaacag ttctggctgg   7200
tgtccggtgc cctgaatgaa ctgcaagacg aggcagcgcg gctatcgtgg ctggccacga   7260
cgggcgttcc ttgcgcagct gtgctcgacg ttgtcactga acaggccacg ggacttactt   7320
gacgttctgc tccgtcgcgc cgatagcacc gaccggtgct gcccgcaagg aacgcgtcga   7380
cacgagctgc aacagtgact agcgggaagg gactggctgc tattgggcga agtgccgggg   7440
caggatctcc tgtcatctca ccttgctcct gccgagaaag tatccatcat ggctgatgca   7500
tcgcccttcc ctgaccgacg ataacccgct tcacggcccc gtcctagagg acagtagagt   7560
ggaacgagga cggctctttc ataggtagta ccgactacgt atgcggcggc tgcatacgct   7620
tgatccggct acctgcccat tcgaccacca agcgaaacat cgcatcgagc gagcacgtac   7680
tcggatggaa gccggtcttg tacgccgccg acgtatgcga actaggccga tggacgggta   7740
agctggtggt tcgctttgta gcgtagctcg ctcgtgcatg agcctacctt cggccagaac   7800
tcgatcagga tgatctggac gaagagcatc aggggctcgc gccagccgaa ctgttcgcca   7860
ggctcaaggc gagcatgccc gacggcgagg atctcgtcgt agctagtcct actagacctg   7920
cttctcgtag tccccgagcg cggtcggctt gacaagcggt ccgagttccg ctcgtacggg   7980
ctgccgctcc tagagcagca gacccatggc gatgcctgct tgccgaatat catggtggaa   8040
aatggccgct tttctggatt catcgactgt ggccggctgg gtgtggcgga ccgctatcag   8100
ctgggtaccg ctacggacga acggcttata gtaccacctt ttaccggcga aaagacctaa   8160
gtagctgaca ccggccgacc cacaccgcct ggcgatagtc gacatagcgt tggctacccg   8220
tgatattgct gaagagcttg gcggcgaatg ggctgaccgc ttcctcgtgc tttacggtat   8280
cgccgctccc gattcgcagc ctgtatcgca accgatgggc actataacga cttctcgaac   8340
cgccgcttac ccgactggcg aaggagcacg aaatgccata gcggcgaggg ctaagcgtcg   8400
gcatcgcctt ctatcgcctt cttgacgagt tcttctgagc gggactctgg ggttcgggcc   8460
gcactcgagc ataaacttgt ttattgcagc ttataatggt cgtagcggaa gatagcggaa   8520
gaactgctca agaagactcg ccctgagacc ccaagcccgg cgtgagctcg tatttgaaca   8580
```

-continued

```
aataacgtcg aatattacca tacaaataaa gcaatagcat cacaaatttc acaaataaag    8640
catttttttc actgcattct agttgtggtt tgtccaaact catcaatgta tcttaagtag    8700
atgtttattt cgttatcgta gtgtttaaag tgtttatttc gtaaaaaaag tgacgtaaga    8760
tcaacaccaa acaggtttga gtagttacat agaattcatc ggataacagg gtaattttgt    8820
taaatcagct catttttttaa ccaataggaa cgccatcaaa aataattcgc gtctggcctt   8880
cctgtagcca gctttcatca cctattgtcc cattaaaaca atttagtcga gtaaaaaatt    8940
ggttatcctt gcggtagttt ttattaagcg cagaccggaa ggacatcggt cgaaagtagt    9000
acattaaatg tgagcgagta acaacccgtc ggattctccg tgggaacaaa cggcggattg    9060
accgtaatgg gataggttac gttggtgtag atgggcgcat tgtaatttac actcgctcat    9120
tgttgggcag cctaagaggc acccttgttt gccgcctaac tggcattacc ctatccaatg    9180
caaccacatc tacccgcgta cgtaaccgtg catctgccag tttgagggga cgacgaccgt    9240
atcggcctca ggaagatcgc actccagcca gctttccggc accgcttctg gtgccggaaa    9300
gcattggcac gtagacggtc aaactcccct gctgctggca tagccggagt ccttctagcg    9360
tgaggtcggt cgaaaggccg tggcgaagac cacggccttt ccaggcaaag cgccattcgc    9420
cattcaggct gcgcaactgt tgggaagggc gatcggtgcg ggcctcttcg ctattacgcc    9480
agctggcgaa agggggatgt ggtccgtttc gcggtaagcg gtaagtccga cgcgttgaca    9540
acccttcccg ctagccacgc ccggagaagc gataatgcgg tcgaccgctt tccccctaca    9600
gctgcaaggc gattaagttg ggtaacgcca gggttttccc agtcacgacg ttgtaaaacg    9660
acggccagtg aattgcaatt cgtaatcatg gtcatagctg cgacgttccg ctaattcaac    9720
ccattgcggt cccaaaaggg tcagtgctgc aacattttgc tgccggtcac ttaacgttaa    9780
gcattagtac cagtatcgac tttcctgtgt gaaattgtta tccgctcaca attccacaca    9840
acatacgagc cggaagcata aagtgtaaag cctggggtgc ctaatgagtg agctaactca    9900
aaaggacaca ctttaacaat aggcgagtgt taaggtgtgt tgtatgctcg gccttcgtat    9960
ttcacatttc ggaccccacg gattactcac tcgattgagt cattaattgc gttgcgctca   10020
ctgccattac cctgttatcc ctagtgaacc atcaccctaa tcaagttttt tggggtcgag   10080
gtgccgtaaa gcactaaatc gtaattaacg caacgcgagt gacggtaatg ggacaatagg   10140
gatcacttgg tagtgggatt agttcaaaaa accccagctc cacggcattt cgtgatttag   10200
ggaaccctaa agggagcccc cgatttagag cttgacgggg aaagccggcg aacgtggcga   10260
gaaaggaagg gaagaaagcg aaaggagcgg gcgctagggc ccttgggatt tccctcgggg   10320
gctaaatctc gaactgcccc tttcggccgc ttgcaccgct ctttccttcc cttctttcgc   10380
tttcctcgcc cgcgatcccg gctggcaagt gtagcggtca cgctgcgcgt aaccaccaca   10440
cccgccgcgc ttaatgcgcc gctacagggc gcgtcaggtg gcacttttcg gggaaatgtg   10500
cgaccgttca catcgccagt gcgacgcgca ttggtggtgt gggcggcgcg aattacgcgg   10560
cgatgtcccg cgcagtccac cgtgaaaagc ccctttacac cgcggaaccc ctatttgttt   10620
atttttctaa atacattcaa atatgtatcc gctcatgaga caataaccct gataaatgct   10680
tcaataataa cgaccggtaa gcgccttggg gataaacaaa taaaaagatt tatgtaagtt   10740
tatacatagg cgagtactct gttattggga ctatttacga agttattatt gctggccatt   10800
tgaaaaagga agagtatgag tattcaacat ttccgtgtcg cccttattcc cttttttgcg   10860
gcattttgcc ttcctgtttt tgctcaccca gaaacgctgg actttttcct tctcatactc   10920
```

-continued

```
ataagttgta aaggcacagc gggaataagg gaaaaaacgc cgtaaaacgg aaggacaaaa  10980
acgagtgggt ctttgcgacc tgaaagtaaa agatgctgaa gatcagttgg gtgcacgagt  11040
gggttacatc gaactggatc tcaacagcgg taagatcctt gagagttttc gccccgaaga  11100
actttcattt tctacgactt ctagtcaacc cacgtgctca cccaatgtag cttgacctag  11160
agttgtcgcc attctaggaa ctctcaaaag cggggcttct acgttttcca atgatgagca  11220
cttttaaagt tctgctatgt ggcgcggtat tatcccgtat tgacgccggg caagagcaac  11280
tcggtcgccg catacactat tgcaaaaggt tactactcgt gaaaatttca agacgataca  11340
ccgcgccata atagggcata actgcggccc gttctcgttg agccagcggc gtatgtgata  11400
tctcagaatg acttggttga gtctagcgtt gatcggcacg taagaggttc caactttcac  11460
cataatgaaa taagatcact accgggcgta ttttttgagt agagtcttac tgaaccaact  11520
cagatcgcaa ctagccgtgc attctccaag gttgaaagtg gtattacttt attctagtga  11580
tggcccgcat aaaaaactca tatcgagatt ttcaggagct aaggaagcta aaatggagaa  11640
aaaaatcact ggatatacca ccgttgatat atcccaatgg catcgtaaag aacattttga  11700
atagctctaa aagtcctcga ttccttcgat ttacctctt tttttagtga cctatatggt  11760
ggcaactata tagggttacc gtagcatttc ttgtaaaact ggcatttcag tcagttgctc  11820
aatgtaccta taaccagacc gttcagctgg atattacggc ctttttaaag accgtaaaga  11880
aaaataagca caagttttat ccgtaaagtc agtcaacgag ttacatggat attggtctgg  11940
caagtcgacc tataatgccg gaaaaatttc tggcatttct ttttattcgt gttcaaaata  12000
ccggccttta ttcacattct tgcccgcctg atgaatgctc atccggaatt ccgtatggca  12060
atgaaagacg gtgagctggt gatatgggat agtgttcacc ggccggaaat aagtgtaaga  12120
acgggcggac tacttacgag taggccttaa ggcataccgt tactttctgc cactcgacca  12180
ctatacccta tcacaagtgg cttgttacac cgttttccat gagcaaactg aaacgttttc  12240
atcgctctgg agtgaatacc acgacgattt ccggcagttt ctacacatat attcgcaaga  12300
gaacaatgtg gcaaaaggta ctcgtttgac tttgcaaaag tagcgagacc tcacttatgg  12360
tgctgctaaa ggccgtcaaa gatgtgtata taagcgttct tgtggcgtgt tacggtgaaa  12420
acctggccta tttccctaaa gggtttattg agaatatgtt tttcgtatca gccaatccct  12480
gggtgagttt caccagtttt acaccgcaca atgccacttt tggaccggat aaagggattt  12540
cccaaataac tcttatacaa aaagcatagt cggttaggga cccactcaaa gtggtcaaaa  12600
gatttaaacg tggccaatat ggacaacttc ttcgcccccg ttttcaccat gggcaaatat  12660
tatacgcaag gcgacaaggt gctgatgccg ctggcgattc ctaaatttgc accggttata  12720
cctgttgaag aagcgggggc aaaagtggta cccgtttata atatgcgttc cgctgttcca  12780
cgactacggc gaccgctaag aggttcatca tgccgtctgt gatggcttcc atgtcggcag  12840
aatgcttaat gaattacaac agtactgcga tgagtggcag ggcggggcgt aattttttta  12900
tccaagtagt acggcagaca ctaccgaagg tacagccgtc ttacgaatta cttaatgttg  12960
tcatgacgct actcaccgtc ccgccccgca ttaaaaaaat aggcagttat tggtgccctt  13020
aaacgcctgg tgctacgcct gaataagtga taataagcgg atgaatggca gaaattcgaa  13080
atgaccgacc aagcgacgcc tccgtcaata accacgggaa tttgcggacc acgatgcgga  13140
cttattcact attattcgcc tacttaccgt ctttaagctt tactggctgg ttcgctgcgg  13200
caacctgcca tcacgagatt tcgattccac cgccgccttc tatgaaaggt tgggcttcgg  13260
aatcgttttc cgggacgccg gctggatgat cctccagcgc gttggacggt agtgctctaa  13320
```

agctaaggtg gcggcggaag atactttcca acccgaagcc ttagcaaaag gccctgcggc 13380
cgacctacta ggaggtcgcg gggatctca tgctggagtt cttcgcccac cctaggggga 13440
ggctaactga aacacggaag gagacaatac cggaaggaac ccgcgctatg acggcaataa 13500
cccctagagt acgacctcaa gaagcgggtg ggatccccct ccgattgact ttgtgccttc 13560
ctctgttatg gccttccttg ggcgcgatac tgccgttatt aaagacagaa taaaacgcac 13620
ggtgttgggt cgtttgttca taaacgcggg gttcggtccc agggctggca ctctgtcgat 13680
accccaccga gaccccattg tttctgtctt attttgcgtg ccacaaccca gcaaacaagt 13740
atttgcgccc caagccaggg tcccgaccgt gagacagcta tggggtggct ctggggtaac 13800
gggccaatac gcccgcgttt cttccttttc cccaccccac cccccaagtt cgggtgaagg 13860
cccagggctc gcagccaacg tcggggcggc aggccctgcc cccggttatg cgggcgcaaa 13920
gaaggaaaag gggtggggtg gggggttcaa gcccacttcc gggtcccgag cgtcggttgc 13980
agccccgccg tccgggacgg atagcctcag gttactcata tatactttag attgatttaa 14040
aacttcattt ttaatttaaa aggatctagg tgaagatcct ttttgataat ctcatgacca 14100
tatcggagtc caatgagtat atatgaaatc taactaaatt ttgaagtaaa aattaaattt 14160
tcctagatcc acttctagga aaaactatta gagtactggt aaatccctta acgtgagttt 14220
tcgttccact gagcgtcaga ccccgtagaa aagatcaaag gatcttcttg agatcctttt 14280
tttctgcgcg taatctgctg tttagggaat tgcactcaaa agcaaggtga ctcgcagtct 14340
ggggcatctt ttctagtttc ctagaagaac tctaggaaaa aaagacgcgc attagacgac 14400
cttgcaaaca aaaaaaccac cgctaccagc ggtggtttgt ttgccggatc aagagctacc 14460
aactcttttt ccgaaggtaa ctggcttcag cagagcgcag gaacgtttgt ttttttggtg 14520
gcgatggtcg ccaccaaaca aacggcctag ttctcgatgg ttgagaaaaa ggcttccatt 14580
gaccgaagtc gtctcgcgtc ataccaaata ctgtccttct agtgtagccg tagttaggcc 14640
accacttcaa gaactctgta gcaccgccta catacctcgc tctgctaatc ctgttaccag 14700
tatggtttat gacaggaaga tcacatcggc atcaatccgg tggtgaagtt cttgagacat 14760
cgtggcggat gtatggagcg agacgattag gacaatggtc tggctgctgc cagtggcgat 14820
aagtcgtgtc ttaccgggtt ggactcaaga cgatagttac cggataaggc gcagcggtcg 14880
ggctgaacgg ggggttcgtg accgacgacg gtcaccgcta ttcagcacag aatggcccaa 14940
cctgagttct gctatcaatg gcctattccg cgtcgccagc ccgacttgcc ccccaagcac 15000
cacacagccc agcttggagc gaacgaccta caccgaactg agatacctac agcgtgagct 15060
atgagaaagc gccacgcttc ccgaagggag aaaggcggac gtgtgtcggg tcgaacctcg 15120
cttgctggat gtggcttgac tctatggatg tcgcactcga tactctttcg cggtgcgaag 15180
ggcttccctc tttccgcctg aggtatccgg taagcggcag ggtcggaaca ggagagcgca 15240
cgagggagct tccaggggga aacgcctggt atctttatag tcctgtcggg tttcgccacc 15300
tccataggcc attcgccgtc ccagccttgt cctctcgcgt gctccctcga aggtccccct 15360
ttgcggacca tagaaatatc aggacagccc aaagcggtgg tctgacttga gcgtcgattt 15420
ttgtgatgct cgtcaggggg gcggagccta tggaaaaacg ccagcaacgc ggccttttta 15480
cggttcctgg ccttttgctg agactgaact cgcagctaaa aacactacga gcagtccccc 15540
cgcctcggat accttttgc ggtcgttgcg ccggaaaaat gccaaggacc ggaaaacgac 15600
gccttttgct cacatgttct ttcctgcgtt atcccctgat tctgtggata accgtattac 15660

```
cgccatgcat tagttattaa tagtaatcaa ttacggggtc cggaaaacga gtgtacaaga  15720
aaggacgcaa taggggacta agacacctat tggcataatg gcggtacgta atcaataatt  15780
atcattagtt aatgccccag attagttcat agcccatata tggagttccg cgttacataa  15840
cttacggtaa atggcccgcc tggctgaccg cccaacgacc cccgcccatt gacgtcaata  15900
taatcaagta tcgggtatat acctcaaggc gcaatgtatt gaatgccatt taccgggcgg  15960
accgactggc gggttgctgg gggcgggtaa ctgcagttat atgacgtatg ttcccatagt  16020
aacgccaata gggactttcc attgacgtca atgggtggag tatttacggt aaactgccca  16080
cttggcagta catcaagtgt tactgcatac aagggtatca ttgcggttat ccctgaaagg  16140
taactgcagt tacccacctc ataaatgcca tttgacgggt gaaccgtcat gtagttcaca  16200
atcatatgcc aagtacgccc cctattgacg tcaatgacgg taaatggccc gcctggcatt  16260
atgcccagta catgacctta tgggactttc ctacttggca tagtatacgg ttcatgcggg  16320
ggataactgc agttactgcc atttaccggg cggaccgtaa tacgggtcat gtactggaat  16380
accctgaaag gatgaaccgt gtacatctac gtattagtca tcgctattac catggtgatg  16440
cggttttggc agtacatcaa tgggcgtgga tagcggtttg actcacgggg atttccaagt  16500
catgtagatg cataatcagt agcgataatg gtaccactac gccaaaaccg tcatgtagtt  16560
acccgcacct atcgccaaac tgagtgcccc taaaggttca ctccacccca ttgacgtcaa  16620
tgggagtttg ttttggcacc aaaatcaacg ggactttcca aaatgtcgta acaactccgc  16680
cccattgacg caaatgggcg gaggtggggt aactgcagtt accctcaaac aaaaccgtgg  16740
ttttagttgc cctgaaaggt tttacagcat tgttgaggcg ggtaactgc gtttacccgc  16800
gtaggcgtgt acggtgggag gtctatataa gcagagctca tccgcacatg ccaccctcca  16860
gatatattcg tctcga                                                 16876
```

<210> SEQ ID NO 56
<211> LENGTH: 16826
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
ggtttagtga accgtcagat ccgctagacg tctcatatac ctgactggaa tacgacagct     60
cctgcagctt ctgggcgaag accaccgtgg cccattgcgt ccaaatcact tggcagtcta    120
ggcgatctgc agagtatatg gactgacctt atgctgtcga ggacgtcgaa gacccgcttc    180
tggtggcacc gggtaacgca acttagcgat aatctggtcc gcttggaagt tagcacggcg    240
agcgcgctcc agagccaagt cacgcagctt aacagtacct accgcagagc ggtgcatgaa    300
tgaatcgcta ttagaccagg cgaaccttca atcgtgccgc tcgcgcgagg tctcggttca    360
gtgcgtcgaa ttgtcatgga tggcgtctcg ccacgtactt caggccgata acgttgtcct    420
tagcaacctt gacattaccc tcacctttat tggcagggaa gacgtgcttc tgaccagtag    480
tgccctcacg agcggtacca gtccggctat tgcaacagga atcgttggaa ctgtaatggg    540
agtggaaata accgtccctt ctgcacgaag actggtcatc acgggagtgc tcgccatggt    600
gcaccaccag cggtgaggtg cggaacttct acaacctcaa agcccataac gttgcggata    660
gaacccttct cagggtcaat cagagcagcg tagtttgctg cgtggtggtc gccactccac    720
gccttgaaga tgttggagtt tcgggtattg caacgcctat cttgggaaga gtcccagtta    780
```

-continued

```
gtctcgtcgc atcaaacgac cgttcggcat cagtgctgcc agaatcgcag agtagctatc    840
tgggtcacag tagaacacac ggtcagcagc cggaacatag ttcttggtca gagccgcacg    900
gcaagccgta gtcacgacgg tcttagcgtc tcatcgatag acccagtgtc atcttgtgtg    960
ccagtcgtcg gccttgtatc aagaaccagt ctcggcgtgc agccttagtc agagccgcaa   1020
taatctcctt acccagcgca acttggtcgg taagtgcggc cttgttctga gtggtctcaa   1080
ttacggtagc agtacctaag tcggaatcag tctcggcgtt attagaggaa tgggtcgcgt   1140
tgaaccagcc attcacgccg gaacaagact caccagagtt aatgccatcg tcatggattc   1200
ccctcgatgt tctcattata tttgctttcc acgttacaca gaccggcaat ctcagccaga   1260
accgcaccat ccgcagccat cgccagagat tcacccaact gggagctaca agagtaatat   1320
aaacgaaagg tgcaatgtgt ctggccgtta gagtcggtct tggcgtggta ggcgtcggta   1380
gcggtctcta agtgggttga gagaggtata ctcagagcga acgtcgtagt ggttcatcgc   1440
gtcctcaata tcataaatca gaacgtcagc cgtcaggaga ccgtcaatgg tgattacctt   1500
ctctccatat gagtctcgct tgcagcatca ccaagtagcg caggagttat agtatttagt   1560
cttgcagtcg gcagtcctct ggcagttacc actaatggaa ctcggtgtgt ttgatgtcct   1620
tacgtttatc gtcgaggttc tcgcccggag ccagatacgc tgcctgagtg cgacccagaa   1680
cagggaactg agcggattta gagccacaca aactacagga atgcaaatag cagctccaag   1740
agcgggcctc ggtctatgcg acggactcac gctgggtctt gtcccttgac tcgcctaaat   1800
ccgctggaga tggaacgtac catgtggcga gaagtggtca cggaggtacg agcgaacgca   1860
gtcaggactt caccgccaaa taccttcaag aacaacgcca ggcgacctct accttgcatg   1920
gtacaccgct cttcaccagt gcctccatgc tcgcttgcgt cagtcctgaa gtggcggttt   1980
atggaagttc ttgttgcggt gtttatctcc agcagcaact acacctttac cttggttagt   2040
acccatttgc tgtccaccag tcatgctagc catatgtata tctccttctt aaagtcgtct   2100
caaatagagg tcgtcgttga tgtggaaatg gaaccaatca tgggtaaacg acaggtggtc   2160
agtacgatcg gtatacatat agaggaagaa tttcagcaga ccagtgcctc caccaagggc   2220
ccatcggtct tccccctggc gccctgctcc aggagcacct ccgagagcac agcggccctg   2280
ggctgcctgg tcaaggacta ggtcacggag gtggttcccg ggtagccaga agggggaccg   2340
cgggacgagg tcctcgtgga ggctctcgtg tcgccgggac ccgacggacc agttcctgat   2400
cttccccgaa ccggtgacgg tgtcgtggaa ctcaggcgct ctgaccagcg gcgtgcacac   2460
cttcccagct gtcctacagt cctcaggact ctactccctc gaaggggctt ggccactgcc   2520
acagcacctt gagtccgcga gactggtcgc cgcacgtgtg gaagggtcga caggatgtca   2580
ggagtcctga gatgagggag agcagcgtgg tgaccgtgcc ctccagcagc ttgggcaccc   2640
agacctacat ctgcaacgtg aatcacaagc ccagcaacac caaggtggac aagaaagttg   2700
tcgtcgcacc actggcacgg gaggtcgtcg aacccgtggg tctggatgta gacgttgcac   2760
ttagtgttcg ggtcgttgtg gttccacctg ttctttcaac agcccaaatc ttgtgacaaa   2820
actcacacat gcccaccgtg cccagcacct gaactcctgg ggggaccgtc agtcttcctc   2880
ttccccccma aacccaagga tcgggtttag aacactgttt tgagtgtgta cgggtggcac   2940
gggtcgtgga cttgaggacc cccctggcag tcagaaggag aaggggggkt ttgggttcct   3000
caccctcatg atctcccgga cccctgaggt cacatgcgtg gtggtggacg tgagccacga   3060
agaccctgag gtcaagttca actggtacgt ggacggcgtg gtgggagtac tagagggcct   3120
ggggactcca gtgtacgcac caccacctgc actcggtgct tctgggactc cagttcaagt   3180
```

-continued

```
tgaccatgca cctgccgcac gaggtgcata atgccaagac aaagccgcgg gaggagcagt   3240
acaacagcac gtaccgtgtg gtcagcgtcc tcaccgtcct gcaccaggac tggctgaatg   3300
ctccacgtat tacggttctg tttcggcgcc ctcctcgtca tgttgtcgtg catggcacac   3360
cagtcgcagg agtggcagga cgtggtcctg accgacttac gcaaggagta caagtgcaag   3420
gtctccaaca aagccctccc agcccccatc gagaaaacca tctccaaagc caaagggcag   3480
ccccgagaac cacaggtgta cgttcctcat gttcacgttc cagaggttgt ttcgggaggg   3540
tcgggggtag ctcttttggt agaggtttcg gtttcccgtc ggggctcttg gtgtccacat   3600
caccctgccc ccatcccggg atgagctgac caagaaccag gtcagcctga cctgcctggt   3660
caaaggcttc taccccagcg acatcgccgt ggagtgggag gtgggacggg ggtagggccc   3720
tactcgactg gttcttggtc cagtcggact ggacggacca gtttccgaag atggggtcgc   3780
tgtagcggca cctcaccctc agcaatgggc agccggagaa caactacaag accacgcctc   3840
ccatgctgga ctccgacggc tccttcttcc tctacagcaa gctcaccgtg gacaagagca   3900
tcgttacccg tcggcctctt gttgatgttc tggtgcggag ggtacgacct gaggctgccg   3960
aggaagaagg agatgtcgtt cgagtggcac ctgttctcgt ggtggcagca ggggaacgtc   4020
ttctcatgct ccgtgatgca tgaggctctg cacaaccact acacgcagaa gagcctctcc   4080
ctgtctccgg gtaaagggta ccaccgtcgt ccccttgcag aagagtacga ggcactacgt   4140
actccgagac gtgttggtga tgtgcgtctt ctcggagagg gacagaggcc catttcccat   4200
catgtcccat atgctcgaca tggcaagcag cctgagacag attctggact cccagaaaat   4260
ggagtggagg tccaacgccg ggggcagcgg tagggataag gtacagggta tacgagctgt   4320
accgttcgtc ggactctgtc taagacctga gggtctttta cctcacctcc aggttgcggc   4380
ccccgtcgcc atccctattc tggtcagatc ttcgcgacaa ttccaaatca actgagttcg   4440
atcctaacat tgacattgtt ggtttagaag gaaaatttgg tattacaaac ctagaaacgg   4500
accagtctag aagcgctgtt aaggtttagt tgactcaagc taggattgta actgtaacaa   4560
ccaaatcttc cttttaaacc ataatgtttg gatctttgcc atttattcac aatctgggag   4620
acaatggagg tcatgatcaa agcagatatt gcagatactg atagagccag caactttgtt   4680
gcaactgaaa ccgatgctaa taaataagtg ttagaccctc tgttacctcc agtactagtt   4740
tcgtctataa cgtctatgac tatctcggtc gttgaaacaa cgttgacttt ggctacgatt   4800
ccgcggaaaa atgcctggca aaaaactgcc actggcagtt atcatggaaa tggaagccaa   4860
tgctttcaaa gctggctgca ccaggggatg ccttatctgt ggcgcctttt tacggaccgt   4920
tttttgacgg tgaccgtcaa tagtaccttt accttcggtt acgaaagttt cgaccgacgt   4980
ggtcccctac ggaatagaca ctttcaaaaa ttaagtgtac agccaaaatg aaggtataca   5040
ttccaggaag gtgtcacgat tatggtggtg acaagaaaac tggacaggca ggaattgttg   5100
gaaagttttt aattcacatg tcggttttac ttccatatgt aaggtccttc cacagtgcta   5160
ataccaccac tgttcttttg acctgtccgt ccttaacaac gtgcaattgt tgacattccc   5220
gaaatctctg gatttaagga gatggcaccc atggaacagt tcattgctca agttgatcgc   5280
tgcgcttcct gcactactgg cacgttaaca actgtaaggg ctttagagac ctaaattcct   5340
ctaccgtggg taccttgtca agtaacgagt tcaactagcg acgcgaagga cgtgatgacc   5400
atgtctcaaa ggtcttgcca atgttaagtg ctctgaactc ctgaagaaat ggctgcctga   5460
caggtgtgca agttttgctg acaagattca aaaagaagtt tacagagttt ccagaacggt   5520
```

-continued

```
tacaattcac gagacttgag gacttcttta ccgacggact gtccacacgt tcaaaacgac   5580
tgttctaagt ttttcttcaa cacaatatca aaggcatggc cggcgatcga tgagcggccg   5640
caatttaatt ccggttattt tccaccatat tgccgtcttt tggcaatgtg agggcccgga   5700
gtgttatagt ttccgtaccg gccgctagct actcgccggc gttaaattaa ggccaataaa   5760
aggtggtata acggcagaaa accgttacac tcccgggcct aacctggccc tgtcttcttg   5820
acgagcattc ctaggggtct ttcccctctc gccaaaggaa tgcaaggtct gttgaatgtc   5880
gtgaaggaag cagttcctct ttggaccggg acagaagaac tgctcgtaag gatccccaga   5940
aaggggagag cggtttcctt acgttccaga caacttacag cacttccttc gtcaaggaga   6000
ggaagcttct tgaagacaaa caacgtctgt agcgaccctt tgcaggcagc ggaacccccc   6060
acctggcgac aggtgcctct gcggccaaaa gccacgtgta ccttcgaaga acttctgttt   6120
gttgcagaca tcgctgggaa acgtccgtcg ccttgggggg tggaccgctg tccacggaga   6180
cgccggtttt cggtgcacat taagatacac ctgcaaaggc ggcacaaccc cagtgccacg   6240
ttgtgagttg gatagttgtg gaaagagtca aatggctcac ctcaagcgta ttcaacaagg   6300
attctatgtg gacgtttccg ccgtgttggg gtcacggtgc aacactcaac ctatcaacac   6360
ctttctcagt ttaccgagtg gagttcgcat aagttgttcc ggctgaagga tgcccagaag   6420
gtaccccatt gtatgggatc tgatctgggg cctcggtgca catgctttac atgtgtttag   6480
tcgaggttaa aaaacgtcta ccgacttcct acgggtcttc catggggtaa cataccctag   6540
actagacccc ggagccacgt gtacgaaatg tacacaaatc agctccaatt ttttgcagat   6600
ggccccccga accacgggga cgtggttttc ctttgaaaaa cacgatgata atatggccac   6660
cacccatacc taggcttttg caaagatcga tcaagagaca ccggggggct tggtgcccct   6720
gcaccaaaag gaaacttttt gtgctactat tataccggtg gtgggtatgg atccgaaaac   6780
gtttctagct agttctctgt ggatgaggat cgtttcgcat gattgaacaa gatggattgc   6840
acgcaggttc tccggccgct tgggtggaga ggctattcgg ctatgactgg gcacaacaga   6900
cctactccta gcaaagcgta ctaacttgtt ctacctaacg tgcgtccaag aggccggcga   6960
acccacctct ccgataagcc gatactgacc cgtgttgtct caatcggctg ctctgatgcc   7020
gccgtgttcc ggctgtcagc gcaggggcgc ccggttcttt ttgtcaagac cgacctgtcc   7080
ggtgccctga atgaactgca gttagccgac gagactacgg cggcacaagg ccgacagtcg   7140
cgtccccgcg ggccaagaaa aacagttctg gctggacagg ccacgggact tacttgacgt   7200
agacgaggca gcgcggctat cgtggctggc cacgacgggc gttccttgcg cagctgtgct   7260
cgacgttgtc actgaagcgg gaagggactg gctgctattg tctgctccgt cgcgccgata   7320
gcaccgaccg gtgctgcccg caaggaacgc gtcgacacga gctgcaacag tgacttcgcc   7380
cttccctgac cgacgataac ggcgaagtgc cggggcagga tctcctgtca tctcaccttg   7440
ctcctgccga gaaagtatcc atcatggctg atgcaatgcg gcggctgcat acgcttgatc   7500
ccgcttcacg gccccgtcct agaggacagt agagtggaac gaggacggct ctttcatagg   7560
tagtaccgac tacgttacgc cgccgacgta tgcgaactag cggctacctg cccattcgac   7620
caccaagcga aacatcgcat cgagcgagca cgtactcgga tggaagccgg tcttgtcgat   7680
caggatgatc tggacgaaga gccgatggac gggtaagctg gtggttcgct ttgtagcgta   7740
gctcgctcgt gcatgagcct accttcggcc agaacagcta gtcctactag acctgcttct   7800
gcatcagggg ctcgcgccag ccgaactgtt cgccaggctc aaggcgagca tgcccgacgg   7860
cgaggatctc gtcgtgaccc atggcgatgc ctgcttgccg cgtagtcccc gagcgcggtc   7920
```

```
ggcttgacaa gcggtccgag ttccgctcgt acgggctgcc gctcctagag cagcactggg   7980
taccgctacg gacgaacggc aatatcatgg tggaaaatgg ccgcttttct ggattcatcg   8040
actgtggccg gctgggtgtg gcggaccgct atcaggacat agcgttggct acccgtgata   8100
ttatagtacc accttttacc ggcgaaaaga cctaagtagc tgacaccggc cgacccacac   8160
cgcctggcga tagtcctgta tcgcaaccga tgggcactat ttgctgaaga gcttggcggc   8220
gaatgggctg accgcttcct cgtgctttac ggtatcgccg ctcccgattc gcagcgcatc   8280
gccttctatc gccttcttga aacgacttct cgaaccgccg cttacccgac tggcgaagga   8340
gcacgaaatg ccatagcggc gagggctaag cgtcgcgtag cggaagatag cggaagaact   8400
cgagttcttc tgagcgggac tctggggttc gggccgcact cgagcataaa cttgtttatt   8460
gcagcttata atggttacaa ataaagcaat agcatcacaa gctcaagaag actcgccctg   8520
agaccccaag cccggcgtga gctcgtattt gaacaaataa cgtcgaatat taccaatgtt   8580
tatttcgtta tcgtagtgtt atttcacaaa taaagcattt ttttcactgc attctagttg   8640
tggtttgtcc aaactcatca atgtatctta agtagggata acagggtaat tttgttaaat   8700
taaagtgttt atttcgtaaa aaaagtgacg taagatcaac accaaacagg tttgagtagt   8760
tacatagaat tcatccctat tgtcccatta aaacaattta cagctcattt tttaaccaat   8820
aggaacgcca tcaaaaataa ttcgcgtctg gccttcctgt agccagcttt catcaacatt   8880
aaatgtgagc gagtaacaac gtcgagtaaa aaattggtta tccttgcggt agtttttatt   8940
aagcgcagac cggaaggaca tcggtcgaaa gtagttgtaa tttacactcg ctcattgttg   9000
ccgtcggatt ctccgtggga acaaacggcg gattgaccgt aatgggatag gttacgttgg   9060
tgtagatggg cgcatcgtaa ccgtgcatct gccagtttga ggcagcctaa gaggcaccct   9120
tgtttgccgc ctaactggca ttaccctatc caatgcaacc acatctaccc gcgtagcatt   9180
ggcacgtaga cggtcaaact ggggacgacg accgtatcgg cctcaggaag atcgcactcc   9240
agccagcttt ccggcaccgc ttctggtgcc ggaaaccagg caaagcgcca ttcgccattc   9300
cccctgctgc tggcatagcc ggagtccttc tagcgtgagg tcggtcgaaa ggccgtggcg   9360
aagaccacgg cctttggtcc gtttcgcggt aagcggtaag aggctgcgca actgttggga   9420
agggcgatcg gtgcgggcct cttcgctatt acgccagctg gcgaaagggg gatgtgctgc   9480
aaggcgatta agttgggtaa tccgacgcgt tgacaaccct tcccgctagc cacgcccgga   9540
gaagcgataa tgcggtcgac cgctttcccc ctacacgacg ttccgctaat tcaacccatt   9600
cgccagggtt ttcccagtca cgacgttgta aaacgacggc cagtgaattg caattcgtaa   9660
tcatggtcat agctgtttcc tgtgtgaaat tgttatccgc gcggtcccaa aagggtcagt   9720
gctgcaacat tttgctgccg gtcacttaac gttaagcatt agtaccagta tcgacaaagg   9780
acacacttta acaataggcg tcacaattcc acacaacata cgagccggaa gcataaagtg   9840
taaagcctgg ggtgcctaat gagtgagcta actcacatta attgcgttgc gctcactgcc   9900
agtgttaagg tgtgttgtat gctcggcctt cgtatttcac atttcggacc ccacggatta   9960
ctcactcgat tgagtgtaat taacgcaacg cgagtgacgg attaccctgt tatccctagt  10020
gaaccatcac cctaatcaag ttttttgggg tcgaggtgcc gtaaagcact aaatcggaac  10080
cctaaaggga gcccccgatt taatgggaca atagggatca cttggtagtg ggattagttc  10140
aaaaaacccc agctccacgg catttcgtga tttagccttg ggatttccct cgggggctaa  10200
tagagcttga cggggaaagc cggcgaacgt ggcgagaaag gaagggaaga aagcgaaagg  10260
```

-continued

```
agcgggcgct agggcgctgg caagtgtagc ggtcacgctg atctcgaact gccccctttcg  10320
gccgcttgca ccgctctttc cttcccttct ttcgctttcc tcgcccgcga tcccgcgacc  10380
gttcacatcg ccagtgcgac cgcgtaacca ccacacccgc cgcgcttaat gcgccgctac  10440
agggcgcgtc aggtggcact tttcggggaa atgtgcgcgg aacccctatt tgtttatttt  10500
gcgcattggt ggtgtgggcg gcgcgaatta cgcggcgatg tcccgcgcag tccaccgtga  10560
aaagcccctt tacacgcgcc ttggggataa acaaataaaa tctaaataca ttcaaatatg  10620
tatccgctca tgagacaata accctgataa atgcttcaat aataacgacc ggtaatgaaa  10680
aaggaagagt atgagtattc agatttatgt aagtttatac ataggcgagt actctgttat  10740
tgggactatt tacgaagtta ttattgctgg ccattacttt ttccttctca tactcataag  10800
aacatttccg tgtcgccctt attccctttt ttgcggcatt ttgccttcct gtttttgctc  10860
acccagaaac gctggtgaaa gtaaaagatg ctgaagatca ttgtaaaggc acagcgggaa  10920
taagggaaaa aacgccgtaa aacggaagga caaaaacgag tgggtctttg cgaccacttt  10980
cattttctac gacttctagt gttgggtgca cgagtgggtt acatcgaact ggatctcaac  11040
agcggtaaga tccttgagag ttttcgcccc gaagaacgtt ttccaatgat gagcactttt  11100
caacccacgt gctcacccaa tgtagcttga cctagagttg tcgccattct aggaactctc  11160
aaaagcgggg cttcttgcaa aaggttacta ctcgtgaaaa aaagttctgc tatgtggcgc  11220
ggtattatcc cgtattgacg ccgggcaaga gcaactcggt cgccgcatac actattctca  11280
gaatgacttg gttgagtcta tttcaagacg atacaccgcg ccataatagg gcataactgc  11340
ggcccgttct cgttgagcca gcggcgtatg tgataagagt cttactgaac caactcagat  11400
gcgttgatcg gcacgtaaga ggttccaact ttcaccataa tgaaataaga tcactaccgg  11460
gcgtattttt tgagttatcg agattttcag gagctaagga cgcaactagc cgtgcattct  11520
ccaaggttga aagtggtatt actttattct agtgatggcc cgcataaaaa actcaatagc  11580
tctaaaagtc ctcgattcct agctaaaatg gagaaaaaaa tcactggata taccaccgtt  11640
gatatatccc aatggcatcg taaagaacat tttgaggcat ttcagtcagt tgctcaatgt  11700
tcgattttac ctcttttttt agtgacctat atggtggcaa ctatataggg ttaccgtagc  11760
atttcttgta aaactccgta aagtcagtca acgagttaca acctataacc agaccgttca  11820
gctggatatt acggcctttt taaagaccgt aaagaaaaat aagcacaagt tttatccggc  11880
ctttattcac attcttgccc tggatattgg tctggcaagt cgacctataa tgccggaaaa  11940
atttctggca tttcttttta ttcgtgttca aaataggccg gaaataagtg taagaacggg  12000
gcctgatgaa tgctcatccg gaattccgta tggcaatgaa agacggtgag ctggtgatat  12060
gggatagtgt tcacccttgt tacaccgttt tccatgagca cggactactt acgagtaggc  12120
cttaaggcat accgttactt tctgccactc gaccactata ccctatcaca agtgggaaca  12180
atgtggcaaa aggtactcgt aactgaaacg ttttcatcgc tctggagtga ataccacgac  12240
gatttccggc agtttctaca catatattcg caagatgtgg cgtgttacgg tgaaaacctg  12300
ttgactttgc aaaagtagcg agacctcact tatggtgctg ctaaaggccg tcaaagatgt  12360
gtatataagc gttctacacc gcacaatgcc acttttggac gcctatttcc ctaaagggtt  12420
tattgagaat atgtttttcg tatcagccaa tccctgggtg agtttcacca gttttgattt  12480
aaacgtggcc aatatggaca cggataaagg gatttcccaa ataactctta tacaaaaagc  12540
atagtcggtt agggacccac tcaaagtggt caaaactaaa tttgcaccgg ttatacctgt  12600
acttcttcgc ccccgttttc accatgggca aatattatac gcaaggcgac aaggtgctga  12660
```

-continued tgccgctggc gattcaggtt catcatgccg tctgtgatgg tgaagaagcg ggggcaaaag 12720
tggtacccgt ttataatatg cgttccgctg ttccacgact acggcgaccg ctaagtccaa 12780
gtagtacggc agacactacc cttccatgtc ggcagaatgc ttaatgaatt acaacagtac 12840
tgcgatgagt ggcagggcgg ggcgtaattt ttttaaggca gttattggtg cccttaaacg 12900
gaaggtacag ccgtcttacg aattacttaa tgttgtcatg acgctactca ccgtcccgcc 12960
ccgcattaaa aaaattccgt caataaccac gggaatttgc cctggtgcta cgcctgaata 13020
agtgataata agcggatgaa tggcagaaat tcgaaatgac cgaccaagcg acgcccaacc 13080
tgccatcacg agatttcgat ggaccacgat gcggacttat tcactattat tcgcctactt 13140
accgtcttta agctttactg gctggttcgc tgcgggttgg acggtagtgc tctaaagcta 13200
tccaccgccg ccttctatga aaggttgggc ttcggaatcg ttttccggga cgccggctgg 13260
atgatcctcc agcgcgggga tctcatgctg gagttcttcg aggtggcggc ggaagatact 13320
ttccaacccg aagccttagc aaaaggccct gcggccgacc tactaggagg tcgcgcccct 13380
agagtacgac ctcaagaagc cccaccctag ggggaggcta actgaaacac ggaaggagac 13440
aataccggaa ggaacccgcg ctatgacggc aataaaaaga cagaataaaa cgcacggtgt 13500
gggtgggatc cccctccgat tgactttgtg ccttcctctg ttatggcctt ccttgggcgc 13560
gatactgccg ttatttttct gtcttatttt gcgtgccaca tgggtcgttt gttcataaac 13620
gcggggttcg gtcccagggc tggcactctg tcgataccc accgagaccc cattggggcc 13680
aatacgcccg cgtttcttcc acccagcaaa caagtatttg cgccccaagc cagggtcccg 13740
accgtgagac agctatgggg tggctctggg gtaaccccgg ttatgcgggc gcaaagaagg 13800
ttttccccac cccacccccc aagttcgggt gaaggcccag ggctcgcagc caacgtcggg 13860
gcggcaggcc ctgccatagc ctcaggttac tcatatatac aaaaggggtg gggtgggggg 13920
ttcaagccca cttccgggtc ccgagcgtcg gttgcagccc cgccgtccgg gacggtatcg 13980
gagtccaatg agtatatatg tttagattga tttaaaactt catttttaat ttaaaaggat 14040
ctaggtgaag atcctttttg ataatctcat gaccaaaatc ccttaacgtg agttttcgtt 14100
aaatctaact aaattttgaa gtaaaaatta aattttccta gatccacttc taggaaaaac 14160
tattagagta ctggttttag ggaattgcac tcaaaagcaa ccactgagcg tcagaccccg 14220
tagaaaagat caaaggatct tcttgagatc ctttttttct gcgcgtaatc tgctgcttgc 14280
aaacaaaaaa accaccgcta ggtgactcgc agtctggggc atcttttcta gtttcctaga 14340
agaactctag gaaaaaaaga cgcgcattag acgacgaacg tttgtttttt tggtggcgat 14400
ccagcggtgg tttgtttgcc ggatcaagag ctaccaactc tttttccgaa ggtaactggc 14460
ttcagcagag cgcagatacc aaatactgtc cttctagtgt ggtcgccacc aaacaaacgg 14520
cctagttctc gatggttgag aaaaaggctt ccattgaccg aagtcgtctc gcgtctatgg 14580
tttatgacag gaagatcaca agccgtagtt aggccaccac ttcaagaact ctgtagcacc 14640
gcctacatac ctcgctctgc taatcctgtt accagtggct gctgccagtg gcgataagtc 14700
tcggcatcaa tccggtggtg aagttcttga gacatcgtgg cggatgtatg gagcgagacg 14760
attaggacaa tggtcaccga cgacggtcac cgctattcag gtgtcttacc gggttggact 14820
caagacgata gttaccggat aaggcgcagc ggtcgggctg aacggggggt tcgtgcacac 14880
agcccagctt ggagcgaacg cacagaatgg cccaacctga gttctgctat caatggccta 14940
ttccgcgtcg ccagcccgac ttgcccccca agcacgtgtg tcgggtcgaa cctcgcttgc 15000

-continued acctacaccg aactgagata cctacagcgt gagctatgag aaagcgccac gcttcccgaa 15060
gggagaaagg cggacaggta tccggtaagc ggcagggtcg tggatgtggc ttgactctat 15120
ggatgtcgca ctcgatactc tttcgcggtg cgaagggctt ccctctttcc gcctgtccat 15180
aggccattcg ccgtcccagc gaacaggaga gcgcacgagg gagcttccag gggaaacgc 15240 ctggtatctt tatagtcctg tcgggtttcg ccacctctga cttgagcgtc gatttttgtg 15300
cttgtcctct cgcgtgctcc ctcgaaggtc cccctttgcg gaccatagaa atatcaggac 15360
agcccaaagc ggtggagact gaactcgcag ctaaaaacac atgctcgtca ggggggcgga 15420
gcctatggaa aaacgccagc aacgcggcct ttttacggtt cctggccttt tgctggcctt 15480
ttgctcacat gttctttcct tacgagcagt ccccccgcct cggatacctt tttgcggtcg 15540
ttgcgccgga aaaatgccaa ggaccggaaa acgaccggaa aacgagtgta caagaaagga 15600
gcgttatccc ctgattctgt ggataaccgt attaccgcca tgcattagtt attaatagta 15660
atcaattacg gggtcattag ttcatagccc atatatggag cgcaataggg gactaagaca 15720
cctattggca taatggcggt acgtaatcaa taattatcat tagttaatgc cccagtaatc 15780
aagtatcggg tatatacctc ttccgcgtta cataacttac ggtaaatggc ccgcctggct 15840
gaccgcccaa cgacccccgc ccattgacgt caataatgac gtatgttccc atagtaacgc 15900
aaggcgcaat gtattgaatg ccatttaccg ggcggaccga ctggcgggtt gctgggggcg 15960
ggtaactgca gttattactg catacaaggg tatcattgcg caatagggac tttccattga 16020
cgtcaatggg tggagtattt acggtaaact gcccacttgg cagtacatca agtgtatcat 16080
atgccaagta cgccccctat gttatccctg aaaggtaact gcagttaccc acctcataaa 16140
tgccatttga cgggtgaacc gtcatgtagt tcacatagta tacggttcat gcgggggata 16200
tgacgtcaat gacggtaaat ggcccgcctg gcattatgcc cagtacatga ccttatggga 16260
ctttcctact tggcagtaca tctacgtatt agtcatcgct actgcagtta ctgccattta 16320
ccgggcggac cgtaatacgg gtcatgtact ggaataccct gaaaggatga accgtcatgt 16380
agatgcataa tcagtagcga attaccatgg tgatgcggtt ttggcagtac atcaatgggc 16440
gtggatagcg gtttgactca cggggatttc caagtctcca ccccattgac gtcaatggga 16500
taatggtacc actacgccaa aaccgtcatg tagttacccg cacctatcgc caaactgagt 16560
gcccctaaag gttcagaggt ggggtaactg cagttaccct gtttgttttg gcaccaaaat 16620
caacgggact ttccaaaatg tcgtaacaac tccgccccat tgacgcaaat gggcggtagg 16680
cgtgtacggt gggaggtcta caaacaaaac cgtggtttta gttgccctga aaggttttac 16740
agcattgttg aggcggggta actgcgttta cccgccatcc gcacatgcca ccctccagat 16800
tataagcaga gctatattcg tctcga 16826

<210> SEQ ID NO 57
<211> LENGTH: 16778
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
ggtttagtga accgtcagat ccgctagacg tctcatatac ctgactggaa tacgacagct 60
cctgcagctt ctgggcgaag accaccgtgg cccattgcgt ccaaatcact tggcagtcta 120
ggcgatctgc agagtatatg gactgacctt atgctgtcga ggacgtcgaa gacccgcttc 180

-continued

```
tggtggcacc gggtaacgca acttagcgat aatctggtcc gcttggaagt tagcacggcg    240
agcgcgctcc agagccaagt cacgcagctt aacagtacct accgcagagc ggtgcatgaa    300
tgaatcgcta ttagaccagg cgaaccttca atcgtgccgc tcgcgcgagg tctcggttca    360
gtgcgtcgaa ttgtcatgga tggcgtctcg ccacgtactt caggccgata acgttgtcct    420
tagcaacctt gacattaccc tcacctttat tggcagggaa gacgtgcttc tgaccagtag    480
tgccctcacg agcggtacca gtccggctat tgcaacagga atcgttggaa ctgtaatggg    540
agtggaaata accgtccctt ctgcacgaag actggtcatc acgggagtgc tcgccatggt    600
gcaccaccag cggtgaggtg cggaacttct acaacctcaa agcccataac gttgcggata    660
gaacccttct cagggtcaat cagagcagcg tagtttgctg cgtggtggtc gccactccac    720
gccttgaaga tgttggagtt tcgggtattg caacgcctat cttgggaaga gtcccagtta    780
gtctcgtcgc atcaaacgac cgttcggcat cagtgctgcc agaatcgcag agtagctatc    840
tgggtcacag tagaacacac ggtcagcagc cggaacatag ttcttggtca gagccgcacg    900
gcaagccgta gtcacgacgg tcttagcgtc tcatcgatag acccagtgtc atcttgtgtg    960
ccagtcgtcg gccttgtatc aagaaccagt ctcggcgtgc agccttagtc agagccgcaa   1020
taatctcctt acccagcgca acttggtcgg taagtgcggc cttgttctga gtggtctcaa   1080
ttacggtagc agtacctaag tcggaatcag tctcggcgtt attagaggaa tgggtcgcgt   1140
tgaaccagcc attcacgccg gaacaagact caccagagtt aatgccatcg tcatggattc   1200
ccctcgatgt tctcattata tttgctttcc acgttacaca gaccggcaat ctcagccaga   1260
accgcaccat ccgcagccat cgccagagat tcacccaact gggagctaca agagtaatat   1320
aaacgaaagg tgcaatgtgt ctggccgtta gagtcggtct tggcgtggta ggcgtcggta   1380
gcggtctcta agtgggttga gagaggtata ctcagagcga acgtcgtagt ggttcatcgc   1440
gtcctcaata tcataaatca gaacgtcagc cgtcaggaga ccgtcaatgg tgattacctt   1500
ctctccatat gagtctcgct tgcagcatca ccaagtagcg caggagttat agtatttagt   1560
cttgcagtcg gcagtcctct ggcagttacc actaatggaa ctcggtgtgt ttgatgtcct   1620
tacgtttatc gtcgaggttc tcgcccggag ccagatacgc tgcctgagtg cgacccagaa   1680
cagggaactg agcggattta gagccacaca aactacagga atgcaaatag cagctccaag   1740
agcgggcctc ggtctatgcg acggactcac gctgggtctt gtcccttgac tcgcctaaat   1800
ccgctggaga tggaacgtac catgtggcga gaagtggtca cggaggtacg agcgaacgca   1860
gtcaggactt caccgccaaa taccttcaag aacaacgcca ggcgacctct accttgcatg   1920
gtacaccgct cttcaccagt gcctccatgc tcgcttgcgt cagtcctgaa gtggcggttt   1980
atggaagttc ttgttgcggt gtttatctcc agcagcaact acacctttac cttggttagt   2040
acccatttgc tgtccaccag tcatgctagc catatgtata tctccttctt aaagtcgtct   2100
caaatagagg tcgtcgttga tgtggaaatg gaaccaatca tgggtaaacg acaggtggtc   2160
agtacgatcg gtatacatat agaggaagaa tttcagcaga ccagtgcctc caccaagggc   2220
ccatcggtct tcccccctggc gccctgctcc aggagcacct ccgagagcac agcggccctg   2280
ggctgcctgg tcaaggacta ggtcacggag gtggttcccg ggtagccaga agggggaccg   2340
cgggacgagg tcctcgtgga ggctctcgtg tcgccgggac ccgacggacc agttcctgat   2400
cttccccgaa ccggtgacgg tgtcgtggaa ctcaggcgct ctgaccagcg gcgtgcacac   2460
cttcccagct gtcctacagt cctcaggact ctactccctc gaaggggctt ggccactgcc   2520
acagcacctt gagtccgcga gactggtcgc cgcacgtgtg gaagggtcga caggatgtca   2580
```

-continued

```
ggagtcctga gatgagggag agcagcgtgg tgaccgtgcc ctccagcagc ttgggcaccc   2640
agacctacat ctgcaacgtg aatcacaagc ccagcaacac caaggtggac aagaaagttg   2700
tcgtcgcacc actggcacgg gaggtcgtcg aacccgtggg tctggatgta gacgttgcac   2760
ttagtgttcg ggtcgttgtg gttccacctg ttctttcaac agcccaaatc ttgtgacaaa   2820
actcacacat gcccaccgtg cccagcacct gaactcctgg ggggaccgtc agtcttcctc   2880
ttccccccma aacccaagga tcgggtttag aacactgttt tgagtgtgta cgggtggcac   2940
gggtcgtgga cttgaggacc cccctggcag tcagaaggag aagggggkt ttgggttcct   3000
caccctcatg atctcccgga cccctgaggt cacatgcgtg gtggtggacg tgagccacga   3060
agaccctgag gtcaagttca actggtacgt ggacggcgtg gtgggagtac tagagggcct   3120
ggggactcca gtgtacgcac caccacctgc actcggtgct tctgggactc cagttcaagt   3180
tgaccatgca cctgccgcac gaggtgcata atgccaagac aaagccgcgg gaggagcagt   3240
acaacagcac gtaccgtgtg gtcagcgtcc tcaccgtcct gcaccaggac tggctgaatg   3300
ctccacgtat tacggttctg tttcggcgcc ctcctcgtca tgttgtcgtg catggcacac   3360
cagtcgcagg agtggcagga cgtggtcctg accgacttac gcaaggagta caagtgcaag   3420
gtctccaaca aagccctccc agcccccatc gagaaaacca tctccaaagc caaagggcag   3480
ccccgagaac cacaggtgta cgttcctcat gttcacgttc cagaggttgt ttcgggaggg   3540
tcgggggtag ctcttttggt agaggtttcg gtttcccgtc ggggctcttg gtgtccacat   3600
caccctgccc ccatcccggg atgagctgac caagaaccag gtcagcctga cctgcctggt   3660
caaaggcttc taccccagcg acatcgccgt ggagtgggag gtgggacggg ggtagggccc   3720
tactcgactg gttcttggtc cagtcggact ggacggacca gtttccgaag atggggtcgc   3780
tgtagcggca cctcaccctc agcaatgggc agccggagaa caactacaag accacgcctc   3840
ccatgctgga ctccgacggc tccttcttcc tctacagcaa gctcaccgtg gacaagagca   3900
tcgttacccg tcggcctctt gttgatgttc tggtgcggag ggtacgacct gaggctgccg   3960
aggaagaagg agatgtcgtt cgagtggcac ctgttctcgt ggtggcagca ggggaacgtc   4020
ttctcatgct ccgtgatgca tgaggctctg cacaaccact acacgcagaa gagcctctcc   4080
ctgtctccgg gtaaagggta ccaccgtcgt ccccttgcag aagagtacga ggcactacgt   4140
actccgagac gtgttggtga tgtgcgtctt ctcggagagg gacagaggcc catttcccat   4200
catgtcccat atgctcgaca tggcaagcag cctgagacag attctggact cccagaaaat   4260
ggagtggagg tccaacgccg gggcagcgg tagggataag gtacagggta tacgagctgt   4320
accgttcgtc ggactctgtc taagacctga gggtctttta cctcacctcc aggttgcggc   4380
ccccgtcgcc atccctattc tggtcagatc ttcgcatggg cagcagccat catcatcatc   4440
atcacagcag cggcatggca agcagcctga gacagattct ggactcccag aaaatggagt   4500
accagtctag aagcgtaccc gtcgtcggta gtagtagtag tagtgtcgtc gccgtaccgt   4560
tcgtcggact ctgtctaaga cctgagggtc ttttacctca ggaggtccaa cgccgggggc   4620
agcggtaggg ataacagggt aatccatatg ctcgaggggg ccaaggccgc gccggcctgc   4680
aggcatgcaa gcttggcgta cctccaggtt gcggccccg tcgccatccc tattgtccca   4740
ttaggtatac gagctccccc ggttccggcg cggccggacg tccgtacgtt cgaaccgcat   4800
atcatggtca tagctgtttc ctgtgtgaaa ttgttatccg ctcacaattc cacacaacat   4860
acgagccgga agcataaagt gtaaagcctg gggtgcctaa tagtaccagt atcgacaaag   4920
```

-continued

```
gacacacttt aacaataggc gagtgttaag gtgtgttgta tgctcggcct tcgtatttca   4980
catttcggac cccacggatt tgagtgagct aactcacatt aattgcgttg cgctcactgc   5040
ccgctttcca gtcgggaaac ctgtcgtgcc agcgagctcg aattgttgac attcccgaaa   5100
actcactcga ttgagtgtaa ttaacgcaac gcgagtgacg ggcgaaaggt cagccctttg   5160
gacagcacgg tcgctcgagc ttaacaactg taagggcttt tctctggatt taaggagatg   5220
gcacccatgg aacagttcat tgctcaagtt gatcgctgcg cttcctgcac tactggatgt   5280
ctcaaaggtc ttgccaatgt agagacctaa attcctctac cgtgggtacc ttgtcaagta   5340
acgagttcaa ctagcgacgc gaaggacgtg atgacctaca gagtttccag aacggttaca   5400
taagtgctct gaactcctga agaaatggct gcctgacagg tgtgcaagtt ttgctgacaa   5460
gattcaaaaa gaagttcaca atatcaaagg catggccggc attcacgaga cttgaggact   5520
tctttaccga cggactgtcc acacgttcaa aacgactgtt ctaagttttt cttcaagtgt   5580
tatagtttcc gtaccggccg gatcgatgag cggccgcaat ttaattccgg ttattttcca   5640
ccatattgcc gtcttttggc aatgtgaggg cccggaaacc tggccctgtc ttcttgacga   5700
ctagctactc gccggcgtta aattaaggcc aataaaaggt ggtataacgg cagaaaaccg   5760
ttacactccc gggcctttgg accgggacag aagaactgct gcattcctag ggtctttcc    5820
cctctcgcca aaggaatgca aggtctgttg aatgtcgtga aggaagcagt tcctctggaa   5880
gcttcttgaa gacaaacaac cgtaaggatc cccagaaagg ggagagcggt ttccttacgt   5940
tccagacaac ttacagcact tccttcgtca aggagacctt cgaagaactt ctgtttgttg   6000
gtctgtagcg accctttgca ggcagcggaa ccccccacct ggcgacaggt gcctctgcgg   6060
ccaaaagcca cgtgtataag atacacctgc aaaggcggca cagacatcgc tgggaaacgt   6120
ccgtcgcctt ggggggtgga ccgctgtcca cggagacgcc ggttttcggt gcacatattc   6180
tatgtggacg tttccgccgt caaccccagt gccacgttgt gagttggata gttgtggaaa   6240
gagtcaaatg gctcacctca agcgtattca acaaggggct gaaggatgcc cagaaggtac   6300
gttggggtca cggtgcaaca ctcaacctat caacaccttt ctcagtttac cgagtggagt   6360
tcgcataagt tgttccccga cttcctacgg gtcttccatg cccattgtat gggatctgat   6420
ctggggcctc ggtgcacatg ctttacatgt gtttagtcga ggttaaaaaa cgtctaggcc   6480
ccccgaacca cggggacgtg gggtaacata ccctagacta gaccccggag ccacgtgtac   6540
gaaatgtaca caaatcagct ccaatttttt gcagatccgg ggggcttggt gcccctgcac   6600
gttttccttt gaaaaacacg atgataatat ggccaccacc catacctagg cttttgcaaa   6660
gatcgatcaa gagacaggat gaggatcgtt tcgcatgatt caaaaggaaa ctttttgtgc   6720
tactattata ccggtggtgg gtatggatcc gaaaacgttt ctagctagtt ctctgtccta   6780
ctcctagcaa agcgtactaa gaacaagatg gattgcacgc aggttctccg gccgcttggg   6840
tggagaggct attcggctat gactgggcac aacagacaat cggctgctct gatgccgccg   6900
cttgttctac ctaacgtgcg tccaagaggc cggcgaaccc acctctccga taagccgata   6960
ctgacccgtg ttgtctgtta gccgacgaga ctacggcggc tgttccggct gtcagcgcag   7020
gggcgcccgg ttctttttgt caagaccgac ctgtccggtg ccctgaatga actgcaagac   7080
gaggcagcgc ggctatcgtg acaaggccga cagtcgcgtc cccgcgggcc aagaaaaaca   7140
gttctggctg gacaggccac gggacttact tgacgttctg ctccgtcgcg ccgatagcac   7200
gctggccacg acgggcgttc cttgcgcagc tgtgctcgac gttgtcactg aagcgggaag   7260
ggactggctg ctattgggcg aagtgccggg gcaggatctc cgaccggtgc tgcccgcaag   7320
```

-continued gaacgcgtcg acacgagctg caacagtgac ttcgcccttc cctgaccgac gataacccgc 7380
ttcacggccc cgtcctagag ctgtcatctc accttgctcc tgccgagaaa gtatccatca 7440
tggctgatgc aatgcggcgg ctgcatacgc ttgatccggc tacctgccca ttcgaccacc 7500
gacagtagag tggaacgagg acggctcttt cataggtagt accgactacg ttacgccgcc 7560
gacgtatgcg aactaggccg atggacgggt aagctggtgg aagcgaaaca tcgcatcgag 7620
cgagcacgta ctcggatgga agccggtctt gtcgatcagg atgatctgga cgaagagcat 7680
caggggctcg cgccagccga ttcgctttgt agcgtagctc gctcgtgcat gagcctacct 7740
tcggccagaa cagctagtcc tactagacct gcttctcgta gtccccgagc gcggtcggct 7800
actgttcgcc aggctcaagg cgagcatgcc cgacggcgag gatctcgtcg tgacccatgg 7860
cgatgcctgc ttgccgaata tcatggtgga aaatggccgc tgacaagcgg tccgagttcc 7920
gctcgtacgg gctgccgctc ctagagcagc actgggtacc gctacggacg aacggcttat 7980
agtaccacct tttaccggcg ttttctggat tcatcgactg tggccggctg ggtgtggcgg 8040
accgctatca ggacatagcg ttggctaccc gtgatattgc tgaagagctt ggcggcgaat 8100
aaaagaccta agtagctgac accggccgac ccacaccgcc tggcgatagt cctgtatcgc 8160
aaccgatggg cactataacg acttctcgaa ccgccgctta gggctgaccg cttcctcgtg 8220
ctttacggta tcgccgctcc cgattcgcag cgcatcgcct tctatcgcct tcttgacgag 8280
ttcttctgag cgggactctg cccgactggc gaaggagcac gaaatgccat agcggcgagg 8340
gctaagcgtc gcgtagcgga agatagcgga agaactgctc aagaagactc gccctgagac 8400
gggttcgggc cgcactcgag cataaacttg tttattgcag cttataatgg ttacaaataa 8460
agcaatagca tcacaaattt cacaaataaa gcattttttt cccaagcccg gcgtgagctc 8520
gtatttgaac aaataacgtc gaatattacc aatgtttatt tcgttatcgt agtgtttaaa 8580
gtgtttattt cgtaaaaaaa cactgcattc tagttgtggt ttgtccaaac tcatcaatgt 8640
atcttaagta gggataacag ggtaattttg ttaaatcagc tcattttttta accaatagga 8700 gtgacgtaag atcaacacca aacaggtttg agtagttaca tagaattcat ccctattgtc 8760
ccattaaaac aatttagtcg agtaaaaaat tggttatcct acgccatcaa aaataattcg 8820
cgtctggcct tcctgtagcc agctttcatc aacattaaat gtgagcgagt aacaacccgt 8880
cggattctcc gtgggaacaa tgcggtagtt tttattaagc gcagaccgga aggacatcgg 8940
tcgaaagtag ttgtaattta cactcgctca ttgttgggca gcctaagagg caccccttgtt 9000 acggcggatt gaccgtaatg ggataggtta cgttggtgta gatgggcgca tcgtaaccgt 9060
gcatctgcca gtttgagggg acgacgaccg tatcggcctc tgccgcctaa ctggcattac 9120
cctatccaat gcaaccacat ctacccgcgt agcattggca cgtagacggt caaactcccc 9180
tgctgctggc atagccggag aggaagatcg cactccagcc agctttccgg caccgcttct 9240
ggtgccggaa accaggcaaa gcgccattcg ccattcaggc tgcgcaactg ttgggaaggg 9300
tccttctagc gtgaggtcgg tcgaaaggcc gtggcgaaga ccacggcctt tggtccgttt 9360
cgcggtaagc ggtaagtccg acgcgttgac aacccttccc cgatcggtgc gggcctcttc 9420
gctattacgc cagctggcga aagggggatg tgctgcaagg cgattaagtt gggtaacgcc 9480
agggttttcc cagtcacgac gctagccacg cccggagaag cgataatgcg gtcgaccgct 9540
ttccccctac acgacgttcc gctaattcaa cccattgcgg tcccaaaagg gtcagtgctg 9600
gttgtaaaac gacggccagt gaattgcaat tcgtaatcat ggtcatagct gtttcctgtg 9660

-continued

```
tgaaattgtt atccgctcac aattccacac aacatacgag caacattttg ctgccggtca   9720
cttaacgtta agcattagta ccagtatcga caaaggacac actttaacaa taggcgagtg   9780
ttaaggtgtg ttgtatgctc ccggaagcat aaagtgtaaa gcctggggtg cctaatgagt   9840
gagctaactc acattaattg cgttgcgctc actgccatta ccctgttatc cctagtgaac   9900
ggccttcgta tttcacattt cggaccccac ggattactca ctcgattgag tgtaattaac   9960
gcaacgcgag tgacggtaat gggacaatag ggatcacttg catcacccta atcaagtttt  10020
ttggggtcga ggtgccgtaa agcactaaat cggaacccta aagggagccc ccgatttaga  10080
gcttgacggg gaaagccggc gtagtgggat tagttcaaaa aaccccagct ccacggcatt  10140
tcgtgattta gccttgggat ttccctcggg ggctaaatct cgaactgccc ctttcggccg  10200
gaacgtggcg agaaaggaag ggaagaaagc gaaaggagcg ggcgctaggg cgctggcaag  10260
tgtagcggtc acgctgcgcg taaccaccac acccgccgcg cttgcaccgc tctttccttc  10320
ccttctttcg ctttcctcgc ccgcgatccc gcgaccgttc acatcgccag tgcgacgcgc  10380
attggtggtg tgggcggcgc cttaatgcgc cgctacaggg cgcgtcaggt ggcacttttc  10440
ggggaaatgt gcgcggaacc cctatttgtt tatttttcta aatacattca aatatgtatc  10500
gaattacgcg gcgatgtccc gcgcagtcca ccgtgaaaag cccctttaca cgcgccttgg  10560
ggataaacaa ataaaaagat ttatgtaagt ttatacatag cgctcatgag acaataaccc  10620
tgataaatgc ttcaataata acgaccggta atgaaaaagg aagagtatga gtattcaaca  10680
tttccgtgtc gcccttattc gcgagtactc tgttattggg actatttacg aagttattat  10740
tgctggccat tactttttcc ttctcatact cataagttgt aaaggcacag cgggaataag  10800
cctttttgc ggcattttgc cttcctgttt ttgctcaccc agaaacgctg gtgaaagtaa  10860
aagatgctga agatcagttg ggtgcacgag tgggttacat ggaaaaaacg ccgtaaaacg  10920
gaaggacaaa aacgagtggg tctttgcgac cactttcatt ttctacgact tctagtcaac  10980
ccacgtgctc acccaatgta cgaactggat ctcaacagcg gtaagatcct tgagagtttt  11040
cgccccgaag aacgttttcc aatgatgagc acttttaaag ttctgctatg tggcgcggta  11100
gcttgaccta gagttgtcgc cattctagga actctcaaaa gcggggcttc ttgcaaaagg  11160
ttactactcg tgaaaatttc aagacgatac accgcgccat ttatcccgta ttgacgccgg  11220
gcaagagcaa ctcggtcgcc gcatacacta ttctcagaat gacttggttg agtctagcgt  11280
tgatcggcac gtaagaggtt aatagggcat aactgcggcc cgttctcgtt gagccagcgg  11340
cgtatgtgat aagagtctta ctgaaccaac tcagatcgca actagccgtg cattctccaa  11400
ccaactttca ccataatgaa ataagatcac taccgggcgt attttttgag ttatcgagat  11460
tttcaggagc taaggaagct aaaatggaga aaaaaatcac ggttgaaagt ggtattactt  11520
tattctagtg atggcccgca taaaaaactc aatagctcta aaagtcctcg attccttcga  11580
ttttacctct ttttttagtg tggatatacc accgttgata tatcccaatg gcatcgtaaa  11640
gaacattttg aggcatttca gtcagttgct caatgtacct ataaccagac cgttcagctg  11700
acctatatgg tggcaactat atagggttac cgtagcattt cttgtaaaac tccgtaaagt  11760
cagtcaacga gttacatgga tattggtctg gcaagtcgac gatattacgg cctttttaaa  11820
gaccgtaaag aaaaataagc acaagtttta tccggccttt attcacattc ttgcccgcct  11880
gatgaatgct catccggaat ctataatgcc ggaaaaattt ctggcatttc tttttattcg  11940
tgttcaaaat aggccggaaa taagtgtaag aacgggcgga ctacttacga gtaggcctta  12000
tccgtatggc aatgaaagac ggtgagctgg tgatatggga tagtgttcac ccttgttaca  12060
```

-continued

```
ccgttttcca tgagcaaact gaaacgtttt catcgctctg aggcataccg ttactttctg  12120
ccactcgacc actataccct atcacaagtg ggaacaatgt ggcaaaaggt actcgtttga  12180
ctttgcaaaa gtagcgagac gagtgaatac cacgacgatt tccggcagtt tctacacata  12240
tattcgcaag atgtggcgtg ttacggtgaa aacctggcct atttccctaa agggtttatt  12300
ctcacttatg gtgctgctaa aggccgtcaa agatgtgtat ataagcgttc tacaccgcac  12360
aatgccactt ttggaccgga taaagggatt tcccaaataa gagaatatgt ttttcgtatc  12420
agccaatccc tgggtgagtt tcaccagttt tgatttaaac gtggccaata tggacaactt  12480
cttcgccccc gttttcacca ctcttataca aaaagcatag tcggttaggg acccactcaa  12540
agtggtcaaa actaaatttg caccggttat acctgttgaa gaagcggggg caaaagtggt  12600
tgggcaaata ttatacgcaa ggcgacaagg tgctgatgcc gctggcgatt caggttcatc  12660
atgccgtctg tgatggcttc catgtcggca gaatgcttaa acccgtttat aatatgcgtt  12720
ccgctgttcc acgactacgg cgaccgctaa gtccaagtag tacggcagac actaccgaag  12780
gtacagccgt cttacgaatt tgaattacaa cagtactgcg atgagtggca gggcggggcg  12840
taattttttt aaggcagtta ttggtgccct taaacgcctg gtgctacgcc tgaataagtg  12900
acttaatgtt gtcatgacgc tactcaccgt cccgccccgc attaaaaaaa ttccgtcaat  12960
aaccacggga atttgcggac cacgatgcgg acttattcac ataataagcg gatgaatggc  13020
agaaattcga aatgaccgac caagcgacgc ccaacctgcc atcacgagat ttcgattcca  13080
ccgccgcctt ctatgaaagg tattattcgc ctacttaccg tctttaagct ttactggctg  13140
gttcgctgcg ggttggacgg tagtgctcta aagctaaggt ggcggcggaa gatactttcc  13200
ttgggcttcg gaatcgtttt ccgggacgcc ggctggatga tcctccagcg cggggatctc  13260
atgctggagt tcttcgccca ccctaggggg aggctaactg aacccgaagc cttagcaaaa  13320
ggccctgcgg ccgacctact aggaggtcgc gcccctagag tacgacctca agaagcgggt  13380
gggatccccc tccgattgac aaacacggaa ggagacaata ccggaaggaa cccgcgctat  13440
gacggcaata aaaagacaga ataaaacgca cggtgttggg tcgtttgttc ataaacgcgg  13500
tttgtgcctt cctctgttat ggccttcctt gggcgcgata ctgccgttat ttttctgtct  13560
tattttgcgt gccacaaccc agcaaacaag tatttgcgcc ggttcggtcc cagggctggc  13620
actctgtcga taccccaccg agaccccatt ggggccaata cgcccgcgtt tcttcctttt  13680
ccccacccca ccccccaagt ccaagccagg gtcccgaccg tgagacagct atggggtggc  13740
tctggggtaa ccccggttat gcgggcgcaa agaaggaaaa ggggtggggt ggggggttca  13800
tcgggtgaag gcccagggct cgcagccaac gtcggggcgg caggccctgc catagcctca  13860
ggttactcat atatacttta gattgattta aaacttcatt agcccacttc cgggtcccga  13920
gcgtcggttg cagccccgcc gtccgggacg gtatcggagt ccaatgagta tatatgaaat  13980
ctaactaaat tttgaagtaa tttaatttaa aaggatctag gtgaagatcc tttttgataa  14040
tctcatgacc aaaatccctt aacgtgagtt ttcgttccac tgagcgtcag accccgtaga  14100
aaattaaatt ttcctagatc cacttctagg aaaaactatt agagtactgg ttttagggaa  14160
ttgcactcaa aagcaaggtg actcgcagtc tggggcatct aaagatcaaa ggatcttctt  14220
gagatccttt ttttctgcgc gtaatctgct gcttgcaaac aaaaaaacca ccgctaccag  14280
cggtggtttg tttgccggat tttctagttt cctagaagaa ctctaggaaa aaaagacgcg  14340
cattagacga cgaacgtttg tttttttggt ggcgatggtc gccaccaaac aaacggccta  14400
```

-continued

```
caagagctac caactctttt tccgaaggta actggcttca gcagagcgca gataccaaat  14460
actgtccttc tagtgtagcc gtagttaggc caccacttca gttctcgatg gttgagaaaa  14520
aggcttccat tgaccgaagt cgtctcgcgt ctatggttta tgacaggaag atcacatcgg  14580
catcaatccg gtggtgaagt agaactctgt agcaccgcct acatacctcg ctctgctaat  14640
cctgttacca gtggctgctg ccagtggcga taagtcgtgt cttaccgggt tggactcaag  14700
tcttgagaca tcgtggcgga tgtatggagc gagacgatta ggacaatggt caccgacgac  14760
ggtcaccgct attcagcaca gaatggccca acctgagttc acgatagtta ccggataagg  14820
cgcagcggtc gggctgaacg gggggttcgt gcacacagcc cagcttggag cgaacgacct  14880
acaccgaact gagataccta tgctatcaat ggcctattcc gcgtcgccag cccgacttgc  14940
cccccaagca cgtgtgtcgg gtcgaacctc gcttgctgga tgtggcttga ctctatggat  15000
cagcgtgagc tatgagaaag cgccacgctt cccgaaggga gaaaggcgga caggtatccg  15060
gtaagcggca gggtcggaac aggagagcgc acgagggagc gtcgcactcg atactctttc  15120
gcggtgcgaa gggcttccct ctttccgcct gtccataggc cattcgccgt cccagccttg  15180
tcctctcgcg tgctccctcg ttccaggggg aaacgcctgg tatctttata gtcctgtcgg  15240
gtttcgccac ctctgacttg agcgtcgatt tttgtgatgc tcgtcagggg ggcggagcct  15300
aaggtccccc tttgcggacc atagaaatat caggacagcc caaagcggtg gagactgaac  15360
tcgcagctaa aaacactacg agcagtcccc ccgcctcgga atggaaaaac gccagcaacg  15420
cggccttttt acggttcctg gccttttgct ggccttttgc tcacatgttc tttcctgcgt  15480
tatcccctga ttctgtggat tacctttttg cggtcgttgc gccggaaaaa tgccaaggac  15540
cggaaaacga ccggaaaacg agtgtacaag aaaggacgca ataggggact aagacaccta  15600
aaccgtatta ccgccatgca ttagttatta atagtaatca attacggggt cattagttca  15660
tagcccatat atggagttcc gcgttacata acttacggta ttggcataat ggcggtacgt  15720
aatcaataat tatcattagt taatgcccca gtaatcaagt atcgggtata tacctcaagg  15780
cgcaatgtat tgaatgccat aatggcccgc ctggctgacc gcccaacgac ccccgcccat  15840
tgacgtcaat aatgacgtat gttcccatag taacgccaat agggactttc cattgacgtc  15900
ttaccgggcg gaccgactgg cgggttgctg gggcgggta actgcagtta ttactgcata  15960
caagggtatc attgcggtta tccctgaaag gtaactgcag aatgggtgga gtatttacgg  16020
taaactgccc acttggcagt acatcaagtg tatcatatgc caagtacgcc ccctattgac  16080
gtcaatgacg gtaaatggcc ttacccacct cataaatgcc atttgacggg tgaaccgtca  16140
tgtagttcac atagtatacg gttcatgcgg gggataactg cagttactgc catttaccgg  16200
cgcctggcat tatgcccagt acatgacctt atgggacttt cctacttggc agtacatcta  16260
cgtattagtc atcgctatta ccatggtgat gcggttttgg gcggaccgta atacgggtca  16320
tgtactggaa taccctgaaa ggatgaaccg tcatgtagat gcataatcag tagcgataat  16380
ggtaccacta cgccaaaacc cagtacatca atgggcgtgg atagcggttt gactcacggg  16440
gatttccaag tctccacccc attgacgtca atgggagttt gttttggcac caaaatcaac  16500
gtcatgtagt tacccgcacc tatcgccaaa ctgagtgccc ctaaaggttc agaggtgggg  16560
taactgcagt taccctcaaa caaaaccgtg gttttagttg ggactttcc aaaatgtcgt  16620
aacaactccg ccccattgac gcaaatgggc ggtaggcgtg tacggtggga ggtctatata  16680
agcagagctc cctgaaaggt tttacagcat tgttgaggcg ggtaactgc gtttacccgc  16740
catccgcaca tgccaccctc cagatatatt cgtctcga                        16778
```

<210> SEQ ID NO 58
<211> LENGTH: 16582
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
ggtttagtga accgtcagat ccgctagacg tctcatatac ctgactggaa tacgacagct 60
cctgcagctt ctgggcgaag accaccgtgg cccattgcgt ccaaatcact tggcagtcta 120
ggcgatctgc agagtatatg gactgacctt atgctgtcga ggacgtcgaa gacccgcttc 180
tggtggcacc gggtaacgca acttagcgat aatctggtcc gcttggaagt tagcacggcg 240
agcgcgctcc agagccaagt cacgcagctt aacagtacct accgcagagc ggtgcatgaa 300
tgaatcgcta ttagaccagg cgaaccttca atcgtgccgc tcgcgcgagg tctcggttca 360
gtgcgtcgaa ttgtcatgga tggcgtctcg ccacgtactt caggccgata acgttgtcct 420
tagcaacctt gacattaccc tcacctttat tggcagggaa gacgtgcttc tgaccagtag 480
tgccctcacg agcggtacca gtccggctat tgcaacagga atcgttggaa ctgtaatggg 540
agtggaaata accgtccctt ctgcacgaag actggtcatc acgggagtgc tcgccatggt 600
gcaccaccag cggtgaggtg cggaacttct acaacctcaa agcccataac gttgcggata 660
gaacccttct cagggtcaat cagagcagcg tagtttgctg cgtggtggtc gccactccac 720
gccttgaaga tgttggagtt tcgggtattg caacgcctat cttgggaaga gtcccagtta 780
gtctcgtcgc atcaaacgac cgttcggcat cagtgctgcc agaatcgcag agtagctatc 840
tgggtcacag tagaacacac ggtcagcagc cggaacatag ttcttggtca gagccgcacg 900
gcaagccgta gtcacgacgg tcttagcgtc tcatcgatag acccagtgtc atcttgtgtg 960
ccagtcgtcg gccttgtatc aagaaccagt ctcggcgtgc agccttagtc agagccgcaa 1020
taatctcctt acccagcgca acttggtcgg taagtgcggc cttgttctga gtggtctcaa 1080
ttacggtagc agtacctaag tcggaatcag tctcggcgtt attagaggaa tgggtcgcgt 1140
tgaaccagcc attcacgccg gaacaagact caccagagtt aatgccatcg tcatggattc 1200
ccctcgatgt tctcattata tttgctttcc acgttacaca gaccggcaat ctcagccaga 1260
accgcaccat ccgcagccat cgccagagat tcacccaact gggagctaca agagtaatat 1320
aaacgaaagg tgcaatgtgt ctggccgtta gagtcggtct tggcgtggta ggcgtcggta 1380
gcggtctcta agtgggttga gagaggtata ctcagagcga acgtcgtagt ggttcatcgc 1440
gtcctcaata tcataaatca gaacgtcagc cgtcaggaga ccgtcaatgg tgattacctt 1500
ctctccatat gagtctcgct tgcagcatca ccaagtagcg caggagttat agtatttagt 1560
cttgcagtcg gcagtcctct ggcagttacc actaatggaa ctcggtgtgt ttgatgtcct 1620
tacgtttatc gtcgaggttc tcgcccggag ccagatacgc tgcctgagtg cgacccagaa 1680
cagggaactg agcggattta gagccacaca aactacagga atgcaaatag cagctccaag 1740
agcgggcctc ggtctatgcg acggactcac gctgggtctt gtcccttgac tcgcctaaat 1800
ccgctggaga tggaacgtac catgtggcga gaagtggtca cggaggtacg agcgaacgca 1860
gtcaggactt caccgccaaa taccttcaag aacaacgcca ggcgacctct accttgcatg 1920
gtacaccgct cttcaccagt gcctccatgc tcgcttgcgt cagtcctgaa gtggcggttt 1980
atggaagttc ttgttgcggt gtttatctcc agcagcaact acacctttac cttggttagt 2040

-continued

```
acccatttgc tgtccaccag tcatgctagc catatgtata tctccttctt aaagtcgtct   2100
caaatagagg tcgtcgttga tgtggaaatg gaaccaatca tgggtaaacg acaggtggtc   2160
agtacgatcg gtatacatat agaggaagaa tttcagcaga ccagtgcctc caccaagggc   2220
ccatcggtct tccccctggc gccctgctcc aggagcacct ccgagagcac agcggccctg   2280
ggctgcctgg tcaaggacta ggtcacggag gtggttcccg ggtagccaga agggggaccg   2340
cgggacgagg tcctcgtgga ggctctcgtg tcgccgggac ccgacggacc agttcctgat   2400
cttccccgaa ccggtgacgg tgtcgtggaa ctcaggcgct ctgaccagcg gcgtgcacac   2460
cttcccagct gtcctacagt cctcaggact ctactccctc gaaggggctt ggccactgcc   2520
acagcacctt gagtccgcga gactggtcgc cgcacgtgtg gaagggtcga caggatgtca   2580
ggagtcctga gatgagggag agcagcgtgg tgaccgtgcc ctccagcagc ttgggcaccc   2640
agacctacat ctgcaacgtg aatcacaagc ccagcaacac caaggtggac aagaaagttg   2700
tcgtcgcacc actggcacgg gaggtcgtcg aacccgtggg tctggatgta gacgttgcac   2760
ttagtgttcg ggtcgttgtg gttccacctg ttctttcaac agcccaaatc ttgtgacaaa   2820
actcacacat gcccaccgtg cccagcacct gaactcctgg ggggaccgtc agtcttcctc   2880
ttccccccma aacccaagga tcgggtttag aacactgttt tgagtgtgta cgggtggcac   2940
gggtcgtgga cttgaggacc cccctggcag tcagaaggag aagggggkt ttgggttcct   3000
caccctcatg atctcccgga cccctgaggt cacatgcgtg gtggtggacg tgagccacga   3060
agaccctgag gtcaagttca actggtacgt ggacggcgtg gtgggagtac tagagggcct   3120
ggggactcca gtgtacgcac caccacctgc actcggtgct tctgggactc cagttcaagt   3180
tgaccatgca cctgccgcac gaggtgcata atgccaagac aaagccgcgg gaggagcagt   3240
acaacagcac gtaccgtgtg gtcagcgtcc tcaccgtcct gcaccaggac tggctgaatg   3300
ctccacgtat tacggttctg tttcggcgcc ctcctcgtca tgttgtcgtg catggcacac   3360
cagtcgcagg agtggcagga cgtggtcctg accgacttac gcaaggagta caagtgcaag   3420
gtctccaaca aagccctccc agcccccatc gagaaaacca tctccaaagc caaagggcag   3480
ccccgagaac cacaggtgta cgttcctcat gttcacgttc cagaggttgt ttcgggaggg   3540
tcgggggtag ctcttttggt agaggtttcg gtttcccgtc ggggctcttg gtgtccacat   3600
caccctgccc ccatcccggg atgagctgac caagaaccag gtcagcctga cctgcctggt   3660
caaaggcttc taccccagcg acatcgccgt ggagtgggag gtgggacggg ggtagggccc   3720
tactcgactg gttcttggtc cagtcggact ggacggacca gtttccgaag atggggtcgc   3780
tgtagcggca cctcaccctc agcaatgggc agccggagaa caactacaag accacgcctc   3840
ccatgctgga ctccgacggc tccttcttcc tctacagcaa gctcaccgtg gacaagagca   3900
tcgttacccg tcggcctctt gttgatgttc tggtgcggag ggtacgacct gaggctgccg   3960
aggaagaagg agatgtcgtt cgagtggcac ctgttctcgt ggtggcagca ggggaacgtc   4020
ttctcatgct ccgtgatgca tgaggctctg cacaaccact acacgcagaa gagcctctcc   4080
ctgtctccgg gtaaagggta ccaccgtcgt ccccttgcag aagagtacga ggcactacgt   4140
actccgagac gtgttggtga tgtgcgtctt ctcggagagg gacagaggcc catttcccat   4200
catgtcccat atgctcgaca tggcaagcag cctgagacag attctggact cccagaaaat   4260
ggagtggagg tccaacgccg ggggcagcgg tagggataag gtacagggta tacgagctgt   4320
accgttcgtc ggactctgtc taagacctga gggtctttta cctcacctcc aggttgcggc   4380
```

-continued

```
ccccgtcgcc atccctattc tggtcagatc tggtaccgcg ggcggcgacc agcagcatga   4440
gcgtggaatt ttataacagc aacaaaagcg cgcagaccaa cagcattacc ccgattatta   4500
accagtctag accatggcgc ccgccgctgg tcgtcgtact cgcaccttaa aatattgtcg   4560
ttgttttcgc gcgtctggtt gtcgtaatgg ggctaataat aaattaccaa caccagcgat   4620
agcgatctga acctgaacga tgtgaaagtg cgctattatt ataccagcga tggcacccag   4680
ggccagacct tttggtgcga tttaatggtt gtggtcgcta tcgctagact tggacttgct   4740
acactttcac gcgataataa tatggtcgct accgtgggtc ccggtctgga aaaccacgct   4800
tcatgcgggc gcgctgctgg gcaacagcta tgtggataac accagcaaag tgaccgcgaa   4860
ctttgtgaaa gaaaccgcga gcccgaccag cacctatgat agtacgcccg cgcgacgacc   4920
cgttgtcgat acacctattg tggtcgtttc actggcgctt gaaacacttt ctttggcgct   4980
cgggctggtc gtggatacta acctatgtgg aatttggctt tgcgagtggc cgcgcgaccc   5040
tgaaaaaagg ccagtttatt accattcagg gccgcattac caaaagcgat tggagcaact   5100
tggatacacc ttaaaccgaa acgctcaccg gcgcgctggg acttttttcc ggtcaaataa   5160
tggtaagtcc cggcgtaatg gttttcgcta acctcgttga atacccagac caacgattat   5220
agctttgatg cgagcagcag caccccggtg gtgaacccga aagtgaccgg ctatattggc   5280
ggcgcgaaag tgctgggcac tatgggtctg gttgctaata tcgaaactac gctcgtcgtc   5340
gtggggccac cacttgggct ttcactggcc gatataaccg ccgcgctttc acgacccgtg   5400
cgcgccgtaa agcggccgca atttaattcc ggttattttc caccatattg ccgtcttttg   5460
gcaatgtgag ggcccggaaa cctggccctg tcttcttgac gcgcggcatt tcgccggcgt   5520
taaattaagg ccaataaaag gtggtataac ggcagaaaac cgttacactc ccgggccttt   5580
ggaccgggac agaagaactg gagcattcct aggggtcttt cccctctcgc caaaggaatg   5640
caaggtctgt tgaatgtcgt gaaggaagca gttcctctgg aagcttcttg aagacaaaca   5700
ctcgtaagga tccccagaaa ggggagagcg gtttccttac gttccagaca acttacagca   5760
cttccttcgt caaggagacc ttcgaagaac ttctgtttgt acgtctgtag cgaccctttg   5820
caggcagcgg aaccccccac ctggcgacag gtgcctctgc ggccaaaagc cacgtgtata   5880
agatacacct gcaaaggcgg tgcagacatc gctgggaaac gtccgtcgcc ttggggggtg   5940
gaccgctgtc cacggagacg ccggttttcg gtgcacatat tctatgtgga cgtttccgcc   6000
cacaacccca gtgccacgtt gtgagttgga tagttgtgga aagagtcaaa tggctcacct   6060
caagcgtatt caacaagggg ctgaaggatg cccagaaggt gtgttggggt cacggtgcaa   6120
cactcaacct atcaacacct ttctcagttt accgagtgga gttcgcataa gttgttcccc   6180
gacttcctac gggtcttcca accccattgt atgggatctg atctggggcc tcggtgcaca   6240
tgctttacat gtgtttagtc gaggttaaaa aacgtctagg ccccccgaac cacggggacg   6300
tggggtaaca taccctagac tagaccccgg agccacgtgt acgaaatgta cacaaatcag   6360
ctccaatttt ttgcagatcc ggggggcttg gtgcccctgc tggttttcct ttgaaaaaca   6420
cgatgataat atggccacca cccataccta ggcttttgca aagatcgatc aagagacagg   6480
atgaggatcg tttcgcatga accaaaagga aactttttgt gctactatta taccggtggt   6540
gggtatggat ccgaaaacgt ttctagctag ttctctgtcc tactcctagc aaagcgtact   6600
ttgaacaaga tggattgcac gcaggttctc cggccgcttg ggtggagagg ctattcggct   6660
atgactgggc acaacagaca atcggctgct ctgatgccgc aacttgttct acctaacgtg   6720
cgtccaagag gccggcgaac ccacctctcc gataagccga tactgacccg tgttgtctgt   6780
```

-continued

```
tagccgacga gactacggcg cgtgttccgg ctgtcagcgc aggggcgccc ggttcttttt   6840
gtcaagaccg acctgtccgg tgccctgaat gaactgcaag acgaggcagc gcggctatcg   6900
gcacaaggcc gacagtcgcg tccccgcggg ccaagaaaaa cagttctggc tggacaggcc   6960
acgggactta cttgacgttc tgctccgtcg cgccgatagc tggctggcca cgacgggcgt   7020
tccttgcgca gctgtgctcg acgttgtcac tgaagcggga agggactggc tgctattggg   7080
cgaagtgccg gggcaggatc accgaccggt gctgcccgca aggaacgcgt cgacacgagc   7140
tgcaacagtg acttcgccct tccctgaccg acgataaccc gcttcacggc cccgtcctag   7200
tcctgtcatc tcaccttgct cctgccgaga aagtatccat catggctgat gcaatgcggc   7260
ggctgcatac gcttgatccg gctacctgcc cattcgacca aggacagtag agtggaacga   7320
ggacggctct ttcataggta gtaccgacta cgttacgccg ccgacgtatg cgaactaggc   7380
cgatggacgg gtaagctggt ccaagcgaaa catcgcatcg agcgagcacg tactcggatg   7440
gaagccggtc ttgtcgatca ggatgatctg gacgaagagc atcaggggct cgcgccagcc   7500
ggttcgcttt gtagcgtagc tcgctcgtgc atgagcctac cttcggccag aacagctagt   7560
cctactagac ctgcttctcg tagtccccga gcgcggtcgg gaactgttcg ccaggctcaa   7620
ggcgagcatg cccgacggcg aggatctcgt cgtgacccat ggcgatgcct gcttgccgaa   7680
tatcatggtg gaaaatggcc cttgacaagc ggtccgagtt ccgctcgtac gggctgccgc   7740
tcctagagca gcactgggta ccgctacgga cgaacggctt atagtaccac cttttaccgg   7800
gcttttctgg attcatcgac tgtggccggc tgggtgtggc ggaccgctat caggacatag   7860
cgttggctac ccgtgatatt gctgaagagc ttggcggcga cgaaaagacc taagtagctg   7920
acaccggccg acccacaccg cctggcgata gtcctgtatc gcaaccgatg ggcactataa   7980
cgacttctcg aaccgccgct atgggctgac cgcttcctcg tgctttacgg tatcgccgct   8040
cccgattcgc agcgcatcgc cttctatcgc cttcttgacg agttcttctg agcgggactc   8100
tacccgactg gcgaaggagc acgaaatgcc atagcggcga gggctaagcg tcgcgtagcg   8160
gaagatagcg gaagaactgc tcaagaagac tcgccctgag tggggttcgg gccgcactcg   8220
agcataaact tgtttattgc agcttataat ggttacaaat aaagcaatag catcacaaat   8280
ttcacaaata aagcattttt accccaagcc cggcgtgagc tcgtatttga acaaataacg   8340
tcgaatatta ccaatgttta tttcgttatc gtagtgttta aagtgtttat ttcgtaaaaa   8400
ttcactgcat tctagttgtg gtttgtccaa actcatcaat gtatcttaag tagggataac   8460
agggtaattt tgttaaatca gctcattttt taaccaatag aagtgacgta agatcaacac   8520
caaacaggtt tgagtagtta catagaattc atccctattg tcccattaaa acaatttagt   8580
cgagtaaaaa attggttatc gaacgccatc aaaaataatt cgcgtctggc cttcctgtag   8640
ccagctttca tcaacattaa atgtgagcga gtaacaaccc gtcggattct ccgtgggaac   8700
cttgcggtag tttttattaa gcgcagaccg gaaggacatc ggtcgaaagt agttgtaatt   8760
tacactcgct cattgttggg cagcctaaga ggcacccttg aaacggcgga ttgaccgtaa   8820
tgggataggt tacgttggtg tagatgggcg catcgtaacc gtgcatctgc cagtttgagg   8880
ggacgacgac cgtatcggcc tttgccgcct aactggcatt accctatcca atgcaaccac   8940
atctacccgc gtagcattgg cacgtagacg gtcaaactcc cctgctgctg gcatagccgg   9000
tcaggaagat cgcactccag ccagctttcc ggcaccgctt ctggtgccgg aaaccaggca   9060
aagcgccatt cgccattcag gctgcgcaac tgttgggaag agtccttcta gcgtgaggtc   9120
```

```
ggtcgaaagg ccgtggcgaa gaccacggcc tttggtccgt ttcgcggtaa gcggtaagtc   9180
cgacgcgttg acaacccttc ggcgatcggt gcgggcctct tcgctattac gccagctggc   9240
gaaaggggga tgtgctgcaa ggcgattaag ttgggtaacg ccagggtttt cccagtcacg   9300
ccgctagcca cgcccggaga agcgataatg cggtcgaccg ctttcccccct acacgacgtt   9360
ccgctaattc aacccattgc ggtcccaaaa gggtcagtgc acgttgtaaa acgacggcca   9420
gtgaattgca attcgtaatc atggtcatag ctgtttcctg tgtgaaattg ttatccgctc   9480
acaattccac acaacatacg tgcaacattt tgctgccggt cacttaacgt taagcattag   9540
taccagtatc gacaaaggac acactttaac aataggcgag tgttaaggtg tgttgtatgc   9600
agccggaagc ataaagtgta aagcctgggg tgcctaatga gtgagctaac tcacattaat   9660
tgcgttgcgc tcactgccat taccctgtta tccctagtga tcggccttcg tatttcacat   9720
ttcggacccc acggattact cactcgattg agtgtaatta acgcaacgcg agtgacggta   9780
atgggacaat agggatcact accatcaccc taatcaagtt ttttggggtc gaggtgccgt   9840
aaagcactaa atcggaaccc taaagggagc ccccgattta gagcttgacg gggaaagccg   9900
tggtagtggg attagttcaa aaaaccccag ctccacggca tttcgtgatt tagccttggg   9960
atttccctcg gggctaaat ctcgaactgc ccctttcggc gcgaacgtgg cgagaaagga  10020
agggaagaaa gcgaaaggag cgggcgctag ggcgctggca agtgtagcgg tcacgctgcg  10080
cgtaaccacc acacccgccg cgcttgcacc gctctttcct tcccttcttt cgctttcctc  10140
gcccgcgatc ccgcgaccgt tcacatcgcc agtgcgacgc gcattggtgg tgtgggcggc  10200
cgcttaatgc gccgctacag ggcgcgtcag gtggcacttt tcggggaaat gtgcgcggaa  10260
cccctatttg tttatttttc taaatacatt caaatatgta gcgaattacg cggcgatgtc  10320
ccgcgcagtc caccgtgaaa agcccctta cacgcgcctt ggggataaac aaataaaaag  10380
atttatgtaa gtttatacat tccgctcatg agacaataac cctgataaat gcttcaataa  10440
taacgaccgg taatgaaaaa ggaagagtat gagtattcaa catttccgtg tcgcccttat  10500
aggcgagtac tctgttattg ggactattta cgaagttatt attgctggcc attacttttt  10560
ccttctcata ctcataagtt gtaaaggcac agcgggaata tcccttttt gcggcatttt  10620
gccttcctgt ttttgctcac ccagaaacgc tggtgaaagt aaaagatgct gaagatcagt  10680
tgggtgcacg agtgggttac agggaaaaaa cgccgtaaaa cggaaggaca aaaacgagtg  10740
ggtctttgcg accactttca ttttctacga cttctagtca acccacgtgc tcacccaatg  10800
atcgaactgg atctcaacag cggtaagatc cttgagagtt ttcgccccga agaacgtttt  10860
ccaatgatga gcacttttaa agttctgcta tgtggcgcgg tagcttgacc tagagttgtc  10920
gccattctag gaactctcaa aagcggggct tcttgcaaaa ggttactact cgtgaaaatt  10980
tcaagacgat acaccgcgcc tattatcccg tattgacgcc gggcaagagc aactcggtcg  11040
ccgcatacac tattctcaga atgacttggt tgagtctagc gttgatcggc acgtaagagg  11100
ataatagggc ataactgcgg cccgttctcg ttgagccagc ggcgtatgtg ataagagtct  11160
tactgaacca actcagatcg caactagccg tgcattctcc ttccaacttt caccataatg  11220
aaataagatc actaccgggc gtattttttg agttatcgag attttcagga gctaaggaag  11280
ctaaaatgga gaaaaaaatc aaggttgaaa gtggtattac tttattctag tgatggcccg  11340
cataaaaaac tcaatagctc taaaagtcct cgattccttc gattttacct cttttttag  11400
actggatata ccaccgttga tatatcccaa tggcatcgta aagaacattt tgaggcattt  11460
cagtcagttg ctcaatgtac ctataaccag accgttcagc tgacctatat ggtggcaact  11520
```

-continued atatagggtt accgtagcat ttcttgtaaa actccgtaaa gtcagtcaac gagttacatg 11580
gatattggtc tggcaagtcg tggatattac ggccttttta aagaccgtaa agaaaaataa 11640
gcacaagttt tatccggcct ttattcacat tcttgcccgc ctgatgaatg ctcatccgga 11700
acctataatg ccggaaaaat ttctggcatt tctttttatt cgtgttcaaa ataggccgga 11760
aataagtgta agaacgggcg gactacttac gagtaggcct attccgtatg gcaatgaaag 11820
acggtgagct ggtgatatgg gatagtgttc acccttgtta caccgttttc catgagcaaa 11880
ctgaaacgtt ttcatcgctc taaggcatac cgttactttc tgccactcga ccactatacc 11940
ctatcacaag tgggaacaat gtggcaaaag gtactcgttt gactttgcaa aagtagcgag 12000
tggagtgaat accacgacga tttccggcag tttctacaca tatattcgca agatgtggcg 12060
tgttacggtg aaaacctggc ctatttccct aaagggttta acctcactta tggtgctgct 12120
aaaggccgtc aaagatgtgt atataagcgt tctacaccgc acaatgccac ttttggaccg 12180
gataaaggga tttcccaaat ttgagaatat gtttttcgta tcagccaatc cctgggtgag 12240
tttcaccagt tttgatttaa acgtggccaa tatggacaac ttcttcgccc ccgttttcac 12300
aactcttata caaaaagcat agtcggttag ggacccactc aaagtggtca aaactaaatt 12360
tgcaccggtt atacctgttg aagaagcggg ggcaaaagtg catgggcaaa tattatacgc 12420
aaggcgacaa ggtgctgatg ccgctggcga ttcaggttca tcatgccgtc tgtgatggct 12480
tccatgtcgg cagaatgctt gtacccgttt ataatatgcg ttccgctgtt ccacgactac 12540
ggcgaccgct aagtccaagt agtacggcag acactaccga aggtacagcc gtcttacgaa 12600
aatgaattac aacagtactg cgatgagtgg cagggcgggg cgtaattttt ttaaggcagt 12660
tattggtgcc cttaaacgcc tggtgctacg cctgaataag ttacttaatg ttgtcatgac 12720
gctactcacc gtcccgcccc gcattaaaaa aattccgtca ataaccacgg gaatttgcgg 12780
accacgatgc ggacttattc tgataataag cggatgaatg gcagaaattc gaaatgaccg 12840
accaagcgac gcccaacctg ccatcacgag atttcgattc caccgccgcc ttctatgaaa 12900
actattattc gcctacttac cgtctttaag ctttactggc tggttcgctg cgggttggac 12960
ggtagtgctc taaagctaag gtggcggcgg aagatacttt ggttgggctt cggaatcgtt 13020
ttccgggacg ccggctggat gatcctccag cgcggggatc tcatgctgga gttcttcgcc 13080
caccctaggg ggaggctaac ccaacccgaa gccttagcaa aaggccctgc ggccgaccta 13140
ctaggaggtc gcgcccctag agtacgacct caagaagcgg gtgggatccc cctccgattg 13200
tgaaacacgg aaggagacaa taccggaagg aacccgcgct atgacggcaa taaaaagaca 13260
gaataaaacg cacggtgttg ggtcgtttgt tcataaacgc actttgtgcc ttcctctgtt 13320
atggccttcc ttgggcgcga tactgccgtt atttttctgt cttattttgc gtgccacaac 13380
ccagcaaaca agtatttgcg gggttcggt cccagggctg gcactctgtc gataccccac 13440
cgagacccca ttggggccaa tacgcccgcg tttcttcctt ttccccaccc caccccccaa 13500
ccccaagcca gggtcccgac cgtgagacag ctatggggtg gctctggggt aaccccggtt 13560
atgcgggcgc aaagaaggaa aaggggtggg gtggggggtt gttcgggtga aggcccaggg 13620
ctcgcagcca acgtcggggc ggcaggccct gccatagcct caggttactc atatatactt 13680
tagattgatt taaaacttca caagcccact tccgggtccc gagcgtcggt tgcagccccg 13740
ccgtccggga cggtatcgga gtccaatgag tatatatgaa atctaactaa attttgaagt 13800
tttttaattt aaaaggatct aggtgaagat cctttttgat aatctcatga ccaaaatccc 13860

-continued ttaacgtgag ttttcgttcc actgagcgtc agaccccgta aaaaattaaa ttttcctaga 13920
tccacttcta ggaaaaacta ttagagtact ggttttaggg aattgcactc aaaagcaagg 13980
tgactcgcag tctggggcat gaaaagatca aaggatcttc ttgagatcct ttttttctgc 14040
gcgtaatctg ctgcttgcaa acaaaaaaac caccgctacc agcggtggtt tgtttgccgg 14100
cttttctagt ttcctagaag aactctagga aaaaaagacg cgcattagac gacgaacgtt 14160
tgtttttttg gtggcgatgg tcgccaccaa acaaacggcc atcaagagct accaactctt 14220
tttccgaagg taactggctt cagcagagcg cagataccaa atactgtcct tctagtgtag 14280
ccgtagttag gccaccactt tagttctcga tggttgagaa aaaggcttcc attgaccgaa 14340
gtcgtctcgc gtctatggtt tatgacagga agatcacatc ggcatcaatc cggtggtgaa 14400
caagaactct gtagcaccgc ctacatacct cgctctgcta atcctgttac cagtggctgc 14460
tgccagtggc gataagtcgt gtcttaccgg gttggactca gttcttgaga catcgtggcg 14520
gatgtatgga gcgagacgat taggacaatg gtcaccgacg acggtcaccg ctattcagca 14580
cagaatggcc caacctgagt agacgatagt taccggataa ggcgcagcgg tcgggctgaa 14640
cggggggttc gtgcacacag cccagcttgg agcgaacgac ctacaccgaa ctgagatacc 14700
tctgctatca atggcctatt ccgcgtcgcc agcccgactt gccccccaag cacgtgtgtc 14760
gggtcgaacc tcgcttgctg gatgtggctt gactctatgg tacagcgtga gctatgagaa 14820
agcgccacgc ttcccgaagg gagaaaggcg gacaggtatc cggtaagcgg cagggtcgga 14880
acaggagagc gcacgaggga atgtcgcact cgatactctt tcgcggtgcg aagggcttcc 14940
ctctttccgc ctgtccatag gccattcgcc gtcccagcct tgtcctctcg cgtgctccct 15000
gcttccaggg ggaaacgcct ggtatcttta tagtcctgtc gggtttcgcc acctctgact 15060
tgagcgtcga tttttgtgat gctcgtcagg ggggcggagc cgaaggtccc cctttgcgga 15120
ccatagaaat atcaggacag cccaaagcgg tggagactga actcgcagct aaaaacacta 15180
cgagcagtcc ccccgcctcg ctatggaaaa acgccagcaa cgcggccttt ttacggttcc 15240
tggccttttg ctggcctttt gctcacatgt tctttcctgc gttatcccct gattctgtgg 15300
gataaccttt tgcggtcgtt gcgccggaaa aatgccaagg accggaaaac gaccggaaaa 15360
cgagtgtaca agaaaggacg caatagggga ctaagacacc ataaccgtat taccgccatg 15420
cattagttat taatagtaat caattacggg gtcattagtt catagcccat atatggagtt 15480
ccgcgttaca taacttacgg tattggcata atggcggtac gtaatcaata attatcatta 15540
gttaatgccc cagtaatcaa gtatcgggta tatacctcaa ggcgcaatgt attgaatgcc 15600
taaatggccc gcctggctga ccgcccaacg acccccgccc attgacgtca ataatgacgt 15660
atgttcccat agtaacgcca atagggactt tccattgacg atttaccggg cggaccgact 15720
ggcgggttgc tgggggcggg taactgcagt tattactgca tacaagggta tcattgcggt 15780
tatccctgaa aggtaactgc tcaatgggtg gagtatttac ggtaaactgc ccacttggca 15840
gtacatcaag tgtatcatat gccaagtacg ccccctattg acgtcaatga cggtaaatgg 15900
agttacccac ctcataaatg ccatttgacg ggtgaaccgt catgtagttc acatagtata 15960
cggttcatgc gggggataac tgcagttact gccatttacc cccgcctggc attatgccca 16020
gtacatgacc ttatgggact ttcctacttg gcagtacatc tacgtattag tcatcgctat 16080
taccatggtg atgcggtttt gggcggaccg taatacgggt catgtactgg aataccctga 16140
aaggatgaac cgtcatgtag atgcataatc agtagcgata atggtaccac tacgccaaaa 16200
ggcagtacat caatgggcgt ggatagcggt ttgactcacg ggatttccaa agtctccacc 16260
ccattgacgt caatgggagt ttgttttggc accaaaatca ccgtcatgta gttacccgca 16320
cctatcgcca aactgagtgc ccctaaaggt tcagaggtgg ggtaactgca gttaccctca 16380
aacaaaaccg tggttttagt acgggacttt ccaaaatgtc gtaacaactc cgccccattg 16440
acgcaaatgg gcggtaggcg tgtacggtgg gaggtctata taagcagagc ttgccctgaa 16500
aggttttaca gcattgttga ggcggggtaa ctgcgtttac ccgccatccg cacatgccac 16560
cctccagata tattcgtctc ga 16582

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Met Asp Thr Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Gln Ser
35 40 45

Val Ser Ser Tyr Leu Ala Trp Tyr Gln Gln Lys Pro Gly Gln Ala Pro
50 55 60

Arg Leu Leu Thr Tyr Asp Ala Ser Asn Arg Ala Thr Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln Gln Arg Ser
100 105 110

Asn Trp Gln Arg Thr Phe Gly Gly Gly Thr Lys Val Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys
210

<210> SEQ ID NO 60
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Gln Ser
35 40 45

Val Ser Ser Tyr Leu Ala Trp Tyr Gln Gln Lys Pro Gly Gln Ala Pro
50 55 60

Arg Leu Leu Ile Tyr Asp Ala Ser Asn Arg Ala Thr Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln Gln Arg Ser
100 105 110

Asn Trp Pro Ala Leu Thr Phe Gly Gly Gly Thr Lys Val Glu Ile Lys
115 120 125

Arg Thr Val Ala Ala Pro Ser Val Phe Ile Phe Pro Pro Ser Asp Glu
130 135 140

Gln Leu Lys Ser Gly Thr Ala Ser Val Val Cys Leu Leu Asn Asn Phe
145 150 155 160

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Gly Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys
225 230 235

<210> SEQ ID NO 61
<211> LENGTH: 254
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Gln Ser
35 40 45

Val Gly Ser Ser Leu Ala Trp Tyr Gln Gln Lys Pro Gly Gln Pro Pro
50 55 60

Arg Leu Leu Leu Tyr Glu Thr Ser Lys Arg Ala Thr Gly Ile Pro Ala
65 70 75 80

Arg Phe Arg Gly Ser Gly Ser Gly Thr Asp Phe Thr Leu Thr Ile Asn
85 90 95

Ser Leu Glu Pro Asp Asp Phe Ala Val Tyr Tyr Cys Gln Glu Arg His
100 105 110

Asn Phe Asn Trp Arg Thr Phe Gly Pro Gly Thr Lys Val Glu Ile Lys
115 120 125

Arg Thr Val Ala Ala Pro Ser Val Phe Ile Phe Pro Pro Ser Asp Glu

-continued

```
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Ser Val Arg Pro Leu Arg Asp
225                 230                 235                 240

Ala Arg Asp Pro His Gln Ser Met Leu Phe Ser Val Cys Pro
                245                 250


<210> SEQ ID NO 62
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Asp Met Arg Val Pro Ala Gln Leu Leu Gly Leu Leu Met Leu Trp
1               5                   10                  15

Val Ser Gly Ser Ser Gly Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Pro Phe Thr Phe Gly Pro
        115                 120                 125

Gly Thr Lys Val Asp Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240
```

Glu Cys

<210> SEQ ID NO 63
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Asp Met Arg Val Pro Ala Gln Leu Leu Gly Leu Leu Met Leu Trp
1               5                   10                  15

Val Ser Gly Ser Ser Gly Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro His Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Asp Met Arg Val Pro Ala Gln Leu Leu Gly Leu Leu Leu Leu Trp
1               5                   10                  15

Leu Pro Gly Thr Val Ala Ala Pro Ser Val Phe Ile Phe Pro Pro Ser
            20                  25                  30

Asp Glu Gln Leu Lys Ser Gly Thr Ala Ser Val Val Cys Leu Leu Asn
        35                  40                  45
```

Asn Phe Tyr Pro Arg Glu Ala Lys Val Gln Trp Lys Val Asp Asn Ala
    50                  55                  60

Leu Gln Ser Gly Asn Ser Gln Glu Ser Val Thr Glu Gln Asp Ser Lys
65                  70                  75                  80

Asp Ser Thr Tyr Ser Leu Ser Ser Thr Leu Thr Leu Ser Lys Ala Asp
                85                  90                  95

Tyr Glu Lys His Lys Val Tyr Ala Cys Glu Val Thr His Gln Gly Leu
            100                 105                 110

Ser Ser Pro Val Thr Lys Ser Phe Asn Arg Gly Glu Cys
        115                 120                 125

<210> SEQ ID NO 65
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Gln Ser Ile Ser Ser Trp Leu Ala Trp Tyr Gln Gln Lys Pro Gly Lys
    50                  55                  60

Ala Pro Lys Leu Leu Ile Tyr Lys Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 66
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Gln Ser Ile Ser Ser Trp Leu Ala Trp Tyr Gln Gln Lys Pro Gly Lys
    50                  55                  60

Ala Pro Lys Leu Leu Ile Tyr Lys Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Glu Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Ile Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Asp Thr Lys Ser Phe Asn Arg Gly Glu Cys
225                 230                 235
```

<210> SEQ ID NO 67
<211> LENGTH: 255
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 67

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Gln Ser Ile Ser Ser Trp Leu Ala Trp Tyr Gln Gln Lys Pro Gly Lys
    50                  55                  60

Ala Pro Lys Leu Leu Ile Tyr Lys Ala Ser Ser Leu Glu Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Asp Asp Phe Ala Thr Tyr Tyr Cys Gln Gln
```

```
            100                 105                 110

Tyr Asn Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Ser Thr Gly Glu Ser Val Arg Pro Leu Arg
225                 230                 235                 240

Asp Ala Arg Asp Pro His Gln Ser Met Leu Phe Ser Val Cys Pro
                245                 250                 255


<210> SEQ ID NO 68
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Asp Met Arg Val Pro Ala Gln Leu Leu Gly Leu Leu Leu Leu Trp
1               5                   10                  15

Leu Pro Gly Ala Arg Cys Ala Ile Arg Met Thr Gln Ser Pro Ser Ser
            20                  25                  30

Phe Ser Ala Ser Thr Gly Asp Arg Val Thr Ile Thr Cys Arg Ala Ser
        35                  40                  45

Gln Gly Ile Ser Thr Tyr Leu Ala Trp Tyr Gln Gln Lys Pro Gly Lys
    50                  55                  60

Ala Pro Asn Phe Leu Ile Phe Ala Ala Ser Thr Leu Gln Ser Gly Val
65                  70                  75                  80

Pro Ser Arg Phe Ser Gly Ser Gly Ser Gly Thr Asp Phe Thr Leu Asn
                85                  90                  95

Ile Ser Ser Leu Gln Ser Glu Asp Phe Ala Thr Tyr Tyr Cys Gln Gln
            100                 105                 110

Tyr Tyr Thr Tyr Pro Pro Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Arg Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Pro Ser Lys Ala Asp Tyr
        195                 200                 205
```

```
Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 69
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Gly
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Leu Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Thr Pro Pro Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 70
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Asp Met Arg Val Pro Ala Gln Leu Leu Gly Leu Leu Leu Leu Cys
1               5                   10                  15

Phe Pro Asp Ala Arg Cys Asp Ile Gln Met Thr Gln Ser Pro Ser Ser
            20                  25                  30
```

```
Leu Ser Ala Ser Val Gly Asp Arg Val Thr Ile Thr Cys Arg Ala Ser
        35                  40                  45

Gln Asp Ile Gly Asn Ser Leu Thr Trp Phe Gln Gln Glu Pro Gly Lys
    50                  55                  60

Ala Pro Lys Ser Leu Ile Tyr Asp Ala Ser Ser Leu Gln Thr Gly Ala
65                  70                  75                  80

Pro Ser Lys Phe Ser Gly Ser Gly Ser Gly Thr Asp Phe Thr Leu Thr
                85                  90                  95

Ile Ser Ser Leu Gln Pro Glu Asp Phe Ala Thr Tyr Phe Cys Gln Gln
            100                 105                 110

Tyr Lys Asn Tyr Pro Tyr Thr Phe Gly Pro Gly Thr Lys Val Asp Ile
        115                 120                 125

Thr Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 71
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Gly Gln Ser
        35                  40                  45

Ile Arg Ser Asp Tyr Leu Ala Trp Tyr Gln Gln Lys Pro Gly Gln Ala
    50                  55                  60

Pro Arg Leu Leu Met Tyr Gly Glu Ser Arg Arg Pro Ser Gly Ile Pro
65                  70                  75                  80

Asp Arg Phe Ser Gly Ser Gly Ser Gly Thr Asp Phe Thr Leu Thr Ile
                85                  90                  95

Ser Arg Leu Gly Pro Glu Asp Phe Ala Val Tyr Tyr Cys His Gln Tyr
            100                 105                 110

Gly Ser Ser Thr Arg Thr Phe Gly Gln Gly Thr Lys Val Glu Val Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160
```

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Ser Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys
225 230 235

<210> SEQ ID NO 72
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Gly Thr Leu Ser
20 25 30

Leu Ser Pro Gly Glu Arg Ala Thr Leu Ser Cys Arg Ala Ser Ser Val
35 40 45

Ser Ser Ser Tyr Leu Ala Trp Tyr Gln Gln Lys Pro Gly Gln Ala Pro
50 55 60

Arg Leu Leu Ile Tyr Gly Ala Ser Ser Arg Ala Thr Gly Ile Pro Asp
65 70 75 80

Lys Phe Ser Gly Ser Gly Ser Gly Thr Asp Phe Thr Leu Thr Ile Ser
85 90 95

Arg Leu Glu Pro Glu Asp Phe Ala Val Tyr Tyr Cys Gln Gln Tyr Gly
100 105 110

Ser Ser Leu Thr Phe Gly Gly Gly Thr Lys Val Glu Ile Lys Arg Thr
115 120 125

Val Ala Ala Pro Ser Val Phe Ile Phe Pro Pro Ser Asp Glu Gln Leu
130 135 140

Lys Ser Gly Thr Ala Ser Val Val Cys Leu Leu Asn Asn Phe Tyr Pro
145 150 155 160

Arg Glu Ala Lys Val Gln Trp Lys Val Asp Asn Ala Leu Gln Ser Gly
165 170 175

Asn Ser

<210> SEQ ID NO 73
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Gly Thr Leu Ser
20 25 30

```
Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

Arg Thr Val Ala Ala Pro Ser Val Phe Ile Phe Thr Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 74
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Leu Thr Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 75
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Ala Glu Gln Asp Ser Lys Asp
            180                 185                 190

Ser Thr Tyr Ser Leu Ser Gly Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Lys Gly Glu Ser Val Arg Pro Leu Arg
225                 230                 235                 240

Asp Ala Arg Asp Pro His Gln Ser Met Leu Phe Ser Val Cys Pro
                245                 250                 255
```

<210> SEQ ID NO 76
<211> LENGTH: 217
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 76

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Met Ser Leu Arg Leu Ser Cys Glu Ala Ser Gly Phe Asn Phe
        35                  40                  45

Asn Met Tyr Gly Leu His Trp Ala Arg Gln Ala Pro Gly Lys Gly Leu
    50                  55                  60

Glu Trp Val Ala Val Ile Thr Phe Asp Gly Gly Asn Lys Leu Tyr Ala
65                  70                  75                  80

Asp Ser Val Arg Gly Arg Phe Ser Ile Ser Arg Asp Asn Ser Lys Asn
                85                  90                  95

Thr Val Tyr Leu Gln Met Asn Ser Leu Arg Thr Asp Asp Thr Ala Val
            100                 105                 110

Tyr Tyr Cys Ala Arg Asp Trp Ser Gly Gly Ile Arg Leu Gly Glu Leu
        115                 120                 125

Ser Ala His Phe Asp Tyr Trp Gly Gln Gly Thr Leu Val Thr Val Ser
    130                 135                 140

Ser Val Ser Ala Asn Thr Arg Arg Ser Thr Leu Glu Asp Pro Arg Val
145                 150                 155                 160

Pro Ala Pro Ala Ala Ser Ser Gly Leu Thr Thr Phe Gly Ser Arg Trp
                165                 170                 175

Arg Ser Leu Leu Gln Pro Pro Pro Arg Ala His Arg Ser Ser Pro Trp
            180                 185                 190

Arg Pro Ala Pro Gly Ala Pro Pro Arg Ala Gln Arg Pro Trp Ala Ala
        195                 200                 205

Trp Ser Arg Thr Thr Ser Pro Asn Arg
    210                 215
```

<210> SEQ ID NO 77
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Met Glu Phe Gly Leu Ser Trp Val Phe Leu Ile Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ser Asn Tyr Glu Met Asn Trp Val Arg Gln Ala Pro Gly Lys Gly Leu
    50                  55                  60

Glu Trp Val Ser Tyr Ile Ser Pro Ser Gly Asp Pro Thr Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Val Glu Asp Thr Ala Val
```

```
            100                 105                 110

Tyr Tyr Cys Ala Arg Asp Pro Pro Glu Cys Cys Thr Gly Ala Ile Cys
        115                 120                 125

Val His Phe Asp Tyr Trp Gly Gln Gly Thr Leu Val Thr Val Ser Ser
    130                 135                 140

Val Ser Ala Asn Thr Arg Arg Ser Thr Leu Glu Asp Pro Arg Val Pro
145                 150                 155                 160

Ala Pro Ala Ala Ser Ser Gly Leu Thr Thr Phe Gly Ser Arg Trp Arg
                165                 170                 175

Ser Leu Leu Gln Pro Pro Pro Arg Ala His Arg Ser Ser Pro Trp Arg
            180                 185                 190

Pro Ala Pro Gly Ala Pro Pro Arg Ala Gln Arg Pro Trp Ala Ala Trp
        195                 200                 205

Ser Arg Thr Thr Ser Pro Asn Arg
    210                 215
```

<210> SEQ ID NO 78
<211> LENGTH: 208
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Met Asp Ile Leu Cys Ser Thr Leu Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr Ser Gly Val Gly Val Gly Trp Ile Arg Gln Pro Pro Gly Lys
    50                  55                  60

Ala Leu Glu Trp Leu Ala Leu Ile Tyr Trp Asp Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala His Arg Tyr Tyr Tyr Phe Asp Tyr Trp Gly Gln
        115                 120                 125

Gly Thr Val Val Thr Val Ser Ser Val Ser Ala Asn Thr Arg Arg Ser
    130                 135                 140

Thr Leu Glu Asp Pro Arg Val Pro Ala Pro Ala Ala Ser Ser Gly Leu
145                 150                 155                 160

Thr Thr Phe Gly Ser Arg Trp Arg Ser Leu Leu Gln Pro Pro Pro Arg
                165                 170                 175

Ala His Arg Ser Ser Pro Trp Arg Pro Ala Pro Gly Ala Pro Pro Arg
            180                 185                 190

Ala Gln Arg Pro Trp Ala Ala Trp Ser Arg Thr Thr Ser Pro Asn Arg
        195                 200                 205
```

<210> SEQ ID NO 79
<211> LENGTH: 147
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 79

Met Glu Phe Gly Leu Ser Trp Val Phe Leu Val Ala Ile Leu Glu Gly
1 5 10 15

Val Gln Cys Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Cys Tyr Trp Met Ser Trp Val Arg Gln Ala Pro Gly Lys Gly Leu
50 55 60

Glu Trp Val Ala Asn Ile Lys Gln Asp Gly Ser Glu Lys Tyr Tyr Val
65 70 75 80

Asp Ser Val Lys Gly Arg Phe Thr Ile Ser Arg Asp Asn Ala Lys Asn
85 90 95

Ser Leu Tyr Leu Gln Met Asn Ser Leu Arg Ala Gly Asp Thr Ala Ala
100 105 110

Tyr Tyr Cys Ala Arg Met Ser Gly Ser Gly Tyr Asp Ser Glu Tyr Tyr
115 120 125

Gly Met Asp Val Trp Gly Gln Gly Thr Leu Val Thr Val Ser Ser Val
130 135 140

Ser Ala Asn
145

<210> SEQ ID NO 80
<211> LENGTH: 141
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Met Glu Phe Gly Leu Ser Trp Val Phe Leu Val Val Ile Leu Gln Gly
1 5 10 15

Val Gln Cys Glu Val Gln Leu Val Glu Ser Gly Gly Asp Leu Val Gln
20 25 30

Pro Gly Gly Ser Leu Arg Leu Ser Cys Thr Thr Ser Gly Phe Thr Phe
35 40 45

Ser Asp His His Met Asp Trp Val Arg Gln Ala Pro Gly Lys Gly Leu
50 55 60

Glu Trp Val Gly Arg Ala Arg Gly Arg Ala Ser Arg Tyr Thr Ala Gln
65 70 75 80

Tyr Ala Ala Ser Val Glu Gly Arg Phe Ser Val Ser Arg Asp Glu Ser
85 90 95

Lys Ala Ser Phe Tyr Leu His Met Arg Ser Leu Lys Thr Glu Asp Ala
100 105 110

Ala Thr Tyr Tyr Cys Val Arg Gly Tyr His Gly Phe Asp Val Trp Gly
115 120 125

Gln Gly Thr Leu Val Thr Val Ser Ser Val Ser Ala Asn
130 135 140

<210> SEQ ID NO 81
<211> LENGTH: 142
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 81

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Pro Ala Ala Gly His Met Asp Val Trp
        115                 120                 125

Gly Gln Gly Thr Leu Val Thr Val Ser Ser Val Ser Ala Asn
    130                 135                 140
```

<210> SEQ ID NO 82
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Pro Gly Tyr Ser Phe
        35                  40                  45

Thr Ser Tyr Trp Ile Gly Trp Val Arg Gln Thr Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Leu Tyr Cys Ser Ser Thr Ser Cys Tyr Thr Gly
        115                 120                 125

Gly Tyr Tyr Phe Asp Tyr Trp Gly Gln Gly Thr Leu Val Thr Val Ser
    130                 135                 140

Ser Val Ser Ala Asn Thr Arg Arg Ser Thr Leu Glu Asp Pro Arg Val
145                 150                 155                 160

Pro Ala Pro Ala Ala Ser Ser Gly Leu Thr Thr Phe Gly Ser Arg Trp
                165                 170                 175

Arg Ser Leu Leu Gln Pro Pro Pro Arg Ala His Arg Ser Ser Pro Trp
            180                 185                 190
```

Arg Pro Ala Pro Gly Ala Pro Pro Arg Ala Gln Arg Pro Trp Ala Ala
        195                 200                 205

Trp Ser Arg Thr Thr Ser Pro Asn Arg
    210                 215

<210> SEQ ID NO 83
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Lys Leu Leu Trp Phe Leu Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Ser Val Ser Gly Gly Ser Val
        35                  40                  45

Ser Ser Tyr Tyr Trp Ser Trp Ile Arg Gln Pro Pro Gly Lys Gly Leu
    50                  55                  60

Glu Trp Ile Gly Tyr Phe His Tyr Ser Gly Ser Thr Asn Tyr Asn Pro
65                  70                  75                  80

Ser Leu Arg Ser Arg Val Ser Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Arg Val Gly Ala Ile Pro Tyr Trp Gly Gln Gly
        115                 120                 125

Thr Leu Val Thr Val Ser Ser Val Ser Ala Asn Thr Arg Arg Ser Thr
    130                 135                 140

Leu Glu Asp Pro Arg Val Pro Ala Pro Ala Ala Ser Ser Gly Leu Thr
145                 150                 155                 160

Thr Phe Gly Ser Arg Trp Arg Ser Leu Leu Gln Pro Pro Pro Arg Ala
                165                 170                 175

His Arg Ser Ser Pro Trp Arg Pro Ala Pro Gly Ala Pro Pro Arg Ala
            180                 185                 190

Gln Arg Pro Trp Ala Ala Trp Ser Arg Thr Thr Ser Pro Asn Arg
        195                 200                 205

<210> SEQ ID NO 84
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Glu
            20                  25                  30

Pro Gly Glu Ser Leu Arg Val Ser Cys Lys Ala Tyr Gly Tyr Thr Phe
        35                  40                  45

Thr Ser Tyr Trp Ile Thr Trp Val Arg Gln Met Pro Gly Arg Gly Leu
    50                  55                  60

Glu Tyr Met Gly Arg Ile Ser Pro Gly Asp Ser Tyr Thr Glu Tyr Ser
65 70 75 80

Pro Ser Phe Gln Gly His Val Thr Ile Ser Thr Asp Lys Ser Ile Asn
85 90 95

Thr Ala Tyr Leu Gln Trp Ser Ser Leu Lys Ala Ser Asp Thr Ala Val
100 105 110

Tyr Phe Cys Ala Arg Met Gly Ala Trp Glu Val Pro Asp Phe Trp Gly
115 120 125

Gln Gly Thr Leu Val Thr Val Ser Ser Val Ser Ala Asn Thr Arg Arg
130 135 140

Ser Thr Leu Glu Asp Pro Arg Val Pro Ala Pro Ala Ala Ser Ser Gly
145 150 155 160

Leu Thr Thr Phe Gly Ser Arg Trp Arg Ser Leu Leu Gln Pro Pro Pro
165 170 175

Arg Ala His Arg Ser Ser Pro Trp Arg Pro Ala Pro Gly Ala Pro Pro
180 185 190

Arg Ala Gln Arg Pro Trp Ala Ala Trp Ser Arg Thr Thr Ser Pro Asn
195 200 205

Arg

<210> SEQ ID NO 85
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Met Glu Phe Gly Leu Ser Trp Val Phe Leu Val Ala Ile Ile Lys Gly
1 5 10 15

Val Gln Cys Gln Val Gln Leu Val Glu Ser Gly Gly Gly Leu Val Lys
20 25 30

Pro Gly Gly Ser Leu Arg Leu Ser Cys Ala Ala Ser Gly Phe Thr Phe
35 40 45

Ser Asp Tyr Tyr Met Ser Trp Ile Arg Gln Ala Pro Gly Lys Gly Leu
50 55 60

Glu Trp Val Ser Tyr Ile Ser Ser Ser Ser Ser Tyr Thr Asn Tyr Ala
65 70 75 80

Asp Ser Val Lys Gly Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Arg Val Phe Gly Asp Thr Ala Met Gly Pro Ala Phe
115 120 125

Asp Tyr Trp Gly Gln Gly Thr Leu Val Thr Val Ser Ser Val Ser Ala
130 135 140

Asn Thr Arg Arg Ser Thr Leu Glu Asp Pro Arg Val Pro Ala Pro Ala
145 150 155 160

Ala Ser Ser Gly Leu Thr Thr Phe Gly Ser Arg Trp Arg Ser Leu Leu
165 170 175

Gln Pro Pro Pro Arg Ala His Arg Ser Ser Pro Trp Arg Pro Ala Pro
180 185 190

Gly Ala Pro Pro Arg Ala Gln Arg Pro Trp Ala Ala Trp Ser Arg Thr
195 200 205

```
Thr Ser Pro Asn Arg
    210


<210> SEQ ID NO 86
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Thr Pro Thr Ala Arg Val Val Val Pro Pro Phe
        115                 120                 125

Asp Tyr Trp Gly Gln Gly Thr Leu Val Thr Val Ser Ser Val Ser Ala
    130                 135                 140

Asn Thr Arg Arg Ser Thr Leu Glu Asp Pro Arg Val Pro Ala Pro Ala
145                 150                 155                 160

Ala Ser Ser Gly Leu Thr Thr Phe Gly Ser Arg Trp Arg Ser Leu Leu
                165                 170                 175

Gln Pro Pro Pro Arg Ala His Arg Ser Ser Pro Trp Arg Pro Ala Pro
            180                 185                 190

Gly Ala Pro Pro Arg Ala Gln Arg Pro Trp Ala Ala Trp Ser Arg Thr
        195                 200                 205

Thr Ser Pro Asn Arg
    210


<210> SEQ ID NO 87
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60
```

```
Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Tyr Tyr Tyr Glu Gly Gly Ser His Ala Phe
        115                 120                 125

Asp Ile Trp Gly Gln Gly Thr Leu Val Thr Val Ser Ser Val Ser Ala
    130                 135                 140

Asn Thr Arg Arg Ser Thr Leu Glu Asp Pro Arg Val Pro Ala Pro Ala
145                 150                 155                 160

Ala Ser Ser Gly Leu Thr Thr Phe Gly Ser Arg Trp Arg Ser Leu Leu
                165                 170                 175

Gln Pro Pro Pro Arg Ala His Arg Ser Ser Pro Trp Arg Pro Ala Pro
            180                 185                 190

Gly Ala Pro Pro Arg Ala Gln Arg Pro Trp Ala Ala Trp Ser Arg Thr
        195                 200                 205

Thr Ser Pro Asn Arg
    210


<210> SEQ ID NO 88
<211> LENGTH: 13478
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

ggaaaaatgc ctggcaaaaa actgccactg gcagttatca tggaaatgga agccaatgct     60

ttcaaagctg gctgcaccag gggatgcctt atctgtcttt cctttttacg gaccgttttt    120

tgacggtgac cgtcaatagt acctttacct tcggttacga aagtttcgac cgacgtggtc    180

ccctacggaa tagacagaaa caaaaattaa gtgtacagcc aaaatgaagg tatacattcc    240

aggaaggtgt cacgattatg gtggtgacaa gaaaactgga caggcaggaa ttgttggtgc    300

gtttttaatt cacatgtcgg ttttacttcc atatgtaagg tccttccaca gtgctaatac    360

caccactgtt cttttgacct gtccgtcctt aacaaccacg aattgttgac attcccgaaa    420

tctctggatt taaggagatg gcacccatgg aacagttcat tgctcaagtt gatcgctgcg    480

cttcctgcac tactggatgt ttaacaactg taagggcttt agagacctaa attcctctac    540

cgtgggtacc ttgtcaagta acgagttcaa ctagcgacgc gaaggacgtg atgacctaca    600

ctcaaaggtc ttgccaatgt taagtgctct gaactcctga agaaatggct gcctgacagg    660

tgtgcaagtt ttgctgacaa gattcaaaaa gaagttcaca gagtttccag aacggttaca    720

attcacgaga cttgaggact tctttaccga cggactgtcc acacgttcaa aacgactgtt    780

ctaagttttt cttcaagtgt atatcaaagg catggccgta cagctgcagg tcgagcacca    840

ccaccaccac cactgagatc cggctgctaa caaagcccga aaggaagctg agttggctgc    900

tatagtttcc gtaccggcat gtcgacgtcc agctcgtggt ggtggtggtg gtgactctag    960

gccgacgatt gtttcgggct ttccttcgac tcaaccgacg tgccaccgct gagcaataac   1020

tagcataacc ccttggggcc tctaaacggg tcttgagggg ttttttgctg aaaggaggaa   1080

ctatatccgg attggcgaat acggtggcga ctcgttattg atcgtattgg ggaaccccgg   1140
```

-continued

```
agatttgccc agaactcccc aaaaaacgac tttcctcctt gatataggcc taaccgctta    1200
gggacgcgcc ctgtagcggc gcattaagcg cggcgggtgt ggtggttacg cgcagcgtga    1260
ccgctacact tgccagcgcc ctagcgcccg ctcctttcgc ccctgcgcgg gacatcgccg    1320
cgtaattcgc gccgcccaca ccaccaatgc gcgtcgcact ggcgatgtga acggtcgcgg    1380
gatcgcgggc gaggaaagcg tttcttccct tcctttctcg ccacgttcgc cggctttccc    1440
cgtcaagctc taaatcgggg gctcccttta gggttccgat ttagtgcttt acggcacctc    1500
aaagaaggga aggaaagagc ggtgcaagcg gccgaaaggg gcagttcgag atttagcccc    1560
cgagggaaat cccaaggcta aatcacgaaa tgccgtggag gaccccaaaa aacttgatta    1620
gggtgatggt tcacgtagtg ggccatcgcc ctgatagacg gtttttcgcc ctttgacgtt    1680
ggagtccacg ttctttaata ctggggtttt ttgaactaat cccactacca agtgcatcac    1740
ccggtagcgg gactatctgc caaaaagcgg gaaactgcaa cctcaggtgc aagaaattat    1800
gtggactctt gttccaaact ggaacaacac tcaaccctat ctcggtctat tcttttgatt    1860
tataagggat tttgccgatt tcggcctatt ggttaaaaaa cacctgagaa caaggtttga    1920
ccttgttgtg agttgggata gagccagata agaaaactaa atattcccta aaacggctaa    1980
agccggataa ccaatttttt tgagctgatt taacaaaaat ttaacgcgaa ttttaacaaa    2040
atattaacgt ttacaatttc aggtggcact tttcggggaa atgtgcgcgg aacccctatt    2100
actcgactaa attgttttta aattgcgctt aaaattgttt tataattgca aatgttaaag    2160
tccaccgtga aaagcccctt tacacgcgcc ttggggataa tgtttatttt tctaaataca    2220
ttcaaatatg tatccgctca tgaattaatt cttagaaaaa ctcatcgagc atcaaatgaa    2280
actgcaattt attcatatca acaaataaaa agatttatgt aagtttatac ataggcgagt    2340
acttaattaa gaatcttttt gagtagctcg tagtttactt tgacgttaaa taagtatagt    2400
ggattatcaa taccatattt ttgaaaaagc cgtttctgta atgaaggaga aaactcaccg    2460
aggcagttcc ataggatggc aagatcctgg tatcggtctg cctaatagtt atggtataaa    2520
aactttttcg gcaaagacat tacttcctct tttgagtggc tccgtcaagg tatcctaccg    2580
ttctaggacc atagccagac cgattccgac tcgtccaaca tcaatacaac ctattaattt    2640
cccctcgtca aaaataaggt tatcaagtga gaaatcacca tgagtgacga ctgaatccgg    2700
gctaaggctg agcaggttgt agttatgttg gataattaaa ggggagcagt ttttattcca    2760
atagttcact ctttagtggt actcactgct gacttaggcc tgagaatggc aaaagtttat    2820
gcatttcttt ccagacttgt tcaacaggcc agccattacg ctcgtcatca aaatcactcg    2880
catcaaccaa accgttattc actcttaccg ttttcaaata cgtaaagaaa ggtctgaaca    2940
agttgtccgg tcggtaatgc gagcagtagt tttagtgagc gtagttggtt tggcaataag    3000
attcgtgatt gcgcctgagc gagacgaaat acgcgatcgc tgttaaaagg acaattacaa    3060
acaggaatcg aatgcaaccg gcgcaggaac actgccagcg taagcactaa cgcggactcg    3120
ctctgcttta tgcgctagcg acaattttcc tgttaatgtt tgtccttagc ttacgttggc    3180
cgcgtccttg tgacggtcgc catcaacaat attttcacct gaatcaggat attcttctaa    3240
tacctggaat gctgttttcc cggggatcgc agtggtgagt aaccatgcat catcaggagt    3300
gtagttgtta taaaagtgga cttagtccta taagaagatt atggacctta cgacaaaagg    3360
gcccctagcg tcaccactca ttggtacgta gtagtcctca acggataaaa tgcttgatgg    3420
tcggaagagg cataaattcc gtcagccagt ttagtctgac catctcatct gtaacatcat    3480
tggcaacgct acctttgcca tgcctatttt acgaactacc agccttctcc gtatttaagg    3540
```

```
cagtcggtca aatcagactg gtagagtaga cattgtagta accgttgcga tggaaacggt   3600

tgtttcagaa acaactctgg cgcatcgggc ttcccataca atcgatagat tgtcgcacct   3660

gattgcccga cattatcgcg agcccattta tacccatata acaaagtctt tgttgagacc   3720

gcgtagcccg aagggtatgt tagctatcta acagcgtgga ctaacgggct gtaatagcgc   3780

tcgggtaaat atgggtatat aatcagcatc catgttggaa tttaatcgcg gcctagagca   3840

agacgtttcc cgttgaatat ggctcataac accccttgta ttactgttta tgtaagcaga   3900

ttagtcgtag gtacaacctt aaattagcgc cggatctcgt tctgcaaagg gcaacttata   3960

ccgagtattg tggggaacat aatgacaaat acattcgtct cagttttatt gttcatgacc   4020

aaaatccctt aacgtgagtt ttcgttccac tgagcgtcag accccgtaga aaagatcaaa   4080

ggatcttctt gagatccttt gtcaaaataa caagtactgg ttttagggaa ttgcactcaa   4140

aagcaaggtg actcgcagtc tggggcatct tttctagttt cctagaagaa ctctaggaaa   4200

ttttctgcgc gtaatctgct gcttgcaaac aaaaaaacca ccgctaccag cggtggtttg   4260

tttgccggat caagagctac caactctttt tccgaaggta aaaagacgcg cattagacga   4320

cgaacgtttg ttttttggt ggcgatggtc gccaccaaac aaacggccta gttctcgatg    4380

gttgagaaaa aggcttccat actggcttca gcagagcgca gataccaaat actgtccttc   4440

tagtgtagcc gtagttaggc caccacttca agaactctgt agcaccgcct acatacctcg   4500

tgaccgaagt cgtctcgcgt ctatggttta tgacaggaag atcacatcgg catcaatccg   4560

gtggtgaagt tcttgagaca tcgtggcgga tgtatggagc ctctgctaat cctgttacca   4620

gtggctgctg ccagtggcga taagtcgtgt cttaccgggt tggactcaag acgatagtta   4680

ccggataagg cgcagcggtc gagacgatta ggacaatggt caccgacgac ggtcaccgct   4740

attcagcaca gaatggccca acctgagttc tgctatcaat ggcctattcc gcgtcgccag   4800

gggctgaacg gggggttcgt gcacacagcc cagcttggag cgaacgacct acaccgaact   4860

gagataccta cagcgtgagc tatgagaaag cgccacgctt cccgacttgc cccccaagca   4920

cgtgtgtcgg gtcgaacctc gcttgctgga tgtggcttga ctctatggat gtcgcactcg   4980

atactctttc gcggtgcgaa cccgaaggga gaaaggcgga caggtatccg gtaagcggca   5040

gggtcggaac aggagagcgc acgagggagc ttccaggggg aaacgcctgg tatctttata   5100

gggcttccct ctttccgcct gtccataggc cattcgccgt cccagccttg tcctctcgcg   5160

tgctccctcg aaggtccccc tttgcggacc atagaaatat gtcctgtcgg gtttcgccac   5220

ctctgacttg agcgtcgatt tttgtgatgc tcgtcagggg ggcggagcct atggaaaaac   5280

gccagcaacg cggccttttt caggacagcc caaagcggtg gagactgaac tcgcagctaa   5340

aaacactacg agcagtcccc ccgcctcgga taccttttg cggtcgttgc gccggaaaaa    5400

acggttcctg gccttttgct ggccttttgc tcacatgttc tttcctgcgt tatcccctga   5460

ttctgtggat aaccgtatta ccgcctttga gtgagctgat tgccaaggac cggaaaacga   5520

ccggaaaacg agtgtacaag aaaggacgca ataggggact aagacaccta ttggcataat   5580

ggcggaaact cactcgacta accgctcgcc gcagccgaac gaccgagcgc agcgagtcag   5640

tgagcgagga agcggaagag cgcctgatgc ggtattttct ccttacgcat ctgtgcggta   5700

tggcgagcgg cgtcggcttg ctggctcgcg tcgctcagtc actcgctcct tcgccttctc   5760

gcggactacg ccataaaaga ggaatgcgta gacacgccat tttcacaccg catatatggt   5820

gcactctcag tacaatctgc tctgatgccg catagttaag ccagtataca ctccgctatc   5880
```

-continued

```
gctacgtgac tgggtcatgg aaagtgtggc gtatatacca cgtgagagtc atgttagacg   5940
agactacggc gtatcaattc ggtcatatgt gaggcgatag cgatgcactg acccagtacc   6000
ctgcgccccg acacccgcca acacccgctg acgcgccctg acgggcttgt ctgctcccgg   6060
catccgctta cagacaagct gtgaccgtct ccgggagctg gacgcggggc tgtgggcggt   6120
tgtgggcgac tgcgcgggac tgcccgaaca gacgagggcc gtaggcgaat gtctgttcga   6180
cactggcaga ggccctcgac catgtgtcag aggttttcac cgtcatcacc gaaacgcgcg   6240
aggcagctgc ggtaaagctc atcagcgtgg tcgtgaagcg attcacagat gtctgcctgt   6300
gtacacagtc tccaaaagtg gcagtagtgg ctttgcgcgc tccgtcgacg ccatttcgag   6360
tagtcgcacc agcacttcgc taagtgtcta cagacggaca tcatccgcgt ccagctcgtt   6420
gagtttctcc agaagcgtta atgtctggct tctgataaag cgggccatgt taagggcggt   6480
tttttcctgt ttggtcactg agtaggcgca ggtcgagcaa ctcaaagagg tcttcgcaat   6540
tacagaccga agactatttc gcccggtaca attcccgcca aaaaaggaca aaccagtgac   6600
atgcctccgt gtaaggggga tttctgttca tgggggtaat gataccgatg aaacgagaga   6660
ggatgctcac gatacgggtt actgatgatg aacatgcccg tacggaggca cattccccct   6720
aaagacaagt acccccatta ctatggctac tttgctctct cctacgagtg ctatgcccaa   6780
tgactactac ttgtacgggc gttactggaa cgttgtgagg gtaaacaact ggcggtatgg   6840
atgcggcggg accagagaaa aatcactcag ggtcaatgcc agcgcttcgt taatacagat   6900
caatgacctt gcaacactcc catttgttga ccgccatacc tacgccgccc tggtctcttt   6960
ttagtgagtc ccagttacgg tcgcgaagca attatgtcta gtaggtgttc cacagggtag   7020
ccagcagcat cctgcgatgc agatccggaa cataatggtg cagggcgctg acttccgcgt   7080
ttccagactt tacgaaacac catccacaag gtgtcccatc ggtcgtcgta ggacgctacg   7140
tctaggcctt gtattaccac gtcccgcgac tgaaggcgca aaggtctgaa atgctttgtg   7200
ggaaaccgaa gaccattcat gttgttgctc aggtcgcaga cgttttgcag cagcagtcgc   7260
ttcacgttcg ctcgcgtatc ggtgattcat tctgctaacc cctttggctt ctggtaagta   7320
caacaacgag tccagcgtct gcaaaacgtc gtcgtcagcg aagtgcaagc gagcgcatag   7380
ccactaagta agacgattgg agtaaggcaa ccccgccagc ctagccgggt cctcaacgac   7440
aggagcacga tcatgcgcac ccgtggggcc gccatgccgg cgataatggc ctgcttctcg   7500
tcattccgtt ggggcggtcg gatcggccca ggagttgctg tcctcgtgct agtacgcgtg   7560
ggcaccccgg cggtacggcc gctattaccg gacgaagagc ccgaaacgtt tggtggcggg   7620
accagtgacg aaggcttgag cgagggcgtg caagattccg aataccgcaa gcgacaggcc   7680
gatcatcgtc gcgctccagc ggctttgcaa accaccgccc tggtcactgc ttccgaactc   7740
gctcccgcac gttctaaggc ttatggcgtt cgctgtccgg ctagtagcag cgcgaggtcg   7800
gaaagcggtc ctcgccgaaa atgacccaga gcgctgccgg cacctgtcct acgagttgca   7860
tgataaagaa gacagtcata agtgcggcga cgatagtcat ctttcgccag gagcggcttt   7920
tactgggtct cgcgacggcc gtggacagga tgctcaacgt actatttctt ctgtcagtat   7980
tcacgccgct gctatcagta gccccgcgcc caccggaagg agctgactgg gttgaaggct   8040
ctcaagggca tcggtcgaga tcccggtgcc taatgagtga gctaacttac attaattgcg   8100
cggggcgcgg gtggccttcc tcgactgacc caacttccga gagttcccgt agccagctct   8160
agggccacgg attactcact cgattgaatg taattaacgc ttgcgctcac tgcccgcttt   8220
ccagtcggga aacctgtcgt gccagctgca ttaatgaatc ggccaacgcg cggggagagg   8280
```

-continued

```
cggtttgcgt attgggcgcc aacgcgagtg acgggcgaaa ggtcagccct ttggacagca   8340
cggtcgacgt aattacttag ccggttgcgc gcccctctcc gccaaacgca taacccgcgg   8400
agggtggttt ttcttttcac cagtgagacg ggcaacagct gattgccctt caccgcctgg   8460
ccctgagaga gttgcagcaa gcggtccacg ctggtttgcc tcccaccaaa aagaaaagtg   8520
gtcactctgc ccgttgtcga ctaacgggaa gtggcggacc gggactctct caacgtcgtt   8580
cgccaggtgc gaccaaacgg ccagcaggcg aaaatcctgt ttgatggtgg ttaacggcgg   8640
gatataacat gagctgtctt cggtatcgtc gtatcccact accgagatat ccgcaccaac   8700
ggtcgtccgc ttttaggaca aactaccacc aattgccgcc ctatattgta ctcgacagaa   8760
gccatagcag catagggtga tggctctata ggcgtggttg gcgcagcccg gactcggtaa   8820
tggcgcgcat tgcgcccagc gccatctgat cgttggcaac cagcatcgca gtgggaacga   8880
tgccctcatt cagcatttgc cgcgtcgggc ctgagccatt accgcgcgta acgcgggtcg   8940
cggtagacta gcaaccgttg gtcgtagcgt cacccttgct acgggagtaa gtcgtaaacg   9000
atggtttgtt gaaaaccgga catggcactc cagtcgcctt cccgttccgc tatcggctga   9060
atttgattgc gagtgagata tttatgccag ccagccagac taccaaacaa cttttggcct   9120
gtaccgtgag gtcagcggaa gggcaaggcg atagccgact taaactaacg ctcactctat   9180
aaatacggtc ggtcggtctg gcagacgcgc cgagacagaa cttaatgggc ccgctaacag   9240
cgcgatttgc tggtgaccca atgcgaccag atgctccacg cccagtcgcg taccgtcttc   9300
cgtctgcgcg gctctgtctt gaattacccg ggcgattgtc gcgctaaacg accactgggt   9360
tacgctggtc tacgaggtgc gggtcagcgc atggcagaag atgggagaaa ataatactgt   9420
tgatgggtgt ctggtcagag acatcaagaa ataacgccgg aacattagtg caggcagctt   9480
ccacagcaat ggcatcctgg taccctcttt tattatgaca actacccaca gaccagtctc   9540
tgtagttctt tattgcggcc ttgtaatcac gtccgtcgaa ggtgtcgtta ccgtaggacc   9600
tcatccagcg gatagttaat gatcagccca ctgacgcgtt gcgcgagaag attgtgcacc   9660
gccgctttac aggcttcgac gccgcttcgt tctaccatcg agtaggtcgc ctatcaatta   9720
ctagtcgggt gactgcgcaa cgcgctcttc taacacgtgg cggcgaaatg tccgaagctg   9780
cggcgaagca agatggtagc acaccaccac gctggcaccc agttgatcgg cgcgagattt   9840
aatcgccgcg acaatttgcg acggcgcgtg cagggccaga ctggaggtgg caacgccaat   9900
tgtggtggtg cgaccgtggg tcaactagcc gcgctctaaa ttagcggcgc tgttaaacgc   9960
tgccgcgcac gtcccggtct gacctccacc gttgcggtta cagcaacgac tgtttgcccg  10020
ccagttgttg tgccacgcgg ttgggaatgt aattcagctc cgccatcgcc gcttccactt  10080
tttcccgcgt tttcgcagaa gtcgttgctg acaaacgggc ggtcaacaac acggtgcgcc  10140
aacccttaca ttaagtcgag gcggtagcgg cgaaggtgaa aaagggcgca aaagcgtctt  10200
acgtggctgg cctggttcac cacgcgggaa acggtctgat aagagacacc ggcatactct  10260
gcgacatcgt ataacgttac tggtttcaca ttcaccaccc tgcaccgacc ggaccaagtg  10320
gtgcgccctt tgccagacta ttctctgtgg ccgtatgaga cgctgtagca tattgcaatg  10380
accaaagtgt aagtggtggg tgaattgact ctcttccggg cgctatcatg ccataccgcg  10440
aaaggttttg cgccattcga tggtgtccgg gatctcgacg ctctccctta tgcgactcct  10500
acttaactga gagaaggccc gcgatagtac ggtatggcgc tttccaaaac gcggtaagct  10560
accacaggcc ctagagctgc gagagggaat acgctgagga gcattaggaa gcagcccagt  10620
```

-continued

```
agtaggttga ggccgttgag caccgccgcc gcaaggaatg gtgcatgcaa ggagatggcg  10680
cccaacagtc ccccggccac cgtaatcctt cgtcgggtca tcatccaact ccggcaactc  10740
gtggcggcgg cgttccttac cacgtacgtt cctctaccgc gggttgtcag gggccggtg  10800
ggggcctgcc accataccca cgccgaaaca agcgctcatg agcccgaagt ggcgagcccg  10860
atcttcccca tcggtgatgt cggcgatata ggcgccagca ccccggacgg tggtatgggt  10920
gcggctttgt tcgcgagtac tcgggcttca ccgctcgggc tagaaggggt agccactaca  10980
gccgctatat ccgcggtcgt accgcacctg tggcgccggt gatgccggcc acgatgcgtc  11040
cggcgtagag gatcgagatc tcgatcccgc gaaattaata cgactcacta taggggaatt  11100
tggcgtggac accgcggcca ctacggccgg tgctacgcag gccgcatctc ctagctctag  11160
agctagggcg ctttaattat gctgagtgat atccccttaa gtgagcggat aacaattccc  11220
ctctagaaat aattttgttt aactttaaga aggagatata ccatgggcag cagccatcat  11280
catcatcatc acagcagcgg cactcgccta ttgttaaggg gagatcttta ttaaaacaaa  11340
ttgaaattct tcctctatat ggtacccgtc gtcggtagta gtagtagtag tgtcgtcgcc  11400
cctggtgccg cgcggcagcc ataggtcgac tctagaggat ccaagccaaa gcactaacgt  11460
tttaggtgaa gctaaaaaat taaacgaatc tcaagcaccg ggaccacggc gcgccgtcgg  11520
tatccagctg agatctccta ggttcggttt cgtgattgca aaatccactt cgattttta  11580
atttgcttag agttcgtggc aaagctgaca acaatttcaa caaagaacaa caaaatgctt  11640
tctatgaaat cttgaacatg cctaacttga acgaagaaca acgcaatggt ttcatccaaa  11700
tttcgactgt tgttaaagtt gtttcttgtt gttttacgaa agatacttta gaacttgtac  11760
ggattgaact tgcttcttgt tgcgttacca aagtaggttt gcttaaaaga tgacccaagt  11820
caaagtgcta accttttagc agaagctaaa aagttaaatg aatctcaagc accgaaagct  11880
gataacaaat tcaacaaaga cgaattttct actgggttca gtttcacgat tggaaaatcg  11940
tcttcgattt ttcaatttac ttagagttcg tggctttcga ctattgttta agttgtttct  12000
acaacaaaat gctttctatg aaatcttaca tttacctaac ttaaatgaag aacaacgcaa  12060
tggtttcatc caaagcttaa aagatgaccc aagccaaagc tgttgtttta cgaaagatac  12120
tttagaatgt aaatggattg aatttacttc ttgttgcgtt accaaagtag gtttcgaatt  12180
ttctactggg ttcggtttcg gctaaccttt tagcagaagc taaaaagcta aatgatgcac  12240
aagcaccaaa agctgacaac aaattcaaca aagaacaaca aaatgctttc tatgaaattt  12300
cgattggaaa atcgtcttcg atttttcgat ttactacgtg ttcgtggttt tcgactgttg  12360
tttaagttgt ttcttgttgt tttacgaaag atactttaaa tacatttacc taacttaact  12420
gaagaacaac gtaacggctt catccaaagc cttaaagacg atccccggtc gactctagcg  12480
gcagcttccg gtgctagcac atgtaaatgg attgaattga cttcttgttg cattgccgaa  12540
gtaggtttcg gaatttctgc taggggccag ctgagatcgc cgtcgaaggc cacgatcgtg  12600
tgacacttac aaattaatcc ttaatggtaa aacattgaaa ggcgaaacaa ctactgaagc  12660
tgttgatgct gctactgcag aaaaagtctt caaacaatac actgtgaatg tttaattagg  12720
aattaccatt ttgtaacttt ccgctttgtt gatgacttcg acaactacga cgatgacgtc  12780
tttttcagaa gtttgttatg gctaacgaca acggtgttga cggtgaatgg acttacgacg  12840
atgcgactaa gacctttaca gttactgaaa aaccagaagt gatcgatgcg tctgaattaa  12900
cgattgctgt tgccacaact gccacttacc tgaatgctgc tacgctgatt ctggaaatgt  12960
caatgacttt ttggtcttca ctagctacgc agacttaatt caccagccgt gacaacttac  13020
```

aaacttgtta ttaatggtaa aacattgaaa ggcgaaacaa ctactaaagc agtagacgca 13080
gaaactgcag aaaaagcctt gtggtcggca ctgttgaatg tttgaacaat aattaccatt 13140
ttgtaacttt ccgctttgtt gatgatttcg tcatctgcgt ctttgacgtc tttttcggaa 13200
caaacaatac gctaacgaca acggtgttga tggtgtttgg acttatgatg atgcgactaa 13260
gacctttacg gtaactgaaa tggttacaga ggtaccagat gtttgttatg cgattgctgt 13320
tgccacaact accacaaacc tgaatactac tacgctgatt ctggaaatgc cattgacttt 13380
accaatgtct ccatggtcta cttagcaact ttgttgcaac tgaaaccgat gctaaccgcg 13440
aatcgttgaa acaacgttga ctttggctac gattggcg 13478

<210> SEQ ID NO 89
<211> LENGTH: 14500
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89
agcgcccaat acgcaaaccg cctctccccg cgcgttggcc gattcattaa tgcagctggc 60
acgacaggtt tcccgactgg aaagcgggca gtgagcgcaa tcgcgggtta tgcgtttggc 120
ggagaggggc gcgcaaccgg ctaagtaatt acgtcgaccg tgctgtccaa agggctgacc 180
tttcgcccgt cactcgcgtt cgcaattaat gtgagttagc tcactcatta ggcaccccag 240
gctttacact ttatgcttcc ggctcgtatg ttgtgtggaa ttgtgagcgg ataacaattt 300
gcgttaatta cactcaatcg agtgagtaat ccgtggggtc cgaaatgtga aatacgaagg 360
ccgagcatac aacacacctt aacactcgcc tattgttaaa cacacaggaa acagctatga 420
ccatgattac gccaagcttt agggataaca gggtaatcgc catgcattag ttattaatag 480
taatcaatta cggggtcatt gtgtgtcctt tgtcgatact ggtactaatg cggttcgaaa 540
tccctattgt cccattagcg gtacgtaatc aataattatc attagttaat gccccagtaa 600
agttcatagc ccatatatgg agttccgcgt tacataactt acggtaaatg gcccgcctgg 660
ctgaccgccc aacgaccccc gcccattgac gtcaataatg tcaagtatcg ggtatatacc 720
tcaaggcgca atgtattgaa tgccatttac cgggcggacc gactggcggg ttgctggggg 780
cgggtaactg cagttattac acgtatgttc ccatagtaac gccaataggg actttccatt 840
gacgtcaatg ggtggagtat ttacggtaaa ctgcccactt ggcagtacat caagtgtatc 900
tgcatacaag ggtatcattg cggttatccc tgaaaggtaa ctgcagttac ccacctcata 960
aatgccattt gacgggtgaa ccgtcatgta gttcacatag atatgccaag tacgccccct 1020
attgacgtca atgacggtaa atggcccgcc tggcattatg cccagtacat gaccttatgg 1080
gactttccta cttggcagta tatacggttc atgcggggga taactgcagt tactgccatt 1140
taccgggcgg accgtaatac gggtcatgta ctggaatacc ctgaaaggat gaaccgtcat 1200
catctacgta ttagtcatcg ctattaccat ggtgatgcgg ttttggcagt acatcaatgg 1260
gcgtggatag cggtttgact cacggggatt tccaagtctc gtagatgcat aatcagtagc 1320
gataatggta ccactacgcc aaaaccgtca tgtagttacc cgcacctatc gccaaactga 1380
gtgcccctaa aggttcagag caccccattg acgtcaatgg gagtttgttt tggcaccaaa 1440
atcaacggga ctttccaaaa tgtcgtaaca actccgcccc attgacgcaa atgggcggta 1500
gtggggtaac tgcagttacc ctcaaacaaa accgtggttt tagttgccct gaaaggtttt 1560
acagcattgt tgaggcgggg taactgcgtt tacccgccat ggcgtgtacg gtgggaggtc 1620
tatataagca gagctggttt agtgaaccgt cagatccgct agacgtctca tttaggcatg 1680
gaaaccccag cgcagcttct ccgcacatgc caccctccag atatattcgt ctcgaccaaa 1740
tcacttggca gtctaggcga tctgcagagt aaatccgtac ctttggggtc gcgtcgaaga 1800
cttcctcctg ctactctgga tcccagacac cattgaagaa atagtgatga cgcagtctcc 1860
agccaccctg tctgtgtctc caggggaaag agtcaccctc gaaggaggac gatgagacct 1920
agggtctgtg gtaacttctt tatcactact gcgtcagagg tcggtgggac agacacagag 1980
gtcccctttc tcagtgggag tccagcagcc atcatcatca tcatcacagc agcggcctgg 2040
tgccgcgcgg cagccatagg tcgactctag aggatccaag ccaaagcact aacgttttag 2100
aggtcgtcgg tagtagtagt agtagtgtcg tcgccggacc acggcgcgcc gtcggtatcc 2160
agctgagatc tcctaggttc ggtttcgtga ttgcaaaatc gtgaagctaa aaaattaaac 2220
gaatctcaag caccgaaagc tgacaacaat ttcaacaaag aacaacaaaa tgctttctat 2280
gaaatcttga acatgcctaa cacttcgatt ttttaatttg cttagagttc gtggctttcg 2340
actgttgtta aagttgtttc ttgttgtttt acgaaagata ctttagaact tgtacggatt 2400
cttgaacgaa gaacaacgca atggtttcat ccaaagctta aaagatgacc caagtcaaag 2460
tgctaacctt ttagcagaag ctaaaaagtt aaatgaatct gaacttgctt cttgttgcgt 2520
taccaaagta ggtttcgaat tttctactgg gttcagtttc acgattggaa aatcgtcttc 2580
gatttttcaa tttacttaga caagcaccga aagctgataa caaattcaac aaagaacaac 2640
aaaatgcttt ctatgaaatc ttacatttac ctaacttaaa tgaagaacaa cgcaatggtt 2700
gttcgtggct ttcgactatt gtttaagttg tttcttgttg ttttacgaaa gatactttag 2760
aatgtaaatg gattgaattt acttcttgtt gcgttaccaa tcatccaaag cttaaaagat 2820
gacccaagcc aaagcgctaa ccttttagca gaagctaaaa agctaaatga tgcacaagca 2880
ccaaaagctg acaacaaatt agtaggtttc gaattttcta ctgggttcgg tttcgcgatt 2940
ggaaaatcgt cttcgatttt tcgatttact acgtgttcgt ggttttcgac tgttgtttaa 3000
caacaaagaa caacaaaatg ctttctatga aattttacat ttacctaact taactgaaga 3060
acaacgtaac ggcttcatcc aaagccttaa agacgatccc gttgtttctt gttgttttac 3120
gaaagatact ttaaaatgta aatggattga attgacttct tgttgcattg ccgaagtagg 3180
tttcggaatt tctgctaggg cggtcgactc tagcggcagc ttccggtgct agcactgaca 3240
cttacaaatt aatccttaat ggtaaaacat tgaaaggcga aacaactact gaagctgttg 3300
gccagctgag atcgccgtcg aaggccacga tcgtgactgt gaatgtttaa ttaggaatta 3360
ccattttgta actttccgct ttgttgatga cttcgacaac atgctgctac tgcagaaaaa 3420
gtcttcaaac aatacgctaa cgacaacggt gttgacggtg aatggactta cgacgatgcg 3480
actaagacct ttacagttac tacgacgatg acgtcttttt cagaagtttg ttatgcgatt 3540
gctgttgcca caactgccac ttacctgaat gctgctacgc tgattctgga aatgtcaatg 3600
tgaaaaacca gaagtgatcg atgcgtctga attaacacca gccgtgacaa cttacaaact 3660
tgttattaat ggtaaaacat tgaaaggcga aacaactact actttttggt cttcactagc 3720
tacgcagact taattgtggt cggcactgtt gaatgtttga acaataatta ccattttgta 3780
actttccgct ttgttgatga aaagcagtag acgcagaaac tgcagaaaaa gccttcaaac 3840
aatacgctaa cgacaacggt gttgatggtg tttggactta tgatgatgcg actaagacct 3900

-continued

```
tttcgtcatc tgcgtctttg acgtcttttt cggaagtttg ttatgcgatt gctgttgcca   3960
caactaccac aaacctgaat actactacgc tgattctgga ttacggtaac tgaaatggtt   4020
acagaggtac cgcgggcccg ggatccaccg gctagcggga attccaaatc aactgagttc   4080
gatcctaaca ttgacattgt aatgccattg actttaccaa tgtctccatg gcgcccgggc   4140
cctaggtggc cgatcgccct taaggtttag ttgactcaag ctaggattgt aactgtaaca   4200
tggtttagaa ggaaaatttg gtattacaaa cctagagacg gatttattca caatctggga   4260
gacaatggag gtcatgatca aagcagatat tgcagatact accaaatctt ccttttaaac   4320
cataatgttt ggatctctgc ctaaataagt gttagaccct ctgttacctc cagtactagt   4380
ttcgtctata acgtctatga gatagagcca gcaactttgt tgcaactgaa accgatgcta   4440
accgcggaaa aatgcctggc aaaaaactgc cactggcagt tatcatggaa atggaagcca   4500
ctatctcggt cgttgaaaca acgttgactt tggctacgat tggcgccttt ttacggaccg   4560
tttttgacg gtgaccgtca atagtacctt taccttcggt atgctttcaa agctggctgc   4620
accaggggat gccttatctg tctttcaaaa attaagtgta cagccaaaat gaaggtatac   4680
attccaggaa ggtgtcacga tacgaaagtt tcgaccgacg tggtccccta cggaatagac   4740
agaaagtttt taattcacat gtcggtttta cttccatatg taaggtcctt ccacagtgct   4800
ttatggtggt gacaagaaaa ctggacaggc aggaattgtt ggtgcaattg ttgacattcc   4860
cgaaatctct ggatttaagg agatggcacc catggaacag aataccacca ctgttctttt   4920
gacctgtccg tccttaacaa ccacgttaac aactgtaagg gctttagaga cctaaattcc   4980
tctaccgtgg gtaccttgtc ttcattgctc aagttgatcg ctgcgcttcc tgcactactg   5040
gatgtctcaa aggtcttgcc aatgttaagt gctctgaact cctgaagaaa tggctgcctg   5100
aagtaacgag ttcaactagc gacgcgaagg acgtgatgac ctacagagtt tccagaacgg   5160
ttacaattca cgagacttga ggacttcttt accgacggac acaggtgtgc aagttttgct   5220
gacaagattc aaaaagaagt tcacaatatc aaaggcatgg ccggcgatcg atgagcggcc   5280
gcaatttaat tccggttatt tgtccacacg ttcaaaacga ctgttctaag tttttcttca   5340
agtgttatag tttccgtacc ggccgctagc tactcgccgg cgttaaatta aggccaataa   5400
ttccaccata ttgccgtctt ttggcaatgt gagggcccgg aaacctggcc ctgtcttctt   5460
gacgagcatt cctaggggtc tttcccctct cgccaaagga aaggtggtat aacggcagaa   5520
aaccgttaca ctcccgggcc tttggaccgg gacagaagaa ctgctcgtaa ggatccccag   5580
aaaggggaga gcggtttcct atgcaaggtc tgttgaatgt cgtgaaggaa gcagttcctc   5640
tggaagcttc ttgaagacaa acaacgtctg tagcgaccct ttgcaggcag cggaaccccc   5700
tacgttccag acaacttaca gcacttcctt cgtcaaggag accttcgaag aacttctgtt   5760
tgttgcagac atcgctggga aacgtccgtc gccttggggg cacctggcga caggtgcctc   5820
tgcggccaaa agccacgtgt ataagataca cctgcaaagg cggcacaacc ccagtgccac   5880
gttgtgagtt ggatagttgt gtggaccgct gtccacggag acgccggttt tcggtgcaca   5940
tattctatgt ggacgtttcc gccgtgttgg ggtcacggtg caacactcaa cctatcaaca   6000
ggaaagagtc aaatggctca cctcaagcgt attcaacaag ggctgaagg atgcccagaa   6060
ggtaccccat tgtatgggat ctgatctggg gcctcggtgc cctttctcag tttaccgagt   6120
ggagttcgca taagttgttc cccgacttcc tacgggtctt ccatggggta acatacccta   6180
gactagaccc cggagccacg acatgcttta catgtgttta gtcgaggtta aaaaacgtct   6240
aggccccccg aaccacgggg acgtggtttt cctttgaaaa acacgatgat aatatggcca   6300
```

```
tgtacgaaat gtacacaaat cagctccaat tttttgcaga tccggggggc ttggtgcccc   6360
tgcaccaaaa ggaaactttt tgtgctacta ttataccggt ccacccatac ctaggctttt   6420
gcaaagatcg atcagatccc ggggggcaat gagatatgaa aaagcctgaa ctcaccgcga   6480
cgtctgtcga gaagtttctg ggtgggtatg gatccgaaaa cgtttctagc tagtctaggg   6540
ccccccgtta ctctatactt tttcggactt gagtggcgct gcagacagct cttcaaagac   6600
atcgaaaagt tcgacagcgt ctccgacctg atgcagctct cggagggcga agaatctcgt   6660
gctttcagct tcgatgtagg agggcgtgga tatgtcctgc tagcttttca agctgtcgca   6720
gaggctggac tacgtcgaga gcctcccgct tcttagagca cgaaagtcga agctacatcc   6780
tcccgcacct atacaggacg gggtaaatag ctgcgccgat ggtttctaca aagatcgtta   6840
tgtttatcgg cactttgcat cggccgcgct cccgattccg gaagtgcttg acattgggga   6900
cccatttatc gacgcggcta ccaaagatgt ttctagcaat acaaatagcc gtgaaacgta   6960
gccggcgcga gggctaaggc cttcacgaac tgtaacccct attcagcgag agcctgacct   7020
attgcatctc ccgccgtgca cagggtgtca cgttgcaaga cctgcctgaa accgaactgc   7080
ccgctgttct gcagccggtc taagtcgctc tcggactgga taacgtagag ggcggcacgt   7140
gtcccacagt gcaacgttct ggacggactt tggcttgacg ggcgacaaga cgtcggccag   7200
gcggaggcca tggatgcgat cgctgcggcc gatcttagcc agacgagcgg gttcggccca   7260
ttcggaccgc aaggaatcgg tcaatacact acatggcgtg cgcctccggt acctacgcta   7320
gcgacgccgg ctagaatcgg tctgctcgcc caagccgggt aagcctggcg ttccttagcc   7380
agttatgtga tgtaccgcac atttcatatg cgcgattgct gatccccatg tgtatcactg   7440
gcaaactgtg atggacgaca ccgtcagtgc gtccgtcgcg caggctctcg atgagctgat   7500
taaagtatac gcgctaacga ctaggggtac acatagtgac cgtttgacac tacctgctgt   7560
ggcagtcacg caggcagcgc gtccgagagc tactcgacta gctttgggcc gaggactgcc   7620
ccgaagtccg gcacctcgtg cacgcggatt tcggctccaa caatgtcctg acggacaatg   7680
gccgcataac agcggtcatt cgaaacccgg ctcctgacgg ggcttcaggc cgtggagcac   7740
gtgcgcctaa agccgaggtt gttacaggac tgcctgttac cggcgtattg tcgccagtaa   7800
gactggagcg aggcgatgtt cggggattcc caatacgagg tcgccaacat cttcttctgg   7860
aggccgtggt tggcttgtat ggagcagcag acgcgctact ctgacctcgc tccgctacaa   7920
gcccctaagg gttatgctcc agcggttgta gaagaagacc tccggcacca accgaacata   7980
cctcgtcgtc tgcgcgatga tcgagcggag gcatccggag cttgcaggat cgccgcggct   8040
ccgggcgtat atgctccgca ttggtcttga ccaactctat cagagcttgg ttgacggcaa   8100
agctcgcctc cgtaggcctc gaacgtccta gcggcgccga ggcccgcata tacgaggcgt   8160
aaccagaact ggttgagata gtctcgaacc aactgccgtt tttcgatgat gcagcttggg   8220
cgcagggtcg atgcgacgca atcgtccgat ccggagccgg gactgtcggg cgtacacaaa   8280
tcgcccgcag aagcgcggcc aaagctacta cgtcgaaccc gcgtcccagc tacgctgcgt   8340
tagcaggcta ggcctcggcc ctgacagccc gcatgtgttt agcgggcgtc ttcgcgccgg   8400
gtctggaccg atggctgtgt agaagtactc gccgatagtg gaaaccgacg ccccagcact   8460
cgtccggatc gggagatggg ggaggctaac tgaaacacgg cagacctggc taccgacaca   8520
tcttcatgag cggctatcac ctttggctgc ggggtcgtga gcaggcctag ccctctaccc   8580
cctccgattg actttgtgcc aaggagacaa taccggaagg aacctcgacg ttaacttgtt   8640
```

-continued

```
tattgcagct tataatggtt acaaataaag caatagcatc acaaatttca caaataaagc   8700
ttcctctgtt atggccttcc ttggagctgc aattgaacaa ataacgtcga atattaccaa   8760
tgtttatttc gttatcgtag tgtttaaagt gtttatttcg atttattacc ctgttatccc   8820
tagaattcac tggccgtcgt tttacaacgt cgtgactggg aaaaccctgg cgttacccaa   8880
cttaatcgcc ttgcagcaca taaataatgg gacaataggg atcttaagtg accggcagca   8940
aaatgttgca gcactgaccc ttttgggacc gcaatgggtt gaattagcgg aacgtcgtgt   9000
tccccctttc gccagctggc gtaatagcga agaggcccgc accgatcgcc cttcccaaca   9060
gttgcgcagc ctgaatggcg aatggcgcct gatgcggtat agggggaaag cggtcgaccg   9120
cattatcgct tctccgggcg tggctagcgg gaagggttgt caacgcgtcg gacttaccgc   9180
ttaccgcgga ctacgccata tttctcctta cgcatctgtg cggtatttca caccgcatac   9240
gtcaaagcaa ccatagtacg cgccctgtag cggcgcatta agcgcggcgg gtgtggtggt   9300
aaagaggaat gcgtagacac gccataaagt gtggcgtatg cagtttcgtt ggtatcatgc   9360
gcgggacatc gccgcgtaat tcgcgccgcc cacaccacca tacgcgcagc gtgaccgcta   9420
cacttgccag cgccctagcg cccgctcctt tcgctttctt cccttccttt ctcgccacgt   9480
tcgccggctt tccccgtcaa atgcgcgtcg cactggcgat gtgaacggtc gcgggatcgc   9540
gggcgaggaa agcgaaagaa gggaaggaaa gagcggtgca agcggccgaa aggggcagtt   9600
gctctaaatc gggggctccc tttagggttc cgatttagtg ctttacggca cctcgacccc   9660
aaaaaacttg atttgggtga tggttcacgt agtgggccat cgagatttag cccccgaggg   9720
aaatcccaag gctaaatcac gaaatgccgt ggagctgggg ttttttgaac taaacccact   9780
accaagtgca tcacccggta cgccctgata gacggttttt cgccctttga cgttggagtc   9840
cacgttcttt aatagtggac tcttgttcca aactggaaca acactcaacc ctatctcggg   9900
gcgggactat ctgccaaaaa gcgggaaact gcaacctcag gtgcaagaaa ttatcacctg   9960
agaacaaggt ttgaccttgt tgtgagttgg gatagagccc ctattctttt gatttataag  10020
ggattttgcc gatttcggcc tattggttaa aaaatgagct gatttaacaa aaatttaacg  10080
cgaattttaa caaaatatta gataagaaaa ctaaatattc cctaaaacgg ctaaagccgg  10140
ataaccaatt ttttactcga ctaaattgtt tttaaattgc gcttaaaatt gttttataat  10200
acgtttacaa ttttatggtg cactctcagt acaatctgct ctgatgccgc atagttaagc  10260
cagccccgac acccgccaac acccgctgac gcgccctgac tgcaaatgtt aaaataccac  10320
gtgagagtca tgttagacga gactacggcg tatcaattcg gtcggggctg tgggcggttg  10380
tgggcgactg cgcgggactg gggcttgtct gctcccggca tccgcttaca gacaagctgt  10440
gaccgtctag acgaaagggc ctcgtgatac gcctattttt ataggttaat gtcatgataa  10500
cccgaacaga cgagggccgt aggcgaatgt ctgttcgaca ctggcagatc tgctttcccg  10560
gagcactatg cggataaaaa tatccaatta cagtactatt taatggtttc ttagacgtca  10620
ggtggcactt ttcggggaaa tgtgcgcgga acccctattt gtttattttt ctaaatacat  10680
tcaaatatgt atccgctcat attaccaaag aatctgcagt ccaccgtgaa aagccccttt  10740
acacgcgcct tggggataaa caaataaaaa gatttatgta agtttataca taggcgagta  10800
gagacaataa ccctgataaa tgcttcaata atattgaaaa aggaagagta tgagtattca  10860
acatttccgt gtcgccctta ttcccttttt tgcggcattt ctctgttatt gggactattt  10920
acgaagttat tataactttt tccttctcat actcataagt tgtaaaggca cagcgggaat  10980
aagggaaaaa acgccgtaaa tgccttcctg tttttgctca cccagaaacg ctggtgaaag  11040
```

taaaagatgc tgaagatcag ttgggtgcac gagtgggtta catcgaactg gatctcaaca 11100
acggaaggac aaaaacgagt gggtctttgc gaccactttc attttctacg acttctagtc 11160
aacccacgtg ctcacccaat gtagcttgac ctagagttgt gcggtaagat ccttgagagt 11220
tttcgccccg aagaacgttt tccaatgatg agcactttta aagttctgct atgtggcgcg 11280
gtattatccc gtattgacgc cgccattcta ggaactctca aaagcggggc ttcttgcaaa 11340
aggttactac tcgtgaaaat ttcaagacga tacaccgcgc cataataggg cataactgcg 11400
cgggcaagag caactcggtc gccgcataca ctattctcag aatgacttgg ttgagtactc 11460
accagtcaca gaaaagcatc ttacggatgg catgacagta gcccgttctc gttgagccag 11520
cggcgtatgt gataagagtc ttactgaacc aactcatgag tggtcagtgt cttttcgtag 11580
aatgcctacc gtactgtcat agagaattat gcagtgctgc cataaccatg agtgataaca 11640
ctgcggccaa cttacttctg acaacgatcg gaggaccgaa ggagctaacc gctttttttgc 11700
tctcttaata cgtcacgacg gtattggtac tcactattgt gacgccggtt gaatgaagac 11760
tgttgctagc ctcctggctt cctcgattgg cgaaaaaacg acaacatggg ggatcatgta 11820
actcgccttg atcgttggga accggagctg aatgaagcca taccaaacga cgagcgtgac 11880
accacgatgc ctgtagcaat tgttgtaccc cctagtacat tgagcggaac tagcaaccct 11940
tggcctcgac ttacttcggt atggtttgct gctcgcactg tggtgctacg gacatcgtta 12000
ggcaacaacg ttgcgcaaac tattaactgg cgaactactt actctagctt cccggcaaca 12060
attaatagac tggatggagg cggataaagt tgcaggacca ccgttgttgc aacgcgtttg 12120
ataattgacc gcttgatgaa tgagatcgaa gggccgttgt taattatctg acctacctcc 12180
gcctatttca acgtcctggt cttctgcgct cggcccttcc ggctggctgg tttattgctg 12240
ataaatctgg agccggtgag cgtgggtctc gcggtatcat tgcagcactg gggccagatg 12300
gaagacgcga gccgggaagg ccgaccgacc aaataacgac tatttagacc tcggccactc 12360
gcacccagag cgccatagta acgtcgtgac cccggtctac gtaagccctc ccgtatcgta 12420
gttatctaca cgacggggag tcaggcaact atggatgaac gaaatagaca gatcgctgag 12480
ataggtgcct cactgattaa cattcgggag ggcatagcat caatagatgt gctgcccctc 12540
agtccgttga tacctacttg ctttatctgt ctagcgactc tatccacgga gtgactaatt 12600
gcattggtaa ctgtcagacc aagtttactc atatatactt tagattgatt taaaacttca 12660
tttttaattt aaaaggatct aggtgaagat cctttttgat cgtaaccatt gacagtctgg 12720
ttcaaatgag tatatatgaa atctaactaa attttgaagt aaaaattaaa ttttcctaga 12780
tccacttcta ggaaaaacta aatctcatga ccaaaatccc ttaacgtgag ttttcgttcc 12840
actgagcgtc agaccccgta gaaaagatca aaggatcttc ttgagatcct ttttttctgc 12900
ttagagtact ggttttaggg aattgcactc aaaagcaagg tgactcgcag tctggggcat 12960
cttttctagt ttcctagaag aactctagga aaaaaagacg gcgtaatctg ctgcttgcaa 13020
acaaaaaaac caccgctacc agcggtggtt tgtttgccgg atcaagagct accaactctt 13080
tttccgaagg taactggctt cgcattagac gacgaacgtt tgttttttttg gtggcgatgg 13140
tcgccaccaa acaaacggcc tagttctcga tggttgagaa aaaggcttcc attgaccgaa 13200
cagcagagcg cagataccaa atactgtcct tctagtgtag ccgtagttag gccaccactt 13260
caagaactct gtagcaccgc ctacatacct cgctctgcta gtcgtctcgc gtctatggtt 13320
tatgacagga agatcacatc ggcatcaatc cggtggtgaa gttcttgaga catcgtggcg 13380

-continued gatgtatgga gcgagacgat atcctgttac cagtggctgc tgccagtggc gataagtcgt 13440
gtcttaccgg gttggactca agacgatagt taccggataa ggcgcagcgg tcgggctgaa 13500
taggacaatg gtcaccgacg acggtcaccg ctattcagca cagaatggcc caacctgagt 13560
tctgctatca atggcctatt ccgcgtcgcc agcccgactt cggggggttc gtgcacacag 13620
cccagcttgg agcgaacgac ctacaccgaa ctgagatacc tacagcgtga gctatgagaa 13680
agcgccacgc ttcccgaagg gcccccccaag cacgtgtgtc gggtcgaacc tcgcttgctg 13740
gatgtggctt gactctatgg atgtcgcact cgatactctt tcgcggtgcg aagggcttcc 13800
gagaaaggcg gacaggtatc cggtaagcgg cagggtcgga acaggagagc gcacgaggga 13860
gcttccaggg ggaaacgcct ggtatcttta tagtcctgtc ctctttccgc ctgtccatag 13920
gccattcgcc gtcccagcct tgtcctctcg cgtgctccct cgaaggtccc cctttgcgga 13980
ccatagaaat atcaggacag ggtttcgcc acctctgact tgagcgtcga tttttgtgat 14040
gctcgtcagg ggggcggagc ctatggaaaa acgccagcaa cgcggccttt ttacggttcc 14100
cccaaagcgg tggagactga actcgcagct aaaaacacta cgagcagtcc ccccgcctcg 14160 gataccttt tgcggtcgtt gcgccggaaa aatgccaagg tggcctttg ctggcctttt 14220 gctcacatgt tctttcctgc gttatcccct gattctgtgg ataaccgtat taccgccttt 14280
gagtgagctg ataccgctcg accggaaaac gaccggaaaa cgagtgtaca agaaaggacg 14340
caatagggga ctaagacacc tattggcata atggcggaaa ctcactcgac tatggcgagc 14400
ccgcagccga acgaccgagc gcagcgagtc agtgagcgag gaagcggaag ggcgtcggct 14460
tgctggctcg cgtcgctcag tcactcgctc cttcgccttc 14500

<210> SEQ ID NO 90
<211> LENGTH: 14158
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
agcgcccaat acgcaaaccg cctctccccg cgcgttggcc gattcattaa tgcagctggc 60
acgacaggtt tcccgactgg aaagcgggca gtgagcgcaa tcgcgggtta tgcgtttggc 120
ggagaggggc gcgcaaccgg ctaagtaatt acgtcgaccg tgctgtccaa agggctgacc 180
tttcgcccgt cactcgcgtt cgcaattaat gtgagttagc tcactcatta ggcaccccag 240
gctttacact ttatgcttcc ggctcgtatg ttgtgtggaa ttgtgagcgg ataacaattt 300
gcgttaatta cactcaatcg agtgagtaat ccgtggggtc cgaaatgtga aatacgaagg 360
ccgagcatac aacacacctt aacactcgcc tattgttaaa cacacaggaa acagctatga 420
ccatgattac gccaagcttt agggataaca gggtaatcgc catgcattag ttattaatag 480
taatcaatta cggggtcatt gtgtgtcctt tgtcgatact ggtactaatg cggttcgaaa 540
tccctattgt cccattagcg gtacgtaatc aataattatc attagttaat gccccagtaa 600
agttcatagc ccatatatgg agttccgcgt tacataactt acggtaaatg gcccgcctgg 660
ctgaccgccc aacgaccccc gcccattgac gtcaataatg tcaagtatcg ggtatatacc 720
tcaaggcgca atgtattgaa tgccatttac cgggcggacc gactggcggg ttgctggggg 780
cgggtaactg cagttattac acgtatgttc ccatagtaac gccaataggg actttccatt 840
gacgtcaatg ggtggagtat ttacggtaaa ctgcccactt ggcagtacat caagtgtatc 900

-continued

```
tgcatacaag ggtatcattg cggttatccc tgaaaggtaa ctgcagttac ccacctcata    960
aatgccattt gacgggtgaa ccgtcatgta gttcacatag atatgccaag tacgcccccct  1020
attgacgtca atgacggtaa atggcccgcc tggcattatg cccagtacat gaccttatgg  1080
gactttccta cttggcagta tatacggttc atgcgggggga taactgcagt tactgccatt  1140
taccgggcgg accgtaatac gggtcatgta ctggaatacc ctgaaaggat gaaccgtcat  1200
catctacgta ttagtcatcg ctattaccat ggtgatgcgg ttttggcagt acatcaatgg  1260
gcgtggatag cggtttgact cacggggatt tccaagtctc gtagatgcat aatcagtagc  1320
gataatggta ccactacgcc aaaaccgtca tgtagttacc cgcacctatc gccaaactga  1380
gtgcccctaa aggttcagag caccccattg acgtcaatgg gagtttgttt tggcaccaaa  1440
atcaacggga ctttccaaaa tgtcgtaaca actccgcccc attgacgcaa atgggcggta  1500
gtggggtaac tgcagttacc ctcaaacaaa accgtggttt tagttgccct gaaaggtttt  1560
acagcattgt tgaggcgggg taactgcgtt tacccgccat ggcgtgtacg gtgggaggtc  1620
tatataagca gagctggttt agtgaaccgt cagatccgct agacgtctca tttaggcatg  1680
gaaaccccag cgcagcttct ccgcacatgc caccctccag atatattcgt ctcgaccaaa  1740
tcacttggca gtctaggcga tctgcagagt aaatccgtac ctttggggtc gcgtcgaaga  1800
cttcctcctg ctactctgga tcccagacac cattgaagaa atagtgatga cgcagtctcc  1860
agccaccctg tctgtgtctc caggggaaag agtcaccctc gaaggaggac gatgagacct  1920
agggtctgtg gtaacttctt tatcactact gcgtcagagg tcggtgggac agacacagag  1980
gtccccttttc tcagtgggag tccagcagcc atcatcatca tcatcacagc agcggcctgg  2040
tgccgcgcgg cagccatagg tcgactctag aggatccaag ccaaagcact aacgttttag  2100
aggtcgtcgg tagtagtagt agtagtgtcg tcgccggacc acggcgcgcc gtcggtatcc  2160
agctgagatc tcctaggttc ggtttcgtga ttgcaaaatc gtgaagctaa aaaattaaac  2220
gaatctcaag caccgaaagc tgacaacaat ttcaacaaag aacaacaaaa tgctttctat  2280
gaaatcttga acatgcctaa cacttcgatt ttttaatttg cttagagttc gtggctttcg  2340
actgttgtta aagttgtttc ttgttgtttt acgaaagata ctttagaact tgtacggatt  2400
cttgaacgaa gaacaacgca atggtttcat ccaaagctta aaagatgacc caagtcaaag  2460
tgctaacctt ttagcagaag ctaaaaagtt aaatgaatct gaacttgctt cttgttgcgt  2520
taccaaagta ggtttcgaat tttctactgg gttcagtttc acgattggaa aatcgtcttc  2580
gatttttcaa tttacttaga caagcaccga aagctgataa caaattcaac aaagaacaac  2640
aaaatgcttt ctatgaaatc ttacatttac ctaacttaaa tgaagaacaa cgcaatggtt  2700
gttcgtggct ttcgactatt gtttaagttg tttcttgttg ttttacgaaa gatactttag  2760
aatgtaaatg gattgaattt acttcttgtt gcgttaccaa tcatccaaag cttaaaagat  2820
gacccaagcc aaagcgctaa ccttttagca gaagctaaaa agctaaatga tgcacaagca  2880
ccaaaagctg acaacaaatt agtaggtttc gaattttcta ctgggttcgg tttcgcgatt  2940
ggaaaatcgt cttcgatttt tcgatttact acgtgttcgt ggttttcgac tgttgtttaa  3000
caacaaagaa caacaaaatg ctttctatga aattttacat ttacctaact taactgaaga  3060
acaacgtaac ggcttcatcc aaagccttaa agacgatccc gttgtttctt gttgttttac  3120
gaaagatact ttaaaatgta aatggattga attgacttct tgttgcattg ccgaagtagg  3180
tttcggaatt tctgctaggg cggtcgactc tagcggcagc ttccggtgct agcactgaca  3240
cttacaaatt aatccttaat ggtaaaacat tgaaaggcga aacaactact gaagctgttg  3300
```

```
gccagctgag atcgccgtcg aaggccacga tcgtgactgt gaatgtttaa ttaggaatta   3360
ccattttgta actttccgct ttgttgatga cttcgacaac atgctgctac tgcagaaaaa   3420
gtcttcaaac aatacgctaa cgacaacggt gttgacggtg aatggactta cgacgatgcg   3480
actaagacct ttacagttac tacgacgatg acgtcttttt cagaagtttg ttatgcgatt   3540
gctgttgcca caactgccac ttacctgaat gctgctacgc tgattctgga aatgtcaatg   3600
tgaaaaacca gaagtgatcg atgcgtctga attaacacca gccgtgacaa cttacaaact   3660
tgttattaat ggtaaaacat tgaaaggcga aacaactact actttttggt cttcactagc   3720
tacgcagact taattgtggt cggcactgtt gaatgtttga acaataatta ccattttgta   3780
actttccgct ttgttgatga aaagcagtag acgcagaaac tgcagaaaaa gccttcaaac   3840
aatacgctaa cgacaacggt gttgatggtg tttggactta tgatgatgcg actaagacct   3900
tttcgtcatc tgcgtctttg acgtcttttt cggaagtttg ttatgcgatt gctgttgcca   3960
caactaccac aaacctgaat actactacgc tgattctgga ttacggtaac tgaaatggtt   4020
acagaggtac cagatcttag caactttgtt gcaactgaaa ccgatgctaa ccgcggaaaa   4080
atgcctggca aaaaactgcc aatgccattg actttaccaa tgtctccatg gtctagaatc   4140
gttgaaacaa cgttgacttt ggctacgatt ggcgcctttt tacggaccgt tttttgacgg   4200
actggcagtt atcatggaaa tggaagccaa tgctttcaaa gctggctgca ccaggggatg   4260
ccttatctgt ctttcaaaaa ttaagtgtac agccaaaatg tgaccgtcaa tagtaccttt   4320
accttcggtt acgaaagttt cgaccgacgt ggtcccctac ggaatagaca gaaagttttt   4380
aattcacatg tcggttttac aaggtataca ttccaggaag gtgtcacgat tatggtggtg   4440
acaagaaaac tggacaggca ggaattgttg gtgcaattgt tgacattccc gaaatctctg   4500
ttccatatgt aaggtccttc cacagtgcta ataccaccac tgttcttttg acctgtccgt   4560
ccttaacaac cacgttaaca actgtaaggg ctttagagac gatttaagga gatggcaccc   4620
atggaacagt tcattgctca agttgatcgc tgcgcttcct gcactactgg atgtctcaaa   4680
ggtcttgcca atgttaagtg ctaaattcct ctaccgtggg taccttgtca agtaacgagt   4740
tcaactagcg acgcgaagga cgtgatgacc tacagagttt ccagaacggt tacaattcac   4800
ctctgaactc ctgaagaaat ggctgcctga caggtgtgca agttttgctg acaagattca   4860
aaaagaagtt cacaatatca aaggcatggc cggcgatcga gagacttgag gacttcttta   4920
ccgacggact gtccacacgt tcaaaacgac tgttctaagt tttcttcaa gtgttatagt    4980
ttccgtaccg gccgctagct tgagcggccg caatttaatt ccggttattt tccaccatat   5040
tgccgtcttt tggcaatgtg agggcccgga aacctggccc tgtcttcttg acgagcattc   5100
actcgccggc gttaaattaa ggccaataaa aggtggtata acggcagaaa accgttacac   5160
tcccgggcct ttggaccggg acagaagaac tgctcgtaag ctaggggtct ttcccctctc   5220
gccaaaggaa tgcaaggtct gttgaatgtc gtgaaggaag cagttcctct ggaagcttct   5280
tgaagacaaa caacgtctgt gatccccaga aaggggagag cggtttcctt acgttccaga   5340
caacttacag cacttccttc gtcaaggaga ccttcgaaga acttctgttt gttgcagaca   5400
agcgaccctt tgcaggcagc ggaacccccc acctggcgac aggtgcctct gcggccaaaa   5460
gccacgtgta taagatacac ctgcaaaggc ggcacaaccc tcgctgggaa acgtccgtcg   5520
ccttgggggg tggaccgctg tccacggaga cgccggtttt cggtgcacat attctatgtg   5580
gacgtttccg ccgtgttggg cagtgccacg ttgtgagttg gatagttgtg gaaagagtca   5640
```

-continued aatggctcac ctcaagcgta ttcaacaagg ggctgaagga tgcccagaag gtaccccatt 5700
gtcacggtgc aacactcaac ctatcaacac ctttctcagt ttaccgagtg gagttcgcat 5760
aagttgttcc ccgacttcct acgggtcttc catggggtaa gtatgggatc tgatctgggg 5820
cctcggtgca catgctttac atgtgtttag tcgaggttaa aaaacgtcta ggccccccga 5880
accacgggga cgtggttttc catacccctag actagacccc ggagccacgt gtacgaaatg 5940
tacacaaatc agctccaatt ttttgcagat ccggggggct tggtgcccct gcaccaaaag 6000
ctttgaaaaa cacgatgata atatggccac cacccatacc taggcttttg caaagatcga 6060
tcagatcccg gggggcaatg agatatgaaa aagcctgaac gaaacttttt gtgctactat 6120
tataccggtg gtgggtatgg atccgaaaac gtttctagct agtctagggc cccccgttac 6180
tctatacttt ttcggacttg tcaccgcgac gtctgtcgag aagtttctga tcgaaaagtt 6240
cgacagcgtc tccgacctga tgcagctctc ggagggcgaa gaatctcgtg ctttcagctt 6300
agtggcgctg cagacagctc ttcaaagact agcttttcaa gctgtcgcag aggctggact 6360
acgtcgagag cctcccgctt cttagagcac gaaagtcgaa cgatgtagga gggcgtggat 6420
atgtcctgcg ggtaaatagc tgcgccgatg gtttctacaa agatcgttat gtttatcggc 6480
actttgcatc ggccgcgctc gctacatcct cccgcaccta tacaggacgc ccatttatcg 6540
acgcggctac caaagatgtt tctagcaata caaatagccg tgaaacgtag ccggcgcgag 6600
ccgattccgg aagtgcttga cattggggaa ttcagcgaga gcctgaccta ttgcatctcc 6660
cgccgtgcac agggtgtcac gttgcaagac ctgcctgaaa ggctaaggcc ttcacgaact 6720
gtaacccctt aagtcgctct cggactggat aacgtagagg gcggcacgtg tcccacagtg 6780
caacgttctg gacggacttt ccgaactgcc cgctgttctg cagccggtcg cggaggccat 6840
ggatgcgatc gctgcggccg atcttagcca gacgagcggg ttcggcccat tcggaccgca 6900
ggcttgacgg gcgacaagac gtcggccagc gcctccggta cctacgctag cgacgccggc 6960
tagaatcggt ctgctcgccc aagccgggta agcctggcgt aggaatcggt caatacacta 7020
catggcgtga tttcatatgc gcgattgctg atccccatgt gtatcactgg caaactgtga 7080
tggacgacac cgtcagtgcg tccttagcca gttatgtgat gtaccgcact aaagtatacg 7140
cgctaacgac taggggtaca catagtgacc gtttgacact acctgctgtg gcagtcacgc 7200
tccgtcgcgc aggctctcga tgagctgatg ctttgggccg aggactgccc cgaagtccgg 7260
cacctcgtgc acgcggattt cggctccaac aatgtcctga aggcagcgcg tccgagagct 7320
actcgactac gaaacccggc tcctgacggg gcttcaggcc gtggagcacg tgcgcctaaa 7380
gccgaggttg ttacaggact cggacaatgg ccgcataaca gcggtcattg actggagcga 7440
ggcgatgttc ggggattccc aatacgaggt cgccaacatc ttcttctgga ggccgtggtt 7500
gcctgttacc ggcgtattgt cgccagtaac tgacctcgct ccgctacaag cccctaaggg 7560
ttatgctcca gcggttgtag aagaagacct ccggcaccaa ggcttgtatg gagcagcaga 7620
cgcgctactt cgagcggagg catccggagc ttgcaggatc gccgcggctc cgggcgtata 7680
tgctccgcat tggtcttgac ccgaacatac ctcgtcgtct gcgcgatgaa gctcgcctcc 7740
gtaggcctcg aacgtcctag cggcgccgag gcccgcatat acgaggcgta accagaactg 7800
caactctatc agagcttggt tgacggcaat ttcgatgatg cagcttgggc gcagggtcga 7860
tgcgacgcaa tcgtccgatc cggagccggg actgtcgggc gttgagatag tctcgaacca 7920
actgccgtta aagctactac gtcgaacccg cgtcccagct acgctgcgtt agcaggctag 7980
gcctcggccc tgacagcccg gtacacaaat cgcccgcaga agcgcggccg tctggaccga 8040

```
tggctgtgta gaagtactcg ccgatagtgg aaaccgacgc cccagcactc gtccggatcg   8100
catgtgttta gcgggcgtct tcgcgccggc agacctggct accgacacat cttcatgagc   8160
ggctatcacc tttggctgcg ggtcgtgag caggcctagc ggagatgggg gaggctaact   8220
gaaacacgga aggagacaat accggaagga acctcgacgt taacttgttt attgcagctt   8280
ataatggtta caaataaagc cctctacccc ctccgattga ctttgtgcct tcctctgtta   8340
tggccttcct tggagctgca attgaacaaa taacgtcgaa tattaccaat gtttatttcg   8400
aatagcatca caaatttcac aaataaagca tttattaccc tgttatccct agaattcact   8460
ggccgtcgtt ttacaacgtc gtgactggga aaaccctggc ttatcgtagt gtttaaagtg   8520
tttatttcgt aaataatggg acaataggga tcttaagtga ccggcagcaa aatgttgcag   8580
cactgaccct tttgggaccg gttacccaac ttaatcgcct tgcagcacat ccccctttcg   8640
ccagctggcg taatagcgaa gaggcccgca ccgatcgccc ttcccaacag ttgcgcagcc   8700
caatgggttg aattagcgga acgtcgtgta gggggaaagc ggtcgaccgc attatcgctt   8760
ctccgggcgt ggctagcggg aagggttgtc aacgcgtcgg tgaatggcga atggcgcctg   8820
atgcggtatt ttctccttac gcatctgtgc ggtatttcac accgcatacg tcaaagcaac   8880
catagtacgc gccctgtagc acttaccgct taccgcggac tacgccataa aagaggaatg   8940
cgtagacacg ccataaagtg tggcgtatgc agtttcgttg gtatcatgcg cgggacatcg   9000
ggcgcattaa gcgcggcggg tgtggtggtt acgcgcagcg tgaccgctac acttgccagc   9060
gccctagcgc ccgctccttt cgctttcttc ccttcctttc ccgcgtaatt cgcgccgccc   9120
acaccaccaa tgcgcgtcgc actggcgatg tgaacggtcg cgggatcgcg ggcgaggaaa   9180
gcgaaagaag ggaaggaaag tcgccacgtt cgccggcttt ccccgtcaag ctctaaatcg   9240
ggggctccct ttagggttcc gatttagtgc tttacggcac ctcgacccca aaaaacttga   9300
agcggtgcaa gcggccgaaa ggggcagttc gagatttagc cccgagggga aatcccaagg   9360
ctaaatcacg aaatgccgtg gagctggggt tttttgaact tttgggtgat ggttcacgta   9420
gtgggccatc gccctgatag acggtttttc gccctttgac gttggagtcc acgttcttta   9480
atagtggact cttgttccaa aaacccacta ccaagtgcat cacccggtag cgggactatc   9540
tgccaaaaag cgggaaactg caacctcagg tgcaagaaat tatcacctga gaacaaggtt   9600
actggaacaa cactcaaccc tatctcgggc tattcttttg atttataagg gattttgccg   9660
atttcggcct attggttaaa aaatgagctg atttaacaaa tgaccttgtt gtgagttggg   9720
atagagcccg ataagaaaac taaatattcc ctaaaacggc taaagccgga taaccaattt   9780
tttactcgac taaattgttt aatttaacgc gaattttaac aaaatattaa cgtttacaat   9840
tttatggtgc actctcagta caatctgctc tgatgccgca tagttaagcc agccccgaca   9900
ttaaattgcg cttaaaattg ttttataatt gcaaatgtta aaataccacg tgagagtcat   9960
gttagacgag actacggcgt atcaattcgg tcggggctgt cccgccaaca cccgctgacg   10020
cgccctgacg ggcttgtctg ctcccggcat ccgcttacag acaagctgtg accgtctaga   10080
cgaaagggcc tcgtgatacg ggcggttgt gggcgactgc gcgggactgc ccgaacagac   10140
gagggccgta ggcgaatgtc tgttcgacac tggcagatct gctttcccgg agcactatgc   10200
cctattttta taggttaatg tcatgataat aatggtttct tagacgtcag gtggcacttt   10260
tcggggaaat gtgcgcggaa cccctatttg tttatttttc ggataaaaat atccaattac   10320
agtactatta ttaccaaaga atctgcagtc caccgtgaaa agccccttta cacgcgcctt   10380
```

-continued

```
ggggataaac aaataaaaag taaatacatt caaatatgta tccgctcatg agacaataac  10440
cctgataaat gcttcaataa tattgaaaaa ggaagagtat gagtattcaa catttccgtg  10500
atttatgtaa gtttatacat aggcgagtac tctgttattg ggactattta cgaagttatt  10560
ataacttttt ccttctcata ctcataagtt gtaaaggcac tcgcccttat tccctttttt  10620
gcggcatttt gccttcctgt ttttgctcac ccagaaacgc tggtgaaagt aaaagatgct  10680
gaagatcagt tgggtgcacg agcgggaata agggaaaaaa cgccgtaaaa cggaaggaca  10740
aaaacgagtg ggtctttgcg accactttca ttttctacga cttctagtca acccacgtgc  10800
agtgggttac atcgaactgg atctcaacag cggtaagatc cttgagagtt ttcgccccga  10860
agaacgtttt ccaatgatga gcacttttaa agttctgcta tcacccaatg tagcttgacc  10920
tagagttgtc gccattctag gaactctcaa aagcggggct tcttgcaaaa ggttactact  10980
cgtgaaaatt tcaagacgat tgtggcgcgg tattatcccg tattgacgcc gggcaagagc  11040
aactcggtcg ccgcatacac tattctcaga atgacttggt tgagtactca ccagtcacag  11100
acaccgcgcc ataatagggc ataactgcgg cccgttctcg ttgagccagc ggcgtatgtg  11160
ataagagtct tactgaacca actcatgagt ggtcagtgtc aaaagcatct tacggatggc  11220
atgacagtaa gagaattatg cagtgctgcc ataaccatga gtgataacac tgcggccaac  11280
ttacttctga caacgatcgg ttttcgtaga atgcctaccg tactgtcatt ctcttaatac  11340
gtcacgacgg tattggtact cactattgtg acgccggttg aatgaagact gttgctagcc  11400
aggaccgaag gagctaaccg cttttttgca caacatgggg gatcatgtaa ctcgccttga  11460
tcgttgggaa ccggagctga atgaagccat accaaacgac tcctggcttc ctcgattggc  11520
gaaaaaacgt gttgtacccc ctagtacatt gagcggaact agcaaccctt ggcctcgact  11580
tacttcggta tggtttgctg gagcgtgaca ccacgatgcc tgtagcaatg gcaacaacgt  11640
tgcgcaaact attaactggc gaactactta ctctagcttc ccggcaacaa ttaatagact  11700
ctcgcactgt ggtgctacgg acatcgttac cgttgttgca acgcgtttga taattgaccg  11760
cttgatgaat gagatcgaag ggccgttgtt aattatctga ggatggaggc ggataaagtt  11820
gcaggaccac ttctgcgctc ggcccttccg gctggctggt ttattgctga taaatctgga  11880
gccggtgagc gtgggtctcg cctacctccg cctatttcaa cgtcctggtg aagacgcgag  11940
ccgggaaggc cgaccgacca aataacgact atttagacct cggccactcg cacccagagc  12000
cggtatcatt gcagcactgg ggccagatgg taagccctcc cgtatcgtag ttatctacac  12060
gacggggagt caggcaacta tggatgaacg aaatagacag gccatagtaa cgtcgtgacc  12120
ccggtctacc attcgggagg gcatagcatc aatagatgtg ctgcccctca gtccgttgat  12180
acctacttgc tttatctgtc atcgctgaga taggtgcctc actgattaag cattggtaac  12240
tgtcagacca agtttactca tatatacttt agattgattt aaaacttcat ttttaattta  12300
tagcgactct atccacggag tgactaattc gtaaccattg acagtctggt tcaaatgagt  12360
atatatgaaa tctaactaaa ttttgaagta aaaattaaat aaaggatcta ggtgaagatc  12420
ctttttgata atctcatgac caaaatccct taacgtgagt tttcgttcca ctgagcgtca  12480
gaccccgtag aaaagatcaa tttcctagat ccacttctag gaaaaactat tagagtactg  12540
gttttaggga attgcactca aaagcaaggt gactcgcagt ctggggcatc ttttctagtt  12600
aggatcttct tgagatcctt tttttctgcg cgtaatctgc tgcttgcaaa caaaaaaacc  12660
accgctacca gcggtggttt gtttgccgga tcaagagcta tcctagaaga actctaggaa  12720
aaaaagacgc gcattagacg acgaacgttt gttttttttgg tggcgatggt cgccaccaaa  12780
```

```
caaacggcct agttctcgat ccaactcttt ttccgaaggt aactggcttc agcagagcgc  12840

agataccaaa tactgtcctt ctagtgtagc cgtagttagg ccaccacttc aagaactctg  12900

ggttgagaaa aaggcttcca ttgaccgaag tcgtctcgcg tctatggttt atgacaggaa  12960

gatcacatcg gcatcaatcc ggtggtgaag ttcttgagac tagcaccgcc tacatacctc  13020

gctctgctaa tcctgttacc agtggctgct gccagtggcg ataagtcgtg tcttaccggg  13080

ttggactcaa gacgatagtt atcgtggcgg atgtatggag cgagacgatt aggacaatgg  13140

tcaccgacga cggtcaccgc tattcagcac agaatggccc aacctgagtt ctgctatcaa  13200

accggataag gcgcagcggt cgggctgaac ggggggttcg tgcacacagc ccagcttgga  13260

gcgaacgacc tacaccgaac tgagatacct acagcgtgag tggcctattc cgcgtcgcca  13320

gcccgacttg ccccccaagc acgtgtgtcg ggtcgaacct cgcttgctgg atgtggcttg  13380

actctatgga tgtcgcactc ctatgagaaa gcgccacgct tcccgaaggg agaaaggcgg  13440

acaggtatcc ggtaagcggc agggtcggaa caggagagcg cacgagggag cttccagggg  13500

gatactcttt cgcggtgcga agggcttccc tctttccgcc tgtccatagg ccattcgccg  13560

tcccagcctt gtcctctcgc gtgctccctc gaaggtcccc gaaacgcctg gtatctttat  13620

agtcctgtcg ggtttcgcca cctctgactt gagcgtcgat ttttgtgatg ctcgtcaggg  13680

gggcggagcc tatggaaaaa ctttgcggac catagaaata tcaggacagc ccaaagcggt  13740

ggagactgaa ctcgcagcta aaaacactac gagcagtccc cccgcctcgg ataccttttt  13800

cgccagcaac gcggcctttt tacggttcct ggccttttgc tggccttttg ctcacatgtt  13860

ctttcctgcg ttatcccctg attctgtgga taaccgtatt gcggtcgttg cgccggaaaa  13920

atgccaagga ccggaaaacg accggaaaac gagtgtacaa gaaaggacgc aatagggggac  13980

taagacacct attggcataa accgcctttg agtgagctga taccgctcgc cgcagccgaa  14040

cgaccgagcg cagcgagtca gtgagcgagg aagcggaagt ggcggaaact cactcgacta  14100

tggcgagcgg cgtcggcttg ctggctcgcg tcgctcagtc actcgctcct tcgccttc    14158
```

<210> SEQ ID NO 91
<211> LENGTH: 13882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
agcgcccaat acgcaaaccg cctctccccg cgcgttggcc gattcattaa tgcagctggc     60

acgacaggtt tcccgactgg aaagcgggca gtgagcgcaa tcgcgggtta tgcgtttggc    120

ggagaggggc gcgcaaccgg ctaagtaatt acgtcgaccg tgctgtccaa agggctgacc    180

tttcgcccgt cactcgcgtt cgcaattaat gtgagttagc tcactcatta ggcaccccag    240

gctttacact ttatgcttcc ggctcgtatg ttgtgtggaa ttgtgagcgg ataacaattt    300

gcgttaatta cactcaatcg agtgagtaat ccgtggggtc cgaaatgtga aatacgaagg    360

ccgagcatac aacacacctt aacactcgcc tattgttaaa cacacaggaa acagctatga    420

ccatgattac gccaagcttt agggataaca gggtaatcgc catgcattag ttattaatag    480

taatcaatta cggggtcatt gtgtgtcctt tgtcgatact ggtactaatg cggttcgaaa    540

tccctattgt cccattagcg gtacgtaatc aataattatc attagttaat gccccagtaa    600

agttcatagc ccatatatgg agttccgcgt tacataactt acggtaaatg gcccgcctgg    660
```

```
ctgaccgccc aacgaccccc gcccattgac gtcaataatg tcaagtatcg ggtatatacc    720
tcaaggcgca atgtattgaa tgccatttac cgggcggacc gactggcggg ttgctggggg    780
cgggtaactg cagttattac acgtatgttc ccatagtaac gccaataggg actttccatt    840
gacgtcaatg ggtggagtat ttacggtaaa ctgcccactt ggcagtacat caagtgtatc    900
tgcatacaag ggtatcattg cggttatccc tgaaaggtaa ctgcagttac ccacctcata    960
aatgccattt gacgggtgaa ccgtcatgta gttcacatag atatgccaag tacgccccct   1020
attgacgtca atgacggtaa atggcccgcc tggcattatg cccagtacat gaccttatgg   1080
gactttccta cttggcagta tatacggttc atgcgggga taactgcagt tactgccatt   1140
taccgggcgg accgtaatac gggtcatgta ctggaatacc ctgaaaggat gaaccgtcat   1200
catctacgta ttagtcatcg ctattaccat ggtgatgcgg ttttggcagt acatcaatgg   1260
gcgtggatag cggtttgact cacggggatt tccaagtctc gtagatgcat aatcagtagc   1320
gataatggta ccactacgcc aaaaccgtca tgtagttacc cgcacctatc gccaaactga   1380
gtgcccctaa aggttcagag caccccattg acgtcaatgg gagtttgttt tggcaccaaa   1440
atcaacggga ctttccaaaa tgtcgtaaca actccgcccc attgacgcaa atgggcggta   1500
gtggggtaac tgcagttacc ctcaaacaaa accgtggttt tagttgccct gaaaggtttt   1560
acagcattgt tgaggcgggg taactgcgtt tacccgccat ggcgtgtacg gtgggaggtc   1620
tatataagca gagctggttt agtgaaccgt cagatccgct agacgtctca tttaggcatg   1680
gaaaccccag cgcagcttct ccgcacatgc caccctccag atatattcgt ctcgaccaaa   1740
tcacttggca gtctaggcga tctgcagagt aaatccgtac ctttggggtc gcgtcgaaga   1800
cttcctcctg ctactctgga tcccagacac cattgaagaa atagtgatga cgcagtctcc   1860
agccaccctg tctgtgtctc caggggaaag agtcaccctc gaaggaggac gatgagacct   1920
agggtctgtg gtaacttctt tatcactact gcgtcagagg tcggtgggac agacacagag   1980
gtcccctttc tcagtgggag tcctcaggcg gcgcaagcag cctgagacag attctggact   2040
cccagaaaat ggagtggagg tccaacgccg ggggcagcgg tagggataac agggtaatcg   2100
aggagtccgc cgcgttcgtc ggactctgtc taagacctga gggtctttta cctcacctcc   2160
aggttgcggc ccccgtcgcc atccctattg tcccattagc ccgaggacgc agacatgcgt   2220
aatgaactgg aggagatgca gaggagggct gaccagctgg ctgatgagtc cctggaaagc   2280
acccgtcgca tgctgcagct ggctcctgcg tctgtacgca ttacttgacc tcctctacgt   2340
ctcctcccga ctggtcgacc gactactcag ggacctttcg tgggcagcgt acgacgtcga   2400
ggtcgaagag agtaaagatg ctggcatcag gactttggtt atgttggatg agcaaggcga   2460
acaactggaa cgcattgagg aagggatgga ccaaatcaat ccagcttctc tcatttctac   2520
gaccgtagtc ctgaaaccaa tacaacctac tcgttccgct tgttgacctt gcgtaactcc   2580
ttccctacct ggtttagtta aaggatatga aagaagcaga aaagaatttg acggacctag   2640
gaaaattctg cgggctttgt gtgtgtccct gtaacaagct taaatccagt gatgcttaca   2700
ttcctatact ttcttcgtct tttcttaaac tgcctggatc cttttaagac gcccgaaaca   2760
cacacaggga cattgttcga atttaggtca ctacgaatgt aaaaagcctg gggcaataat   2820
caggatggag tagtggccag ccagcctgcc cgtgtggtgg atgaacggga gcagatggcc   2880
atcagtggtg gcttcatccg tttttcggac cccgttatta gtcctacctc atcaccggtc   2940
ggtcggacgg gcacaccacc tacttgccct cgtctaccgg tagtcaccac cgaagtaggc   3000
```

-continued

```
cagggtaaca aacgatgccc gggaaaatga aatggatgaa aacctagagc aggtgagcgg   3060
catcatcgga aacctccgtc atatggccct agacatgggc gtcccattgt ttgctacggg   3120
ccctttact ttacctactt ttggatctcg tccactcgcc gtagtagcct ttggaggcag    3180
tataccggga tctgtacccg aatgagattg acacccagaa tcgccagatt gacaggatca   3240
tggagaaggc tgactccaac aaaaccagaa ttgatgaagc caaccaacgt gcaacaaaga   3300
ttactctaac tgtgggtctt agcggtctaa ctgtcctagt acctcttccg actgaggttg   3360
ttttggtctt aactacttcg gttggttgca cgttgtttct tgctgggaag tggggagatc   3420
tccgcggccc gggatccacc ggctagcggg aattccaaat caactgagtt cgatcctaac   3480
attgacattg ttggtttaga acgacccttc acccctctag aggcgccggg ccctaggtgg   3540
ccgatcgccc ttaaggttta gttgactcaa gctaggattg taactgtaac aaccaaatct   3600
aggaaaattt ggtattacaa acctagagac ggatttattc acaatctggg agacaatgga   3660
ggtcatgatc aaagcagata ttgcagatac tgatagagcc tccttttaaa ccataatgtt   3720
tggatctctg cctaaataag tgttagaccc tctgttacct ccagtactag tttcgtctat   3780
aacgtctatg actatctcgg agcaactttg ttgcaactga aaccgatgct aaccgcggaa   3840
aaatgcctgg caaaaaactg ccactggcag ttatcatgga aatggaagcc aatgctttca   3900
tcgttgaaac aacgttgact ttggctacga ttggcgcctt tttacggacc gttttttgac   3960
ggtgaccgtc aatagtacct ttaccttcgg ttacgaaagt aagctggctg caccagggga   4020
tgccttatct gtctttcaaa aattaagtgt acagccaaaa tgaaggtata cattccagga   4080
aggtgtcacg attatggtgg ttcgaccgac gtggtcccct acggaataga cagaaagttt   4140
ttaattcaca tgtcggtttt acttccatat gtaaggtcct tccacagtgc taataccacc   4200
tgacaagaaa actggacagg caggaattgt tggtgcaatt gttgacattc ccgaaatctc   4260
tggatttaag gagatggcac ccatggaaca gttcattgct actgttcttt tgacctgtcc   4320
gtccttaaca accacgttaa caactgtaag ggctttagag acctaaattc ctctaccgtg   4380
ggtaccttgt caagtaacga caagttgatc gctgcgcttc ctgcactact ggatgtctca   4440
aaggtcttgc caatgttaag tgctctgaac tcctgaagaa atggctgcct gacaggtgtg   4500
gttcaactag cgacgcgaag gacgtgatga cctacagagt ttccagaacg gttacaattc   4560
acgagacttg aggacttctt taccgacgga ctgtccacac caagttttgc tgacaagatt   4620
caaaaagaag ttcacaatat caaaggcatg gccggcgatc gatgagcggc cgcaatttaa   4680
ttccggttat tttccaccat gttcaaaacg actgttctaa gtttttcttc aagtgttata   4740
gtttccgtac cggccgctag ctactcgccg gcgttaaatt aaggccaata aaaggtggta   4800
attgccgtct tttggcaatg tgagggcccg gaaacctggc cctgtcttct tgacgagcat   4860
tcctaggggt ctttcccctc tcgccaaagg aatgcaaggt taacggcaga aaaccgttac   4920
actcccgggc ctttggaccg ggacagaaga actgctcgta aggatcccca gaaaggggag   4980
agcggtttcc ttacgttcca ctgttgaatg tcgtgaagga agcagttcct ctggaagctt   5040
cttgaagaca aacaacgtct gtagcgaccc tttgcaggca gcggaacccc ccacctggcg   5100
gacaacttac agcacttcct tcgtcaagga gaccttcgaa gaacttctgt ttgttgcaga   5160
catcgctggg aaacgtccgt cgccttgggg ggtggaccgc acaggtgcct ctgcggccaa   5220
aagccacgtg tataagatac acctgcaaag gcggcacaac cccagtgcca cgttgtgagt   5280
tggatagttg tggaaagagt tgtccacgga gacgccggtt ttcggtgcac atattctatg   5340
tggacgtttc cgccgtgttg ggtcacggt  gcaacactca acctatcaac acctttctca   5400
```

-continued caaatggctc acctcaagcg tattcaacaa ggggctgaag gatgcccaga aggtacccca 5460
ttgtatggga tctgatctgg ggcctcggtg cacatgcttt gtttaccgag tggagttcgc 5520
ataagttgtt ccccgacttc ctacgggtct tccatggggt aacataccct agactagacc 5580
ccggagccac gtgtacgaaa acatgtgttt agtcgaggtt aaaaaacgtc taggcccccc 5640
gaaccacggg gacgtggttt tcctttgaaa aacacgatga taatatggcc accacccata 5700
tgtacacaaa tcagctccaa ttttttgcag atccgggggg cttggtgccc ctgcaccaaa 5760
aggaaacttt ttgtgctact attataccgg tggtgggtat cctaggcttt tgcaaagatc 5820
gatcagatcc cggggggcaa tgagatatga aaaagcctga actcaccgcg acgtctgtcg 5880
agaagtttct gatcgaaaag ggatccgaaa acgtttctag ctagtctagg gccccccgtt 5940
actctatact ttttcggact tgagtggcgc tgcagacagc tcttcaaaga ctagcttttc 6000
ttcgacagcg tctccgacct gatgcagctc tcggagggcg aagaatctcg tgctttcagc 6060
ttcgatgtag gagggcgtgg atatgtcctg cgggtaaata aagctgtcgc agaggctgga 6120
ctacgtcgag agcctcccgc ttcttagagc acgaaagtcg aagctacatc ctcccgcacc 6180
tatacaggac gcccatttat gctgcgccga tggtttctac aaagatcgtt atgtttatcg 6240
gcactttgca tcggccgcgc tcccgattcc ggaagtgctt gacattgggg aattcagcga 6300
cgacgcggct accaaagatg tttctagcaa tacaaatagc cgtgaaacgt agccggcgcg 6360
agggctaagg ccttcacgaa ctgtaacccc ttaagtcgct gagcctgacc tattgcatct 6420
cccgccgtgc acagggtgtc acgttgcaag acctgcctga aaccgaactg cccgctgttc 6480
tgcagccggt cgcggaggcc ctcggactgg ataacgtaga gggcggcacg tgtcccacag 6540
tgcaacgttc tggacggact ttggcttgac gggcgacaag acgtcggcca gcgcctccgg 6600
atggatgcga tcgctgcggc cgatcttagc cagacgagcg ggttcggccc attcggaccg 6660
caaggaatcg gtcaatacac tacatggcgt gatttcatat tacctacgct agcgacgccg 6720
gctagaatcg gtctgctcgc ccaagccggg taagcctggc gttccttagc cagttatgtg 6780
atgtaccgca ctaaagtata gcgcgattgc tgatccccat gtgtatcact ggcaaactgt 6840
gatggacgac accgtcagtg cgtccgtcgc gcaggctctc gatgagctga tgctttgggc 6900
cgcgctaacg actaggggta cacatagtga ccgtttgaca ctacctgctg tggcagtcac 6960
gcaggcagcg cgtccgagag ctactcgact acgaaacccg cgaggactgc cccgaagtcc 7020
ggcacctcgt gcacgcggat ttcggctcca acaatgtcct gacggacaat ggccgcataa 7080
cagcggtcat tgactggagc gctcctgacg gggcttcagg ccgtggagca cgtgcgccta 7140
aagccgaggt tgttacagga ctgcctgtta ccggcgtatt gtcgccagta actgacctcg 7200
gaggcgatgt tcggggattc ccaatacgag gtcgccaaca tcttcttctg gaggccgtgg 7260
ttggcttgta tggagcagca gacgcgctac ttcgagcgga ctccgctaca agcccctaag 7320
ggttatgctc cagcggttgt agaagaagac ctccggcacc aaccgaacat acctcgtcgt 7380
ctgcgcgatg aagctcgcct ggcatccgga gcttgcagga tcgccgcggc tccgggcgta 7440
tatgctccgc attggtcttg accaactcta tcagagcttg gttgacggca atttcgatga 7500
ccgtaggcct cgaacgtcct agcggcgccg aggcccgcat atacgaggcg taaccagaac 7560
tggttgagat agtctcgaac caactgccgt taaagctact tgcagcttgg gcgcagggtc 7620
gatgcgacgc aatcgtccga tccggagccg ggactgtcgg gcgtacacaa atcgcccgca 7680
gaagcgcggc cgtctggacc acgtcgaacc cgcgtcccag ctacgctgcg ttagcaggct 7740

-continued

```
aggcctcggc cctgacagcc cgcatgtgtt tagcgggcgt cttcgcgccg gcagacctgg   7800
gatggctgtg tagaagtact cgccgatagt ggaaaccgac gccccagcac tcgtccggat   7860
cgggagatgg gggaggctaa ctgaaacacg gaaggagaca ctaccgacac atcttcatga   7920
gcggctatca cctttggctg cggggtcgtg agcaggccta gccctctacc ccctccgatt   7980
gactttgtgc cttcctctgt ataccggaag gaacctcgac gttaacttgt ttattgcagc   8040
ttataatggt tacaaataaa gcaatagcat cacaaatttc acaaataaag catttattac   8100
tatggccttc cttggagctg caattgaaca aataacgtcg aatattacca atgtttattt   8160
cgttatcgta gtgtttaaag tgtttatttc gtaaataatg cctgttatcc ctagaattca   8220
ctggccgtcg ttttacaacg tcgtgactgg gaaaaccctg gcgttaccca acttaatcgc   8280
cttgcagcac atcccccttt ggacaatagg gatcttaagt gaccggcagc aaaatgttgc   8340
agcactgacc cttttgggac cgcaatgggt tgaattagcg gaacgtcgtg taggggggaaa  8400
cgccagctgg cgtaatagcg aagaggcccg caccgatcgc ccttcccaac agttgcgcag   8460
cctgaatggc gaatggcgcc tgatgcggta ttttctcctt gcggtcgacc gcattatcgc   8520
ttctccgggc gtggctagcg ggaagggttg tcaacgcgtc ggacttaccg cttaccgcgg   8580
actacgccat aaaagaggaa acgcatctgt gcggtatttc acaccgcata cgtcaaagca   8640
accatagtac gcgccctgta gcggcgcatt aagcgcggcg ggtgtggtgg ttacgcgcag   8700
tgcgtagaca cgccataaag tgtggcgtat gcagtttcgt tggtatcatg cgcgggacat   8760
cgccgcgtaa ttcgcgccgc ccacaccacc aatgcgcgtc cgtgaccgct acacttgcca   8820
gcgccctagc gcccgctcct ttcgctttct tcccttcctt tctcgccacg ttcgccggct   8880
ttccccgtca agctctaaat gcactggcga tgtgaacggt cgcgggatcg cgggcgagga   8940
aagcgaaaga agggaaggaa agagcggtgc aagcggccga aaggggcagt tcgagattta   9000
cgggggctcc ctttagggtt ccgatttagt gctttacggc acctcgaccc caaaaaactt   9060
gatttgggtg atggttcacg tagtgggcca tcgccctgat gcccccgagg gaaatcccaa   9120
ggctaaatca cgaaatgccg tggagctggg gttttttgaa ctaaacccac taccaagtgc   9180
atcacccggt agcgggacta agacggtttt tcgccctttg acgttggagt ccacgttctt   9240
taatagtgga ctcttgttcc aaactggaac aacactcaac cctatctcgg gctattcttt   9300
tctgccaaaa agcgggaaac tgcaacctca ggtgcaagaa attatcacct gagaacaagg   9360
tttgaccttg ttgtgagttg ggatagagcc cgataagaaa tgatttataa gggattttgc   9420
cgatttcggc ctattggtta aaaaatgagc tgatttaaca aaaatttaac gcgaatttta   9480
acaaaatatt aacgtttaca actaaatatt ccctaaaacg gctaaagccg gataaccaat   9540
tttttactcg actaaattgt ttttaaattg cgcttaaaat tgttttataa ttgcaaatgt   9600
attttatggt gcactctcag tacaatctgc tctgatgccg catagttaag ccagccccga   9660
cacccgccaa cacccgctga cgcgccctga cgggcttgtc taaaatacca cgtgagagtc   9720
atgttagacg agactacggc gtatcaattc ggtcggggct gtgggcggtt gtgggcgact   9780
gcgcgggact gcccgaacag tgctcccggc atccgcttac agacaagctg tgaccgtcta   9840
gacgaaaggg cctcgtgata cgcctatttt tataggttaa tgtcatgata ataatggttt   9900
acgagggccg taggcgaatg tctgttcgac actggcagat ctgctttccc ggagcactat   9960
gcggataaaa atatccaatt acagtactat tattaccaaa cttagacgtc aggtggcact  10020
tttcggggaa atgtgcgcgg aacccctatt tgtttatttt tctaaataca ttcaaatatg  10080
tatccgctca tgagacaata gaatctgcag tccaccgtga aaagcccctt tacacgcgcc  10140
```

ttggggataa acaaataaaa agatttatgt aagtttatac ataggcgagt actctgttat 10200
accctgataa atgcttcaat aatattgaaa aaggaagagt atgagtattc aacatttccg 10260
tgtcgccctt attccctttt ttgcggcatt ttgccttcct tgggactatt tacgaagtta 10320
ttataacttt ttccttctca tactcataag ttgtaaaggc acagcgggaa taagggaaaa 10380
aacgccgtaa aacggaagga gtttttgctc acccagaaac gctggtgaaa gtaaaagatg 10440
ctgaagatca gttgggtgca cgagtgggtt acatcgaact ggatctcaac agcggtaaga 10500
caaaaacgag tgggtctttg cgaccacttt cattttctac gacttctagt caacccacgt 10560
gctcacccaa tgtagcttga cctagagttg tcgccattct tccttgagag ttttcgcccc 10620
gaagaacgtt ttccaatgat gagcactttt aaagttctgc tatgtggcgc ggtattatcc 10680
cgtattgacg ccgggcaaga aggaactctc aaaagcgggg cttcttgcaa aaggttacta 10740
ctcgtgaaaa tttcaagacg atacaccgcg ccataatagg gcataactgc ggcccgttct 10800
gcaactcggt cgccgcatac actattctca gaatgacttg gttgagtact caccagtcac 10860
agaaaagcat cttacggatg gcatgacagt aagagaatta cgttgagcca gcggcgtatg 10920
tgataagagt cttactgaac caactcatga gtggtcagtg tcttttcgta gaatgcctac 10980
cgtactgtca ttctcttaat tgcagtgctg ccataaccat gagtgataac actgcggcca 11040
acttacttct gacaacgatc ggaggaccga aggagctaac cgcttttttg cacaacatgg 11100
acgtcacgac ggtattggta ctcactattg tgacgccggt tgaatgaaga ctgttgctag 11160
cctcctggct tcctcgattg gcgaaaaaac gtgttgtacc gggatcatgt aactcgcctt 11220
gatcgttggg aaccggagct gaatgaagcc ataccaaacg acgagcgtga caccacgatg 11280
cctgtagcaa tggcaacaac ccctagtaca ttgagcggaa ctagcaaccc ttggcctcga 11340
cttacttcgg tatggtttgc tgctcgcact gtggtgctac ggacatcgtt accgttgttg 11400
gttgcgcaaa ctattaactg gcgaactact tactctagct tcccggcaac aattaataga 11460
ctggatggag gcggataaag ttgcaggacc acttctgcgc caacgcgttt gataattgac 11520
cgcttgatga atgagatcga agggccgttg ttaattatct gacctacctc cgcctatttc 11580
aacgtcctgg tgaagacgcg tcggcccttc cggctggctg gtttattgct gataaatctg 11640
gagccggtga gcgtgggtct cgcggtatca ttgcagcact ggggccagat ggtaagccct 11700
agccgggaag gccgaccgac caaataacga ctatttagac ctcggccact cgcacccaga 11760
gcgccatagt aacgtcgtga ccccggtcta ccattcggga cccgtatcgt agttatctac 11820
acgacgggga gtcaggcaac tatggatgaa cgaaatagac agatcgctga gataggtgcc 11880
tcactgatta agcattggta gggcatagca tcaatagatg tgctgcccct cagtccgttg 11940
atacctactt gctttatctg tctagcgact ctatccacgg agtgactaat tcgtaaccat 12000
actgtcagac caagtttact catatatact ttagattgat ttaaaacttc atttttaatt 12060
taaaaggatc taggtgaaga tcctttttga taatctcatg tgacagtctg gttcaaatga 12120
gtatatatga aatctaacta aattttgaag taaaaattaa attttcctag atccacttct 12180
aggaaaaact attagagtac accaaaatcc cttaacgtga gttttcgttc cactgagcgt 12240
cagaccccgt agaaaagatc aaaggatctt cttgagatcc tttttttctg cgcgtaatct 12300
tggttttagg gaattgcact caaaagcaag gtgactcgca gtctggggca tcttttctag 12360
tttcctagaa gaactctagg aaaaaaagac gcgcattaga gctgcttgca aacaaaaaaa 12420
ccaccgctac cagcggtggt ttgtttgccg gatcaagagc taccaactct ttttccgaag 12480

-continued gtaactggct tcagcagagc cgacgaacgt ttgttttttt ggtggcgatg gtcgccacca 12540
aacaaacggc ctagttctcg atggttgaga aaaaggcttc cattgaccga agtcgtctcg 12600
gcagatacca aatactgtcc ttctagtgta gccgtagtta ggccaccact tcaagaactc 12660
tgtagcaccg cctacatacc tcgctctgct aatcctgtta cgtctatggt ttatgacagg 12720
aagatcacat cggcatcaat ccggtggtga agttcttgag acatcgtggc ggatgtatgg 12780
agcgagacga ttaggacaat ccagtggctg ctgccagtgg cgataagtcg tgtcttaccg 12840
ggttggactc aagacgatag ttaccggata aggcgcagcg gtcgggctga acggggggtt 12900
ggtcaccgac gacggtcacc gctattcagc acagaatggc ccaacctgag ttctgctatc 12960
aatggcctat tccgcgtcgc cagcccgact tgcccccaa cgtgcacaca gcccagcttg 13020
gagcgaacga cctacaccga actgagatac ctacagcgtg agctatgaga aagcgccacg 13080
cttcccgaag ggagaaaggc gcacgtgtgt cgggtcgaac ctcgcttgct ggatgtggct 13140
tgactctatg gatgtcgcac tcgatactct ttcgcggtgc gaagggcttc cctctttccg 13200
ggacaggtat ccggtaagcg gcagggtcgg aacaggagag cgcacgaggg agcttccagg 13260
gggaaacgcc tggtatcttt atagtcctgt cgggtttcgc cctgtccata ggccattcgc 13320
cgtcccagcc ttgtcctctc gcgtgctccc tcgaaggtcc ccctttgcgg accatagaaa 13380
tatcaggaca gcccaaagcg cacctctgac ttgagcgtcg atttttgtga tgctcgtcag 13440
gggggcggag cctatggaaa aacgccagca acgcggcctt tttacggttc ctggcctttt 13500
gtggagactg aactcgcagc taaaaacact acgagcagtc cccccgcctc ggataccttt 13560
ttgcggtcgt tgcgccggaa aaatgccaag gaccggaaaa gctggccttt tgctcacatg 13620
ttctttcctg cgttatcccc tgattctgtg gataaccgta ttaccgcctt tgagtgagct 13680
gataccgctc gccgcagccg cgaccggaaa acgagtgtac aagaaaggac gcaatagggg 13740
actaagacac ctattggcat aatggcggaa actcactcga ctatggcgag cggcgtcggc 13800
aacgaccgag cgcagcgagt cagtgagcga ggaagcggaa gttgctggct cgcgtcgctc 13860
agtcactcgc tccttcgcct tc 13882

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
cgtctcatat a 11

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
cgtctccagt g 11

<210> SEQ ID NO 94
<211> LENGTH: 11
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 94

tatatgagac g                                                          11


<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95

cactggagac g                                                          11


<210> SEQ ID NO 96
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

cgtctcatat ag                                                         12


<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

ctatatgaga cg                                                         12
```

SYSTEM FOR PRODUCTION OF ANTIBODIES AND THEIR DERIVATIVES

CROSS-REFERENCE TO RELATED APPLICATIONS

This application claims priority to U.S. Provisional Application No. 61/733,358, filed Dec. 4, 2012, the content of which is incorporated herein in its entirety.

SEQUENCE LISTING

The instant application contains a Sequence Listing which has been submitted electronically in ASCII format and is hereby incorporated by reference in its entirety. Said ASCII copy, created on Mar. 31, 2014, is named 099523_0105_SL.txt and is 270,890 bytes in size.

TECHNICAL FIELD

The present disclosure relates to methods and compositions for producing chimeric antibodies that specifically bind an antigen of interest.

BACKGROUND

Prior to Sep. 11, 2001 the list of pathogens that humanity was threatened by on a day-to-day basis was relatively short and people had found means of decreasing the threat from these pathogens by developing corresponding vaccines. Nowadays this list has swelled many times from its pre-September 11 size and the threat of exposure of populations to agents from this list has grown immensely. Many vaccines are so old that they have lost their potency, while vaccines for other agents simply do not exist. The situation with the anti-BoNT vaccine is a perfect example of the former situation. As a result, the traditional vaccination approach can no longer be used to the full extent to protect society from such threats.

BoNTs are classified as Category A agents, one of the 6 highest risk threat agents for bioterrorism (2). These homologous, but serologically distinct toxins (serotypes A, B, C, D, E, F and G), specifically target neurons and, through interruption of neurotransmission, cause muscle paralysis, which leads to death from asphyxiation. It has been estimated that aerosol exposure of 100,000 individuals to the toxin, as could occur with an aerosol release over a metropolitan area, would result in 50,000 cases of illness with 30,000 fatalities (3). Such an exposure would result in 4.2 million hospital days and an estimated cost of $8.6 billion.

Pentavalent *botulinum* toxoid was generated over 30 years ago via chemical inactivation of native toxins of five different serotypes. This vaccine received Investigational New Drug status from the CDC (for at-risk workers), and from the United States Army's Office of the Surgeon General (for military deployment). It was stockpiled and over years was used more than 20,000 times (4). However, it was also losing its potency over the years and the CDC recently issued a notice of its discontinuation (5). The first reports of efforts to generate a new recombinant substitute for pentavalent toxoid were published almost 17 years ago (6). However, no new anti-BoNT vaccines have been approved yet. BoNTs of serotypes A and B are currently used under trade names BOTOX® and MIOBLOCK® in medicine as potent drugs and rejuvenation agents in cosmetics. Thus, it is unlikely that many people would be willing to undergo vaccination and give up the current benefits of these "miracle" drugs even if new anti-BoNT vaccines were to be developed. A more realistic strategy for raising preparedness against the threat of a bioterrorist attack would include stockpiling pathogen-specific antibodies and using them in case of an immediate threat of bioterrorist attack or soon after it.

The injection of heterologous antibodies, however, causes acute or delayed hypersensitivity reactions in 9% of cases, including serum sickness (3.7%) and anaphylactic shock (1.9%) (7). Further, application of non-human antibodies might trigger the development of an immunologic response, which will reduce or eliminate the benefit of repeating applications of such antibodies. Securing substantial quantities of human antigen-specific serums, however, may be an extremely expensive endeavor. For example, Orphan Drug human Botulism Immune Globulin has been approved by the FDA for treatment of infant botulism. It was formulated on the basis of serum obtained from human volunteers vaccinated with pentavalent *botulinum* toxoid. The price of this drug for treatment of one patient is $45,300.

SUMMARY

In one aspect, the present disclosure provides a method for producing a chimeric immunoglobulin-G (IgG) antibody that specifically binds an antigen of interest comprising: a) isolating nucleic acid sequences encoding IgG heavy and light chain variable regions from a single immune cell producing an IgG that specifically binds the antigen of interest; b) cloning the nucleic acid sequences of part a) into separate expression vectors comprising the IgG heavy or light chain constant regions, or into a single expression vector comprising both the IgG heavy and light chain constant regions; c) introducing the expression vector(s) of part b) into a host cell; d) establishing a stable cell line from the host cell of part c); and e) isolating the IgG produced by the stable cell line of part d), wherein the method comprises simultaneous cloning of the IgG heavy and light chain variable regions isolated from the immune cell of part a), and wherein the expression vector of part b) allows for (i) unidirectional insertion of the IgG heavy and light chain variable regions into the vector, and (i) positive selection of expression vectors comprising cloned sequences.

In some embodiments, the antigen of interest is derived from a pathogen. In some embodiments, the antigen of interest is a *Clostridium botulinum* neurotoxin.

In some embodiments, the expression vector is selected from the group consisting of pVLentry-Hyg10, pVHentry-Cm5, pVHentry-GFP1, pVHentry-MLuc7, pVHentry-His-bio1, and pVHentry-CBD1.

In some embodiments, the stable cell line of part d) is established through expression of an antibiotic resistance gene present in the expression vector of part b). In some embodiments, the level of expression of the antibiotic resistance gene by the stable cell line correlates to the level of IgG production by the stable cell line.

In some embodiments, parts a) and b) comprise the steps of: i) reverse-transcription of mRNA released from the immune cell upon exposure to perfingolysin O; ii) simultaneous amplification of cDNAs produced in part i) encoding the IgG heavy chain variable region ($V_H$) and the IgG light chain variable region ($V_L$); iii) separate re-amplification of the $V_H$ and $V_L$ sequences of part ii), and iv) insertion of the re-amplified sequences of part iii) into the expression vector of part b).

In some embodiments, the reverse transcription is performed using a primer selected from the group consisting of IgG-CHH, Cm1, and Clv-3.

In some embodiments, the simultaneous amplification is performed using primers selected from the group consisting of pVk-1, pVk-2, pVk-3, pVk-4, hIgGk-3, IgGH-1, IgGH-2, IgGH-3, IgGH-4, IgGH-5, IgG-CHH, M1, M2, M3, M4, Cm1, V11-5T7, V12-5T7, V13-5T7, V14-5T7, V15-5T7, and C1-3.

In some embodiments, the re-amplification is performed using primers selected from the group consisting of Vk-1/2-5T7, Vk-3-5T7, Vk-4-5T7, hIgGk-3, IgG-CH, Vh-1-3T7, Vh-1-3T75, Vh-1-5T7, Vh-2-5T7, Vh-3-5T7, Vh-4-5T7, Vh-5-5T7, Vh-6-5T7, Vh-7-5T7, Vh-8-5T7, Vh-1-3T75, Vm-1-5T7, Vm-2-5T7, Vm-3-5T7, Vh-1-3T75, V11-5T7, V12-5T7, V13-5T7, V14-5T7, V15-5T7, and hIgGl-3.

In some embodiments, the method further comprises formulating the chimeric IgG into a therapeutic composition. In some embodiments, the method further comprises formulating the chimeric IgG into an antigen-specific resin or system for detecting corresponding antigens.

In some embodiments, the immune cell is selected from the group consisting of a plasma cell, a B-cell, or any other cell that secretes or displays on the cell surface immunoglobulins specific for the antigen of interest.

In some embodiments, the host cell is selected from the group consisting of a Chinese hamster ovary (CHO) cell, a human embryonic kidney (HEK), a mouse NS1/1-Ag 4-1 cell, a NSO/u cell, an X63/Ag 8.653 cell, an SP2/0 Ag14 cell, a rat Y3 (210.RCY3.Ag 1.2.3) cell, a YB213.0Ag3 (Y0) cell, and any other mammalian secondary cell line capable of producing immunoglobulins.

In some embodiments, the method allows for high-throughput production of antibodies against the antigen of interest.

In one aspect, the present disclosure provides a method for detecting an antigen of interest in a sample, comprising the steps of (a) contacting the sample with an antibody that specifically binds the antigen under conditions that promote the formation of an antibody-antigen complex, (b) contacting the antibody-antigen complex with a fusion protein comprising (i) the immunoglobulin-binding domains of staphylococcal protein A and streptococcal protein G, and (ii) *Metridia longa* luciferase or a derivative lacking the N-terminal region, under conditions that promote binding of the fusion protein to the antibody-antigen complex, and (c) detecting the *Metridia longa* luciferase.

In some embodiments, the fusion protein is encoded by a vector selected from the group consisting of pS14L-spAG-MLuc16, pETspAG-ΔN-MLuc1, and pS14L-spAG-ΔN-MLuc15. In some embodiments, the fusion protein is encoded by pS14L-spAG-MLuc16 or pETspAG-ΔN-MLuc1. In some embodiments, the fusion protein is encoded by pS14L-spAG-ΔN-MLuc15.

In one aspect, the present disclosure provides an IgG fusion protein comprising IgG heavy chains fused with a peptide or polypeptide selected from the group consisting of green fluorescent protein (GFP), *Metridia longa* luciferase, cellulose binding domain, 6× histidine (SEQ ID NO: 1), or a biotinylatable peptide.

BRIEF DESCRIPTION OF THE FIGURES

FIG. 2 shows SEQ ID NOs: 92-95, 94, 96-97, in order of appearance.

DETAILED DESCRIPTION

Figure 1:
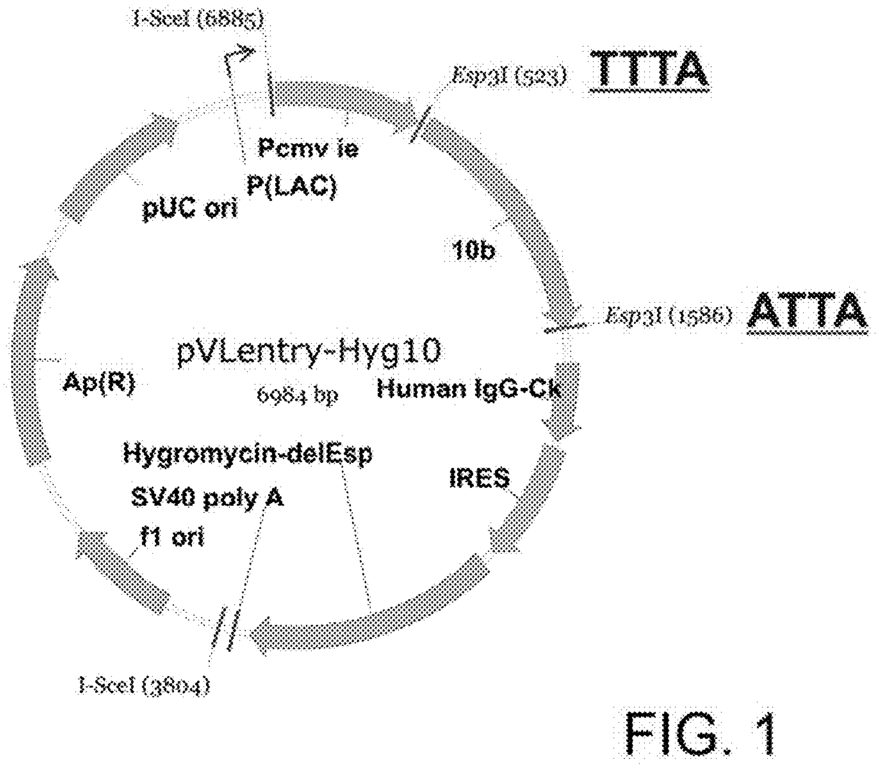
FIG. 1 shows the structure of the pVLentry-Hyg10 and pVHentry-Cm5 vectors. Plac and Pamp—bacterial promoters; PCMV ie—the immediate early promoter of CMV; IRES—internal ribosome entry site; SV40 poly A and HSV TK polyA—transcription terminators; fl ori and pUC ori—phage and plasmid origins of replication; 10b, IGHG1, and lacZ'—sequences encoding phage T7 protein 10b, constant part of human IgG and α-peptide of β-galactosidase, respectively; Ap(R), CM(R), Km(R) and Hygromycin-delEsp—sequences encoding resistance to antibiotics ampicillin, chloramphenicol, G418 and Hygromycin B (this sequence was modified to remove Esp3I site), respectively. Underlined are sequences of cohesive ends generated by Esp3I.
Figure 1:
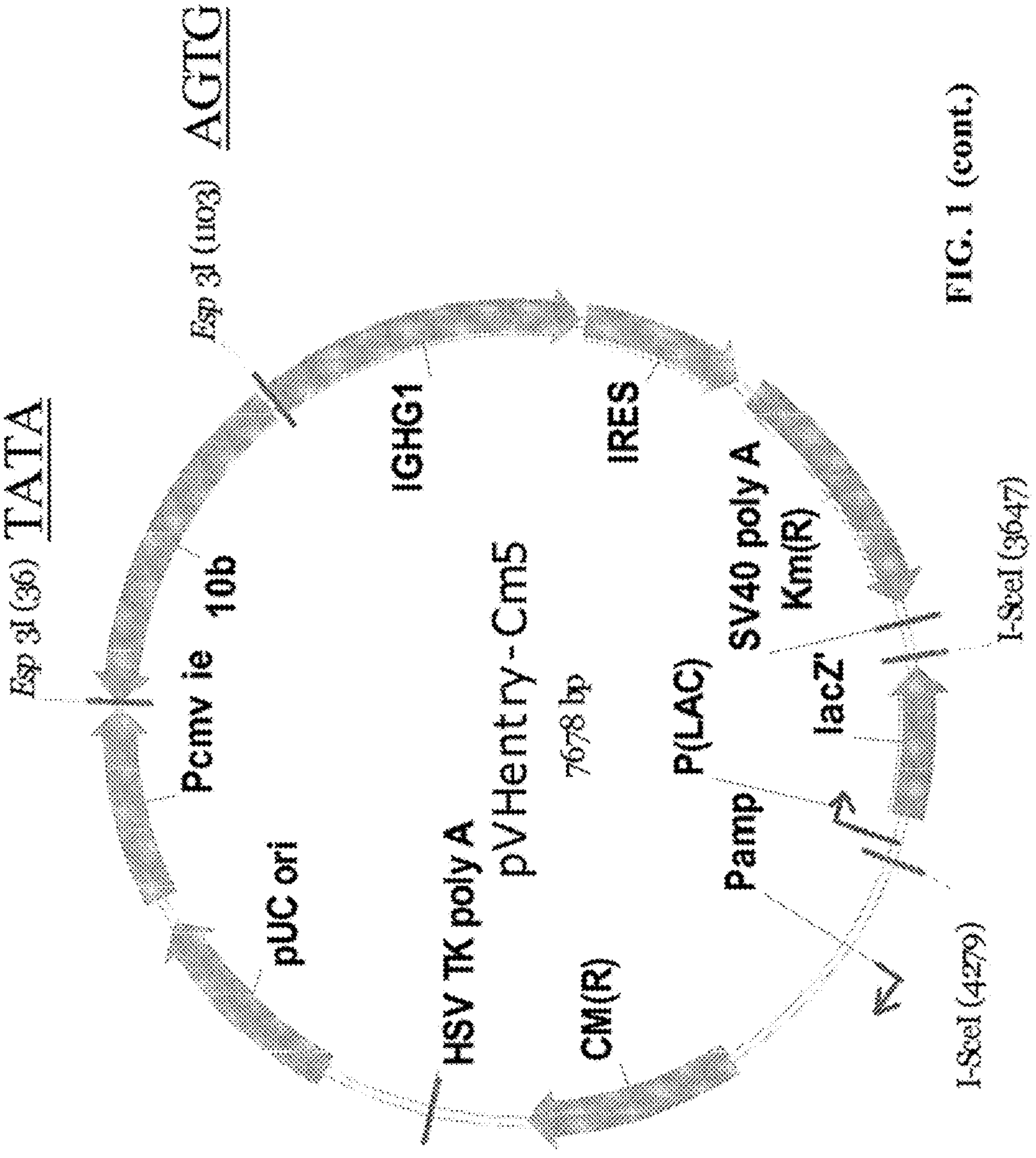

The present disclosure provides methods and compositions for robust generation of human monoclonal antibodies targeted at pathogens of interest.

In addition to the set of products that address existing needs, this technology advances our understanding of structure-function relationships in the neurotoxin molecule and provides information about mechanisms of inactivation of this molecule by antibodies.

In practicing the present disclosure, many conventional techniques in cell biology, molecular biology, protein biochemistry, immunology, and bacteriology are used. These techniques are well-known in the art and are provided in any number of available publications, including Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y., 1989).

Certain terms used herein are defined below. Unless defined otherwise, all technical and scientific terms used herein have the same general meaning as commonly understood by one skilled in the art.

Unless defined otherwise, all technical and scientific terms used herein generally have the same meaning as commonly understood by one of ordinary skill in the art to which this technology belongs. As used in this specification and the appended claims, the singular forms “a”, “an” and “the” include plural referents unless the content clearly dictates otherwise. For example, reference to “a cell” includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. All references cited herein are incorporated by reference in their entirety for all purposes to the same extent as if each individual publication, patent, or patent application were specifically and individually incorporated by reference in its entirety for all purposes.

As used herein, “about” will be understood by persons of ordinary skill in the art and will vary to some extent depending upon the context in which it is used. If there are uses of the term which are not clear to persons of ordinary skill in the art, given the context in which it is used, “about” will mean up to plus or minus 10% of the particular term.

As used herein, “administration” of a composition to a subject includes any route of delivering the compound to the subject to perform its intended function. Administration can be carried out by any suitable route including oral, intranasal, parenteral (intravenous, intramuscular, intraperitoneal, or subcutaneous), or topical. Administration includes self-administration and administration by another.

As used herein, the terms “antigen” and “antigenic” refer to molecules with the capacity to be recognized by an antibody or otherwise act as a member of an antibody-ligand pair. “Specific binding” refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encodes an antigen. The artisan will further understand that antigens are not limited to full-length proteins, but can also include partial amino acid sequences. Moreover, sequences from different sources may be combined to generate mosaic antigens, depending on the specific intended use. In some embodiments, the mosaic antigen will include epitopes derived from different proteins. In some embodiments, the mosaic antigen will include epitopes derived from the same protein. The term “antigenic” is an adjectival reference to molecules having the properties of an antigen. In some embodiments, the antigen of interest is a bacterial toxin. In some embodiments the antigen of interest is a *botulinum* neurotoxin.

As used herein, the term “epitope” refers to that portion of a molecule that forms a site specifically recognized by an antibody or immune cell. A protein epitope may comprise amino acid residues directly involved in antibody binding, as well as residues not directly involved in binding that are nonetheless included in the antibody-epitope footprint and excluded from the solvent surface. Epitopes may derive from a variety of physical characteristics of a protein, including primary, secondary, and tertiary amino acid structure, and amino acid/protein charge. Epitopes present within a molecule are referred to as “real epitopes.” Real epitopes encompass wild-type sequences and variants of wild-type sequences. Real epitopes may exist within a wild-type protein, a naturally occurring variant of a wild-type protein, or an engineered variant of a wild-type protein. The term “mimetic epitope” refers to a molecule whose primary structure is unrelated to the primary structure of a given real epitope that nonetheless specifically binds to antibodies that recognize the real epitope. Epitopes may be isolated, purified, or otherwise prepared by those skilled in the art. They may be obtained from natural sources including cells and tissues, or they may be isolated from host cells expressing a recombinant form of the epitope.

As used herein, “effective amount” refers to a quantity sufficient to achieve a desired effect. In the context of therapeutic or prophylactic applications, the effective amount will depend on the type and severity of the condition at issue and on the characteristics of the individual subject, such as general health, age, sex, body weight, and tolerance to pharmaceutical compositions. In the context of an antigenic composition, in some embodiments, an effective amount is an amount sufficient to result in a protective response against a pathogen. In other embodiments, an effective amount of an antigenic composition is an amount sufficient to result in antibody generation against the antigen. With respect to antigenic compositions, in some embodiments, an effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors. In the case of a biochemical application, in some embodiments, an effective amount will depend on the size and nature of the sample in question. It will also depend on the nature and sensitivity of the methods in use. The skilled artisan will be able to determine the effective amount based on these and other considerations.

As used herein, the term “polymer resin” refers to resins, such as, but not limited to polysaccharide polymers such as agarose, cellulose, and Sepharose™. The skilled artisan will understand that proteins may be covalently attached to the resin using methods well known in the art, including but not limited to cyanogen bromide activation, reductive animation of aldehydes, and the addition of iodoacetyl functional groups. The skilled artisan will further understand that functional equivalents of polysaccharide polymers may also be to immobilize proteins.

As used herein, the term “BoNT” refers to any of the seven serologically distinct *botulinum* neurotoxins produced by *Clostridium botulinum, Clostridium argentiensis*, and *Clostridium baratti*. Individual serotypes are referred to as BoNT/A, BoNT/B, BoNT/C, BoNT/D, BoNT/E, BoNT/F, and BoNT/G. Exemplary, non-limiting nucleic acid sequences of BoNT/A, /B, /C, /D, /E, /F, and /G are found in GenBank Accession numbers DQ409059, FM865705, AB200364, NZ ACSJ01000015, AM695754, X81714, and X74162, respectively. Exemplary, non-limiting amino acid sequences of BoNT/A, /B, /C, /D, /E, /F, and /G are found in GenBank Accession numbers ABD65472, CAR97779, BAD90572, ZP 04863672, CAM91137, CAA57358, and CAA52275, respectively. Exemplary, non-limiting nucleic and amino acid sequences of *C. tetani* tetanus toxin are found in GenBank Accession numbers AF154828 and AAF73267, respectively. As used herein, the term "BoNT/A-L" refers to the full-length *botulinum* neurotoxin A light chain. As used herein, the term "BoNT/B-L" refers to the full-length *botulinum* neurotoxin B light chain.

As used herein, the term "anti-BoNT antibody" refers to an antibody capable of specifically binding to BoNT. As used herein, an antibody includes a polyclonal antibody, a monoclonal antibody, and also refers to functional fragments (e.g., fragments which bind an antigen/epitope), such as Fv, Fab, Fc and CDRs.

As used herein, the terms "immunogen" and "immunogenic" refer to molecules with the capacity to elicit an immune response. The response may involve antibody production or the activation of immune cells. The response may occur in vivo or in vitro. The skilled artisan will understand that a variety of macromolecule, including proteins, have the potential to be immunogenic. The skilled artisan will further understand that nucleic acids encoding a molecule capable of eliciting an immune response necessarily encodes an immunogen. The artisan will further understand that immunogens are not limited to full-length molecules, but may include partial amino acid sequences (e.g., epitopes). Moreover, sequences from different sources may be combined to generate mosaic immunogens, depending on the specific intended use.

As used herein, the terms "isolate" and "purify" refer to processes of obtaining a biological substance that is substantially free of material and/or contaminants normally found in its natural environment (e.g., from the cells or tissues from which a protein is derived, or substantially free from chemical precursors or other chemicals when chemically synthesized).

As used herein, the term the terms "polypeptide," "peptide," and "protein" are used interchangeable to mean a polymer comprising two or more amino acids joined to each other by peptide bonds or modified peptide bonds (i.e., peptide isosteres). Polypeptides may include amino acids other than the naturally-occurring amino acids, as well as amino acid analogs and mimetics prepared by techniques that are well known in the art. The skilled artisan will understand that polypeptides, peptides, and proteins may be obtained in a variety of ways including isolation from cells and tissues expressing the protein endogenously, isolation from cell or tissues expressing a recombinant form of the molecule, or synthesized chemically.

As used herein, the term "subject" refers to a member of any vertebrate species. In some embodiments, the subject is avian and includes domestic (e.g., chicken, turkey) and wild bird species. In some embodiments, subjects include mammals such as humans, as well as those mammals of importance due to being endangered, of economic importance (animals raised on farms for consumption by humans) and/or social importance (animals kept as pets or in zoos) to humans. In particular embodiments, the subject is a human. In other embodiments, the subject is not human.

As used herein, the term "pathogen" refers to any entity that causes disease, including, for example, but not limited to, mycoplasma, fungi, bacteria, viruses, viroids, virus-like organisms, protozoa, and nematodes, toxins, and prions. In some embodiments, the pathogen is a *Clostridium*. In some embodiments, the pathogen is *Clostridium botulinum*.

As used herein, the term "chimera" and "chimeric" refers to biological molecules comprising materials derived from two or more organisms of the same or different species. For example, the terms "chimeric antibody," and "chimeric IgG" refer to antibodies comprising amino acid sequences derived from two or more organisms of the same or different species. In some embodiments, the organisms are both of the same species. In some embodiments, the organisms are both human. In some embodiments, the organisms are from different species. In some embodiments, the terms refer to nucleic acid sequences encoding chimeric polypeptide sequences.

The present disclosure provides methods and compositions for high-throughput production of chimeric antibodies that specifically bind to an antigen of interest. The methods combine three procedures into one streamlined process: 1) isolation of lymphocytes producing antibodies of interest from the blood of immunized individuals, 2) amplification of sequences encoding variable domains of light and heavy chains of immunoglobulin from individual isolated cells, and 3) assembly of amplified sequences into specially designed vectors and construction of cells encoding human/human chimeras targeted at antigens of interest. The uniqueness of this process is its ability to generate multiple (up to 100) immunoglobulin-producing clones within a very short time (one-two months). Each such clone encodes an IgG whose variable domains of light and heavy chains originate from the same lymphocyte.

Since the required antibody-producing blood cells could come from a patient recovered from the infection, this system does not depend on the availability of a developed vaccine. Consequently, this system could be used to develop protective entities against rare and even new natural and engineered pathogens at very early signs of appearance. Additionally, the system does not involve use of viruses and, consequently, is safe to use.

The methods allow for rapid generation of IgGs whose heavy chains carry additional polypeptides at the C-termini. This grants the opportunity to produce derivatives of antibodies that can be used to monitor corresponding antigens (IgGs fused with reporter molecules) or to immobilize those pathogens (IgGs fused with polypeptides like Cellulose Binding Domain). Among other fusions, the system allows creation of fusions with *Metridia longa* luciferase, which allows fast and inexpensive examination of conditions to identify those for optimal production of antibodies. Also, the methods allow for the use of fluorescence activated cell sorting (FACS) for fast selection of clones producing increased levels of IgGs.

The present disclosure provides methods and compositions for robust development of human antibodies targeted at specific antigens of interest. The chosen approach required the ability to 1) isolate individual human lymphocytes specific to the chosen antigen, 2) isolate immunoglobulin-encoding sequences from a single selected cell, and 3) assemble immunoglobulin-encoding constructs that can be introduced into chosen cell cultures for production of corresponding antibodies. Prior to this work, it was unknown whether the dynamics of antibody secretion and the limited number of antigen-specific lymphocytes in the peripheral blood would permit efficient separation of these specific cells from all others. It was unclear whether protocols for rtPCR at the single cell level would be robust enough to allow their application in a high throughput format. Finally, described procedures for assembling expression vectors carrying IgG-encoding sequences were suitable for manipulation with just a very small number of IgG-encoding sequences at a time. By contrast, suitable methods for high throughput production must be capable of simultaneous handling of tens and even hundreds of different sequences.

In some embodiments, the compositions comprise expression vectors encoding constant regions of either light or heavy chains of human IgG. In some embodiments, the compositions comprise an expression vector encoding the constant regions of both the IgG heavy and light chains.

In some embodiments, the methods comprise isolating sequences encoding variable domains of light and heavy chains of IgG from single cells and assembly of Ig-encoding vectors.

In some embodiments, the methods comprise introducing designed IgG-encoding constructs into mammalian cells and evaluation of conditions for efficient IgG production. In some embodiments, the methods comprise producing and characterizing chimeric IgGs. In some embodiments, the chimeric IgGs are specific for *botulinum* neurotoxin serotype A (BoNT/A).

Embodiments described herein are set forth in the following non-limiting examples.

EXAMPLES

Example 1

Development of Expression Vectors

This Example demonstrates the construction of expression vectors for the cloning and production of chimeric IgG antibodies that specifically bind an antigen of interest.

In order to create a system for generation of human antibodies that is capable of working in a high throughput format, vectors were necessary that would allow 1) a 100%-certain assembly of sequences encoding light and heavy chains of immunoglobulins, 2) simple assembly of such sequences into one plasmid, and 3) robust selection of cells carrying such plasmids and expressing both chains of immunoglobulins. Plasmids pVLentry-Hyg10 and pVHentry-Cm5 are designed for assembly of expression-competent sequences for light and heavy chains of IgG, respectively, meet all of these requirements (FIG. 1). Specifically, both of these plasmids possess two recognition sites for restriction endonuclease Esp3I per plasmid and these sites flank the sequence encoding protein 10b of bacteriophage T7. These two features ensure that practically 100% of colonies growing after cloning experiments utilizing vectors pVLentry-Hyg10 and pVHentry-Cm5 carry inserts of interest in a pre-determined orientation.

Figure 2:
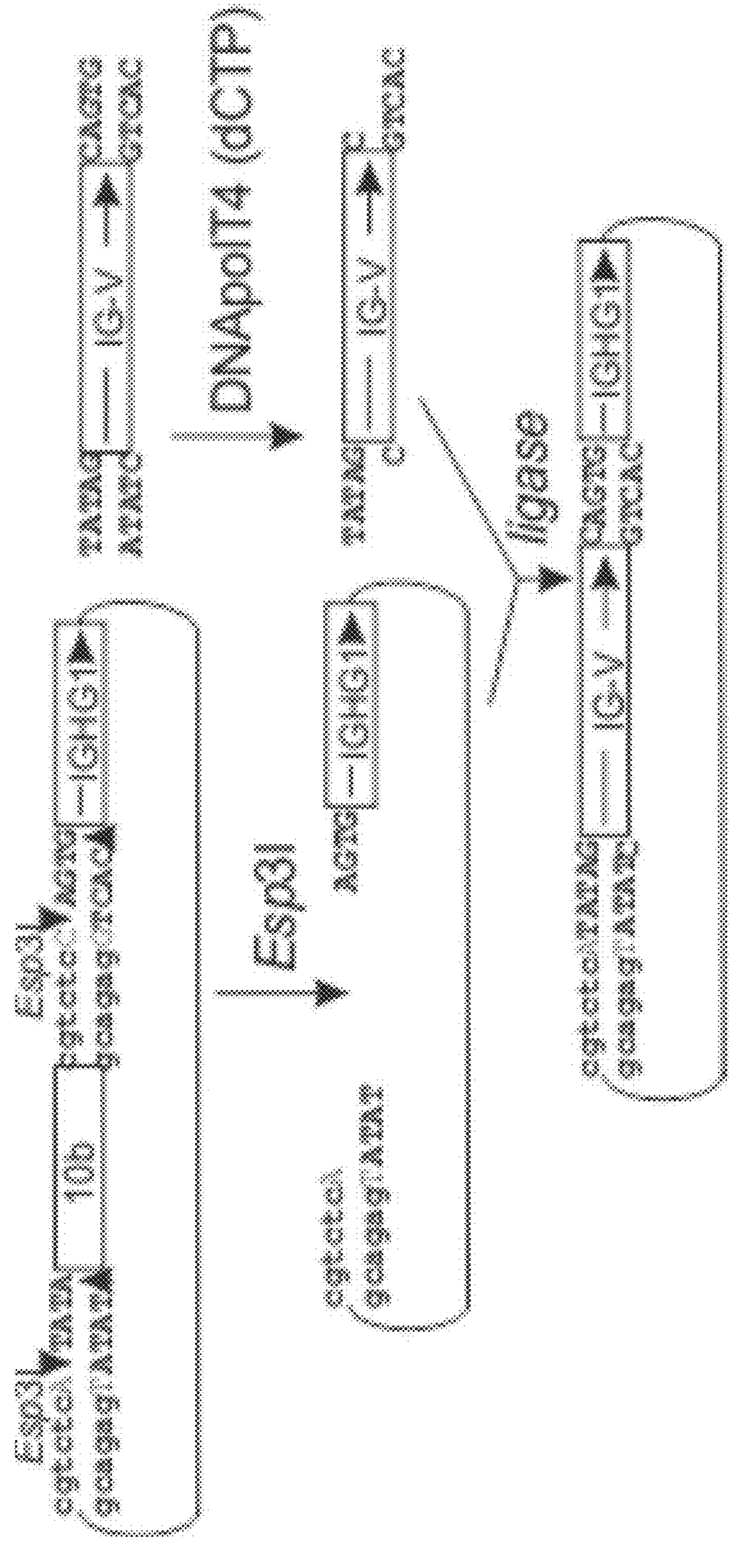
FIG. 2 shows the assembly of IgG-encoding sequences using cohesive ends generated by DNA polymerase T4. DNApolT4 (dCTP)—designates treatment with DNA polymerase T4 in the mixture containing only dCTP. Esp3I and ligase—two additional types of treatments with endonuclease Esp3I and DNA ligase, respectively, that are required for assembly of IgG-encoding sequences. IG-V, IGHG1 and 10b—sequences encoding variable and constant parts of IgG chain and protein 10b, respectively.

Restriction endonuclease Esp3I cuts DNA outside of its recognition sequence and generates four nucleotide-long cohesive 5'-overhanging ends. As depicted in FIG. 1, each Esp3I cleavage site in plasmids pVLentry-Hyg10 and pVHentry-Cm5 is unique. Therefore, fragments generated as a result of treatment of these plasmids with Esp3I and removal of the protein 10b-encoding sequence are not able to form a viable circular DNA unless the reaction is supplemented with a DNA fragment carrying appropriate sticky ends. As demonstrated in FIG. 2, the insertion of such a DNA fragment will occur only in one orientation, thus eliminating the need for following analysis of recombinant clones. The sequence encoding protein 10b of bacteriophage T7 functions as a safeguard, preventing re-assembly of the original vector.

In our vectors, its expression is controlled by the lactose promoter. Expression of this sequence is lethal to F plasmid-containing *E. coli* (17). Therefore, while our vectors are maintained in F-negative cells, cloning experiments require strains carrying F factor and, after transformation, cells are grown in the presence of IPTG and the corresponding antibiotic (ampicillin in the case of plasmid pVLentry-Hyg10 and chloramphenicol in the case of plasmid pVHentry-Cm5). Under these conditions, only cells carrying plasmids in which the protein 10b-encoding fragment has been substituted with a new insert survive.

Another important element of our vectors is a strong promoter that can direct transcription of the inserted sequence in mammalian cells. In vectors pVLentry-Hyg10 and pVHentry-Cm5, this role is served by the sequence from cytomegalovirus (CMV). However, we also designed plasmids in which a sequence from Rouse Sarcoma virus is used for this purpose. Plasmids pVLentry-Hyg10 and pVHentry-Cm5 are designed in such a way that transcripts initiated from the CMV promoter incorporate not only a sequence lying immediately downstream of the promoter, but also an Internal Ribosome Entry Site (IRES) and sequence for antibiotic resistance. In the case of plasmid pVLentry-Hyg10, this is resistance to Hygromycin B and, in the case of plasmid pVHentry-Cm5, this sequence confers resistance to G418. Presence of IRES makes synthesis of antibiotic-inactivating protein proportional to synthesis of protein encoded by the preceding portion of the transcript (immunoglobulin chain in the derivatives of these plasmids). This feature is not absolutely necessary for selection of stable transfectants (in some of our plasmids it is not present), however, it makes further maintenance of selected clones easier and opens opportunities for their further improvement.

In addition, design of our vectors allows simple combination of sequences encoding light and heavy chains of IgG in the same plasmid, which, in turn, ensures equal amounts of IgG chain-encoding sequences to be introduced into the cell during transfection. I-SceI recognition sites are one of elements enabling such combination.

I-SceI is a site-specific homing endonuclease that recognizes an 18 nucleotide-long sequence and generates DNAs with cohesive ends that can be used for cloning. Due to the length of the target sequence, its occurrence in the sequence encoding a variable domain of Ig is practically impossible. Therefore, using this enzyme enabled transfer of entire IgG-encoding sequences from one plasmid into another without destroying the integrity of these sequences. Non-symmetrical cohesive ends generated by the I-SceI 1 ensure that, in all generated plasmids, relative orientation of IgG-encoding sequences is the same. This feature allows further improvement of the reproducibility of IgG production experiments. As shown in FIG. 1, plasmids pVLentry-Hyg10 and pVHentry-Cm5 possess two I-SceI sites each. However, in plasmid pVLentry-Hyg10, I-SceI sites flank the Ig-encoding cassette, while in plasmid pVHentry-Cm5, both I-SceI sites are located on one side of the Ig-encoding cassette and flank the gene of the alpha peptide of beta-galactosidase (lacZ').

In addition to differences in location of I-SceI sites, both plasmids possess different antibiotic-resistance markers. Both of these plasmids use the same origin of replication for propagation in *E. coli* cells and therefore are not be able to coexist in the same cell. All of these features allow us to speed up the process of assembly and identification of the plasmid carrying both L- and H-chain encoding sequences. Indeed, a simple treatment of the mixture of L- and H-chain encoding plasmids with I-SceI and ligase generates the required hybrid plasmid. Similarly to one of its parents, this plasmid inherits the chloramphenicol-resistance gene, while, unlike this parent, it will not be able to produce the alpha-peptide of beta-galactosidase. As a result, only cells carrying the required plasmid and not the three others present in the mixture are able to form white colonies on the media supplemented with chloramphenicol, X-Gal and isopropyl-β-D-thiogalactopyranoside (IPTG).

Also disclosed are four derivatives of plasmid pVHentry-Cm5. These derivatives have all elements described above. However, instead of the sequence encoding the constant part of IgG heavy chain alone, all these plasmids contain sequences that encode fusions of the same part of IgG heavy chain with different polypeptides. One of them encodes a fusion with green fluorescent protein (GFP), the second—a fusion with luciferase from *Metridia longa* (MLuc) (18, 19), the third—a fusion with His-tag and a peptide that can be biotinylated by biotin ligase, and the fourth—a fusion with a polypeptide that specifically binds cellulose (20, 21).

Example 2

Figure 3:
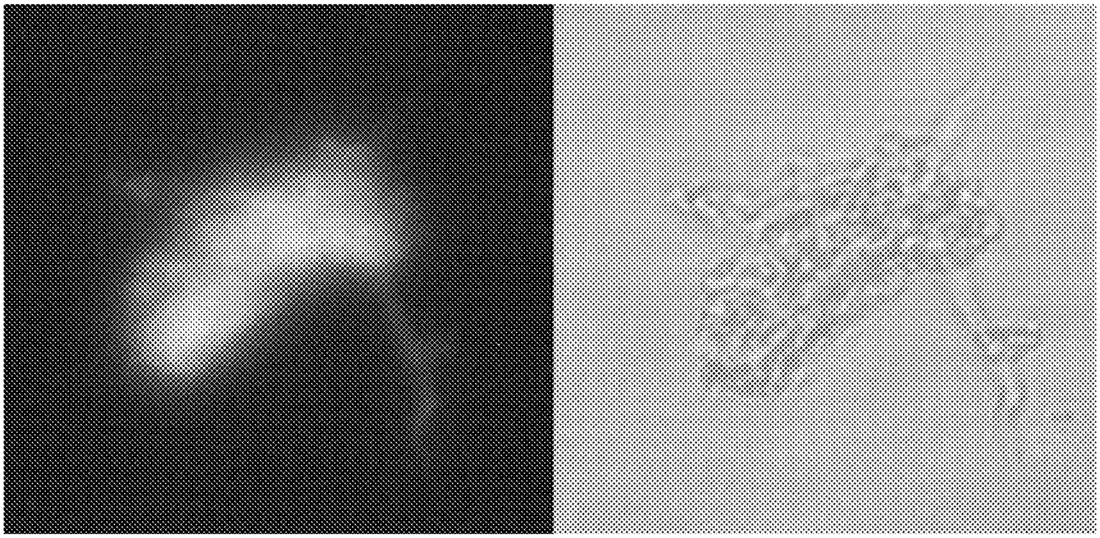
FIG. 3 shows the interaction of gfpBoNT/A-CH5 with its receptors on the surface of the neuroblastoma cell. gfp-BONT/A-CH5 was added to SH-SY5Y cells and after 15 minutes cells were subject to microscopy.

Isolation of Sequences Encoding Variable Domains of Light and Heavy Chains of IgG A single individual who was vaccinated with pentavalent *botulinum* toxoid vaccine six years prior received several boosts and served as a donor of blood cells. These cells were subject to fractionation on Ficoll gradient, enrichment on BD IMag™ Anti-human CD19 Particles-DM, and, finally, cell sorting. As a marker for cells producing anti-BoNT/A, we used a fusion between Green Fluorescent Protein and the receptor-recognizing domain of BoNT/A (gfpBoNT/A-CH5). This protein was constructed in our lab and, prior to use in cell sorting experiments, was tested for the ability to recognize specific receptors present in neuroblastoma cells (FIG. 3).

Cells simultaneously binding APC-Mouse-anti-human CD19 and gfpBoNT/A-CH5 were sorted into wells of a 96-well plate, one cell per well.

Isolated cells were used as a source of sequences encoding $V_H$- and $V_L$-regions. We have developed a procedure for rtPCR of these sequences that includes three steps: 1) reverse transcription of mRNA released from the cell by perfringolysin 0, 2) simultaneous amplification of cDNAs encoding $V_H$- and $V_L$-regions in the same tube by PCR and 3) re-amplification of sequences encoding each region in its own tube. Each step has its own set of primers. The whole procedure takes less than 8 hours. The number of cells that can be processed during this time is mostly limited by the capacity of the available thermo-cycler. Primers were designed based on the analysis of available human Ig-encoding sequences known in the art (8, 22). Primers used during each step are summarized in Table 1. Primers used in the re-amplification step were designed to introduce unique sequences, which can be converted into four-nucleotide-long cohesive ends compatible with ends generated by Esp3I restriction endonuclease in the corresponding vectors (see previous section), into the ends of amplified fragments. The conversion occurs as a result of treatment of purified DNA fragments by DNA polymerase T4 in the presence of dCTP as demonstrated in FIG. 2. The lack of restriction endonucleases at this stage guarantees that none of the sequences is lost due to the presence of sites for corresponding restriction endonucleases in some of them.

TABLE 1

Primers used for amplification of sequences encoding variable domains of human immunoglobulins.

| | | SEQ ID NO: |
|---|---|---|
| Primers used for reverse transcription | | |
| IgG-CHH | GGGGAAGAGGAAGACTGACGGTC | 2 |
| Cm1 | CAGTACTGCGATGAGTGGCA | 3 |
| Clv-3 | TGTGGCCTTGTTGGCTTG | 4 |
| Oligo dT | | |
| Primers used at the PCR amplification stage | | |
| pVk-1 | GAGTCAGDYYCDRYCAGGACACAGCATG | 5 |
| pVk-2 | AGACCCTGTCAGGACACAGCATAGACATG | 6 |
| pVk-3 | GGACTCCTCAGTTCACCTTCTCACAATG | 7 |
| pVk-4 | TGCTCAGTTAGGACCCAGAGGAACCATG | 8 |
| hIgGk-3 | TAATGGCCTAACACTCTCCCCTGTTGAAGCTCTT | 9 |
| IgGH-1 | TGAGVDMMGYWCHTCACCATGGACTG | 10 |
| IgGH-2 | ACTGAACACAGAGGACTCACCATGGA | 11 |
| IgGH-3 | CAGTGACTCCTGTGCCCCACCATGGACA | 12 |
| IgGH-4 | TTTCTGTCCTCCACCATCATGGGGTC | 13 |
| IgGH-5 | GCACTGAACACAGACCACCAATCATGG | 14 |
| IgG-CHH | GGGGAAGAGGAAGACTGACGGTC | 15 |
| M1 | CCTGGGAGCACAGCTCATCACCATGGA | 16 |
| M2 | CACTGAACACAGAGGACTCACCATGGA | 17 |
| M3 | CATGGACCTCCTGCACAAGAACATGAA | 18 |
| M4 | ACTGAACAGAGAGAACTCACCATGGA | 19 |
| Cm1 | CAGTACTGCGATGAGTGGCA | 20 |
| Vl1-5T7 | TTTAGGCCATGGCCTGGACCCCTCTCCTGCTC | 21 |
| Vl2-5T7 | TTTAGGCCATGGCCTGGACCKTTCTCCTCCTC | 22 |
| Vl3-5T7 | TTTAGGCCATGGCCTGGDCTCYKCTCCTYCTC | 23 |
| Vl4-5T7 | TTTAGGCCATGGCATGGCCAGCTTCCCTCTCCTCCTC | 24 |
| Vl5-5T7 | TTTAGGCCATGACCTGCTCCCCTCTCCTCCTC | 25 |
| Cl-3 | CCTGCAGCTCTAGTCTCCCGTGG | 26 |
| Primers used at the re-amplification stage | | |
| Vk-1/2-5T7 | TTTAGGCATGGACATGAGGGTCCCCGCTCAGCTCCTGG | 27 |
| Vk-3-5T7 | TTTAGGCATGGAAACCCCAGCGCAGCTTCT | 28 |
| Vk-4-5T7 | TTTAGGCATGGTGTTGCAGACCCAGGTCTT | 29 |
| hIgGk-3 | TAATGGCCTAACACTCTCCCCTGTT-GAAGCTCTT | 30 |
| IgG-CH | TATTGGCGAGCTGGCCTCTCACCAACTGTCTTGTCCACCTTGGTGTTG | 31 |
| Vh-1-3T7 | CACTGGAGACGGTGACCAGBGTBCCYTGKC-CCCA | 32 |
| Vh-1-3T75 | TATTGGCactcacggaagagacggtgaccagBgtBccYtg | 33 |
| Vh-1-5T7 | TATAGccatggactggacctgga | 34 |
| Vh-2-5T7 | TATAGccatggacatactttgttccac | 35 |
| Vh-3-5T7 | TATAGccatggagtttgggctgagc | 36 |
| Vh-4-5T7 | TATAGccatgaaacacctgtggttctt | 37 |
| Vh-5-5T7 | TATAGccatggggtcaaccgccatcct | 38 |
| Vh-6-5T7 | TATAGccatgtctgtctccttcctcat | 39 |
| Vh-7-5T7 | TATAGccatggaatttgggcttagct | 40 |
| Vh-8-5T7 | TATAGccatggaattggggctgag | 41 |
| Vh-1-3T75 | TATTGGCactcacggaagagacggtgaccagBgtBccYtg | 42 |
| Vm-1-5T7 | TATAGaccatggactggacctggaggttcct | 43 |
| Vm-2-5T7 | TATAGaccatggagtttgggctgagctgggt | 44 |
| Vm-3-5T7 | TATAGaacatgaaacacctgtggttcttcct | 45 |
| Vh-1-3T75 | TATTGGCactcacggaagagacggtgaccagBgtBccYtg | 46 |
| V11-5T7 | TTTAGGccatggcctggacccctctcctgctc | 47 |
| V12-5T7 | TTTAGGccatggcctggacckttctcctcctc | 48 |
| V13-5T7 | TTTAGGccatggcctggdctcykctcctyctc | 49 |
| V14-5T7 | TTTAGGccatggcatggccagcttccctctcctcctc | 50 |
| V15-5T7 | TTTAGGccatgacctgctcccctctcctcctc | 51 |
| hIgG1-3 | taatggcCTATGAACATTCTGTAGGGGCCAC | 52 |

In the end, only 24% of originally sorted cells produced sequences for both $V_H$- and $V_L$-regions. This may sound like a relatively low success rate. However, given the potential of collecting hundreds of cells and the ability to process them in just few days, this allows the accumulation of tens of pairs of sequences for further antibody assembly. In the future, we expect to increase this rate by including anti-CD27 or anti-B220 monoclonal antibodies in the cell sorting protocol and thus increase the number of those among selected cells that produce antibodies versus those that may just absorb them.

Sequencing of 11 pairs of isolated DNA fragments revealed that practically all pairs were unique. Even when two pairs had one identical chain, the second chains were different (Sequences of variable domains of light and heavy chains are listed in Appendix 2 and 3).

Example 3

Introduction of Designed IgG-Encoding Constructs into Mammalian Cells and Evaluation of Conditions for Efficient IgG Production Eight pairs of isolated sequences were incorporated into the previously-described vectors and the resulting plasmids were introduced into CHO and HEK cells. ELISA registered accumulation of human antibodies in media of both of these cultures. In isolated stable cell lines, the level of production varied but did not exceed 1-2 μg/ml (the level of production was determined on the basis of the amount of anti-BoNT/A purified from 100 ml of culture media—will be described below). In our experience, HEK cells proved to be more robust and capable of producing more antibodies from the same volume of media. Also, these cells were easier to adapt to grow and produce IgGs in the serum-free media. This is why, in most of our later analyses, we preferred to use HEK cells.

Figure 4:
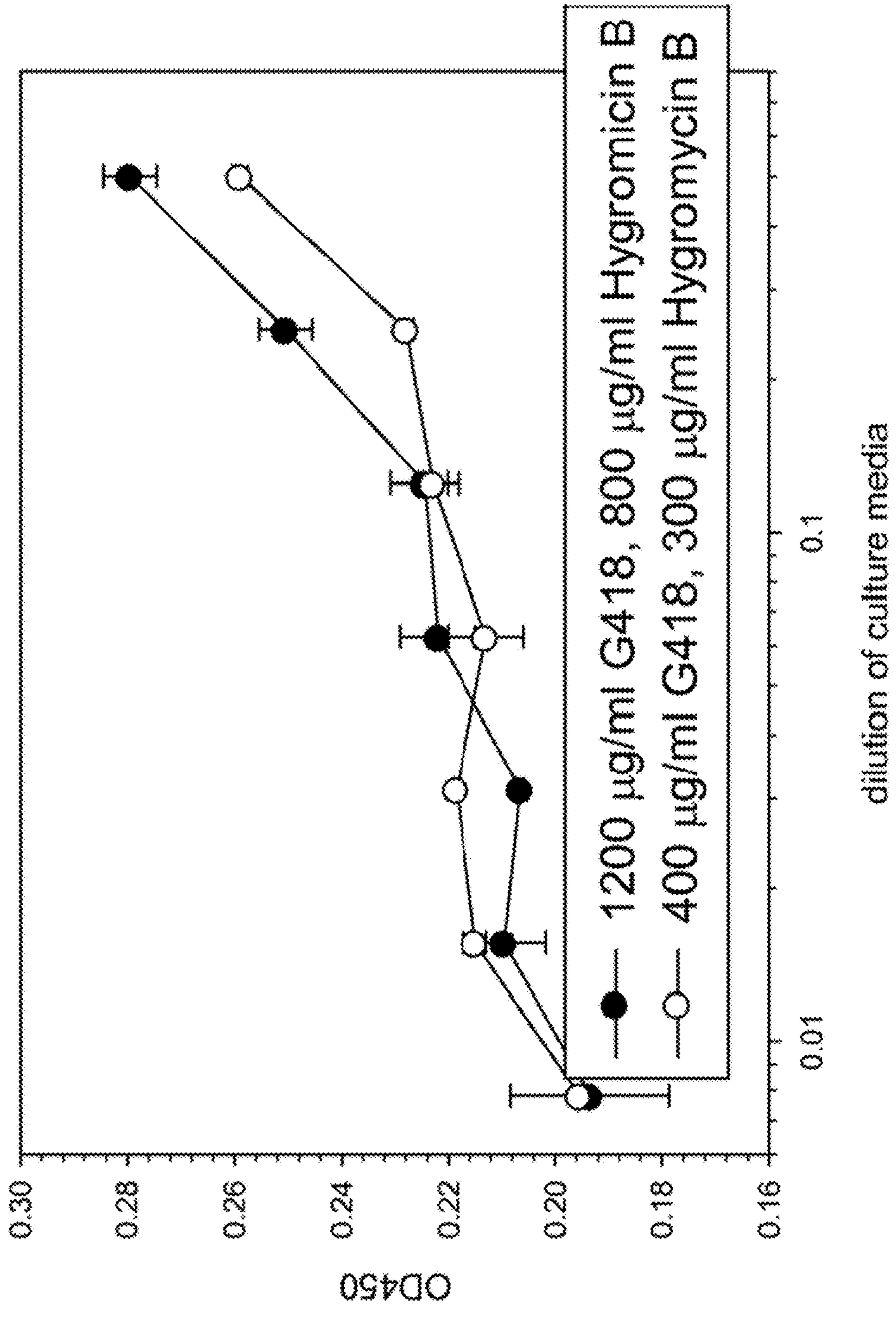
FIG. 4 shows the effect of antibiotic resistance selection on production of human IgG by CHO cells. Dilutions of media from the original IgG-producing culture and its derivative selected at higher concentrations of antibiotics were loaded into wells of a 96-well plate covered with BoNT/A-CH. Immobilized IgGs were visualized by treatment of wells with biotinylated anti-human antibodies followed by treatment with streptavidin-horse radish peroxidase and 1-STEP™ Slow TMB-ELISA (Pierce, Inc.).

To select clones with higher production, we decided to use correlation between translations of sequences encoding light and heavy chains of IgGs and those encoding antibiotic-inactivating proteins, built into our system and discussed earlier. Specifically, by gradually increasing amounts of antibiotics in the culture media, we were able to select cell lines whose resistance to antibiotics is 3-4 times higher than resistance of originally selected cultures. As demonstrated in FIG. 4, ELISA revealed that cells with increased resistance to antibiotics did not produce substantially more immunoglobulins than cells possessing a lower level of resistance to these antibiotics.

This data suggest that the bottleneck of production lies somewhere at the post-translational level. The conventional way for identifying cells with increased production of IgGs is a limiting dilution cloning. The low throughput nature of this method significantly limits the number of clones that can feasibly be screened. We tested whether fluorescence activated cell sorting (FACS) can be used to increase throughput. As a marker for IgG-producing cells, we used previously mentioned gfpBoNT/A-CH5. Cells were released from the solid support via treatment with trypsin and washed two times with fresh RPMI media to remove trypsin. Then, cells were incubated in RPMI media for 1 hour, co-incubated with gfpBoNT/A-CH5 for 10 minutes and subject to FACS. Out of the 1% of cells with the highest fluorescence intensity, corresponding to the highest antibody production rates, single cells were sorted directly into 96-well plates at one cell per well. One plate was assembled per each IgG-producing cell line. Table 2 demonstrates that we were able to find clones with increased production of IgG-luciferase hybrids for five cell lines out of seven used in the experiment. These results clearly demonstrate the potential of FACS for further development of cell lines producing high quantities of IgGs.

TABLE 2

Production of IgG-MLuc by original cultures and individual clones selected from these cultures

| Original culture | Luminescence | Clone | Luminescence |
|---|---|---|---|
| HEK-1HL-MLuc | 657,148 | 1E7 | 1,641,522 |
| HEK-7HL-MLuc | 1,387,980 | 7B8 | 8,013,339 |
| HEK-8HL-MLuc | 981,702 | 8E8 | 3,783,486 |
| HEK-9HL-MLuc | 1,991,512 | 9F6 | 2,778,794 |
| HEK-14HL-MLuc | 951,132 | 14G11 | 721,576 |
| HEK-15HL-MLuc | 104,466 | 15F2 | 594,677 |
| HEK-41HL-MLuc | 3,274,119 | 41C9 | 3,163,750 |

Production of the Chimera IgGs and their Characterization.

As result of the reasons mentioned in the previous section, most of the IgG constructs were purified from culture media of HEK cells. Our analysis of accumulation of luciferase activity in the culture media of two cell lines encoding IgG-MLuc fusions revealed that the accumulation in both continued for seven days. Therefore, all HEK cultures were grown for seven days in the same media, which was then passed through a column containing the hybrid between staphylococcal protein A and streptococcal protein G. In the case of CHO cells, the media was collected after three days. Elution of absorbed IgGs was achieved by a buffer change to 0.1 M glycine HCl (pH 2.3). Immediately after elution, the pH of collected fractions was increased by addition of 1 M Tris-Base. Then, fractions were subjected to buffer exchange and concentrated by ultrafiltration.

Figure 5:
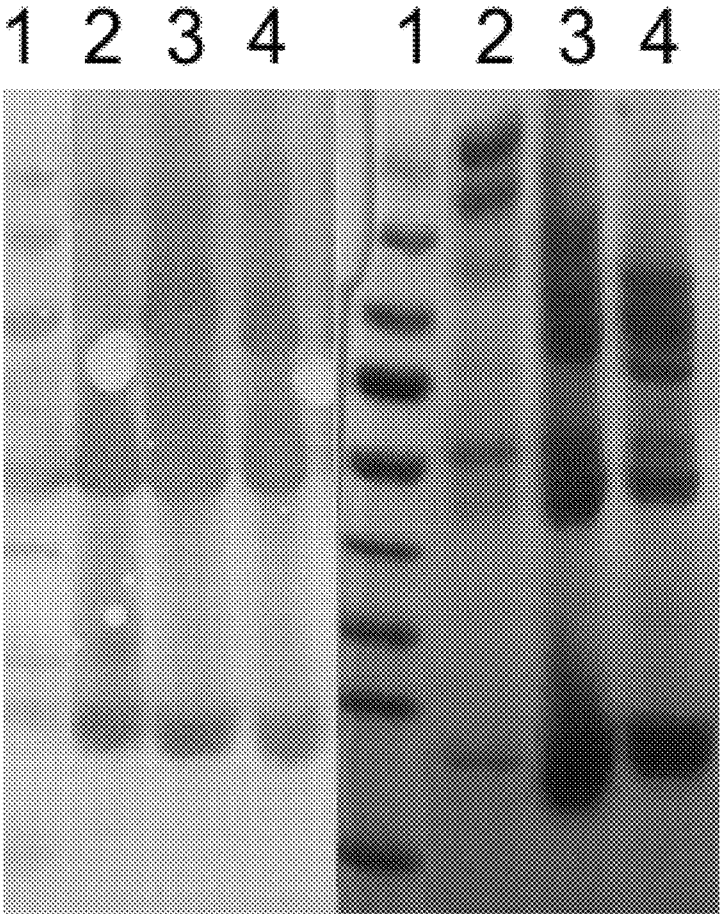
FIG. 5 shows the composition of proteins purified from cell culture media. Proteins were separated by SDS-PAGE and were either stained by Coomassie (right portion) or transferred onto a nitrocellulose membrane and treated with biotinylated anti-human IgG. Bound antibodies were visualized by treatment with streptavidin-horse radish peroxidase conjugate and 1-STEP™ Slow TMB-ELISA (Pierce, Inc.) and 1-STEP™ Ultra TMB (Pierce, Inc.). Line 1 contains pre-stained molecular weight markers from Fermentas, Inc.; 2—protein purified from media of cells generated by transfection with plasmid encoding both chains of IgG; 3—protein from cells transfected with plasmid encoding human IgG whose heavy chain is fused with GFP; 4—protein from cells transfected with plasmid encoding human IgG whose heavy chain is fused with MLuc.

In addition to IgGs alone, we purified fusions of these IgGs with luciferase, GFP, and His-tag connected to the peptide that serves as a target for biotin ligase (BirA). Analysis confirmed the presence of polypeptides with expected molecular weights and recognized by anti-human antibodies in isolated fractions (FIG. 5).

Fractions with IgG-MLuc fusions produced light in the presence of luciferase's substrate-coelenterazine. The IgG-GFP fusion emitted the green light characteristic of GFP upon illumination with UV light. Finally, the IgG fusion with His-tag and BirA substrate interacted with Ni-column and, after treatment with BirA in the presence of biotin and ATP, was recognized by streptavidin-alkaline phosphatase substrate (data not presented).

Figure 6:
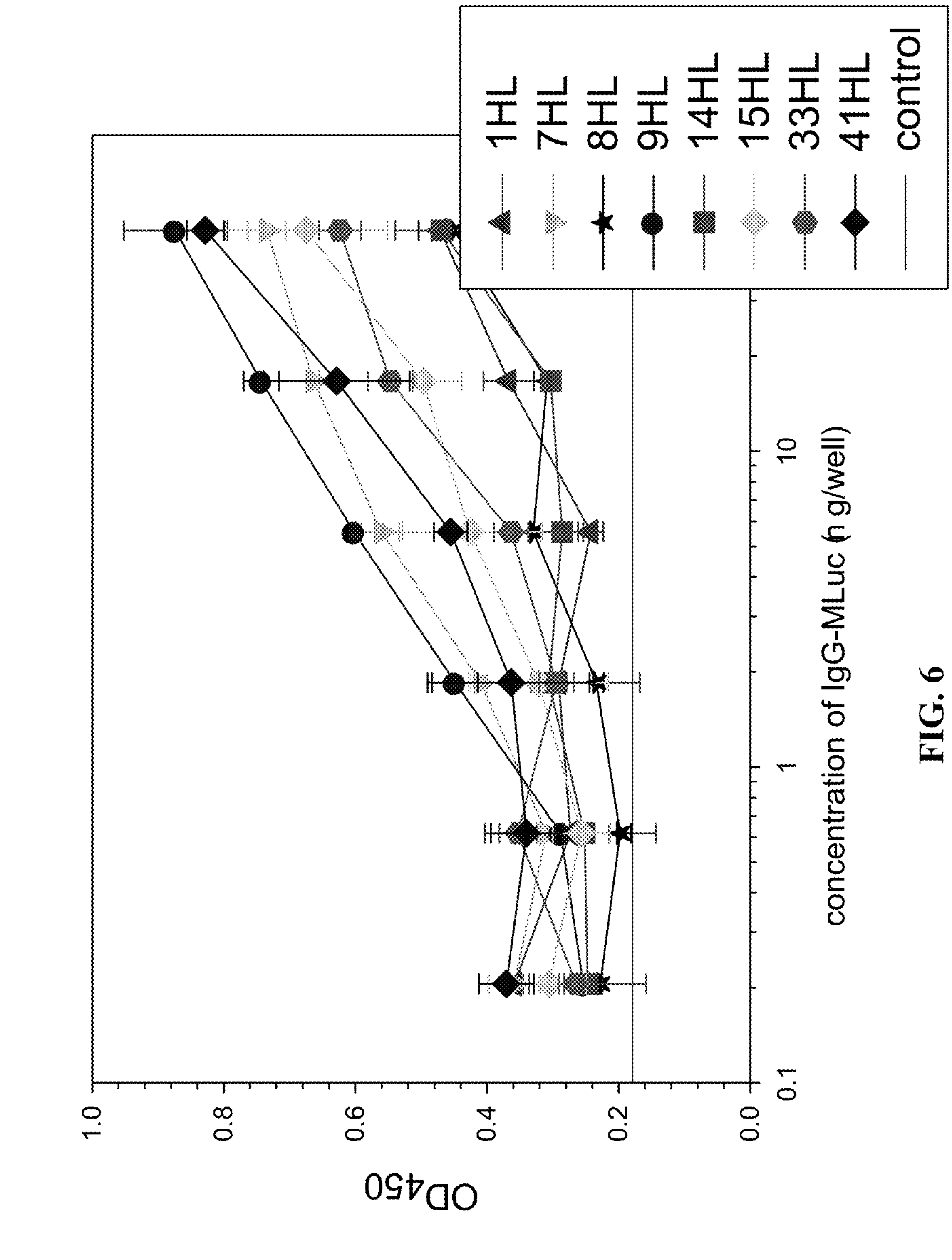
FIG. 6 shows the interaction of purified human IgGs with receptor-recognizing domain of BoNT/A. Dilutions of IgGs purified from media of isolated cell cultures were loaded into wells of a 96-well plate covered with BoNT/A-CH5. Immobilized IgGs were visualized by treatment of wells with biotinylated anti-human antibodies followed by treatment with streptavidin-horse radish peroxidase and Metal Enhanced DAB Substrate Kit (Pierce, Inc.). The control line corresponds to the highest $OD_{450}$ of wells that were treated the same way as others but did not contain BoNT/A-CH5.

ELISA revealed that out of eight different IgGs that we purified, all eight recognize the receptor-recognizing domain of BoNT/A (FIG. 6). This data suggests that practically all isolated cells from which we were able to recover IgG-encoding sequences produced BoNT/A-specific antibodies.

IgGs were recognized by hybrid proteins composed of staphylococcal protein A, streptococcal protein G and *Metridia longa* luciferase (spAG-MLuc and spAG-ΔN-MLuc) and developed in our lab (sequences of plasmids encoding these proteins are presented in Appendix 4). These hybrids allowed quantitative monitoring of IgG present in wells of 96-well plate. Hybrid spAG-MLuc possessed luciferase activity only when it was purified from culture media of mammalian cells. Hybrid spAG-ΔN-MLuc possesses luciferase activity irrespective to where it was expressed, *E. coli* or mammalian cells.

Examples 1-3 demonstrate 1) the number of peripheral blood cells encoding specific IgGs in blood and the efficiency of cell sorting protocols used are sufficient to produce hundreds of cells that can serve as a source of Ig-encoding sequences; 2) the methods disclosed herein permit reliable isolation of cDNA encoding variable domains of both Ig-chains from ⅕ of all isolated individual lymphocytes; 3) practically all isolated cDNA pairs encode IgG specific to the antigen used in the cell sorting procedure; 4) the expression vectors described herein are suitable for high throughput assembly of plasmids encoding both full size human IgGs, as well as their derivatives carrying polypeptides that allow monitoring or/and specific binding of these IgGs to other molecules; 5) the vectors allow efficient selection of cells producing both IgG chains; and 6) FACS can be used as an efficient tool allowing selection of clones producing increased quantities of IgGs and their derivatives.

Accordingly, the compositions and methods described herein are useful in methods comprising one or more of these aspects.

Example 4

Construction and Expression of Libraries of Anti-*Botulinum* Chimeras that Recognize Regions of BoNT/a This example demonstrates the construction and use of libraries of anti-*botulinum* chimeras that recognize regions of BoNT/A.

First, we will use conventional methods of gene engineering to create fusions of corresponding domains with GFP. Similar to previously-mentioned gfpBoNT/A-CH5, these fusions will be used as markers for lymphocytes producing antibodies specific for catalytic and transport domains of BoNT/A. As a source of lymphocytes, we will use white blood cells from the blood of an immunized individual that were generated and tested previously, and preserved under liquid nitrogen. It has been demonstrated that such cells can be used as a source of immunoglobulin-encoding sequences (25). These cells will be subjected to enrichment on BD IMag™ Anti-human CD19 Particles-DM and then sorted into wells of a 96-well plate, one cell per well. Prior to FACS, cells will be labeled with APC Mouse Anti-Human CD19 (BD Biosciences) and the corresponding GFP-BoNT/A fusion. To increase the level of discrimination of IgG-producing cells from those that do not produce, but instead absorb them from serum, we will include an additional marker—memory B cell marker. Bleesing and Fleisher reported that human B cells expose either B220 or CD27 on their surface [30]. Therefore, as the third component of the cell labeling mixture, we will use anti-CD27 (Ancell Co.) and/or anti-B220 (Beckman Coulter) monoclonal antibodies, each conjugated to R-Phycoerythrin.

Isolated cells will be used as a source of sequences encoding $V_H$- and $V_L$-regions. Isolation and further handling of these sequences will be done according to protocols described above. At this stage, the goal will be to isolate 10-20 $V_H$- and $V_L$-encoding pairs that have unique sequences per each BoNT/A domain.

Unique $V_H$- and $V_L$-encoding pairs will be used to assemble and produce human/human IgG chimeras as described above.

Example 5

Identification of IgGs and their Combinations that can Neutralize Toxic Activity of BoNT/A This Example demonstrates the identification of chimeric IgG antibodies with the capacity to neutralize toxicity of BoNT/A using phage display.

Choosing $V_H$- and $V_L$-encoding pairs with unique sequences does not guarantee that they will recognize different epitopes. Therefore, prior to conducting expensive toxin neutralizing experiments, we will sort developed IgGs according to their epitope specificities. For this, we will use phage display known in the art. This technology involves a library of random peptides. Sequences of these peptides are incorporated in the region of the phage genome that encodes the capsid protein. As a result, each phage particle in the library encodes and exposes on its surface only one type of peptide. We previously demonstrated that incubation of such a library with immobilized polyclonal antibodies raised against BoNT/A allows isolation of phage particles that encode peptides mimicking BoNT/A epitopes (mimetics).

We will use a similar approach to sort developed IgGs according to their epitope specificities. Specifically, each developed IgG will be purified and immobilized on a solid support. Then, each immobilized IgG will be co-incubated with the phage display library MD-12™ (Alpha Universe, LLC). Phages that do not bind to IgG will be removed by washing and those bound to IgG will be released and grown on appropriate host cells. Following this amplification, phages will be subjected to two additional cycles of the above-described screening procedure. According to our previous experience, practically all phages released after the third cycle will possess affinity to the IgG used in selection. To ensure that selected phages carry mimetics of BoNT/A, we have to prevent isolation of phages that interact with IgG parts other than the antigen-binding region. In order to do this, phages will be subject to depletion with human naïve serum every time prior to incubation with immobilized developed IgG. After mixing with phages, components of human naïve serum, as well as phage particles bound to them, will be removed by addition of magnetic beads with immobilized staphylococcal protein A-streptococcal protein G hybrid to the mixture.

Individual phages carrying BoNT/A mimetics will be used for characterization of developed IgGs. Specifically, each IgG will be immobilized on wells of a 96-well plate and each immobilized IgG will be incubated with all chosen mimetic-exposing phages. Wells with bound phages will be identified using M13 phage-specific antibodies conjugated with horse radish peroxidase (GE Healthcare) and 1-Step™ Slow TMB-ELISA (PIERCE). IgGs interacting with the same phage will be considered as recognizing the same epitope.

In addition to classification of developed IgGs according to their epitope (actually, mimetic) specificity, we will characterize these IgGs according to the nature of recognized epitopes (linear or structural). In these experiments, we will compare interaction of developed IgGs with corresponding recombinant domains subjected or not subjected to denaturing treatment. For this, corresponding BoNT/A fragments will be subjected to native or SDS polyacrylamide gel electrophoresis, transferred onto a nitrocellulose membrane and probed with each chosen IgG separately. Then, filters will be treated with biotinylated anti-human IgGs, followed by treatment with streptavidin-horse radish conjugate and Metal Enhanced DAB Substrate Kit (Pierce, Inc.). IgGs recognizing both forms of BoNT/A fragment will be considered as recognizing linear epitopes. Those that recognize only BoNT/A fragments not subjected to denaturing conditions will be considered as recognizing structural epitopes.

The information about the nature of the recognized epitope will not only be used to verify epitope-based grouping of IgGs, but also to gain information about locations of corresponding epitopes on the BoNT/A molecule. Specifically, our previous experience suggests that, in the case of mimetics of linear epitopes, some similarities between sequences of these mimetics and the BoNT/A sequence can be observed. Such similarities may be used as indicators of the location of the corresponding epitope in the structure of the molecule.

After developed IgGs are classified and grouped, representatives from each group will be tested for the ability to neutralize BoNT/A.

It has been demonstrated that even when individual monoclonal antibodies do not have substantial protective activity, their combination may have such activity (24). This is why the analysis will include testing of the BoNT/A-neutralization potential of each chosen IgG separately and, then, testing of such potential for selected groups of IgGs.

The goal of this analysis will be to identify IgGs or their combinations that will be able to protect mice from at least 1000 minimal doses that are lethal to a fifty percentage of mouse ($MLD_{50}$) of BoNT/A. In addition, the aim will be to determine which among three regions of the BoNT/A molecule (catalytic, transport, or receptor-recognizing) contains the highest number of protective epitopes. This information will be instrumental for development of antibodies capable of neutralizing other serotypes of BoNTs.

Example 6

Development of Human/Human IgG Chimeras Capable of Neutralizing BoNT/B

This Example demonstrates the development of human/human IgG chimeras capable of neutralizing BoNT/B.

Previously, we demonstrated that different serotypes of BoNTs have similar epitopes and information about locations of epitopes in one serotype can be used to predict locations of epitopes in other serotypes (26). We will use this phenomenon to speed up the process of development of IgGs capable of neutralizing BoNT serotype B. Specifically, instead of developing IgGs to the whole molecule of BoNT/B, we will focus on just one region. This region will be the same one as that revealed in BoNT/A as possessing the most potent protective epitopes. We will create a fusion between GFP and a fragment of BoNT/B after the targeted region of BoNT/B is determined. This fusion will be used to isolate corresponding lymphocytes from the same cryopreserved fractions of blood cells mentioned earlier. FACS and following isolation of cDNAs, their PCR, cloning, expression of assembled sequences, purification of IgGs, and analysis of their protective properties will be done the same way as described in the previous two sections.

As in case with BoNT/A, our goal will be to identify IgGs or their combinations that will ensure protection of mice from at least 1000 $MLD_{50}$.

Optimization of Protocols for Production of Chosen Chimeras.

The ability to efficiently produce developed protective IgGs is a key element for the system to become a commercially viable. Earlier analysis of different monoclonal antibody-producing cell lines conducted by O'Callaghan and coauthors revealed that each cell line had its own bottleneck, limiting production of antibodies (27). This research supports the approach for selection of high producers from population of cells already producing IgG. This approach has been successfully used by many groups including ourselves. However, such selection often requires multiple cycles and is very lengthy. Development of a strain with bottlenecks that are widened or even removed will substantially increase the potential for high throughput development of cells producing high quantities of IgGs. Recent reports of successful increase of antibody production via introduction of specific DNA sequences into the cells suggest the possibility of such an approach (28-30).

To create a cell line originally capable of producing increased quantities of IgGs, we will produce IgG derivatives carrying different polypeptides on the C-termini of heavy chains. Specifically, we will engineer a plasmid encoding one of the anti-BoNT/A IgGs fused with the trans-membrane domain of platelet derived growth factor receptor (31). This plasmid will allow generation of transiently transfected cells expressing IgG anchored in the cell membrane. Such cells will be stained with gfpBoNT/A-CH5 and subjected to FACS. Individual cells carrying the highest levels of fluorescent label will be sorted into wells of a 96-well plate and allowed to grow. We anticipate that the majority of such cells will lose IgG-encoding plasmids. As a result, such cells will stop producing the corresponding IgG derivative and antibiotic-inactivating enzymes encoded by the plasmid. Cell lines grown from such cells will be transfected again. This time, we will use the plasmid encoding IgG-luciferase hybrid formed by different $V_H$- and $V_L$-pair that was used in the previous transfection. Parental cell lines for those transient transfectants whose culture media contains the highest amounts of luciferase will be tested further for the ability to produce high quantities of other types of IgG-luciferase fusions. Eventually, we expect to be able to isolate a cell line that will produce increased quantities if IgGs irrespective of sequences of their $V_H$- and $V_L$-regions.

To increase the success rate of the above-described selection, we will use a cell line whose diversity will be increased by chemical mutagenesis. Further, to eliminate difficulties associated with sorting originally adherent cells, we will use FREESTYLE™ CHO-S® cells (Invitrogen, Inc.). This cell line has been adapted to grow in suspension in serum-free media. The latter feature will beneficial for future production of antibodies.

Even with a developed host cell line capable of increased production of IgGs, we do not exclude the need for additional selection of super-producers among created IgG-producing cells. Traditionally, such selection is done by Limiting dilution cloning, which is a very labor-intensive process. We will use FACS protocols for the isolation of cells that bind the highest amounts of the label after a very short exposure to it from the population, followed by isolation of cells that lose this label faster than others.

As a result of these activities, we will not only generate cell lines producing high quantities of chosen IgGs, but will also determine the best way to efficiently develop new IgG-producing cell lines.

REFERENCES

1. Smith, K., Garman, L., Wrammert, J., Zheng, N., Capra, J. D., and Wilson, P. C. (2009) *Nat Protoc.* 4, 372-384

2. Amon, S. S., Schechter, R., Inglesby, T. V, Henderson, D. A., Bartlett, J. G., Ascher, M. S., Eitzen, E., Fine, A. D., Hauer, J., Layton, M., Lillibridge, S., Osterholm, M. T., O'Toole, T., Parker, G., Perl, T. M., Russell, P. K., Swerdlow, D. L., and Tonat, K. (2001) *Jama* 285, 1059-1070 [online] http://www.ncbi.nlm.nih.gov/entrez/query.fcgi?cmd=Retrieve&db=PubMed&dopt=Citation&list_uids=11209178.

3. St John, R., Finlay, B., and Blair, C. (2001) *The Canadian journal of infectious diseases=Journal canadien des maladies infectieuses* 12, 275-84 [online] http://www.pubmedcentral.nih.gov/articlerender.fcgi?artid=2094836&tool=pmcentrez&rendertype=abstract (Accessed Nov. 23, 2012).

4. Smith, L. A., and Rusnak, J. M. (2007) *Critical reviews in immunology* 27, 303-18 [online] http://www.ncbi.nlm.nih.gov/pubmed/18197811 (Accessed Nov. 21, 2012).

5. Notice of CDC's discontinuation of investigational pentavalent (ABCDE) *botulinum* toxoid vaccine for workers at risk for occupational exposure to *botulinum* toxins (2011) *MMWR Morb Mortal Wkly Rep* 60, 1454-1455 [online] http://www.ncbi.nlm.nih.gov/entrez/query.fcgi?cmd=Retrieve&db=PubMed&dopt=Citation&list_uids=22031218.

6. Clayton, M. A., Clayton, J. M., Brown, D. R., and Middlebrook, J. L. (1995) *Infect Immun* 63, 2738-42.

7. Black, R. E., and Gunn, R. A. (1980) *The American journal of medicine* 69, 567-70 [online] http://www.ncbi.nlm.nih.gov/pubmed/7191633 (Accessed Nov. 23, 2012).

8. Wang, X., and Stollar, B. D. (2000) 244, 217-225

9. Orlandi, R., Gussow, D. H., Jones, P. T., and Winter, G. (1992) *Biotechnology* 24, 527-31.

10. Beidler, C. B., Ludwig, J. R., Cardenas, J., Phelps, J., Papworth, C. G., Melcher, E., Sierzega, M., Myers, L. J., Unger, B. W., and Fisher, M. (1988) *J Immunol* 141, 4053-60.

11. Zhao, Y., and Hammarström, L. (2003) *Immunology* 108, 288-95 [online] http://www.pubmedcentral.nih.gov/articlerender.fcgi?artid=1782897&tool=pmcentrez&rendertype=abstract (Accessed Nov. 14, 2012).

12. CDC (2011) *MMWR. Morbidity and mortality weekly report* 60, 1454-5 [online] http://www.ncbi.nlm.nih.gov/pubmed/22031218 (Accessed Aug. 24, 2012).

13. Beidler, C. B., Ludwig, J. R., Cardenas, J., Phelps, J., Papworth, C. G., Melcher, E., Sierzega, M., Myers, L. J., Unger, B. W., and Fisher, M. (1988) *Journal of immunology* (Baltimore, Md.: 1950) 141, 4053-60 [online] http://www.ncbi.nlm.nih.gov/pubmed/3141512 (Accessed Nov. 24, 2012).

14. Gillies, S. D., Lo, K. M., and Wesolowski, J. (1989) *Journal of immunological methods* 125, 191-202 [online] http://www.ncbi.nlm.nih.gov/pubmed/2514231 (Accessed Nov. 24, 2012).

15. Norderhaug, L., Olafsen, T., Michaelsen, T. E., and Sandlie, I. (1997) *Journal of immunological methods* 204, 77-87 [online] http://www.ncbi.nlm.nih.gov/pubmed/9202712 (Accessed Nov. 24, 2012).

16. Liu, A. Y., Mack, P. W., Champion, C. I., and Robinson, R. R. (1987) *Gene* 54, 33-40 [online] http://www.ncbi.nlm.nih.gov/pubmed/3111940 (Accessed Nov. 24, 2012).

17. Schmitt, C. K., and Molineux, I. J. (1991) *Journal of bacteriology* 173, 1536-43 [online] http://www.pubmedcentral.nih.gov/articlerender.fcgi?artid=207293&tool=pmcentrez&rendertype=abstract (Accessed Nov. 10, 2012).

18. Markova, S. V, Golz, S., Frank, L. A., Kalthof, B., and Vysotski, E. S. (2004) *The Journal of biological chemistry* 279, 3212-7 [online] http://www.ncbi.nlm.nih.gov/pubmed/14583604 (Accessed Nov. 24, 2012).

19. Markova, S. V, Burakova, L. P., and Vysotski, E. S. (2012) *Biochemical and biophysical research communications* 417, 98-103 [online] http://www.ncbi.nlm.nih.gov/pubmed/22138240 (Accessed Jul. 20, 2012).

20. Shpigel, E., Goldlust, a, Efroni, G., Avraham, a, Eshel, a, Dekel, M., and Shoseyov, O. (1999) *Biotechnology and bioengineering* 65, 17-23 [online] http://www.ncbi.nlm.nih.gov/pubmed/10440667.

21. Cao, Y., Zhang, Q., Wang, C., Zhu, Y., and Bai, G. (2007) *Journal of chromatography. A* 1149, 228-35 [online] http://www.ncbi.nlm.nih.gov/pubmed/17391680 (Accessed Jul. 20, 2012).

22. Smith, K., Garman, L., Wrammert, J., Zheng, N., Capra, J. D., Ahmed, R., and Wilson, P. C. (2009)

23. Adekar, S. P., Takahashi, T., Jones, R. M., Al-Saleem, F. H., Ancharski, D. M., Root, M. J., Kapadnis, B. P., Simpson, L. L., and Dessain, S. K. (2008) *PloS one* 3, e3023 [online] http://dx.plos.org/10.1371/journal.pone.0003023 (Accessed Nov. 15, 2012).

24. Nowakowski, A., Wang, C., Powers, D. B., Amersdorfer, P., Smith, T. J., Montgomery, V. A., Sheridan, R., Blake, R., Smith, L. A., and Marks, J. D. (2002) *Proceedings of the National Academy of Sciences of the United States of America* 99, 11346-50 [online] http://www.pubmedcentral.nih.gov/articlerender.fcgi?artid=123259&tool=pmcentrez&rendertype=abstract (Accessed Nov. 25, 2012).

25. Hansen, A., Reiter, K., Dorner, T., and Pruss, A. (2005) *Cell Tissue Bank* 6, 299-308 [online] http://www.ncbi.nlm.nih.gov/entrez/query.fcgi?cmd=Retrieve&db=PubMed&dopt=Citation&list_uids=16308769.

26. Zdanovsky, A., Zdanovsky, D., and Zdanovskaia, M. (2012) *Toxicon: official journal of the International Society on Toxinology* 60, 1277-86 [online] http://www.ncbi.nlm.nih.gov/pubmed/22922018 (Accessed Nov. 4, 2012).

27. O'Callaghan, P. M., McLeod, J., Pybus, L. P., Lovelady, C. S., Wilkinson, S. J., Racher, A. J., Porter, A., and James, D. C. (2010) *Biotechnology and bioengineering* 106, 938-51 [online] http://www.ncbi.nlm.nih.gov/pubmed/20589672 (Accessed Nov. 26, 2012).

28. Florin, L., Pegel, A., Becker, E., Hausser, A., Olayioye, M. A., and Kaufmann, H. (2009) *Journal of biotechnology* 141, 84-90 [online] http://www.ncbi.nlm.nih.gov/pubmed/19428735 (Accessed Nov. 16, 2012).

29. Peng, R., Abellan, E., and Fussenegger, M. (2011) *Biotechnol Bioeng* 108, 611-620

30. Peng, R.-W., and Fussenegger, M. (2009) *Biotechnology and bioengineering* 102, 1170-81 [online] http://www.ncbi.nlm.nih.gov/pubmed/18989903 (Accessed Nov. 27, 2012).

31. Zhou, C., Jacobsen, F. W., Cai, L., Chen, Q., and Shen, W. D. *mAbs* 2, 508-18 [online] http://www.pubmedcentral.nih.gov/articlerender.fcgi?artid=2958572&tool=pmcentrez&rendertype=abstract (Accessed Nov. 16, 2012).

APPENDIX 1

Nucleotide sequences of constructed plasmids(SEQ ID NOs: 53-58, in order of appearance).

```
pVLentry-Hyg10:
   1     TGGCCCGCCT GGCTGACCGC CCAACGACCC CCGCCCATTG ACGTCAATAA TGACGTATGT TCCCATAGTA ACGCCAATAG GGACTTTCCA TTGACGTCAA
         ACCGGGCGGA CCGACTGGCG GGTTGCTGGG GGCGGGTAAC TGCAGTTATT ACTGCATACA AGGGTATCAT TGCGGTTATC CCTGAAAGGT AACTGCAGTT
 101     TGGGTGGAGT ATTTACGGTA AACTGCCCAC TTGGCAGTAC ATCAAGTGTA TCATATGCCA AGTACGCCCC CTATTGACGT CAATGACGGT AAATGGCCCG
         ACCCACCTCA TAAATGCCAT TTGACGGGTG AACCGTCATG TAGTTCACAT AGTATACGGT TCATGCGGGG GATAACTGCA GTTACTGCCA TTTACCGGGC
 201     CCTGGCATTA TGCCCAGTAC ATGACCTTAT GGGACTTTCC TACTTGGCAG TACATCTACG TATTAGTCAT CGCTATTACC ATGGTGATGC GGTTTTGGCA
         GGACCGTAAT ACGGGTCATG TACTGGAATA CCCTGAAAGG ATGAACCGTC ATGTAGATGC ATAATCAGTA GCGATAATGG TACCACTACG CCAAAACCGT
 301     GTACATCAAT GGGCGTGGAT AGCGGTTTGA CTCACGGGGA TTTCCAAGTC TCCACCCCAT TGACGTCAAT GGGAGTTTGT TTTGGCACCA AAATCAACGG
         CATGTAGTTA CCCGCACCTA TCGCCAAACT GAGTGCCCCT AAAGGTTCAG AGGTGGGGTA ACTGCAGTTA CCCTCAAACA AAACCGTGGT TTTAGTTGCC
 401     GACTTTCCAA AATGTCGTAA CAACTCCGCC CCATTGACGC AAATGGGCGG TAGGCGTGTA CGGTGGGAGG TCTATATAAG CAGAGCTGGT TTAGTGAACC
         CTGAAAGGTT TTACAGCATT GTTGAGGCGG GGTAACTGCG TTTACCCGCC ATCCGCACAT GCCACCCTCC AGATATATTC GTCTCGACCA AATCACTTGG
                             Esp3I
                             ~~~~~~~
 501     GTCAGATCCG CTAGACGTCT CATTTAACTT TAAGAAGGAG ATATACATAT GGCTAGCATG ACTGGTGGAC AGCAAATGGG TACTAACCAA GGTAAAGGTG
         CAGTCTAGGC GATCTGCAGA GTAAATTGAA ATTCTTCCTC TATATGTATA CCGATCGTAC TGACCACCTG TCGTTTACCC ATGATTGGTT CCATTTCCAC
 601     TAGTTGCTGC TGGAGATAAA CTGGCGTTGT TCTTGAAGGT ATTTGGCGGT GAAGTCCTGA CTGCGTTCGC TCGTACCTCC GTGACCACTT CTCGCCACAT
         ATCAACGACG ACCTCTATTT GACCGCAACA AGAACTTCCA TAAACCGCCA CTTCAGGACT GACGCAAGCG AGCATGGAGG CACTGGTGAA GAGCGGTGTA
 701     GGTACGTTCC ATCTCCAGCG GTAAATCCGC TCAGTTCCCT GTTCTGGGTC GCACTCAGGC AGCGTATCTG GCTCCGGGCG AGAACCTCGA CGATAAACGT
         CCATGCAAGG TAGAGGTCGC CATTTAGGCG AGTCAAGGGA CAAGACCCAG CGTGAGTCCG TCGCATAGAC CGAGGCCCGC TCTTGGAGCT GCTATTTGCA
 801     AAGGACATCA AACACACCGA GAAGGTAATC ACCATTGACG GTCTCCTGAC GGCTGACGTT CTGATTTATG ATATTGAGGA CGCGATGAAC CACTACGACG
         TTCCTGTAGT TTGTGTGGCT CTTCCATTAG TGGTAACTGC CAGAGGACTG CCGACTGCAA GACTAAATAC TATAACTCCT GCGCTACTTG GTGATGCTGC
 901     TTCGCTCTGA GTATACCTCT CAGTTGGGTG AATCTCTGGC GATGGCTGCG GATGGTGCGG TTCTGGCTGA GATTGCCGGT CTGTGTAACG TGGAAAGCAA
         AAGCGAGACT CATATGGAGA GTCAACCCAC TTAGAGACCG CTACCGACGC CTACCACGCC AAGACCGACT CTAACGGCCA GACACATTGC ACCTTTCGTT
1001     ATATAATGAG AACATCGAGG GCTTAGGTAC TGCTACCGTA ATTGAGACCA CTCAGAACAA GGCCGCACTT ACCGACCAAG TTGCGCTGGG TAAGGAGATT
         TATATTACTC TTGTAGCTCC CGAATCCATG ACGATGGCAT TAACTCTGGT GAGTCTTGTT CCGGCGTGAA TGGCTGGTTC AACGCGACCC ATTCCTCTAA
1101     ATTGCGGCTC TGACTAAGGC TCGTGCGGCT CTGACCAAGA ACTATGTTCC GGCTGCTGAC CGTGTGTTCT ACTGTGACCC AGATAGCTAC TCTGCGATTC
         TAACGCCGAG ACTGATTCCG AGCACGCCGA GACTGGTTCT TGATACAAGG CCGACGACTG GCACACAAGA TGACACTGGG TCTATCGATG AGACGCTAAG
1201     TGGCAGCACT GATGCCGAAC GCAGCAAACT ACGCTGCTCT GATTGACCCT GAGAAGGGTT CTATCCGCAA CGTTATGGGC TTTGAGGTTG TAGAAGTTCC
         ACCGTCGTGA CTACGGCTTG CGTCGTTTGA TGCGACGAGA CTAACTGGGA CTCTTCCCAA GATAGGCGTT GCAATACCCG AAACTCCAAC ATCTTCAAGG
1301     GCACCTCACC GCTGGTGGTG CTGGTACCGC TCGTGAGGGC ACTACTGGTC AGAAGCACGT CTTCCCTGCC AATAAAGGTG AGGGTAATGT CAAGGTTGCT
         CGTGGAGTGG CGACCACCAC GACCATGGCG AGCACTCCCG TGATGACCAG TCTTCGTGCA GAAGGGACGG TTATTTCCAC TCCCATTACA GTTCCAACGA
1401     AAGGACAACG TTATCGGCCT GTTCATGCAC CGCTCTGCGG TAGGTACTGT TAAGCTGCGT GACTTGGCTC TGGAGCGCGC TCGCCGTGCT AACTTCCAAG
         TTCCTGTTGC AATAGCCGGA CAAGTACGTG GCGAGACGCC ATCCATGACA ATTCGACGCA CTGAACCGAG ACCTCGCGCG AGCGGCACGA TTGAAGGTTC
                                                                                                      Esp3I
                                                                                                      ~~~~~~
1501     CGGACCAGAT TATCGCTAAG TACGCAATGG GCCACGGTGG TCTTCGCCCA GAAGCTGCAG GAGCTGTCGT ATTCCAGTCA GGTTAATTAC GAGACGCTCG
         GCCTGGTCTA ATAGCGATTC ATGCGTTACC CGGTGCCACC AGAAGCGGGT CTTCGACGTC CTCGACAGCA TAAGGTCAGT CCAATTAATG CTCTGCGAGC
1601     AGCCGATCCG CATCAAAGCA TGCTGTTTTC TGTCTGTCCC TAACATGCCC TGTGATTATC CGCAAACAAC ACACCCAAGG GCAGAACTTT GTTACTTAAA
         TCGGCTAGGC GTAGTTTCGT ACGACAAAAG ACAGACAGGG ATTGTACGGG ACACTAATAG GCGTTTGTTG TGTGGGTTCC CGTCTTGAAA CAATGAATTT
1701     CACCATCCTG TTTGCTTCTT TCCTCAGGAA CTGTGGCTGC ACCATCTGTC TTCATCTTCC CGCCATCTGA TGAGCAGTTG AAATCTGGAA CTGCCTCTGT
         GTGGTAGGAC AAACGAAGAA AGGAGTCCTT GACACCGACG TGGTAGACAG AAGTAGAAGG GCGGTAGACT ACTCGTCAAC TTTAGACCTT GACGGAGACA
1801     TGTGTGCCTG CTGAATAACT TCTATCCCAG AGAGGCCAAA GTACAGTGGA AGGTGGATAA CGCCCTCCAA TCGGGTAACT CCCAGGAGAG TGTCACAGAG
         ACACACGGAC GACTTATTGA AGATAGGGTC TCTCCGGTTT CATGTCACCT TCCACCTATT GCGGGAGGTT AGCCCATTGA GGGTCCTCTC ACAGTGTCTC
1901     CAGGACAGCA AGGACAGCAC CTACAGCCTC AGCAGCACCC TGACGCTGAG CAAAGCAGAC TACGAGAAAC ACAAAGTCTA CGCCTGCGAA GTCACCCATC
         GTCCTGTCGT TCCTGTCGTG GATGTCGGAG TCGTCGTGGG ACTGCGACTC GTTTCGTCTG ATGCTCTTTG TGTTTCAGAT GCGGACGCTT CAGTGGGTAG
2001     AGGGCCTGAG CTCGCCCGTC ACAAAGAGCT TCAACAGGGG AGAGTGTTAG CGGCCAATTG GCGGCCGCAA TTTAATTCCG GTTATTTTCC ACCATATTGC
         TCCCGGACTC GAGCGGGCAG TGTTTCTCGA AGTTGTCCCC TCTCACAATC GCCGGTTAAC CGCCGGCGTT AAATTAAGGC CAATAAAAGG TGGTATAACG
2101     CGTCTTTTGG CAATGTGAGG GCCCGGAAAC CTGGCCCTGT CTTCTTGACG AGCATTCCTA GGGGTCTTTC CCCTCTCGCC AAAGGAATGC AAGGTCTGTT
         GCAGAAAACC GTTACACTCC CGGGCCTTTG GACCGGGACA GAAGAACTGC TCGTAAGGAT CCCCAGAAAG GGGAGAGCGG TTTCCTTACG TTCCAGACAA
```

APPENDIX 1 -continued

Nucleotide sequences of constructed plasmids(SEQ ID NOs: 53-58, in order of appearance).

```
2201   GAATGTCGTG AAGGAAGCAG TTCCTCTGGA AGCTTCTTGA AGACAAACAA CGTCTGTAGC GACCCTTTGC AGGCAGCGGA ACCCCCCACC TGGCGACAGG
       CTTACAGCAC TTCCTTCGTC AAGGAGACCT TCGAAGAACT TCTGTTTGTT GCAGACATCG CTGGGAAACG TCCGTCGCCT TGGGGGGTGG ACCGCTGTCC
2301   TGCCTCTGCG GCCAAAAGCC ACGTGTATAA GATACACCTG CAAAGGCGGC ACAACCCCAG TGCCACGTTG TGAGTTGGAT AGTTGTGGAA AGAGTCAAAT
       ACGGAGACGC CGGTTTTCGG TGCACATATT CTATGTGGAC GTTTCCGCCG TGTTGGGGTC ACGGTGCAAC ACTCAACCTA TCAACACCTT TCTCAGTTTA
2401   GGCTCACCTC AAGCGTATTC AACAAGGGGC TGAAGGATGC CCAGAAGGTA CCCCATTGTA TGGGATCTGA TCTGGGGCCT CGGTGCACAT GCTTTACATG
       CCGAGTGGAG TTCGCATAAG TTGTTCCCCG ACTTCCTACG GGTCTTCCAT GGGGTAACAT ACCCTAGACT AGACCCCGGA GCCACGTGTA CGAAATGTAC
2501   TGTTTAGTCG AGGTTAAAAA ACGTCTAGGC CCCCCGAACC ACGGGGACGT GGTTTTCCTT TGAAAAACAC GATGATAATA TGGCCACCAC CCATACCTAG
       ACAAATCAGC TCCAATTTTT TGCAGATCCG GGGGGCTTGG TGCCCCTGCA CCAAAAGGAA ACTTTTTGTG CTACTATTAT ACCGGTGGTG GGTATGGATC
2601   GCTTTTGCAA AGATCGATCA GATCCCGGGG GGCAATGAGA TATGAAAAAG CCTGAACTCA CCGCGACGTC TGTCGAGAAG TTTCTGATCG AAAAGTTCGA
       CGAAAACGTT TCTAGCTAGT CTAGGGCCCC CCGTTACTCT ATACTTTTTC GGACTTGAGT GGCGCTGCAG ACAGCTCTTC AAAGACTAGC TTTTCAAGCT
2701   CAGCGTATCC GACCTGATGC AGCTCTCGGA GGGCGAAGAA TCTCGTGCTT TCAGCTTCGA TGTAGGAGGG CGTGGATATG TCCTGCGGGT AAATAGCTGC
       GTCGCATAGG CTGGACTACG TCGAGAGCCT CCCGCTTCTT AGAGCACGAA AGTCGAAGCT ACATCCTCCC GCACCTATAC AGGACGCCCA TTTATCGACG
2801   GCCGATGGTT TCTACAAAGA TCGTTATGTT TATCGGCACT TTGCATCGGC CGCGCTCCCG ATTCCGGAAG TGCTTGACAT TGGGGAATTC AGCGAGAGCC
       CGGCTACCAA AGATGTTTCT AGCAATACAA ATAGCCGTGA AACGTAGCCG GCGCGAGGGC TAAGGCCTTC ACGAACTGTA ACCCCTTAAG TCGCTCTCGG
2901   TGACCTATTG CATCTCCCGC CGTGCACAGG GTGTCACGTT GCAAGACCTG CCTGAAACCG AACTGCCCGC TGTTCTGCAG CCGGTCGCGG AGGCCATGGA
       ACTGGATAAC GTAGAGGGCG GCACGTGTCC CACAGTGCAA CGTTCTGGAC GGACTTTGGC TTGACGGGCG ACAAGACGTC GGCCAGCGCC TCCGGTACCT
3001   TGCGATCGCT GCGGCCGATC TTAGCCAGAC GAGCGGGTTC GGCCCATTCG GACCGCAAGG AATCGGTCAA TACACTACAT GGCGTGATTT CATATGCGCG
       ACGCTAGCGA CGCCGGCTAG AATCGGTCTG CTCGCCCAAG CCGGGTAAGC CTGGCGTTCC TTAGCCAGTT ATGTGATGTA CCGCACTAAA GTATACGCGC
3101   ATTGCTGATC CCCATGTGTA TCACTGGCAA ACTGTGATGG ACGACACCGT CAGTGCGTCC GTCGCGCAGG CTCTCGATGA GCTGATGCTT TGGGCCGAGG
       TAACGACTAG GGGTACACAT AGTGACCGTT TGACACTACC TGCTGTGGCA GTCACGCAGG CAGCGCGTCC GAGAGCTACT CGACTACGAA ACCCGGCTCC
3201   ACTGCCCCGA AGTCCGGCAC CTCGTGCACG CGGATTTCGG CTCCAACAAT GTCCTGACGG ACAATGGCCG CATAACAGCG GTCATTGACT GGAGCGAGGC
       TGACGGGGCT TCAGGCCGTG GAGCACGTGC GCCTAAAGCC GAGGTTGTTA CAGGACTGCC TGTTACCGGC GTATTGTCGC CAGTAACTGA CCTCGCTCCG
3301   GATGTTCGGG GATTCCCAAT ACGAGGTCGC CAACATCTTC TTCTGGAGGC CGTGGTTGGC TTGTATGGAG CAGCAGACGC GCTACTTCGA GCGGAGGCAT
       CTACAAGCCC CTAAGGGTTA TGCTCCAGCG GTTGTAGAAG AAGACCTCCG GCACCAACCG AACATACCTC GTCGTCTGCG CGATGAAGCT CGCCTCCGTA
3401   CCGGAGCTTG CAGGATCGCC GCGGCTCCGG GCGTATATGC TCCGCATTGG TCTTGACCAA CTCTATCAGA GCTTGGTTGA CGGCAATTTC GATGATGCAG
       GGCCTCGAAC GTCCTAGCGG CGCCGAGGCC CGCATATACG AGGCGTAACC AGAACTGGTT GAGATAGTCT CGAACCAACT GCCGTTAAAG CTACTACGTC
3501   CTTGGGCGCA GGGTCGATGC GACGCAATCG TCCGATCCGG AGCCGGGACT GTCGGGCGTA CACAAATCGC CCGCAGAAGC GCGGCCGTCT GGACCGATGG
       GAACCCGCGT CCCAGCTACG CTGCGTTAGC AGGCTAGGCC TCGGCCCTGA CAGCCCGCAT GTGTTTAGCG GGCGTCTTCG CGCCGGCAGA CCTGGCTACC
3601   CTGTGTAGAA GTACTCGCCG ATAGTGGAAA CCGACGCCCC AGCACTCGTC CGGATCGGGA GATGGGGGAG GCTAACTGAA ACACGGAAGG AGACAATACC
       GACACATCTT CATGAGCGGC TATCACCTTT GGCTGCGGGG TCGTGAGCAG GCCTAGCCCT CTACCCCCTC CGATTGACTT TGTGCCTTCC TCTGTTATGG
                                                                                                            I-SceI
                                                                                                          ~~~~~~~~~~
3701   GGAAGGAACC TCGACGTTAA CTTGTTTATT GCAGCTTATA ATGGTTACAA ATAAAGCAAT AGCATCACAA ATTTCACAAA TAAAGCATTT ATTACCCTGT
       CCTTCCTTGG AGCTGCAATT GAACAAATAA CGTCGAATAT TACCAATGTT TATTTCGTTA TCGTAGTGTT TAAAGTGTTT ATTTCGTAAA TAATGGGACA
       I-SceI
       ~~~~~~~~
3801   TATCCCTAGA ATTCACTGGC CGTCGTTTTA CAACGTCGTG ACTGGGAAAA CCCTGGCGTT ACCCAACTTA ATCGCCTTGC AGCACATCCC CCTTTCGCCA
       ATAGGGATCT TAAGTGACCG GCAGCAAAAT GTTGCAGCAC TGACCCTTTT GGGACCGCAA TGGGTTGAAT TAGCGGAACG TCGTGTAGGG GGAAAGCGGT
3901   GCTGGCGTAA TAGCGAAGAG GCCCGCACCG ATCGCCCTTC CCAACAGTTG CGCAGCCTGA ATGGCGAATG GCGCCTGATG CGGTATTTTC TCCTTACGCA
       CGACCGCATT ATCGCTTCTC CGGGCGTGGC TAGCGGGAAG GGTTGTCAAC GCGTCGGACT TACCGCTTAC CGCGGACTAC GCCATAAAAG AGGAATGCGT
4001   TCTGTGCGGT ATTTCACACC GCATACGTCA AAGCAACCAT AGTACGCGCC CTGTAGCGGC GCATTAAGCG CGGCGGGTGT GGTGGTTACG CGCAGCGTGA
       AGACACGCCA TAAAGTGTGG CGTATGCAGT TTCGTTGGTA TCATGCGCGG GACATCGCCG CGTAATTCGC GCCGCCCACA CCACCAATGC GCGTCGCACT
4101   CCGCTACACT TGCCAGCGCC CTAGCGCCCG CTCCTTTCGC TTTCTTCCCT TCCTTTCTCG CCACGTTCGC CGGCTTTCCC CGTCAAGCTC TAAATCGGGG
       GGCGATGTGA ACGGTCGCGG GATCGCGGGC GAGGAAAGCG AAAGAAGGGA AGGAAAGAGC GGTGCAAGCG GCCGAAAGGG GCAGTTCGAG ATTTAGCCCC
4201   GCTCCCTTTA GGGTTCCGAT TTAGTGCTTT ACGGCACCTC GACCCCAAAA AACTTGATTT GGGTGATGGT TCACGTAGTG GGCCATCGCC CTGATAGACG
       CGAGGGAAAT CCCAAGGCTA AATCACGAAA TGCCGTGGAG CTGGGGTTTT TTGAACTAAA CCCACTACCA AGTGCATCAC CCGGTAGCGG GACTATCTGC
4301   GTTTTTCGCC CTTTGACGTT GGAGTCCACG TTCTTTAATA GTGGACTCTT GTTCCAAACT GGAACAACAC TCAACCCTAT CTCGGGCTAT TCTTTTGATT
       CAAAAAGCGG GAAACTGCAA CCTCAGGTGC AAGAAATTAT CACCTGAGAA CAAGGTTTGA CCTTGTTGTG AGTTGGGATA GAGCCCGATA AGAAAACTAA
4401   TATAAGGGAT TTTGCCGATT TCGGCCTATT GGTTAAAAAA TGAGCTGATT TAACAAAAAT TTAACGCGAA TTTTAACAAA ATATTAACGT TTACAATTTT
       ATATTCCCTA AAACGGCTAA AGCCGGATAA CCAATTTTTT ACTCGACTAA ATTGTTTTTA AATTGCGCTT AAAATTGTTT TATAATTGCA AATGTTAAAA
```

APPENDIX 1 -continued

Nucleotide sequences of constructed plasmids(SEQ ID NOs: 53-58, in order of appearance).

```
4501  ATGGTGCACT CTCAGTACAA TCTGCTCTGA TGCCGCATAG TTAAGCCAGC CCCGACACCC GCCAACACCC GCTGACGCGC CCTGACGGGC TTGTCTGCTC
      TACCACGTGA GAGTCATGTT AGACGAGACT ACGGCGTATC AATTCGGTCG GGGCTGTGGG CGGTTGTGGG CGACTGCGCG GGACTGCCCG AACAGACGAG
4601  CCGGCATCCG CTTACAGACA AGCTGTGACC GTCTAGACGA AAGGGCCTCG TGATACGCCT ATTTTTATAG GTTAATGTCA TGATAATAAT GGTTTCTTAG
      GGCCGTAGGC GAATGTCTGT TCGACACTGG CAGATCTGCT TTCCCGGAGC ACTATGCGGA TAAAAATATC CAATTACAGT ACTATTATTA CCAAAGAATC
4701  ACGTCAGGTG GCACTTTTCG GGGAAATGTG CGCGGAACCC CTATTTGTTT ATTTTTCTAA ATACATTCAA ATATGTATCC GCTCATGAGA CAATAACCCT
      TGCAGTCCAC CGTGAAAAGC CCCTTTACAC GCGCCTTGGG GATAAACAAA TAAAAAGATT TATGTAAGTT TATACATAGG CGAGTACTCT GTTATTGGGA
4801  GATAAATGCT TCAATAATAT TGAAAAAGGA AGAGTATGAG TATTCAACAT TTCCGTGTCG CCCTTATTCC CTTTTTTGCG GCATTTTGCC TTCCTGTTTT
      CTATTTACGA AGTTATTATA ACTTTTTCCT TCTCATACTC ATAAGTTGTA AAGGCACAGC GGGAATAAGG GAAAAAACGC CGTAAAACGG AAGGACAAAA
4901  TGCTCACCCA GAAACGCTGG TGAAAGTAAA AGATGCTGAA GATCAGTTGG GTGCACGAGT GGGTTACATC GAACTGGATC TCAACAGCGG TAAGATCCTT
      ACGAGTGGGT CTTTGCGACC ACTTTCATTT TCTACGACTT CTAGTCAACC CACGTGCTCA CCCAATGTAG CTTGACCTAG AGTTGTCGCC ATTCTAGGAA
5001  GAGAGTTTTC GCCCCGAAGA ACGTTTTCCA ATGATGAGCA CTTTTAAAGT TCTGCTATGT GGCGCGGTAT TATCCCGTAT TGACGCCGGG CAAGAGCAAC
      CTCTCAAAAG CGGGGCTTCT TGCAAAAGGT TACTACTCGT GAAAATTTCA AGACGATACA CCGCGCCATA ATAGGGCATA ACTGCGGCCC GTTCTCGTTG
5101  TCGGTCGCCG CATACACTAT TCTCAGAATG ACTTGGTTGA GTACTCACCA GTCACAGAAA AGCATCTTAC GGATGGCATG ACAGTAAGAG AATTATGCAG
      AGCCAGCGGC GTATGTGATA AGAGTCTTAC TGAACCAACT CATGAGTGGT CAGTGTCTTT TCGTAGAATG CCTACCGTAC TGTCATTCTC TTAATACGTC
5201  TGCTGCCATA ACCATGAGTG ATAACACTGC GGCCAACTTA CTTCTGACAA CGATCGGAGG ACCGAAGGAG CTAACCGCTT TTTTGCACAA CATGGGGGAT
      ACGACGGTAT TGGTACTCAC TATTGTGACG CCGGTTGAAT GAAGACTGTT GCTAGCCTCC TGGCTTCCTC GATTGGCGAA AAAACGTGTT GTACCCCCTA
5301  CATGTAACTC GCCTTGATCG TTGGGAACCG GAGCTGAATG AAGCCATACC AAACGACGAG CGTGACACCA CGATGCCTGT AGCAATGGCA ACAACGTTGC
      GTACATTGAG CGGAACTAGC AACCCTTGGC CTCGACTTAC TTCGGTATGG TTTGCTGCTC GCACTGTGGT GCTACGGACA TCGTTACCGT TGTTGCAACG
5401  GCAAACTATT AACTGGCGAA CTACTTACTC TAGCTTCCCG GCAACAATTA ATAGACTGGA TGGAGGCGGA TAAAGTTGCA GGACCACTTC TGCGCTCGGC
      CGTTTGATAA TTGACCGCTT GATGAATGAG ATCGAAGGGC CGTTGTTAAT TATCTGACCT ACCTCCGCCT ATTTCAACGT CCTGGTGAAG ACGCGAGCCG
5501  CCTTCCGGCT GGCTGGTTTA TTGCTGATAA ATCTGGAGCC GGTGAGCGTG GGTCTCGCGG TATCATTGCA GCACTGGGGC CAGATGGTAA GCCCTCCCGT
      GGAAGGCCGA CCGACCAAAT AACGACTATT TAGACCTCGG CCACTCGCAC CCAGAGCGCC ATAGTAACGT CGTGACCCCG GTCTACCATT CGGGAGGGCA
5601  ATCGTAGTTA TCTACACGAC GGGGAGTCAG GCAACTATGG ATGAACGAAA TAGACAGATC GCTGAGATAG GTGCCTCACT GATTAAGCAT TGGTAACTGT
      TAGCATCAAT AGATGTGCTG CCCCTCAGTC CGTTGATACC TACTTGCTTT ATCTGTCTAG CGACTCTATC CACGGAGTGA CTAATTCGTA ACCATTGACA
5701  CAGACCAAGT TTACTCATAT ATACTTTAGA TTGATTTAAA ACTTCATTTT TAATTTAAAA GGATCTAGGT GAAGATCCTT TTTGATAATC TCATGACCAA
      GTCTGGTTCA AATGAGTATA TATGAAATCT AACTAAATTT TGAAGTAAAA ATTAAATTTT CCTAGATCCA CTTCTAGGAA AAACTATTAG AGTACTGGTT
5801  AATCCCTTAA CGTGAGTTTT CGTTCCACTG AGCGTCAGAC CCCGTAGAAA AGATCAAAGG ATCTTCTTGA GATCCTTTTT TTCTGCGCGT AATCTGCTGC
      TTAGGGAATT GCACTCAAAA GCAAGGTGAC TCGCAGTCTG GGGCATCTTT TCTAGTTTCC TAGAAGAACT CTAGGAAAAA AAGACGCGCA TTAGACGACG
5901  TTGCAAACAA AAAAACCACC GCTACCAGCG GTGGTTTGTT TGCCGGATCA AGAGCTACCA ACTCTTTTTC CGAAGGTAAC TGGCTTCAGC AGAGCGCAGA
      AACGTTTGTT TTTTTGGTGG CGATGGTCGC CACCAAACAA ACGGCCTAGT TCTCGATGGT TGAGAAAAAG GCTTCCATTG ACCGAAGTCG TCTCGCGTCT
6001  TACCAAATAC TGTCCTTCTA GTGTAGCCGT AGTTAGGCCA CCACTTCAAG AACTCTGTAG CACCGCCTAC ATACCTCGCT CTGCTAATCC TGTTACCAGT
      ATGGTTTATG ACAGGAAGAT CACATCGGCA TCAATCCGGT GGTGAAGTTC TTGAGACATC GTGGCGGATG TATGGAGCGA GACGATTAGG ACAATGGTCA
6101  GGCTGCTGCC AGTGGCGATA AGTCGTGTCT TACCGGGTTG GACTCAAGAC GATAGTTACC GGATAAGGCG CAGCGGTCGG GCTGAACGGG GGGTTCGTGC
      CCGACGACGG TCACCGCTAT TCAGCACAGA ATGGCCCAAC CTGAGTTCTG CTATCAATGG CCTATTCCGC GTCGCCAGCC CGACTTGCCC CCCAAGCACG
6201  ACACAGCCCA GCTTGGAGCG AACGACCTAC ACCGAACTGA GATACCTACA GCGTGAGCTA TGAGAAAGCG CCACGCTTCC CGAAGGGAGA AAGGCGGACA
      TGTGTCGGGT CGAACCTCGC TTGCTGGATG TGGCTTGACT CTATGGATGT CGCACTCGAT ACTCTTTCGC GGTGCGAAGG GCTTCCCTCT TTCCGCCTGT
6301  GGTATCCGGT AAGCGGCAGG GTCGGAACAG GAGAGCGCAC GAGGGAGCTT CCAGGGGGAA ACGCCTGGTA TCTTTATAGT CCTGTCGGGT TTCGCCACCT
      CCATAGGCCA TTCGCCGTCC CAGCCTTGTC CTCTCGCGTG CTCCCTCGAA GGTCCCCCTT TGCGGACCAT AGAAATATCA GGACAGCCCA AAGCGGTGGA
6401  CTGACTTGAG CGTCGATTTT TGTGATGCTC GTCAGGGGGG CGGAGCCTAT GGAAAAACGC CAGCAACGCG GCCTTTTTAC GGTTCCTGGC CTTTTGCTGG
      GACTGAACTC GCAGCTAAAA ACACTACGAG CAGTCCCCCC GCCTCGGATA CCTTTTTGCG GTCGTTGCGC CGGAAAAATG CCAAGGACCG GAAAACGACC
6501  CCTTTTGCTC ACATGTTCTT TCCTGCGTTA TCCCCTGATT CTGTGGATAA CCGTATTACC GCCTTTGAGT GAGCTGATAC CGCTCGCCGC AGCCGAACGA
      GGAAAACGAG TGTACAAGAA AGGACGCAAT AGGGGACTAA GACACCTATT GGCATAATGG CGGAAACTCA CTCGACTATG GCGAGCGGCG TCGGCTTGCT
6601  CCGAGCGCAG CGAGTCAGTG AGCGAGGAAG CGGAAGAGCG CCCAATACGC AAACCGCCTC TCCCCGCGCG TTGGCCGATT CATTAATGCA GCTGGCACGA
      GGCTCGCGTC GCTCAGTCAC TCGCTCCTTC GCCTTCTCGC GGGTTATGCG TTTGGCGGAG AGGGGCGCGC AACCGGCTAA GTAATACGT CGACCGTGCT
6701  CAGGTTTCCC GACTGGAAAG CGGGCAGTGA GCGCAACGCA ATTAATGTGA GTTAGCTCAC TCATTAGGCA CCCCAGGCTT TACACTTTAT GCTTCCGGCT
      GTCCAAAGGG CTGACCTTTC GCCCGTCACT CGCGTTGCGT TAATTACACT CAATCGAGTG AGTAATCCGT GGGGTCCGAA ATGTGAAATA CGAAGGCCGA
                                                                                                   I-SceI
                                                                                         ~~~~~~~~~~~~~~~~~~~~
6801  CGTATGTTGT GTGGAATTGT GAGCGGATAA CAATTTCACA CAGGAAACAG CTATGACCAT GATTACGCCA AGCTTTAGGG ATAACAGGGT AATCGCCATG
      GCATACAACA CACCTTAACA CTCGCCTATT GTTAAAGTGT GTCCTTTGTC GATACTGGTA CTAATGCGGT TCGAAATCCC TATTGTCCCA TTAGCGGTAC
```

APPENDIX 1 -continued

Nucleotide sequences of constructed plasmids(SEQ ID NOs: 53-58, in order of appearance).

```
6901  CATTAGTTAT TAATAGTAAT CAATTACGGG GTCATTAGTT CATAGCCCAT ATATGGAGTT CCGCGTTACA TAACTTACGG TAAA
      GTAATCAATA ATTATCATTA GTTAATGCCC CAGTAATCAA GTATCGGGTA TATACCTCAA GGCGCAATGT ATTGAATGCC ATTT

pVHentry-Cm5:
                                  Esp3I
                                  ~~~~~~~
   1  GGTTTAGTGA ACCGTCAGAT CCGCTAGACG TCTCATATAC CTGACTGGAA TACGACAGCT CCTGCAGCTT CTGGGCGAAG ACCACCGTGG CCCATTGCGT
      CCAAATCACT TGGCAGTCTA GGCGATCTGC AGAGTATATG GACTGACCTT ATGCTGTCGA GGACGTCGAA GACCCGCTTC TGGTGGCACC GGGTAACGCA
 101  ACTTAGCGAT AATCTGGTCC GCTTGGAAGT TAGCACGGCG AGCGCGCTCC AGAGCCAAGT CACGCAGCTT AACAGTACCT ACCGCAGAGC GGTGCATGAA
      TGAATCGCTA TTAGACCAGG CGAACCTTCA ATCGTGCCGC TCGCGCGAGG TCTCGGTTCA GTGCGTCGAA TTGTCATGGA TGGCGTCTCG CCACGTACTT
 201  CAGGCCGATA ACGTTGTCCT TAGCAACCTT GACATTACCC TCACCTTTAT TGGCAGGGAA GACGTGCTTC TGACCAGTAG TGCCCTCACG AGCGGTACCA
      GTCCGGCTAT TGCAACAGGA ATCGTTGGAA CTGTAATGGG AGTGGAAATA ACCGTCCCTT CTGCACGAAG ACTGGTCATC ACGGGAGTGC TCGCCATGGT
 301  GCACCACCAG CGGTGAGGTG CGGAACTTCT ACAACCTCAA AGCCCATAAC GTTGCGGATA GAACCCTTCT CAGGGTCAAT CAGAGCAGCG TAGTTTGCTG
      CGTGGTGGTC GCCACTCCAC GCCTTGAAGA TGTTGGAGTT TCGGGTATTG CAACGCCTAT CTTGGGAAGA GTCCCAGTTA GTCTCGTCGC ATCAAACGAC
 401  CGTTCGGCAT CAGTGCTGCC AGAATCGCAG AGTAGCTATC TGGGTCACAG TAGAACACAC GGTCAGCAGC CGGAACATAG TTCTTGGTCA GAGCCGCACG
      GCAAGCCGTA GTCACGACGG TCTTAGCGTC TCATCGATAG ACCCAGTGTC ATCTTGTGTG CCAGTCGTCG GCCTTGTATC AAGAACCAGT CTCGGCGTGC
 501  AGCCTTAGTC AGAGCCGCAA TAATCTCCTT ACCCAGCGCA ACTTGGTCGG TAAGTGCGGC CTTGTTCTGA GTGGTCTCAA TTACGGTAGC AGTACCTAAG
      TCGGAATCAG TCTCGGCGTT ATTAGAGGAA TGGGTCGCGT TGAACCAGCC ATTCACGCCG GAACAAGACT CACCAGAGTT AATGCCATCG TCATGGATTC
 601  CCCTCGATGT TCTCATTATA TTTGCTTTCC ACGTTACACA GACCGGCAAT CTCAGCCAGA ACCGCACCAT CCGCAGCCAT CGCCAGAGAT TCACCCAACT
      GGGAGCTACA AGAGTAATAT AAACGAAAGG TGCAATGTGT CTGGCCGTTA GAGTCGGTCT TGGCGTGGTA GGCGTCGGTA GCGGTCTCTA AGTGGGTTGA
 701  GAGAGGTATA CTCAGAGCGA ACGTCGTAGT GGTTCATCGC GTCCTCAATA TCATAAATCA GAACGTCAGC CGTCAGGAGA CCGTCAATGG TGATTACCTT
      CTCTCCATAT GAGTCTCGCT TGCAGCATCA CCAAGTAGCG CAGGAGTTAT AGTATTTAGT CTTGCAGTCG GCAGTCCTCT GGCAGTTACC ACTAATGGAA
 801  CTCGGTGTGT TTGATGTCCT TACGTTTATC GTCGAGGTTC TCGCCCGGAG CCAGATACGC TGCCTGAGTG CGACCCAGAA CAGGGAACTG AGCGGATTTA
      GAGCCACACA AACTACAGGA ATGCAAATAG CAGCTCCAAG AGCGGGCCTC GGTCTATGCG ACGGACTCAC GCTGGGTCTT GTCCCTTGAC TCGCCTAAAT
 901  CCGCTGGAGA TGGAACGTAC CATGTGGCGA GAAGTGGTCA CGGAGGTACG AGCGAACGCA GTCAGGACTT CACCGCCAAA TACCTTCAAG AACAACGCCA
      GGCGACCTCT ACCTTGCATG GTACACCGCT CTTCACCAGT GCCTCCATGC TCGCTTGCGT CAGTCCTGAA GTGGCGGTTT ATGGAAGTTC TTGTTGCGGT
                                                                                                          Esp3I
                                                                                                          ~~~~~
1001  GTTTATCTCC AGCAGCAACT ACACCTTTAC CTTGGTTAGT ACCCATTTGC TGTCCACCAG TCATGCTAGC CATATGTATA TCTCCTTCTT AAAGTCGTCT
      CAAATAGAGG TCGTCGTTGA TGTGGAAATG GAACCAATCA TGGGTAAACG ACAGGTGGTC AGTACGATCG GTATACATAT AGAGGAAGAA TTTCAGCAGA
      Esp3I
      ~
1101  CCAGTGCCTC CACCAAGGGC CCATCGGTCT TCCCCCTGGC GCCCTGCTCC AGGAGCACCT CCGAGAGCAC AGCGGCCCTG GGCTGCCTGG TCAAGGACTA
      GGTCACGGAG GTGGTTCCCG GGTAGCCAGA AGGGGGACCG CGGGACGAGG TCCTCGTGGA GGCTCTCGTG TCGCCGGGAC CCGACGGACC AGTTCCTGAT
1201  CTTCCCCGAA CCGGTGACGG TGTCGTGGAA CTCAGGCGCT CTGACCAGCG GCGTGCACAC CTTCCCAGCT GTCCTACAGT CCTCAGGACT CTACTCCCTC
      GAAGGGGCTT GGCCACTGCC ACAGCACCTT GAGTCCGCGA GACTGGTCGC CGCACGTGTG GAAGGGTCGA CAGGATGTCA GGAGTCCTGA GATGAGGGAG
1301  AGCAGCGTGG TGACCGTGCC CTCCAGCAGC TTGGGCACCC AGACCTACAT CTGCAACGTG AATCACAAGC CCAGCAACAC CAAGGTGGAC AAGAAAGTTG
      TCGTCGCACC ACTGGCACGG GAGGTCGTCG AACCCGTGGG TCTGGATGTA GACGTTGCAC TTAGTGTTCG GGTCGTTGTG GTTCCACCTG TTCTTTCAAC
1401  AGCCCAAATC TTGTGACAAA ACTCACACAT GCCCACCGTG CCCAGCACCT GAACTCCTGG GGGGACCGTC AGTCTTCCTC TTCCCCCCMA AACCCAAGGA
      TCGGGTTTAG AACACTGTTT TGAGTGTGTA CGGGTGGCAC GGGTCGTGGA CTTGAGGACC CCCCTGGCAG TCAGAAGGAG AAGGGGGGKT TTGGGTTCCT
1501  CACCCTCATG ATCTCCCGGA CCCCTGAGGT CACATGCGTG GTGGTGGACG TGAGCCACGA AGACCCTGAG GTCAAGTTCA ACTGGTACGT GGACGGCGTG
      GTGGGAGTAC TAGAGGGCCT GGGGACTCCA GTGTACGCAC CACCACCTGC ACTCGGTGCT TCTGGGACTC CAGTTCAAGT TGACCATGCA CCTGCCGCAC
1601  GAGGTGCATA ATGCCAAGAC AAAGCCGCGG GAGGAGCAGT ACAACAGCAC GTACCGTGTG GTCAGCGTCC TCACCGTCCT GCACCAGGAC TGGCTGAATG
      CTCCACGTAT TACGGTTCTG TTTCGGCGCC CTCCTCGTCA TGTTGTCGTG CATGGCACAC CAGTCGCAGG AGTGGCAGGA CGTGGTCCTG ACCGACTTAC
1701  GCAAGGAGTA CAAGTGCAAG GTCTCCAACA AAGCCCTCCC AGCCCCCATC GAGAAAACCA TCTCCAAAGC CAAAGGGCAG CCCCGAGAAC CACAGGTGTA
      CGTTCCTCAT GTTCACGTTC CAGAGGTTGT TTCGGGAGGG TCGGGGGTAG CTCTTTTGGT AGAGGTTTCG GTTTCCCGTC GGGGCTCTTG GTGTCCACAT
1801  CACCCTGCCC CCATCCCGGG ATGAGCTGAC CAAGAACCAG GTCAGCCTGA CCTGCCTGGT CAAAGGCTTC TATCCCAGCG ACATCGCCGT GGAGTGGGAG
      GTGGGACGGG GGTAGGGCCC TACTCGACTG GTTCTTGGTC CAGTCGGACT GGACGGACCA GTTTCCGAAG ATAGGGTCGC TGTAGCGGCA CCTCACCCTC
1901  AGCAATGGGC AGCCGGAGAA CAACTACAAG ACCACGCCTC CCGTGCTGGA CTCCGACGGC TCCTTCTTCC TCTACAGCAA GCTCACCGTG GACAAGAGCA
      TCGTTACCCG TCGGCCTCTT GTTGATGTTC TGGTGCGGAG GGCACGACCT GAGGCTGCCG AGGAAGAAGG AGATGTCGTT CGAGTGGCAC CTGTTCTCGT
```

APPENDIX 1 -continued

Nucleotide sequences of constructed plasmids(SEQ ID NOs: 53-58, in order of appearance).

```
2001  GGTGGCAGCA GGGGAACGTC TTCTCATGCT CCGTGATGCA TGAGGCTCTG CACAACCACT ACACGCAGAA GAGCCTCTCC CTGTCTCCGG GTAAATGAGC
      CCACCGTCGT CCCCTTGCAG AAGAGTACGA GGCACTACGT ACTCCGAGAC GTGTTGGTGA TGTGCGTCTT CTCGGAGAGG GACAGAGGCC CATTTACTCG
2101  GGCCGCAATT TAATTCCGGT TATTTTCCAC CATATTGCCG TCTTTTGGCA ATGTGAGGGC CCGGAAACCT GGCCCTGTCT TCTTGACGAG CATTCCTAGG
      CCGGCGTTAA ATTAAGGCCA ATAAAAGGTG GTATAACGGC AGAAAACCGT TACACTCCCG GGCCTTTGGA CCGGGACAGA AGAACTGCTC GTAAGGATCC
2201  GGTCTTTCCC CTCTCGCCAA AGGAATGCAA GGTCTGTTGA ATGTCGTGAA GGAAGCAGTT CCTCTGGAAG CTTCTTGAAG ACAAACAACG TCTGTAGCGA
      CCAGAAAGGG GAGAGCGGTT TCCTTACGTT CCAGACAACT TACAGCACTT CCTTCGTCAA GGAGACCTTC GAAGAACTTC TGTTTGTTGC AGACATCGCT
2301  CCCTTTGCAG GCAGCGGAAC CCCCCACCTG GCGACAGGTG CCTCTGCGGC CAAAAGCCAC GTGTATAAGA TACACCTGCA AAGGCGGCAC AACCCCAGTG
      GGGAAACGTC CGTCGCCTTG GGGGGTGGAC CGCTGTCCAC GGAGACGCCG GTTTTCGGTG CACATATTCT ATGTGGACGT TTCCGCCGTG TTGGGGTCAC
2401  CCACGTTGTG AGTTGGATAG TTGTGGAAAG AGTCAAATGG CTCACCTCAA GCGTATTCAA CAAGGGGCTG AAGGATGCCC AGAAGGTACC CCATTGTATG
      GGTGCAACAC TCAACCTATC AACACCTTTC TCAGTTTACC GAGTGGAGTT CGCATAAGTT GTTCCCCGAC TTCCTACGGG TCTTCCATGG GGTAACATAC
2501  GGATCTGATC TGGGGCCTCG GTGCACATGC TTTACATGTG TTTAGTCGAG GTTAAAAAAC GTCTAGGCCC CCCGAACCAC GGGGACGTGG TTTTCCTTTG
      CCTAGACTAG ACCCCGGAGC CACGTGTACG AAATGTACAC AAATCAGCTC CAATTTTTTG CAGATCCGGG GGGCTTGGTG CCCCTGCACC AAAAGGAAAC
2601  AAAAACACGA TGATAATATG GCCACCACCC ATACCTAGGC TTTTGCAAAG ATCGATCAAG AGACAGGATG AGGATCGTTT CGCATGATTG AACAAGATGG
      TTTTTGTGCT ACTATTATAC CGGTGGTGGG TATGGATCCG AAAACGTTTC TAGCTAGTTC TCTGTCCTAC TCCTAGCAAA GCGTACTAAC TTGTTCTACC
2701  ATTGCACGCA GGTTCTCCGG CCGCTTGGGT GGAGAGGCTA TTCGGCTATG ACTGGGCACA ACAGACAATC GGCTGCTCTG ATGCCGCCGT GTTCCGGCTG
      TAACGTGCGT CCAAGAGGCC GGCGAACCCA CCTCTCCGAT AAGCCGATAC TGACCCGTGT TGTCTGTTAG CCGACGAGAC TACGGCGGCA CAAGGCCGAC
2801  TCAGCGCAGG GGCGCCCGGT TCTTTTTGTC AAGACCGACC TGTCCGGTGC CCTGAATGAA CTGCAAGACG AGGCAGCGCG GCTATCGTGG CTGGCCACGA
      AGTCGCGTCC CCGCGGGCCA AGAAAAACAG TTCTGGCTGG ACAGGCCACG GGACTTACTT GACGTTCTGC TCCGTCGCGC CGATAGCACC GACCGGTGCT
2901  CGGGCGTTCC TTGCGCAGCT GTGCTCGACG TTGTCACTGA AGCGGGAAGG GACTGGCTGC TATTGGGCGA AGTGCCGGGG CAGGATCTCC TGTCATCTCA
      GCCCGCAAGG AACGCGTCGA CACGAGCTGC AACAGTGACT TCGCCCTTCC CTGACCGACG ATAACCCGCT TCACGGCCCC GTCCTAGAGG ACAGTAGAGT
3001  CCTTGCTCCT GCCGAGAAAG TATCCATCAT GGCTGATGCA ATGCGGCGGC TGCATACGCT TGATCCGGCT ACCTGCCCAT TCGACCACCA AGCGAAACAT
      GGAACGAGGA CGGCTCTTTC ATAGGTAGTA CCGACTACGT TACGCCGCCG ACGTATGCGA ACTAGGCCGA TGGACGGGTA AGCTGGTGGT TCGCTTTGTA
3101  CGCATCGAGC GAGCACGTAC TCGGATGGAA GCCGGTCTTG TCGATCAGGA TGATCTGGAC GAAGAGCATC AGGGGCTCGC GCCAGCCGAA CTGTTCGCCA
      GCGTAGCTCG CTCGTGCATG AGCCTACCTT CGGCCAGAAC AGCTAGTCCT ACTAGACCTG CTTCTCGTAG TCCCCGAGCG CGGTCGGCTT GACAAGCGGT
3201  GGCTCAAGGC GAGCATGCCC GACGGCGAGG ATCTCGTCGT GACCCATGGC GATGCCTGCT TGCCGAATAT CATGGTGGAA AATGGCCGCT TTTCTGGATT
      CCGAGTTCCG CTCGTACGGG CTGCCGCTCC TAGAGCAGCA CTGGGTACCG CTACGGACGA ACGGCTTATA GTACCACCTT TTACCGGCGA AAAGACCTAA
3301  CATCGACTGT GGCCGGCTGG GTGTGGCGGA CCGCTATCAG GACATAGCGT TGGCTACCCG TGATATTGCT GAAGAGCTTG GCGGCGAATG GGCTGACCGC
      GTAGCTGACA CCGGCCGACC CACACCGCCT GGCGATAGTC CTGTATCGCA ACCGATGGGC ACTATAACGA CTTCTCGAAC CGCCGCTTAC CCGACTGGCG
3401  TTCCTCGTGC TTTACGGTAT CGCCGCTCCC GATTCGCAGC GCATCGCCTT CTATCGCCTT CTTGACGAGT TCTTCTGAGC GGGACTCTGG GGTTCGGGCC
      AAGGAGCACG AAATGCCATA GCGGCGAGGG CTAAGCGTCG CGTAGCGGAA GATAGCGGAA GAACTGCTCA AGAAGACTCG CCCTGAGACC CCAAGCCCGG
3501  GCACTCGAGC ATAAACTTGT TTATTGCAGC TTATAATGGT TACAAATAAA GCAATAGCAT CACAAATTTC ACAAATAAAG CATTTTTTTC ACTGCATTCT
      CGTGAGCTCG TATTTGAACA AATAACGTCG AATATTACCA ATGTTTATTT CGTTATCGTA GTGTTTAAAG TGTTTATTTC GTAAAAAAAG TGACGTAAGA
                                                    I-SceI
                                             ~~~~~~~~~~~~~~~~~~~~
3601  AGTTGTGGTT TGTCCAAACT CATCAATGTA TCTTAAGTAG GGATAACAGG GTAATTTTGT TAAATCAGCT CATTTTTTAA CCAATAGGAA CGCCATCAAA
      TCAACACCAA ACAGGTTTGA GTAGTTACAT AGAATTCATC CCTATTGTCC CATTAAAACA ATTTAGTCGA GTAAAAAATT GGTTATCCTT GCGGTAGTTT
3701  AATAATTCGC GTCTGGCCTT CCTGTAGCCA GCTTTCATCA ACATTAAATG TGAGCGAGTA ACAACCCGTC GGATTCTCCG TGGGAACAAA CGGCGGATTG
      TTATTAAGCG CAGACCGGAA GGACATCGGT CGAAAGTAGT TGTAATTTAC ACTCGCTCAT TGTTGGGCAG CCTAAGAGGC ACCCTTGTTT GCCGCCTAAC
3801  ACCGTAATGG GATAGGTTAC GTTGGTGTAG ATGGGCGCAT CGTAACCGTG CATCTGCCAG TTTGAGGGGA CGACGACCGT ATCGGCCTCA GGAAGATCGC
      TGGCATTACC CTATCCAATG CAACCACATC TACCCGCGTA GCATTGGCAC GTAGACGGTC AAACTCCCCT GCTGCTGGCA TAGCCGGAGT CCTTCTAGCG
3901  ACTCCAGCCA GCTTTCCGGC ACCGCTTCTG GTGCCGGAAA CCAGGCAAAG CGCCATTCGC CATTCAGGCT GCGCAACTGT TGGGAAGGGC GATCGGTGCG
      TGAGGTCGGT CGAAAGGCCG TGGCGAAGAC CACGGCCTTT GGTCCGTTTC GCGGTAAGCG GTAAGTCCGA CGCGTTGACA ACCCTTCCCG CTAGCCACGC
4001  GGCCTCTTCG CTATTACGCC AGCTGGCGAA AGGGGGATGT GCTGCAAGGC GATTAAGTTG GGTAACGCCA GGGTTTTCCC AGTCACGACG TTGTAAAACG
      CCGGAGAAGC GATAATGCGG TCGACCGCTT TCCCCCTACA CGACGTTCCG CTAATTCAAC CCATTGCGGT CCCAAAAGGG TCAGTGCTGC AACATTTTGC
4101  ACGGCCAGTG AATTGCAATT CGTAATCATG GTCATAGCTG TTTCCTGTGT GAAATTGTTA TCCGCTCACA ATTCCACACA ACATACGAGC CGGAAGCATA
      TGCCGGTCAC TTAACGTTAA GCATTAGTAC CAGTATCGAC AAAGGACACA CTTTAACAAT AGGCGAGTGT TAAGGTGTGT TGTATGCTCG GCCTTCGTAT
                                                                                  I-SceI
                                                                           ~~~~~~~~~~~~~~~~~~~~
4201  AAGTGTAAAG CCTGGGGTGC CTAATGAGTG AGCTAACTCA CATTAATTGC GTTGCGCTCA CTGCCATTAC CCTGTTATCC CTAGTGAACC ATCACCCTAA
      TTCACATTTC GGACCCCACG GATTACTCAC TCGATTGAGT GTAATTAACG CAACGCGAGT GACGGTAATG GGACAATAGG GATCACTTGG TAGTGGGATT
```

APPENDIX 1 -continued

| Nucleotide sequences of constructed plasmids(SEQ ID NOs: 53-58, in order of appearance). | |
|---|---|
| 4301 | TCAAGTTTTT TGGGGTCGAG GTGCCGTAAA GCACTAAATC GGAACCCTAA AGGGAGCCCC CGATTTAGAG CTTGACGGGG AAAGCCGGCG AACGTGGCGA |
| | AGTTCAAAAA ACCCCAGCTC CACGGCATTT CGTGATTTAG CCTTGGGATT TCCCTCGGGG GCTAAATCTC GAACTGCCCC TTTCGGCCGC TTGCACCGCT |
| 4401 | GAAAGGAAGG GAAGAAAGCG AAAGGAGCGG GCGCTAGGGC GCTGGCAAGT GTAGCGGTCA CGCTGCGCGT AACCACCACA CCCGCCGCGC TTAATGCGCC |
| | CTTTCCTTCC CTTCTTTCGC TTTCCTCGCC CGCGATCCCG CGACCGTTCA CATCGCCAGT GCGACGCGCA TTGGTGGTGT GGGCGGCGCG AATTACGCGG |
| 4501 | GCTACAGGGC GCGTCAGGTG GCACTTTTCG GGGAAATGTG CGCGGAACCC CTATTTGTTT ATTTTTCTAA ATACATTCAA ATATGTATCC GCTCATGAGA |
| | CGATGTCCCG CGCAGTCCAC CGTGAAAAGC CCCTTTACAC GCGCCTTGGG GATAAACAAA TAAAAAGATT TATGTAAGTT TATACATAGG CGAGTACTCT |
| 4601 | CAATAACCCT GATAAATGCT TCAATAATAA CGACCGGTAA TGAAAAAGGA AGAGTATGAG TATTCAACAT TTCCGTGTCG CCCTTATTCC CTTTTTTGCG |
| | GTTATTGGGA CTATTTACGA AGTTATTATT GCTGGCCATT ACTTTTTCCT TCTCATACTC ATAAGTTGTA AAGGCACAGC GGGAATAAGG GAAAAAACGC |
| 4701 | GCATTTTGCC TTCCTGTTTT TGCTCACCCA GAAACGCTGG TGAAAGTAAA AGATGCTGAA GATCAGTTGG GTGCACGAGT GGGTTACATC GAACTGGATC |
| | CGTAAAACGG AAGGACAAAA ACGAGTGGGT CTTTGCGACC ACTTTCATTT TCTACGACTT CTAGTCAACC CACGTGCTCA CCCAATGTAG CTTGACCTAG |
| 4801 | TCAACAGCGG TAAGATCCTT GAGAGTTTTC GCCCCGAAGA ACGTTTTCCA ATGATGAGCA CTTTTAAAGT TCTGCTATGT GGCGCGGTAT TATCCCGTAT |
| | AGTTGTCGCC ATTCTAGGAA CTCTCAAAAG CGGGGCTTCT TGCAAAAGGT TACTACTCGT GAAAATTTCA AGACGATACA CCGCGCCATA ATAGGGCATA |
| 4901 | TGACGCCGGG CAAGAGCAAC TCGGTCGCCG CATACACTAT TCTCAGAATG ACTTGGTTGA GTCTAGCGTT GATCGGCACG TAAGAGGTTC CAACTTTCAC |
| | ACTGCGGCCC GTTCTCGTTG AGCCAGCGGC GTATGTGATA AGAGTCTTAC TGAACCAACT CAGATCGCAA CTAGCCGTGC ATTCTCCAAG GTTGAAAGTG |
| 5001 | CATAATGAAA TAAGATCACT ACCGGGCGTA TTTTTTGAGT TATCGAGATT TTCAGGAGCT AAGGAAGCTA AAATGGAGAA AAAAATCACT GGATATACCA |
| | GTATTACTTT ATTCTAGTGA TGGCCCGCAT AAAAAACTCA ATAGCTCTAA AAGTCCTCGA TTCCTTCGAT TTTACCTCTT TTTTTAGTGA CCTATATGGT |
| 5101 | CCGTTGATAT ATCCCAATGG CATCGTAAAG AACATTTTGA GGCATTTCAG TCAGTTGCTC AATGTACCTA TAACCAGACC GTTCAGCTGG ATATTACGGC |
| | GGCAACTATA TAGGGTTACC GTAGCATTTC TTGTAAAACT CCGTAAAGTC AGTCAACGAG TTACATGGAT ATTGGTCTGG CAAGTCGACC TATAATGCCG |
| 5201 | CTTTTTAAAG ACCGTAAAGA AAAATAAGCA CAAGTTTTAT CCGGCCTTTA TTCACATTCT TGCCCGCCTG ATGAATGCTC ATCCGGAATT CCGTATGGCA |
| | GAAAAATTTC TGGCATTTCT TTTTATTCGT GTTCAAAATA GGCCGGAAAT AAGTGTAAGA ACGGGCGGAC TACTTACGAG TAGGCCTTAA GGCATACCGT |
| 5301 | ATGAAAGACG GTGAGCTGGT GATATGGGAT AGTGTTCACC CTTGTTACAC CGTTTTCCAT GAGCAAACTG AAACGTTTTC ATCGCTCTGG AGTGAATACC |
| | TACTTTCTGC CACTCGACCA CTATACCCTA TCACAAGTGG GAACAATGTG GCAAAAGGTA CTCGTTTGAC TTTGCAAAAG TAGCGAGACC TCACTTATGG |
| 5401 | ACGACGATTT CCGGCAGTTT CTACACATAT ATTCGCAAGA TGTGGCGTGT TACGGTGAAA ACCTGGCCTA TTTCCCTAAA GGGTTTATTG AGAATATGTT |
| | TGCTGCTAAA GGCCGTCAAA GATGTGTATA TAAGCGTTCT ACACCGCACA ATGCCACTTT TGGACCGGAT AAAGGGATTT CCCAAATAAC TCTTATACAA |
| 5501 | TTTCGTATCA GCCAATCCCT GGGTGAGTTT CACCAGTTTT GATTTAAACG TGGCCAATAT GGACAACTTC TTCGCCCCCG TTTTCACCAT GGGCAAATAT |
| | AAAGCATAGT CGGTTAGGGA CCCACTCAAA GTGGTCAAAA CTAAATTTGC ACCGGTTATA CCTGTTGAAG AAGCGGGGGC AAAAGTGGTA CCCGTTTATA |
| 5601 | TATACGCAAG GCGACAAGGT GCTGATGCCG CTGGCGATTC AGGTTCATCA TGCCGTCTGT GATGGCTTCC ATGTCGGCAG AATGCTTAAT GAATTACAAC |
| | ATATGCGTTC CGCTGTTCCA CGACTACGGC GACCGCTAAG TCCAAGTAGT ACGGCAGACA CTACCGAAGG TACAGCCGTC TTACGAATTA CTTAATGTTG |
| 5701 | AGTACTGCGA TGAGTGGCAG GGCGGGGCGT AATTTTTTTA AGGCAGTTAT TGGTGCCCTT AAACGCCTGG TGCTACGCCT GAATAAGTGA TAATAAGCGG |
| | TCATGACGCT ACTCACCGTC CCGCCCCGCA TTAAAAAAAT TCCGTCAATA ACCACGGGAA TTTGCGGACC ACGATGCGGA CTTATTCACT ATTATTCGCC |
| 5801 | ATGAATGGCA GAAATTCGAA ATGACCGACC AAGCGACGCC CAACCTGCCA TCACGAGATT TCGATTCCAC CGCCGCCTTC TATGAAAGGT TGGGCTTCGG |
| | TACTTACCGT CTTTAAGCTT TACTGGCTGG TTCGCTGCGG GTTGGACGGT AGTGCTCTAA AGCTAAGGTG GCGGCGGAAG ATACTTTCCA ACCCGAAGCC |
| 5901 | TTAGCAAAAG GCCCTGCGGC CGACCTACTA GGAGGTCGCG CCCCTAGAGT ACGACCTCAA GAAGCGGGTG GGATCCCCCT CCGATTGACT TTGTGCCTTC |
| | GAGACAATAC CGGAAGGAAC CCGCGCTATG ACGGCAATAA AAAGACAGAA TAAAACGCAC GGTGTTGGGT CGTTTGTTCA TAAACGCGGG GTTCGGTCCC |
| 6001 | CTCTGTTATG GCCTTCCTTG GGCGCGATAC TGCCGTTATT TTTCTGTCTT ATTTTGCGTG CCACAACCCA GCAAACAAGT ATTTGCGCCC CAAGCCAGGG |
| | AGGGCTGGCA CTCTGTCGAT ACCCCACCGA GACCCCATTG GGGCCAATAC GCCCGCGTTT CTTCCTTTTC CCCACCCCAC CCCCCAAGTT CGGGTGAAGG |
| 6101 | TCCCGACCGT GAGACAGCTA TGGGGTGGCT CTGGGGTAAC CCCGGTTATG CGGGCGCAAA GAAGGAAAAG GGGTGGGGTG GGGGGTTCAA GCCCACTTCC |
| | CCCAGGGCTC GCAGCCAACG TCGGGGCGGC AGGCCCTGCC ATAGCCTCAG GTTACTCATA TATACTTTAG ATTGATTTAA AACTTCATTT TTAATTTAAA |
| 6201 | GGGTCCCGAG CGTCGGTTGC AGCCCCGCCG TCCGGGACGG TATCGGAGTC CAATGAGTAT ATATGAAATC TAACTAAATT TTGAAGTAAA AATTAAATTT |
| | AGGATCTAGG TGAAGATCCT TTTTGATAAT CTCATGACCA AAATCCCTTA ACGTGAGTTT TCGTTCCACT GAGCGTCAGA CCCCGTAGAA AAGATCAAAG |
| 6301 | TCCTAGATCC ACTTCTAGGA AAAACTATTA GAGTACTGGT TTTAGGGAAT TGCACTCAAA AGCAAGGTGA CTCGCAGTCT GGGGCATCTT TTCTAGTTTC |
| | GATCTTCTTG AGATCCTTTT TTTCTGCGCG TAATCTGCTG CTTGCAAACA AAAAAACCAC CGCTACCAGC GGTGGTTTGT TTGCCGGATC AAGAGCTACC |
| 6401 | CTAGAAGAAC TCTAGGAAAA AAAGACGCGC ATTAGACGAC GAACGTTTGT TTTTTTGGTG GCGATGGTCG CCACCAAACA AACGGCCTAG TTCTCGATGG |
| | AACTCTTTTT CCGAAGGTAA CTGGCTTCAG CAGAGCGCAG ATACCAAATA CTGTCCTTCT AGTGTAGCCG TAGTTAGGCC ACCACTTCAA GAACTCTGTA |
| 6501 | TTGAGAAAAA GGCTTCCATT GACCGAAGTC GTCTCGCGTC TATGGTTTAT GACAGGAAGA TCACATCGGC ATCAATCCGG TGGTGAAGTT CTTGAGACAT |
| | GCACCGCCTA CATACCTCGC TCTGCTAATC CTGTTACCAG TGGCTGCTGC CAGTGGCGAT AAGTCGTGTC TTACCGGGTT GGACTCAAGA CGATAGTTAC |
| 6601 | CGTGGCGGAT GTATGGAGCG AGACGATTAG GACAATGGTC ACCGACGACG GTCACCGCTA TTCAGCACAG AATGGCCCAA CCTGAGTTCT GCTATCAATG |
| | CGGATAAGGC GCAGCGGTCG GGCTGAACGG GGGGTTCGTG CACACAGCCC AGCTTGGAGC GAACGACCTA CACCGAACTG AGATACCTAC AGCGTGAGCT |
| 6701 | GCCTATTCCG CGTCGCCAGC CCGACTTGCC CCCCAAGCAC GTGTGTCGGG TCGAACCTCG CTTGCTGGAT GTGGCTTGAC TCTATGGATG TCGCACTCGA |
| | ATGAGAAAGC GCCACGCTTC CCGAAGGGAG AAAGGCGGAC AGGTATCCGG TAAGCGGCAG GGTCGGAACA GGAGAGCGCA CGAGGGAGCT TCCAGGGGGA |

APPENDIX 1 -continued

Nucleotide sequences of constructed plasmids(SEQ ID NOs: 53-58, in order of appearance).

```
6801  TACTCTTTCG CGGTGCGAAG GGCTTCCCTC TTTCCGCCTG TCCATAGGCC ATTCGCCGTC CCAGCCTTGT CCTCTCGCGT GCTCCCTCGA AGGTCCCCCT
      AACGCCTGGT ATCTTTATAG TCCTGTCGGG TTTCGCCACC TCTGACTTGA GCGTCGATTT TTGTGATGCT CGTCAGGGGG GCGGAGCCTA TGGAAAAACG
6901  TTGCGGACCA TAGAAATATC AGGACAGCCC AAAGCGGTGG AGACTGAACT CGCAGCTAAA AACACTACGA GCAGTCCCCC CGCCTCGGAT ACCTTTTTGC
      CCAGCAACGC GGCCTTTTTA CGGTTCCTGG CCTTTTGCTG GCCTTTTGCT CACATGTTCT TTCCTGCGTT ATCCCCTGAT TCTGTGGATA ACCGTATTAC
7001  GGTCGTTGCG CCGGAAAAAT GCCAAGGACC GGAAAACGAC CGGAAAACGA GTGTACAAGA AAGGACGCAA TAGGGGACTA AGACACCTAT TGGCATAATG
      CGCCATGCAT TAGTTATTAA TAGTAATCAA TTACGGGGTC ATTAGTTCAT AGCCCATATA TGGAGTTCCG CGTTACATAA CTTACGGTAA ATGGCCCGCC
7101  GCGGTACGTA ATCAATAATT ATCATTAGTT AATGCCCCAG TAATCAAGTA TCGGGTATAT ACCTCAAGGC GCAATGTATT GAATGCCATT TACCGGGCGG
      TGGCTGACCG CCCAACGACC CCCGCCCATT GACGTCAATA ATGACGTATG TTCCCATAGT AACGCCAATA GGGACTTTCC ATTGACGTCA ATGGGTGGAG
7201  ACCGACTGGC GGGTTGCTGG GGGCGGGTAA CTGCAGTTAT TACTGCATAC AAGGGTATCA TTGCGGTTAT CCCTGAAAGG TAACTGCAGT TACCCACCTC
      TATTTACGGT AAACTGCCCA CTTGGCAGTA CATCAAGTGT ATCATATGCC AAGTACGCCC CCTATTGACG TCAATGACGG TAAATGGCCC GCCTGGCATT
7301  ATAAATGCCA TTTGACGGGT GAACCGTCAT GTAGTTCACA TAGTATACGG TTCATGCGGG GGATAACTGC AGTTACTGCC ATTTACCGGG CGGACCGTAA
      ATGCCCAGTA CATGACCTTA TGGGACTTTC CTACTTGGCA GTACATCTAC GTATTAGTCA TCGCTATTAC CATGGTGATG CGGTTTTGGC AGTACATCAA
7401  TACGGGTCAT GTACTGGAAT ACCCTGAAAG GATGAACCGT CATGTAGATG CATAATCAGT AGCGATAATG GTACCACTAC GCCAAAACCG TCATGTAGTT
      TGGGCGTGGA TAGCGGTTTG ACTCACGGGG ATTTCCAAGT CTCCACCCCA TTGACGTCAA TGGGAGTTTG TTTTGGCACC AAAATCAACG GGACTTTCCA
7501  ACCCGCACCT ATCGCCAAAC TGAGTGCCCC TAAAGGTTCA GAGGTGGGGT AACTGCAGTT ACCCTCAAAC AAAACCGTGG TTTTAGTTGC CCTGAAAGGT
      AAATGTCGTA ACAACTCCGC CCCATTGACG CAAATGGGCG GTAGGCGTGT ACGGTGGGAG GTCTATATAA GCAGAGCT
7601  TTTACAGCAT TGTTGAGGCG GGGTAACTGC GTTTACCCGC CATCCGCACA TGCCACCCTC CAGATATATT CGTCTCGA

pVHentry-GFP1
                                   Esp3I
                                   ~~~~~~~
   1  GGTTTAGTGA ACCGTCAGAT CCGCTAGACG TCTCATATAC CTGACTGGAA TACGACAGCT CCTGCAGCTT CTGGGCGAAG ACCACCGTGG CCCATTGCGT
      CCAAATCACT TGGCAGTCTA GGCGATCTGC AGAGTATATG GACTGACCTT ATGCTGTCGA GGACGTCGAA GACCCGCTTC TGGTGGCACC GGGTAACGCA
 101  ACTTAGCGAT AATCTGGTCC GCTTGGAAGT TAGCACGGCG AGCGCGCTCC AGAGCCAAGT CACGCAGCTT AACAGTACCT ACCGCAGAGC GGTGCATGAA
      TGAATCGCTA TTAGACCAGG CGAACCTTCA ATCGTGCCGC TCGCGCGAGG TCTCGGTTCA GTGCGTCGAA TTGTCATGGA TGGCGTCTCG CCACGTACTT
 201  CAGGCCGATA ACGTTGTCCT TAGCAACCTT GACATTACCC TCACCTTTAT TGGCAGGGAA GACGTGCTTC TGACCAGTAG TGCCCTCACG AGCGGTACCA
      GTCCGGCTAT TGCAACAGGA ATCGTTGGAA CTGTAATGGG AGTGGAAATA ACCGTCCCTT CTGCACGAAG ACTGGTCATC ACGGGAGTGC TCGCCATGGT
 301  GCACCACCAG CGGTGAGGTG CGGAACTTCT ACAACCTCAA AGCCCATAAC GTTGCGGATA GAACCCTTCT CAGGGTCAAT CAGAGCAGCG TAGTTTGCTG
      CGTGGTGGTC GCCACTCCAC GCCTTGAAGA TGTTGGAGTT TCGGGTATTG CAACGCCTAT CTTGGGAAGA GTCCCAGTTA GTCTCGTCGC ATCAAACGAC
 401  CGTTCGGCAT CAGTGCTGCC AGAATCGCAG AGTAGCTATC TGGGTCACAG TAGAACACAC GGTCAGCAGC CGGAACATAG TTCTTGGTCA GAGCCGCACG
      GCAAGCCGTA GTCACGACGG TCTTAGCGTC TCATCGATAG ACCCAGTGTC ATCTTGTGTG CCAGTCGTCG GCCTTGTATC AAGAACCAGT CTCGGCGTGC
 501  AGCCTTAGTC AGAGCCGCAA TAATCTCCTT ACCCAGCGCA ACTTGGTCGG TAAGTGCGGC CTTGTTCTGA GTGGTCTCAA TTACGGTAGC AGTACCTAAG
      TCGGAATCAG TCTCGGCGTT ATTAGAGGAA TGGGTCGCGT TGAACCAGCC ATTCACGCCG GAACAAGACT CACCAGAGTT AATGCCATCG TCATGGATTC
 601  CCCTCGATGT TCTCATTATA TTTGCTTTCC ACGTTACACA GACCGGCAAT CTCAGCCAGA ACCGCACCAT CCGCAGCCAT CGCCAGAGAT TCACCCAACT
      GGGAGCTACA AGAGTAATAT AAACGAAAGG TGCAATGTGT CTGGCCGTTA GAGTCGGTCT TGGCGTGGTA GGCGTCGGTA GCGGTCTCTA AGTGGGTTGA
 701  GAGAGGTATA CTCAGAGCGA ACGTCGTAGT GGTTCATCGC GTCCTCAATA TCATAAATCA GAACGTCAGC CGTCAGGAGA CCGTCAATGG TGATTACCTT
      CTCTCCATAT GAGTCTCGCT TGCAGCATCA CCAAGTAGCG CAGGAGTTAT AGTATTTAGT CTTGCAGTCG GCAGTCCTCT GGCAGTTACC ACTAATGGAA
 801  CTCGGTGTGT TTGATGTCCT TACGTTTATC GTCGAGGTTC TCGCCCGGAG CCAGATACGC TGCCTGAGTG CGACCCAGAA CAGGGAACTG AGCGGATTTA
      GAGCCACACA AACTACAGGA ATGCAAATAG CAGCTCCAAG AGCGGGCCTC GGTCTATGCG ACGGACTCAC GCTGGGTCTT GTCCCTTGAC TCGCCTAAAT
 901  CCGCTGGAGA TGGAACGTAC CATGTGGCGA GAAGTGGTCA CGGAGGTACG AGCGAACGCA GTCAGGACTT CACCGCCAAA TACCTTCAAG AACAACGCCA
      GGCGACCTCT ACCTTGCATG GTACACCGCT CTTCACCAGT GCCTCCATGC TCGCTTGCGT CAGTCCTGAA GTGGCGGTTT ATGGAAGTTC TTGTTGCGGT
                                                                                                           Esp3I
                                                                                                           ~~~~~
1001  GTTTATCTCC AGCAGCAACT ACACCTTTAC CTTGGTTAGT ACCCATTTGC TGTCCACCAG TCATGCTAGC CATATGTATA TCTCCTTCTT AAAGTCGTCT
      CAAATAGAGG TCGTCGTTGA TGTGGAAATG GAACCAATCA TGGGTAAACG ACAGGTGGTC AGTACGATCG GTATACATAT AGAGGAAGAA TTTCAGCAGA
      Esp3I
      ~
1101  CCAGTGCCTC CACCAAGGGC CCATCGGTCT TCCCCCTGGC GCCCTGCTCC AGGAGCACCT CCGAGAGCAC AGCGGCCCTG GGCTGCCTGG TCAAGGACTA
      GGTCACGGAG GTGGTTCCCG GGTAGCCAGA AGGGGGACCG CGGGACGAGG TCCTCGTGGA GGCTCTCGTG TCGCCGGGAC CCGACGGACC AGTTCCTGAT
1201  CTTCCCCGAA CCGGTGACGG TGTCGTGGAA CTCAGGCGCT CTGACCAGCG GCGTGCACAC CTTCCCAGCT GTCCTACAGT CCTCAGGACT CTACTCCCTC
      GAAGGGGCTT GGCCACTGCC ACAGCACCTT GAGTCCGCGA GACTGGTCGC CGCACGTGTG GAAGGGTCGA CAGGATGTCA GGAGTCCTGA GATGAGGGAG
```

APPENDIX 1 -continued

Nucleotide sequences of constructed plasmids(SEQ ID NOs: 53-58, in order of appearance).

| | |
|---|---|
| 1301 | AGCAGCGTGG TGACCGTGCC CTCCAGCAGC TTGGGCACCC AGACCTACAT CTGCAACGTG AATCACAAGC CCAGCAACAC CAAGGTGGAC AAGAAAGTTG |
| | TCGTCGCACC ACTGGCACGG GAGGTCGTCG AACCCGTGGG TCTGGATGTA GACGTTGCAC TTAGTGTTCG GGTCGTTGTG GTTCCACCTG TTCTTTCAAC |
| 1401 | AGCCCAAATC TTGTGACAAA ACTCACACAT GCCCACCGTG CCCAGCACCT GAACTCCTGG GGGGACCGTC AGTCTTCCTC TTCCCCCCMA AACCCAAGGA |
| | TCGGGTTTAG AACACTGTTT TGAGTGTGTA CGGGTGGCAC GGGTCGTGGA CTTGAGGACC CCCCTGGCAG TCAGAAGGAG AAGGGGGGKT TTGGGTTCCT |
| 1501 | CACCCTCATG ATCTCCCGGA CCCCTGAGGT CACATGCGTG GTGGTGGACG TGAGCCACGA AGACCCTGAG GTCAAGTTCA ACTGGTACGT GGACGGCGTG |
| | GTGGGAGTAC TAGAGGGCCT GGGGACTCCA GTGTACGCAC CACCACCTGC ACTCGGTGCT TCTGGGACTC CAGTTCAAGT TGACCATGCA CCTGCCGCAC |
| 1601 | GAGGTGCATA ATGCCAAGAC AAAGCCGCGG GAGGAGCAGT ACAACAGCAC GTACCGTGTG GTCAGCGTCC TCACCGTCCT GCACCAGGAC TGGCTGAATG |
| | CTCCACGTAT TACGGTTCTG TTTCGGCGCC CTCCTCGTCA TGTTGTCGTG CATGGCACAC CAGTCGCAGG AGTGGCAGGA CGTGGTCCTG ACCGACTTAC |
| 1701 | GCAAGGAGTA CAAGTGCAAG GTCTCCAACA AAGCCCTCCC AGCCCCCATC GAGAAAACCA TCTCCAAAGC CAAAGGGCAG CCCCGAGAAC CACAGGTGTA |
| | CGTTCCTCAT GTTCACGTTC CAGAGGTTGT TTCGGGAGGG TCGGGGGTAG CTCTTTTGGT AGAGGTTTCG GTTTCCCGTC GGGGCTCTTG GTGTCCACAT |
| 1801 | CACCCTGCCC CCATCCCGGG ATGAGCTGAC CAAGAACCAG GTCAGCCTGA CCTGCCTGGT CAAAGGCTTC TACCCCAGCG ACATCGCCGT GGAGTGGGAG |
| | GTGGGACGGG GGTAGGGCCC TACTCGACTG GTTCTTGGTC CAGTCGGACT GGACGGACCA GTTTCCGAAG ATGGGGTCGC TGTAGCGGCA CCTCACCCTC |
| 1901 | AGCAATGGGC AGCCGGAGAA CAACTACAAG ACCACGCCTC CCATGCTGGA CTCCGACGGC TCCTTCTTCC TCTACAGCAA GCTCACCGTG GACAAGAGCA |
| | TCGTTACCCG TCGGCCTCTT GTTGATGTTC TGGTGCGGAG GGTACGACCT GAGGCTGCCG AGGAAGAAGG AGATGTCGTT CGAGTGGCAC CTGTTCTCGT |
| 2001 | GGTGGCAGCA GGGGAACGTC TTCTCATGCT CCGTGATGCA TGAGGCTCTG CACAACCACT ACACGCAGAA GAGCCTCTCC CTGTCTCCGG GTAAAGGGAG |
| | CCACCGTCGT CCCCTTGCAG AAGAGTACGA GGCACTACGT ACTCCGAGAC GTGTTGGTGA TGTGCGTCTT CTCGGAGAGG GACAGAGGCC CATTTCCCTC |
| 2101 | CTCGCCAGAT AAGTGGTCAG ATCCACCGGT CGCCACCATG GTGAGCAAGG GCGAGGAGCT GTTCACCGGG GTGGTGCCCA TCCTGGTCGA GCTGGACGGC |
| | GAGCGGTCTA TTCACCAGTC TAGGTGGCCA GCGGTGGTAC CACTCGTTCC CGCTCCTCGA CAAGTGGCCC CACCACGGGT AGGACCAGCT CGACCTGCCG |
| 2201 | GACGTAAACG GCCACAAGTT CAGCGTGTCC GGCGAGGGCG AGGGCGATGC CACCTACGGC AAGCTGACCC TGAAGTTCAT CTGCACCACC GGCAAGCTGC |
| | CTGCATTTGC CGGTGTTCAA GTCGCACAGG CCGCTCCCGC TCCCGCTACG GTGGATGCCG TTCGACTGGG ACTTCAAGTA GACGTGGTGG CCGTTCGACG |
| 2301 | CCGTGCCCTG GCCCACCCTC GTGACCACCC TGACCTACGG CGTGCAGTGC TTCAGCCGCT ACCCCGACCA CATGAAGCAG CACGACTTCT TCAAGTCCGC |
| | GGCACGGGAC CGGGTGGGAG CACTGGTGGG ACTGGATGCC GCACGTCACG AAGTCGGCGA TGGGGCTGGT GTACTTCGTC GTGCTGAAGA AGTTCAGGCG |
| 2401 | CATGCCCGAA GGCTACGTCC AGGAGCGCAC CATCTTCTTC AAGGACGACG GCAACTACAA GACCCGCGCC GAGGTGAAGT TCGAGGGCGA CACCCTGGTG |
| | GTACGGGCTT CCGATGCAGG TCCTCGCGTG GTAGAAGAAG TTCCTGCTGC CGTTGATGTT CTGGGCGCGG CTCCACTTCA AGCTCCCGCT GTGGGACCAC |
| 2501 | AACCGCATCG AGCTGAAGGG CATCGACTTC AAGGAGGACG GCAACATCCT GGGGCACAAG CTGGAGTACA ACTACAACAG CCACAACGTC TATATCATGG |
| | TTGGCGTAGC TCGACTTCCC GTAGCTGAAG TTCCTCCTGC CGTTGTAGGA CCCCGTGTTC GACCTCATGT TGATGTTGTC GGTGTTGCAG ATATAGTACC |
| 2601 | CCGACAAGCA GAAGAACGGC ATCAAGGTGA ACTTCAAGAT CCGCCACAAC ATCGAGGACG GCAGCGTGCA GCTCGCCGAC CACTACCAGC AGAACACCCC |
| | GGCTGTTCGT CTTCTTGCCG TAGTTCCACT TGAAGTTCTA GGCGGTGTTG TAGCTCCTGC CGTCGCACGT CGAGCGGCTG GTGATGGTCG TCTTGTGGGG |
| 2701 | CATCGGCGAC GGCCCCGTGC TGCTGCCCGA CAACCACTAC CTGAGCACCC AGTCCGCCCT GAGCAAAGAC CCCAACGAGA AGCGCGATCA CATGGTCCTG |
| | GTAGCCGCTG CCGGGGCACG ACGACGGGCT GTTGGTGATG GACTCGTGGG TCAGGCGGGA CTCGTTTCTG GGGTTGCTCT TCGCGCTAGT GTACCAGGAC |
| 2801 | CTGGAGTTCG TGACCGCCGC CGGGATCACT CTCGGCATGG ACGAGCTGTA CAAGTAAAGC GGCCGCAATT TAATTCCGGT TATTTTCCAC CATATTGCCG |
| | GACCTCAAGC ACTGGCGGCG GCCCTAGTGA GAGCCGTACC TGCTCGACAT GTTCATTTCG CCGGCGTTAA ATTAAGGCCA ATAAAAGGTG GTATAACGGC |
| 2901 | TCTTTTGGCA ATGTGAGGGC CCGGAAACCT GGCCCTGTCT TCTTGACGAG CATTCCTAGG GGTCTTTCCC CTCTCGCCAA AGGAATGCAA GGTCTGTTGA |
| | AGAAAACCGT TACACTCCCG GGCCTTTGGA CCGGGACAGA AGAACTGCTC GTAAGGATCC CCAGAAAGGG GAGAGCGGTT TCCTTACGTT CCAGACAACT |
| 3001 | ATGTCGTGAA GGAAGCAGTT CCTCTGGAAG CTTCTTGAAG ACAAACAACG TCTGTAGCGA CCCTTTGCAG GCAGCGGAAC CCCCCACCTG GCGACAGGTG |
| | TACAGCACTT CCTTCGTCAA GGAGACCTTC GAAGAACTTC TGTTTGTTGC AGACATCGCT GGGAAACGTC CGTCGCCTTG GGGGGTGGAC CGCTGTCCAC |
| 3101 | CCTCTGCGGC CAAAAGCCAC GTGTATAAGA TACACCTGCA AAGGCGGCAC AACCCCAGTG CCACGTTGTG AGTTGGATAG TTGTGGAAAG AGTCAAATGG |
| | GGAGACGCCG GTTTTCGGTG CACATATTCT ATGTGGACGT TTCCGCCGTG TTGGGGTCAC GGTGCAACAC TCAACCTATC AACACCTTTC TCAGTTTACC |
| 3201 | CTCACCTCAA GCGTATTCAA CAAGGGGCTG AAGGATGCCC AGAAGGTACC CCATTGTATG GGATCTGATC TGGGGCCTCG GTGCACATGC TTTACATGTG |
| | GAGTGGAGTT CGCATAAGTT GTTCCCCGAC TTCCTACGGG TCTTCCATGG GGTAACATAC CCTAGACTAG ACCCCGGAGC CACGTGTACG AAATGTACAC |
| 3301 | TTTAGTCGAG GTTAAAAAAC GTCTAGGCCC CCCGAACCAC GGGGACGTGG TTTTCCTTTG AAAAACACGA TGATAATATG GCCACCACCC ATACCTAGGC |
| | AAATCAGCTC CAATTTTTTG CAGATCCGGG GGGCTTGGTG CCCCTGCACC AAAAGGAAAC TTTTTGTGCT ACTATTATAC CGGTGGTGGG TATGGATCCG |
| 3401 | TTTTGCAAAG ATCGATCAAG AGACAGGATG AGGATCGTTT CGCATGATTG AACAAGATGG ATTGCACGCA GGTTCTCCGG CCGCTTGGGT GGAGAGGCTA |
| | AAAACGTTTC TAGCTAGTTC TCTGTCCTAC TCCTAGCAAA GCGTACTAAC TTGTTCTACC TAACGTGCGT CCAAGAGGCC GGCGAACCCA CCTCTCCGAT |
| 3501 | TTCGGCTATG ACTGGGCACA ACAGACAATC GGCTGCTCTG ATGCCGCCGT GTTCCGGCTG TCAGCGCAGG GGCGCCCGGT TCTTTTTGTC AAGACCGACC |
| | AAGCCGATAC TGACCCGTGT TGTCTGTTAG CCGACGAGAC TACGGCGGCA CAAGGCCGAC AGTCGCGTCC CCGCGGGCCA AGAAAAACAG TTCTGGCTGG |
| 3601 | TGTCCGGTGC CCTGAATGAA CTGCAAGACG AGGCAGCGCG GCTATCGTGG CTGGCCACGA CGGGCGTTCC TTGCGCAGCT GTGCTCGACG TTGTCACTGA |
| | ACAGGCCACG GGACTTACTT GACGTTCTGC TCCGTCGCGC CGATAGCACC GACCGGTGCT GCCCGCAAGG AACGCGTCGA CACGAGCTGC AACAGTGACT |
| 3701 | AGCGGGAAGG GACTGGCTGC TATTGGGCGA AGTGCCGGGG CAGGATCTCC TGTCATCTCA CCTTGCTCCT GCCGAGAAAG TATCCATCAT GGCTGATGCA |
| | TCGCCCTTCC CTGACCGACG ATAACCCGCT TCACGGCCCC GTCCTAGAGG ACAGTAGAGT GGAACGAGGA CGGCTCTTTC ATAGGTAGTA CCGACTACGT |

APPENDIX 1 -continued

Nucleotide sequences of constructed plasmids(SEQ ID NOs: 53-58, in order of appearance).

```
3801   ATGCGGCGGC TGCATACGCT TGATCCGGCT ACCTGCCCAT TCGACCACCA AGCGAAACAT CGCATCGAGC GAGCACGTAC TCGGATGGAA GCCGGTCTTG
       TACGCCGCCG ACGTATGCGA ACTAGGCCGA TGGACGGGTA AGCTGGTGGT TCGCTTTGTA GCGTAGCTCG CTCGTGCATG AGCCTACCTT CGGCCAGAAC
3901   TCGATCAGGA TGATCTGGAC GAAGAGCATC AGGGGCTCGC GCCAGCCGAA CTGTTCGCCA GGCTCAAGGC GAGCATGCCC GACGGCGAGG ATCTCGTCGT
       AGCTAGTCCT ACTAGACCTG CTTCTCGTAG TCCCCGAGCG CGGTCGGCTT GACAAGCGGT CCGAGTTCCG CTCGTACGGG CTGCCGCTCC TAGAGCAGCA
4001   GACCCATGGC GATGCCTGCT TGCCGAATAT CATGGTGGAA AATGGCCGCT TTTCTGGATT CATCGACTGT GGCCGGCTGG GTGTGGCGGA CCGCTATCAG
       CTGGGTACCG CTACGGACGA ACGGCTTATA GTACCACCTT TTACCGGCGA AAAGACCTAA GTAGCTGACA CCGGCCGACC CACACCGCCT GGCGATAGTC
4101   GACATAGCGT TGGCTACCCG TGATATTGCT GAAGAGCTTG GCGGCGAATG GGCTGACCGC TTCCTCGTGC TTTACGGTAT CGCCGCTCCC GATTCGCAGC
       CTGTATCGCA ACCGATGGGC ACTATAACGA CTTCTCGAAC CGCCGCTTAC CCGACTGGCG AAGGAGCACG AAATGCCATA GCGGCGAGGG CTAAGCGTCG
4201   GCATCGCCTT CTATCGCCTT CTTGACGAGT TCTTCTGAGC GGGACTCTGG GGTTCGGGCC GCACTCGAGC ATAAACTTGT TTATTGCAGC TTATAATGGT
       CGTAGCGGAA GATAGCGGAA GAACTGCTCA AGAAGACTCG CCCTGAGACC CCAAGCCCGG CGTGAGCTCG TATTTGAACA AATAACGTCG AATATTACCA
                                                                                                               I-
       SceI
                                                                                                              ~~~
4301   TACAAATAAA GCAATAGCAT CACAAATTTC ACAAATAAAG CATTTTTTTC ACTGCATTCT AGTTGTGGTT TGTCCAAACT CATCAATGTA TCTTAAGTAG
       ATGTTTATTT CGTTATCGTA GTGTTTAAAG TGTTTATTTC GTAAAAAAAG TGACGTAAGA TCAACACCAA ACAGGTTTGA GTAGTTACAT AGAATTCATC
          I-SceI
       ~~~~~~~~~~~~~~~~
4401   GGATAACAGG GTAATTTTGT TAAATCAGCT CATTTTTTAA CCAATAGGAA CGCCATCAAA AATAATTCGC GTCTGGCCTT CCTGTAGCCA GCTTTCATCA
       CCTATTGTCC CATTAAAACA ATTTAGTCGA GTAAAAAATT GGTTATCCTT GCGGTAGTTT TTATTAAGCG CAGACCGGAA GGACATCGGT CGAAAGTAGT
4501   ACATTAAATG TGAGCGAGTA ACAACCCGTC GGATTCTCCG TGGGAACAAA CGGCGGATTG ACCGTAATGG GATAGGTTAC GTTGGTGTAG ATGGGCGCAT
       TGTAATTTAC ACTCGCTCAT TGTTGGGCAG CCTAAGAGGC ACCCTTGTTT GCCGCCTAAC TGGCATTACC CTATCCAATG CAACCACATC TACCCGCGTA
4601   CGTAACCGTG CATCTGCCAG TTTGAGGGGA CGACGACCGT ATCGGCCTCA GGAAGATCGC ACTCCAGCCA GCTTTCCGGC ACCGCTTCTG GTGCCGGAAA
       GCATTGGCAC GTAGACGGTC AAACTCCCCT GCTGCTGGCA TAGCCGGAGT CCTTCTAGCG TGAGGTCGGT CGAAAGGCCG TGGCGAAGAC CACGGCCTTT
4701   CCAGGCAAAG CGCCATTCGC CATTCAGGCT GCGCAACTGT TGGGAAGGGC GATCGGTGCG GGCCTCTTCG CTATTACGCC AGCTGGCGAA AGGGGGATGT
       GGTCCGTTTC GCGGTAAGCG GTAAGTCCGA CGCGTTGACA ACCCTTCCCG CTAGCCACGC CCGGAGAAGC GATAATGCGG TCGACCGCTT TCCCCCTACA
4801   GCTGCAAGGC GATTAAGTTG GGTAACGCCA GGGTTTTCCC AGTCACGACG TTGTAAAACG ACGGCCAGTG AATTGCAATT CGTAATCATG GTCATAGCTG
       CGACGTTCCG CTAATTCAAC CCATTGCGGT CCCAAAAGGG TCAGTGCTGC AACATTTTGC TGCCGGTCAC TTAACGTTAA GCATTAGTAC CAGTATCGAC
4901   TTTCCTGTGT GAAATTGTTA TCCGCTCACA ATTCCACACA ACATACGAGC CGGAAGCATA AAGTGTAAAG CCTGGGGTGC CTAATGAGTG AGCTAACTCA
       AAAGGACACA CTTTAACAAT AGGCGAGTGT TAAGGTGTGT TGTATGCTCG GCCTTCGTAT TTCACATTTC GGACCCCACG GATTACTCAC TCGATTGAGT
                                       I-SceI
                                ~~~~~~~~~~~~~~~~~~~~
5001   CATTAATTGC GTTGCGCTCA CTGCCATTAC CCTGTTATCC CTAGTGAACC ATCACCCTAA TCAAGTTTTT TGGGGTCGAG GTGCCGTAAA GCACTAAATC
       GTAATTAACG CAACGCGAGT GACGGTAATG GGACAATAGG GATCACTTGG TAGTGGGATT AGTTCAAAAA ACCCCAGCTC CACGGCATTT CGTGATTTAG
5101   GGAACCCTAA AGGGAGCCCC CGATTTAGAG CTTGACGGGG AAAGCCGGCG AACGTGGCGA GAAAGGAAGG GAAGAAAGCG AAAGGAGCGG GCGCTAGGGC
       CCTTGGGATT TCCCTCGGGG GCTAAATCTC GAACTGCCCC TTTCGGCCGC TTGCACCGCT CTTTCCTTCC CTTCTTTCGC TTTCCTCGCC CGCGATCCCG
5201   GCTGGCAAGT GTAGCGGTCA CGCTGCGCGT AACCACCACA CCCGCCGCGC TTAATGCGCC GCTACAGGGC GCGTCAGGTG GCACTTTTCG GGGAAATGTG
       CGACCGTTCA CATCGCCAGT GCGACGCGCA TTGGTGGTGT GGGCGGCGCG AATTACGCGG CGATGTCCCG CGCAGTCCAC CGTGAAAAGC CCCTTTACAC
5301   CGCGGAACCC CTATTTGTTT ATTTTTCTAA ATACATTCAA ATATGTATCC GCTCATGAGA CAATAACCCT GATAAATGCT TCAATAATAA CGACCGGTAA
       GCGCCTTGGG GATAAACAAA TAAAAAGATT TATGTAAGTT TATACATAGG CGAGTACTCT GTTATTGGGA CTATTTACGA AGTTATTATT GCTGGCCATT
5401   TGAAAAAGGA AGAGTATGAG TATTCAACAT TTCCGTGTCG CCCTTATTCC CTTTTTTGCG GCATTTTGCC TTCCTGTTTT TGCTCACCCA GAAACGCTGG
       ACTTTTTCCT TCTCATACTC ATAAGTTGTA AAGGCACAGC GGGAATAAGG GAAAAAACGC CGTAAAACGG AAGGACAAAA ACGAGTGGGT CTTTGCGACC
5501   TGAAAGTAAA AGATGCTGAA GATCAGTTGG GTGCACGAGT GGGTTACATC GAACTGGATC TCAACAGCGG TAAGATCCTT GAGAGTTTTC GCCCCGAAGA
       ACTTTCATTT TCTACGACTT CTAGTCAACC CACGTGCTCA CCCAATGTAG CTTGACCTAG AGTTGTCGCC ATTCTAGGAA CTCTCAAAAG CGGGGCTTCT
5601   ACGTTTTCCA ATGATGAGCA CTTTTAAAGT TCTGCTATGT GGCGCGGTAT TATCCCGTAT TGACGCCGGG CAAGAGCAAC TCGGTCGCCG CATACACTAT
       TGCAAAAGGT TACTACTCGT GAAAATTTCA AGACGATACA CCGCGCCATA ATAGGGCATA ACTGCGGCCC GTTCTCGTTG AGCCAGCGGC GTATGTGATA
5701   TCTCAGAATG ACTTGGTTGA GTCTAGCGTT GATCGGCACG TAAGAGGTTC CAACTTTCAC CATAATGAAA TAAGATCACT ACCGGGCGTA TTTTTTGAGT
       AGAGTCTTAC TGAACCAACT CAGATCGCAA CTAGCCGTGC ATTCTCCAAG GTTGAAAGTG GTATTACTTT ATTCTAGTGA TGGCCCGCAT AAAAAACTCA
5801   TATCGAGATT TTCAGGAGCT AAGGAAGCTA AAATGGAGAA AAAAATCACT GGATATACCA CCGTTGATAT ATCCCAATGG CATCGTAAAG AACATTTTGA
       ATAGCTCTAA AAGTCCTCGA TTCCTTCGAT TTTACCTCTT TTTTTAGTGA CCTATATGGT GGCAACTATA TAGGGTTACC GTAGCATTTC TTGTAAAACT
5901   GGCATTTCAG TCAGTTGCTC AATGTACCTA TAACCAGACC GTTCAGCTGG ATATTACGGC CTTTTTAAAG ACCGTAAAGA AAAATAAGCA CAAGTTTTAT
       CCGTAAAGTC AGTCAACGAG TTACATGGAT ATTGGTCTGG CAAGTCGACC TATAATGCCG GAAAAATTTC TGGCATTTCT TTTTATTCGT GTTCAAAATA
```

APPENDIX 1 -continued

Nucleotide sequences of constructed plasmids(SEQ ID NOs: 53-58, in order of appearance).

```
6001    CCGGCCTTTA TTCACATTCT TGCCCGCCTG ATGAATGCTC ATCCGGAATT CCGTATGGCA ATGAAAGACG GTGAGCTGGT GATATGGGAT AGTGTTCACC
        GGCCGGAAAT AAGTGTAAGA ACGGGCGGAC TACTTACGAG TAGGCCTTAA GGCATACCGT TACTTTCTGC CACTCGACCA CTATACCCTA TCACAAGTGG
6101    CTTGTTACAC CGTTTTCCAT GAGCAAACTG AAACGTTTTC ATCGCTCTGG AGTGAATACC ACGACGATTT CCGGCAGTTT CTACACATAT ATTCGCAAGA
        GAACAATGTG GCAAAAGGTA CTCGTTTGAC TTTGCAAAAG TAGCGAGACC TCACTTATGG TGCTGCTAAA GGCCGTCAAA GATGTGTATA TAAGCGTTCT
6201    TGTGGCGTGT TACGGTGAAA ACCTGGCCTA TTTCCCTAAA GGGTTTATTG AGAATATGTT TTTCGTATCA GCCAATCCCT GGGTGAGTTT CACCAGTTTT
        ACACCGCACA ATGCCACTTT TGGACCGGAT AAAGGGATTT CCCAAATAAC TCTTATACAA AAAGCATAGT CGGTTAGGGA CCCACTCAAA GTGGTCAAAA
6301    GATTTAAACG TGGCCAATAT GGACAACTTC TTCGCCCCCG TTTTCACCAT GGGCAAATAT TATACGCAAG GCGACAAGGT GCTGATGCCG CTGGCGATTC
        CTAAATTTGC ACCGGTTATA CCTGTTGAAG AAGCGGGGGC AAAAGTGGTA CCCGTTTATA ATATGCGTTC CGCTGTTCCA CGACTACGGC GACCGCTAAG
6401    AGGTTCATCA TGCCGTCTGT GATGGCTTCC ATGTCGGCAG AATGCTTAAT GAATTACAAC AGTACTGCGA TGAGTGGCAG GGCGGGGCGT AATTTTTTTA
        TCCAAGTAGT ACGGCAGACA CTACCGAAGG TACAGCCGTC TTACGAATTA CTTAATGTTG TCATGACGCT ACTCACCGTC CCGCCCCGCA TTAAAAAAAT
6501    AGGCAGTTAT TGGTGCCCTT AAACGCCTGG TGCTACGCCT GAATAAGTGA TAATAAGCGG ATGAATGGCA GAAATTCGAA ATGACCGACC AAGCGACGCC
        TCCGTCAATA ACCACGGGAA TTTGCGGACC ACGATGCGGA CTTATTCACT ATTATTCGCC TACTTACCGT CTTTAAGCTT TACTGGCTGG TTCGCTGCGG
6601    CAACCTGCCA TCACGAGATT TCGATTCCAC CGCCGCCTTC TATGAAAGGT TGGGCTTCGG AATCGTTTTC CGGGACGCCG GCTGGATGAT CCTCCAGCGC
        GTTGGACGGT AGTGCTCTAA AGCTAAGGTG GCGGCGGAAG ATACTTTCCA ACCCGAAGCC TTAGCAAAAG GCCCTGCGGC CGACCTACTA GGAGGTCGCG
6701    GGGGATCTCA TGCTGGAGTT CTTCGCCCAC CCTAGGGGGA GGCTAACTGA AACACGGAAG GAGACAATAC CGGAAGGAAC CCGCGCTATG ACGGCAATAA
        CCCCTAGAGT ACGACCTCAA GAAGCGGGTG GGATCCCCCT CCGATTGACT TTGTGCCTTC CTCTGTTATG GCCTTCCTTG GGCGCGATAC TGCCGTTATT
6801    AAAGACAGAA TAAAACGCAC GGTGTTGGGT CGTTTGTTCA TAAACGCGGG GTTCGGTCCC AGGGCTGGCA CTCTGTCGAT ACCCCACCGA GACCCCATTG
        TTTCTGTCTT ATTTTGCGTG CCACAACCCA GCAAACAAGT ATTTGCGCCC CAAGCCAGGG TCCCGACCGT GAGACAGCTA TGGGGTGGCT CTGGGGTAAC
6901    GGGCCAATAC GCCCGCGTTT CTTCCTTTTC CCCACCCCAC CCCCCAAGTT CGGGTGAAGG CCCAGGGCTC GCAGCCAACG TCGGGGCGGC AGGCCCTGCC
        CCCGGTTATG CGGGCGCAAA GAAGGAAAAG GGGTGGGGTG GGGGGTTCAA GCCCACTTCC GGGTCCCGAG CGTCGGTTGC AGCCCCGCCG TCCGGGACGG
7001    ATAGCCTCAG GTTACTCATA TATACTTTAG ATTGATTTAA AACTTCATTT TTAATTTAAA AGGATCTAGG TGAAGATCCT TTTTGATAAT CTCATGACCA
        TATCGGAGTC CAATGAGTAT ATATGAAATC TAACTAAATT TTGAAGTAAA AATTAAATTT TCCTAGATCC ACTTCTAGGA AAAACTATTA GAGTACTGGT
7101    AAATCCCTTA ACGTGAGTTT TCGTTCCACT GAGCGTCAGA CCCCGTAGAA AAGATCAAAG GATCTTCTTG AGATCCTTTT TTTCTGCGCG TAATCTGCTG
        TTTAGGGAAT TGCACTCAAA AGCAAGGTGA CTCGCAGTCT GGGGCATCTT TTCTAGTTTC CTAGAAGAAC TCTAGGAAAA AAAGACGCGC ATTAGACGAC
7201    CTTGCAAACA AAAAAACCAC CGCTACCAGC GGTGGTTTGT TTGCCGGATC AAGAGCTACC AACTCTTTTT CCGAAGGTAA CTGGCTTCAG CAGAGCGCAG
        GAACGTTTGT TTTTTTGGTG GCGATGGTCG CCACCAAACA AACGGCCTAG TTCTCGATGG TTGAGAAAAA GGCTTCCATT GACCGAAGTC GTCTCGCGTC
7301    ATACCAAATA CTGTCCTTCT AGTGTAGCCG TAGTTAGGCC ACCACTTCAA GAACTCTGTA GCACCGCCTA CATACCTCGC TCTGCTAATC CTGTTACCAG
        TATGGTTTAT GACAGGAAGA TCACATCGGC ATCAATCCGG TGGTGAAGTT CTTGAGACAT CGTGGCGGAT GTATGGAGCG AGACGATTAG GACAATGGTC
7401    TGGCTGCTGC CAGTGGCGAT AAGTCGTGTC TTACCGGGTT GGACTCAAGA CGATAGTTAC CGGATAAGGC GCAGCGGTCG GGCTGAACGG GGGGTTCGTG
        ACCGACGACG GTCACCGCTA TTCAGCACAG AATGGCCCAA CCTGAGTTCT GCTATCAATG GCCTATTCCG CGTCGCCAGC CCGACTTGCC CCCCAAGCAC
7501    CACACAGCCC AGCTTGGAGC GAACGACCTA CACCGAACTG AGATACCTAC AGCGTGAGCT ATGAGAAAGC GCCACGCTTC CCGAAGGGAG AAAGGCGGAC
        GTGTGTCGGG TCGAACCTCG CTTGCTGGAT GTGGCTTGAC TCTATGGATG TCGCACTCGA TACTCTTTCG CGGTGCGAAG GGCTTCCCTC TTTCCGCCTG
7601    AGGTATCCGG TAAGCGGCAG GGTCGGAACA GGAGAGCGCA CGAGGGAGCT TCCAGGGGGA AACGCCTGGT ATCTTTATAG TCCTGTCGGG TTTCGCCACC
        TCCATAGGCC ATTCGCCGTC CCAGCCTTGT CCTCTCGCGT GCTCCCTCGA AGGTCCCCCT TTGCGGACCA TAGAAATATC AGGACAGCCC AAAGCGGTGG
7701    TCTGACTTGA GCGTCGATTT TTGTGATGCT CGTCAGGGGG GCGGAGCCTA TGGAAAAACG CCAGCAACGC GGCCTTTTTA CGGTTCCTGG CCTTTTGCTG
        AGACTGAACT CGCAGCTAAA AACACTACGA GCAGTCCCCC CGCCTCGGAT ACCTTTTTGC GGTCGTTGCG CCGGAAAAAT GCCAAGGACC GGAAAACGAC
7801    GCCTTTTGCT CACATGTTCT TTCCTGCGTT ATCCCCTGAT TCTGTGGATA ACCGTATTAC CGCCATGCAT TAGTTATTAA TAGTAATCAA TTACGGGGTC
        CGGAAAACGA GTGTACAAGA AAGGACGCAA TAGGGGACTA AGACACCTAT TGGCATAATG GCGGTACGTA ATCAATAATT ATCATTAGTT AATGCCCCAG
7901    ATTAGTTCAT AGCCCATATA TGGAGTTCCG CGTTACATAA CTTACGGTAA ATGGCCCGCC TGGCTGACCG CCCAACGACC CCCGCCCATT GACGTCAATA
        TAATCAAGTA TCGGGTATAT ACCTCAAGGC GCAATGTATT GAATGCCATT TACCGGGCGG ACCGACTGGC GGGTTGCTGG GGGCGGGTAA CTGCAGTTAT
8001    ATGACGTATG TTCCCATAGT AACGCCAATA GGGACTTTCC ATTGACGTCA ATGGGTGGAG TATTTACGGT AAACTGCCCA CTTGGCAGTA CATCAAGTGT
        TACTGCATAC AAGGGTATCA TTGCGGTTAT CCCTGAAAGG TAACTGCAGT TACCCACCTC ATAAATGCCA TTTGACGGGT GAACCGTCAT GTAGTTCACA
8101    ATCATATGCC AAGTACGCCC CCTATTGACG TCAATGACGG TAAATGGCCC GCCTGGCATT ATGCCCAGTA CATGACCTTA TGGGACTTTC CTACTTGGCA
        TAGTATACGG TTCATGCGGG GGATAACTGC AGTTACTGCC ATTTACCGGG CGGACCGTAA TACGGGTCAT GTACTGGAAT ACCCTGAAAG GATGAACCGT
8201    GTACATCTAC GTATTAGTCA TCGCTATTAC CATGGTGATG CGGTTTTGGC AGTACATCAA TGGGCGTGGA TAGCGGTTTG ACTCACGGGG ATTTCCAAGT
        CATGTAGATG CATAATCAGT AGCGATAATG GTACCACTAC GCCAAAACCG TCATGTAGTT ACCCGCACCT ATCGCCAAAC TGAGTGCCCC TAAAGGTTCA
8301    CTCCACCCCA TTGACGTCAA TGGGAGTTTG TTTTGGCACC AAAATCAACG GGACTTTCCA AAATGTCGTA ACAACTCCGC CCCATTGACG CAAATGGGCG
        GAGGTGGGGT AACTGCAGTT ACCCTCAAAC AAAACCGTGG TTTTAGTTGC CCTGAAAGGT TTTACAGCAT TGTTGAGGCG GGGTAACTGC GTTTACCCGC
```

APPENDIX 1 -continued

Nucleotide sequences of constructed plasmids(SEQ ID NOs: 53-58, in order of appearance).

```
8401    GTAGGCGTGT ACGGTGGGAG GTCTATATAA GCAGAGCT
        CATCCGCACA TGCCACCCTC CAGATATATT CGTCTCGA

pVHentry-MLuc7
                                  Esp3I
                                   ~~~~~~~
   1    GGTTTAGTGA ACCGTCAGAT CCGCTAGACG TCTCATATAC CTGACTGGAA TACGACAGCT CCTGCAGCTT CTGGGCGAAG ACCACCGTGG CCCATTGCGT
        CCAAATCACT TGGCAGTCTA GGCGATCTGC AGAGTATATG GACTGACCTT ATGCTGTCGA GGACGTCGAA GACCCGCTTC TGGTGGCACC GGGTAACGCA
 101    ACTTAGCGAT AATCTGGTCC GCTTGGAAGT TAGCACGGCG AGCGCGCTCC AGAGCCAAGT CACGCAGCTT AACAGTACCT ACCGCAGAGC GGTGCATGAA
        TGAATCGCTA TTAGACCAGG CGAACCTTCA ATCGTGCCGC TCGCGCGAGG TCTCGGTTCA GTGCGTCGAA TTGTCATGGA TGGCGTCTCG CCACGTACTT
 201    CAGGCCGATA ACGTTGTCCT TAGCAACCTT GACATTACCC TCACCTTTAT TGGCAGGGAA GACGTGCTTC TGACCAGTAG TGCCCTCACG AGCGGTACCA
        GTCCGGCTAT TGCAACAGGA ATCGTTGGAA CTGTAATGGG AGTGGAAATA ACCGTCCCTT CTGCACGAAG ACTGGTCATC ACGGGAGTGC TCGCCATGGT
 301    GCACCACCAG CGGTGAGGTG CGGAACTTCT ACAACCTCAA AGCCCATAAC GTTGCGGATA GAACCCTTCT CAGGGTCAAT CAGAGCAGCG TAGTTTGCTG
        CGTGGTGGTC GCCACTCCAC GCCTTGAAGA TGTTGGAGTT TCGGGTATTG CAACGCCTAT CTTGGGAAGA GTCCCAGTTA GTCTCGTCGC ATCAAACGAC
 401    CGTTCGGCAT CAGTGCTGCC AGAATCGCAG AGTAGCTATC TGGGTCACAG TAGAACACAC GGTCAGCAGC CGGAACATAG TTCTTGGTCA GAGCCGCACG
        GCAAGCCGTA GTCACGACGG TCTTAGCGTC TCATCGATAG ACCCAGTGTC ATCTTGTGTG CCAGTCGTCG GCCTTGTATC AAGAACCAGT CTCGGCGTGC
 501    AGCCTTAGTC AGAGCCGCAA TAATCTCCTT ACCCAGCGCA ACTTGGTCGG TAAGTGCGGC CTTGTTCTGA GTGGTCTCAA TTACGGTAGC AGTACCTAAG
        TCGGAATCAG TCTCGGCGTT ATTAGAGGAA TGGGTCGCGT TGAACCAGCC ATTCACGCCG GAACAAGACT CACCAGAGTT AATGCCATCG TCATGGATTC
 601    CCCTCGATGT TCTCATTATA TTTGCTTTCC ACGTTACACA GACCGGCAAT CTCAGCCAGA ACCGCACCAT CCGCAGCCAT CGCCAGAGAT TCACCCAACT
        GGGAGCTACA AGAGTAATAT AAACGAAAGG TGCAATGTGT CTGGCCGTTA GAGTCGGTCT TGGCGTGGTA GGCGTCGGTA GCGGTCTCTA AGTGGGTTGA
 701    GAGAGGTATA CTCAGAGCGA ACGTCGTAGT GGTTCATCGC GTCCTCAATA TCATAAATCA GAACGTCAGC CGTCAGGAGA CCGTCAATGG TGATTACCTT
        CTCTCCATAT GAGTCTCGCT TGCAGCATCA CCAAGTAGCG CAGGAGTTAT AGTATTTAGT CTTGCAGTCG GCAGTCCTCT GGCAGTTACC ACTAATGGAA
 801    CTCGGTGTGT TTGATGTCCT TACGTTTATC GTCGAGGTTC TCGCCCGGAG CCAGATACGC TGCCTGAGTG CGACCCAGAA CAGGGAACTG AGCGGATTTA
        GAGCCACACA AACTACAGGA ATGCAAATAG CAGCTCCAAG AGCGGGCCTC GGTCTATGCG ACGGACTCAC GCTGGGTCTT GTCCCTTGAC TCGCCTAAAT
 901    CCGCTGGAGA TGGAACGTAC CATGTGGCGA GAAGTGGTCA CGGAGGTACG AGCGAACGCA GTCAGGACTT CACCGCCAAA TACCTTCAAG AACAACGCCA
        GGCGACCTCT ACCTTGCATG GTACACCGCT CTTCACCAGT GCCTCCATGC TCGCTTGCGT CAGTCCTGAA GTGGCGGTTT ATGGAAGTTC TTGTTGCGGT
                                                                                                             Esp3I
                                                                                                             ~~~~~
1001    GTTTATCTCC AGCAGCAACT ACACCTTTAC CTTGGTTAGT ACCCATTTGC TGTCCACCAG TCATGCTAGC CATATGTATA TCTCCTTCTT AAAGTCGTCT
        CAAATAGAGG TCGTCGTTGA TGTGGAAATG GAACCAATCA TGGGTAAACG ACAGGTGGTC AGTACGATCG GTATACATAT AGAGGAAGAA TTTCAGCAGA
        Esp3I
        ~
1101    CCAGTGCCTC CACCAAGGGC CCATCGGTCT TCCCCCTGGC GCCCTGCTCC AGGAGCACCT CCGAGAGCAC AGCGGCCCTG GGCTGCCTGG TCAAGGACTA
        GGTCACGGAG GTGGTTCCCG GGTAGCCAGA AGGGGGACCG CGGGACGAGG TCCTCGTGGA GGCTCTCGTG TCGCCGGGAC CCGACGGACC AGTTCCTGAT
1201    CTTCCCCGAA CCGGTGACGG TGTCGTGGAA CTCAGGCGCT CTGACCAGCG GCGTGCACAC CTTCCCAGCT GTCCTACAGT CCTCAGGACT CTACTCCCTC
        GAAGGGGCTT GGCCACTGCC ACAGCACCTT GAGTCCGCGA GACTGGTCGC CGCACGTGTG GAAGGGTCGA CAGGATGTCA GGAGTCCTGA GATGAGGGAG
1301    AGCAGCGTGG TGACCGTGCC CTCCAGCAGC TTGGGCACCC AGACCTACAT CTGCAACGTG AATCACAAGC CCAGCAACAC CAAGGTGGAC AAGAAAGTTG
        TCGTCGCACC ACTGGCACGG GAGGTCGTCG AACCCGTGGG TCTGGATGTA GACGTTGCAC TTAGTGTTCG GGTCGTTGTG GTTCCACCTG TTCTTTCAAC
1401    AGCCCAAATC TTGTGACAAA ACTCACACAT GCCCACCGTG CCCAGCACCT GAACTCCTGG GGGGACCGTC AGTCTTCCTC TTCCCCCCMA AACCCAAGGA
        TCGGGTTTAG AACACTGTTT TGAGTGTGTA CGGGTGGCAC GGGTCGTGGA CTTGAGGACC CCCCTGGCAG TCAGAAGGAG AAGGGGGGKT TTGGGTTCCT
1501    CACCCTCATG ATCTCCCGGA CCCCTGAGGT CACATGCGTG GTGGTGGACG TGAGCCACGA AGACCCTGAG GTCAAGTTCA ACTGGTACGT GGACGGCGTG
        GTGGGAGTAC TAGAGGGCCT GGGGACTCCA GTGTACGCAC CACCACCTGC ACTCGGTGCT TCTGGGACTC CAGTTCAAGT TGACCATGCA CCTGCCGCAC
1601    GAGGTGCATA ATGCCAAGAC AAAGCCGCGG GAGGAGCAGT ACAACAGCAC GTACCGTGTG GTCAGCGTCC TCACCGTCCT GCACCAGGAC TGGCTGAATG
        CTCCACGTAT TACGGTTCTG TTTCGGCGCC CTCCTCGTCA TGTTGTCGTG CATGGCACAC CAGTCGCAGG AGTGGCAGGA CGTGGTCCTG ACCGACTTAC
1701    GCAAGGAGTA CAAGTGCAAG GTCTCCAACA AAGCCCTCCC AGCCCCCATC GAGAAAACCA TCTCCAAAGC CAAAGGGCAG CCCCGAGAAC CACAGGTGTA
        CGTTCCTCAT GTTCACGTTC CAGAGGTTGT TTCGGGAGGG TCGGGGGTAG CTCTTTTGGT AGAGGTTTCG GTTTCCCGTC GGGGCTCTTG GTGTCCACAT
1801    CACCCTGCCC CCATCCCGGG ATGAGCTGAC CAAGAACCAG GTCAGCCTGA CCTGCCTGGT CAAAGGCTTC TACCCCAGCG ACATCGCCGT GGAGTGGGAG
        GTGGGACGGG GGTAGGGCCC TACTCGACTG GTTCTTGGTC CAGTCGGACT GGACGGACCA GTTTCCGAAG ATGGGGTCGC TGTAGCGGCA CCTCACCCTC
1901    AGCAATGGGC AGCCGGAGAA CAACTACAAG ACCACGCCTC CCATGCTGGA CTCCGACGGC TCCTTCTTCC TCTACAGCAA GCTCACCGTG GACAAGAGCA
        TCGTTACCCG TCGGCCTCTT GTTGATGTTC TGGTGCGGAG GGTACGACCT GAGGCTGCCG AGGAAGAAGG AGATGTCGTT CGAGTGGCAC CTGTTCTCGT
```

APPENDIX 1 -continued

Nucleotide sequences of constructed plasmids(SEQ ID NOs: 53-58, in order of appearance).

```
2001  GGTGGCAGCA GGGGAACGTC TTCTCATGCT CCGTGATGCA TGAGGCTCTG CACAACCACT ACACGCAGAA GAGCCTCTCC CTGTCTCCGG GTAAAGGGTA
      CCACCGTCGT CCCCTTGCAG AAGAGTACGA GGCACTACGT ACTCCGAGAC GTGTTGGTGA TGTGCGTCTT CTCGGAGAGG GACAGAGGCC CATTTCCCAT
2101  CATGTCCCAT ATGCTCGACA TGGCAAGCAG CCTGAGACAG ATTCTGGACT CCCAGAAAAT GGAGTGGAGG TCCAACGCCG GGGGCAGCGG TAGGGATAAG
      GTACAGGGTA TACGAGCTGT ACCGTTCGTC GGACTCTGTC TAAGACCTGA GGGTCTTTTA CCTCACCTCC AGGTTGCGGC CCCCGTCGCC ATCCCTATTC
2201  TGGTCAGATC TTCGCGACAA TTCCAAATCA ACTGAGTTCG ATCCTAACAT TGACATTGTT GGTTTAGAAG GAAAATTTGG TATTACAAAC CTAGAAACGG
      ACCAGTCTAG AAGCGCTGTT AAGGTTTAGT TGACTCAAGC TAGGATTGTA ACTGTAACAA CCAAATCTTC CTTTTAAACC ATAATGTTTG GATCTTTGCC
2301  ATTTATTCAC AATCTGGGAG ACAATGGAGG TCATGATCAA AGCAGATATT GCAGATACTG ATAGAGCCAG CAACTTTGTT GCAACTGAAA CCGATGCTAA
      TAAATAAGTG TTAGACCCTC TGTTACCTCC AGTACTAGTT TCGTCTATAA CGTCTATGAC TATCTCGGTC GTTGAAACAA CGTTGACTTT GGCTACGATT
2401  CCGCGGAAAA ATGCCTGGCA AAAAACTGCC ACTGGCAGTT ATCATGGAAA TGGAAGCCAA TGCTTTCAAA GCTGGCTGCA CCAGGGGATG CCTTATCTGT
      GGCGCCTTTT TACGGACCGT TTTTTGACGG TGACCGTCAA TAGTACCTTT ACCTTCGGTT ACGAAAGTTT CGACCGACGT GGTCCCCTAC GGAATAGACA
2501  CTTTCAAAAA TTAAGTGTAC AGCCAAAATG AAGGTATACA TTCCAGGAAG GTGTCACGAT TATGGTGGTG ACAAGAAAAC TGGACAGGCA GGAATTGTTG
      GAAAGTTTTT AATTCACATG TCGGTTTTAC TTCCATATGT AAGGTCCTTC CACAGTGCTA ATACCACCAC TGTTCTTTTG ACCTGTCCGT CCTTAACAAC
2601  GTGCAATTGT TGACATTCCC GAAATCTCTG GATTTAAGGA GATGGCACCC ATGGAACAGT TCATTGCTCA AGTTGATCGC TGCGCTTCCT CACTACTGG
      CACGTTAACA ACTGTAAGGG CTTTAGAGAC CTAAATTCCT CTACCGTGGG TACCTTGTCA AGTAACGAGT TCAACTAGCG ACGCGAAGGA CGTGATGACC
2701  ATGTCTCAAA GGTCTTGCCA ATGTTAAGTG CTCTGAACTC CTGAAGAAAT GGCTGCCTGA CAGGTGTGCA AGTTTTGCTG ACAAGATTCA AAAAGAAGTT
      TACAGAGTTT CCAGAACGGT TACAATTCAC GAGACTTGAG GACTTCTTTA CCGACGGACT GTCCACACGT TCAAAACGAC TGTTCTAAGT TTTTCTTCAA
2801  CACAATATCA AAGGCATGGC CGGCGATCGA TGAGCGGCCG CAATTTAATT CCGGTTATTT TCCACCATAT TGCCGTCTTT TGGCAATGTG AGGGCCCGGA
      GTGTTATAGT TTCCGTACCG GCCGCTAGCT ACTCGCCGGC GTTAAATTAA GGCCAATAAA AGGTGGTATA ACGGCAGAAA ACCGTTACAC TCCCGGGCCT
2901  AACCTGGCCC TGTCTTCTTG ACGAGCATTC CTAGGGGTCT TTCCCCTCTC GCCAAAGGAA TGCAAGGTCT GTTGAATGTC GTGAAGGAAG CAGTTCCTCT
      TTGGACCGGG ACAGAAGAAC TGCTCGTAAG GATCCCCAGA AAGGGGAGAG CGGTTTCCTT ACGTTCCAGA CAACTTACAG CACTTCCTTC GTCAAGGAGA
3001  GGAAGCTTCT TGAAGACAAA CAACGTCTGT AGCGACCCTT TGCAGGCAGC GGAACCCCCC ACCTGGCGAC AGGTGCCTCT GCGGCCAAAA GCCACGTGTA
      CCTTCGAAGA ACTTCTGTTT GTTGCAGACA TCGCTGGGAA ACGTCCGTCG CCTTGGGGGG TGGACCGCTG TCCACGGAGA CGCCGGTTTT CGGTGCACAT
3101  TAAGATACAC CTGCAAAGGC GGCACAACCC CAGTGCCACG TTGTGAGTTG GATAGTTGTG GAAAGAGTCA AATGGCTCAC CTCAAGCGTA TTCAACAAGG
      ATTCTATGTG GACGTTTCCG CCGTGTTGGG GTCACGGTGC AACACTCAAC CTATCAACAC CTTTCTCAGT TTACCGAGTG GAGTTCGCAT AAGTTGTTCC
3201  GGCTGAAGGA TGCCCAGAAG GTACCCCATT GTATGGGATC TGATCTGGGG CCTCGGTGCA CATGCTTTAC ATGTGTTTAG TCGAGGTTAA AAAACGTCTA
      CCGACTTCCT ACGGGTCTTC CATGGGGTAA CATACCCTAG ACTAGACCCC GGAGCCACGT GTACGAAATG TACACAAATC AGCTCCAATT TTTTGCAGAT
3301  CGGCCCCCGA ACCACGGGGA CGTGGTTTTC CTTTGAAAAA CACGATGATA ATATGGCCAC CACCCATACC TAGGCTTTTG CAAAGATCGA TCAAGAGACA
      CCGGGGGGCT TGGTGCCCCT GCACCAAAAG GAAACTTTTT GTGCTACTAT TATACCGGTG GTGGGTATGG ATCCGAAAAC GTTTCTAGCT AGTTCTCTGT
3401  GGATGAGGAT CGTTTCGCAT GATTGAACAA GATGGATTGC ACGCAGGTTC TCCGGCCGCT TGGGTGGAGA GGCTATTCGG CTATGACTGG GCACAACAGA
      CCTACTCCTA GCAAAGCGTA CTAACTTGTT CTACCTAACG TGCGTCCAAG AGGCCGGCGA ACCCACCTCT CCGATAAGCC GATACTGACC CGTGTTGTCT
3501  CAATCGGCTG CTCTGATGCC GCCGTGTTCC GGCTGTCAGC GCAGGGGCGC CCGGTTCTTT TTGTCAAGAC CGACCTGTCC GGTGCCCTGA ATGAACTGCA
      GTTAGCCGAC GAGACTACGG CGGCACAAGG CCGACAGTCG CGTCCCCGCG GGCCAAGAAA AACAGTTCTG GCTGGACAGG CCACGGGACT TACTTGACGT
3601  AGACGAGGCA GCGCGGCTAT CGTGGCTGGC CACGACGGGC GTTCCTTGCG CAGCTGTGCT CGACGTTGTC ACTGAAGCGG GAAGGGACTG GCTGCTATTG
      TCTGCTCCGT CGCGCCGATA GCACCGACCG GTGCTGCCCG CAAGGAACGC GTCGACACGA GCTGCAACAG TGACTTCGCC CTTCCCTGAC CGACGATAAC
3701  GGCGAAGTGC CGGGGCAGGA TCTCCTGTCA TCTCACCTTG CTCCTGCCGA GAAAGTATCC ATCATGGCTG ATGCAATGCG GCGGCTGCAT ACGCTTGATC
      CCGCTTCACG GCCCCGTCCT AGAGGACAGT AGAGTGGAAC GAGGACGGCT CTTTCATAGG TAGTACCGAC TACGTTACGC CGCCGACGTA TGCGAACTAG
3801  CGGCTACCTG CCCATTCGAC CACCAAGCGA AACATCGCAT CGAGCGAGCA CGTACTCGGA TGGAAGCCGG TCTTGTCGAT CAGGATGATC TGGACGAAGA
      GCCGATGGAC GGGTAAGCTG GTGGTTCGCT TTGTAGCGTA GCTCGCTCGT GCATGAGCCT ACCTTCGGCC AGAACAGCTA GTCCTACTAG ACCTGCTTCT
3901  GCATCAGGGG CTCGCGCCAG CCGAACTGTT CGCCAGGCTC AAGGCGAGCA TGCCCGACGG CGAGGATCTC GTCGTGACCC ATGGCGATGC CTGCTTGCCG
      CGTAGTCCCC GAGCGCGGTC GGCTTGACAA GCGGTCCGAG TTCCGCTCGT ACGGGCTGCC GCTCCTAGAG CAGCACTGGG TACCGCTACG GACGAACGGC
4001  AATATCATGG TGGAAAATGG CCGCTTTTCT GGATTCATCG ACTGTGGCCG GCTGGGTGTG GCGGACCGCT ATCAGGACAT AGCGTTGGCT ACCCGTGATA
      TTATAGTACC ACCTTTTACC GGCGAAAAGA CCTAAGTAGC TGACACCGGC CGACCCACAC CGCCTGGCGA TAGTCCTGTA TCGCAACCGA TGGGCACTAT
4101  TTGCTGAAGA GCTTGGCGGC GAATGGGCTG ACCGCTTCCT CGTGCTTTAC GGTATCGCCG CTCCCGATTC GCAGCGCATC GCCTTCTATC GCCTTCTTGA
      AACGACTTCT CGAACCGCCG CTTACCCGAC TGGCGAAGGA GCACGAAATG CCATAGCGGC GAGGGCTAAG CGTCGCGTAG CGGAAGATAG CGGAAGAACT
4201  CGAGTTCTTC TGAGCGGGAC TCTGGGGTTC GGGCCGCACT CGAGCATAAA CTTGTTTATT GCAGCTTATA ATGGTTACAA ATAAAGCAAT AGCATCACAA
      GCTCAAGAAG ACTCGCCCTG AGACCCCAAG CCCGGCGTGA GCTCGTATTT GAACAAATAA CGTCGAATAT TACCAATGTT TATTTCGTTA TCGTAGTGTT
                                                                                    I-SceI
                                                                                ~~~~~~~~~~~~~~~~~~~~
4301  ATTTCACAAA TAAAGCATTT TTTTCACTGC ATTCTAGTTG TGGTTTGTCC AAACTCATCA ATGTATCTTA AGTAGGGATA ACAGGGTAAT TTTGTTAAAT
      TAAAGTGTTT ATTTCGTAAA AAAAGTGACG TAAGATCAAC ACCAAACAGG TTTGAGTAGT TACATAGAAT TCATCCCTAT TGTCCCATTA AAACAATTTA
```

APPENDIX 1 -continued

Nucleotide sequences of constructed plasmids(SEQ ID NOs: 53-58, in order of appearance).

```
4401  CAGCTCATTT TTTAACCAAT AGGAACGCCA TCAAAAATAA TTCGCGTCTG GCCTTCCTGT AGCCAGCTTT CATCAACATT AAATGTGAGC GAGTAACAAC
      GTCGAGTAAA AAATTGGTTA TCCTTGCGGT AGTTTTTATT AAGCGCAGAC CGGAAGGACA TCGGTCGAAA GTAGTTGTAA TTTACACTCG CTCATTGTTG
4501  CCGTCGGATT CTCCGTGGGA ACAAACGGCG GATTGACCGT AATGGGATAG GTTACGTTGG TGTAGATGGG CGCATCGTAA CCGTGCATCT GCCAGTTTGA
      GGCAGCCTAA GAGGCACCCT TGTTTGCCGC CTAACTGGCA TTACCCTATC CAATGCAACC ACATCTACCC GCGTAGCATT GGCACGTAGA CGGTCAAACT
4601  GGGGACGACG ACCGTATCGG CCTCAGGAAG ATCGCACTCC AGCCAGCTTT CCGGCACCGC TTCTGGTGCC GGAAACCAGG CAAAGCGCCA TTCGCCATTC
      CCCCTGCTGC TGGCATAGCC GGAGTCCTTC TAGCGTGAGG TCGGTCGAAA GGCCGTGGCG AAGACCACGG CCTTTGGTCC GTTTCGCGGT AAGCGGTAAG
4701  AGGCTGCGCA ACTGTTGGGA AGGGCGATCG GTGCGGGCCT CTTCGCTATT ACGCCAGCTG GCGAAAGGGG GATGTGCTGC AAGGCGATTA AGTTGGGTAA
      TCCGACGCGT TGACAACCCT TCCCGCTAGC CACGCCCGGA GAAGCGATAA TGCGGTCGAC CGCTTTCCCC CTACACGACG TTCCGCTAAT TCAACCCATT
4801  CGCCAGGGTT TTCCCAGTCA CGACGTTGTA AAACGACGGC CAGTGAATTG CAATTCGTAA TCATGGTCAT AGCTGTTTCC TGTGTGAAAT TGTTATCCGC
      GCGGTCCCAA AAGGGTCAGT GCTGCAACAT TTTGCTGCCG GTCACTTAAC GTTAAGCATT AGTACCAGTA TCGACAAAGG ACACACTTTA ACAATAGGCG
4901  TCACAATTCC ACACAACATA CGAGCCGGAA GCATAAAGTG TAAAGCCTGG GGTGCCTAAT GAGTGAGCTA ACTCACATTA ATTGCGTTGC GCTCACTGCC
      AGTGTTAAGG TGTGTTGTAT GCTCGGCCTT CGTATTTCAC ATTTCGGACC CCACGGATTA CTCACTCGAT TGAGTGTAAT TAACGCAACG CGAGTGACGG
            I-SceI
      ~~~~~~~~~~~~~~~~~~~
5001  ATTACCCTGT TATCCCTAGT GAACCATCAC CCTAATCAAG TTTTTTGGGG TCGAGGTGCC GTAAAGCACT AAATCGGAAC CCTAAAGGGA GCCCCCGATT
      TAATGGGACA ATAGGGATCA CTTGGTAGTG GGATTAGTTC AAAAAACCCC AGCTCCACGG CATTTCGTGA TTTAGCCTTG GGATTTCCCT CGGGGGCTAA
5101  TAGAGCTTGA CGGGGAAAGC CGGCGAACGT GGCGAGAAAG GAAGGGAAGA AAGCGAAAGG AGCGGGCGCT AGGGCGCTGG CAAGTGTAGC GGTCACGCTG
      ATCTCGAACT GCCCCTTTCG GCCGCTTGCA CCGCTCTTTC CTTCCCTTCT TTCGCTTTCC TCGCCCGCGA TCCCGCGACC GTTCACATCG CCAGTGCGAC
5201  CGCGTAACCA CCACACCCGC CGCGCTTAAT GCGCCGCTAC AGGGCGCGTC AGGTGGCACT TTTCGGGGAA ATGTGCGCGG AACCCCTATT TGTTTATTTT
      GCGCATTGGT GGTGTGGGCG GCGCGAATTA CGCGGCGATG TCCCGCGCAG TCCACCGTGA AAAGCCCCTT TACACGCGCC TTGGGGATAA ACAAATAAAA
5301  TCTAAATACA TTCAAATATG TATCCGCTCA TGAGACAATA ACCCTGATAA ATGCTTCAAT AATAACGACC GGTAATGAAA AAGGAAGAGT ATGAGTATTC
      AGATTTATGT AAGTTTATAC ATAGGCGAGT ACTCTGTTAT TGGGACTATT TACGAAGTTA TTATTGCTGG CCATTACTTT TTCCTTCTCA TACTCATAAG
5401  AACATTTCCG TGTCGCCCTT ATTCCCTTTT TTGCGGCATT TTGCCTTCCT GTTTTTGCTC ACCCAGAAAC GCTGGTGAAA GTAAAAGATG CTGAAGATCA
      TTGTAAAGGC ACAGCGGGAA TAAGGGAAAA AACGCCGTAA AACGGAAGGA CAAAAACGAG TGGGTCTTTG CGACCACTTT CATTTTCTAC GACTTCTAGT
5501  GTTGGGTGCA CGAGTGGGTT ACATCGAACT GGATCTCAAC AGCGGTAAGA TCCTTGAGAG TTTTCGCCCC GAAGAACGTT TTCCAATGAT GAGCACTTTT
      CAACCCACGT GCTCACCCAA TGTAGCTTGA CCTAGAGTTG TCGCCATTCT AGGAACTCTC AAAAGCGGGG CTTCTTGCAA AAGGTTACTA CTCGTGAAAA
5601  AAAGTTCTGC TATGTGGCGC GGTATTATCC CGTATTGACG CCGGGCAAGA GCAACTCGGT CGCCGCATAC ACTATTCTCA GAATGACTTG GTTGAGTCTA
      TTTCAAGACG ATACACCGCG CCATAATAGG GCATAACTGC GGCCCGTTCT CGTTGAGCCA GCGGCGTATG TGATAAGAGT CTTACTGAAC CAACTCAGAT
5701  GCGTTGATCG GCACGTAAGA GGTTCCAACT TTCACCATAA TGAAATAAGA TCACTACCGG GCGTATTTTT TGAGTTATCG AGATTTTCAG GAGCTAAGGA
      CGCAACTAGC CGTGCATTCT CCAAGGTTGA AAGTGGTATT ACTTTATTCT AGTGATGGCC CGCATAAAAA ACTCAATAGC TCTAAAAGTC CTCGATTCCT
5801  AGCTAAAATG GAGAAAAAAA TCACTGGATA TACCACCGTT GATATATCCC AATGGCATCG TAAAGAACAT TTTGAGGCAT TTCAGTCAGT TGCTCAATGT
      TCGATTTTAC CTCTTTTTTT AGTGACCTAT ATGGTGGCAA CTATATAGGG TTACCGTAGC ATTTCTTGTA AAACTCCGTA AAGTCAGTCA ACGAGTTACA
5901  ACCTATAACC AGACCGTTCA GCTGGATATT ACGGCCTTTT TAAAGACCGT AAAGAAAAAT AAGCACAAGT TTTATCCGGC CTTTATTCAC ATTCTTGCCC
      TGGATATTGG TCTGGCAAGT CGACCTATAA TGCCGGAAAA ATTTCTGGCA TTTCTTTTTA TTCGTGTTCA AAATAGGCCG GAAATAAGTG TAAGAACGGG
6001  GCCTGATGAA TGCTCATCCG GAATTCCGTA TGGCAATGAA AGACGGTGAG CTGGTGATAT GGGATAGTGT TCACCCTTGT TACACCGTTT TCCATGAGCA
      CGGACTACTT ACGAGTAGGC CTTAAGGCAT ACCGTTACTT TCTGCCACTC GACCACTATA CCCTATCACA AGTGGGAACA ATGTGGCAAA AGGTACTCGT
6101  AACTGAAACG TTTTCATCGC TCTGGAGTGA ATACCACGAC GATTTCCGGC AGTTTCTACA CATATATTCG CAAGATGTGG CGTGTTACGG TGAAAACCTG
      TTGACTTTGC AAAAGTAGCG AGACCTCACT TATGGTGCTG CTAAAGGCCG TCAAAGATGT GTATATAAGC GTTCTACACC GCACAATGCC ACTTTTGGAC
6201  GCCTATTTCC CTAAAGGGTT TATTGAGAAT ATGTTTTTCG TATCAGCCAA TCCCTGGGTG AGTTTCACCA GTTTTGATTT AAACGTGGCC AATATGGACA
      CGGATAAAGG GATTTCCCAA ATAACTCTTA TACAAAAAGC ATAGTCGGTT AGGGACCCAC TCAAAGTGGT CAAAACTAAA TTTGCACCGG TTATACCTGT
6301  ACTTCTTCGC CCCCGTTTTC ACCATGGGCA AATATTATAC GCAAGGCGAC AAGGTGCTGA TGCCGCTGGC GATTCAGGTT CATCATGCCG TCTGTGATGG
      TGAAGAAGCG GGGGCAAAAG TGGTACCCGT TTATAATATG CGTTCCGCTG TTCCACGACT ACGGCGACCG CTAAGTCCAA GTAGTACGGC AGACACTACC
6401  CTTCCATGTC GGCAGAATGC TTAATGAATT ACAACAGTAC TGCGATGAGT GGCAGGGCGG GGCGTAATTT TTTTAAGGCA GTTATTGGTG CCCTTAAACG
      GAAGGTACAG CCGTCTTACG AATTACTTAA TGTTGTCATG ACGCTACTCA CCGTCCCGCC CCGCATTAAA AAAATTCCGT CAATAACCAC GGGAATTTGC
6501  CCTGGTGCTA CGCCTGAATA AGTGATAATA AGCGGATGAA TGGCAGAAAT TCGAAATGAC CGACCAAGCG ACGCCCAACC TGCCATCACG AGATTTCGAT
      GGACCACGAT GCGGACTTAT TCACTATTAT TCGCCTACTT ACCGTCTTTA AGCTTTACTG GCTGGTTCGC TGCGGGTTGG ACGGTAGTGC TCTAAAGCTA
6601  TCCACCGCCG CCTTCTATGA AAGGTTGGGC TTCGGAATCG TTTTCCGGGA CGCCGGCTGG ATGATCCTCC AGCGCGGGGA TCTCATGCTG GAGTTCTTCG
      AGGTGGCGGC GGAAGATACT TTCCAACCCG AAGCCTTAGC AAAAGGCCCT GCGGCCGACC TACTAGGAGG TCGCGCCCCT AGAGTACGAC CTCAAGAAGC
6701  CCCACCCTAG GGGGAGGCTA ACTGAAACAC GGAAGGAGAC AATACCGGAA GGAACCCGCG CTATGACGGC AATAAAAAGA CAGAATAAAA CGCACGGTGT
      GGGTGGGATC CCCCTCCGAT TGACTTTGTG CCTTCCTCTG TTATGGCCTT CCTTGGGCGC GATACTGCCG TTATTTTTCT GTCTTATTTT GCGTGCCACA
```

APPENDIX 1 -continued

Nucleotide sequences of constructed plasmids(SEQ ID NOs: 53-58, in order of appearance).

```
6801  TGGGTCGTTT GTTCATAAAC GCGGGGTTCG GTCCCAGGGC TGGCACTCTG TCGATACCCC ACCGAGACCC CATTGGGGCC AATACGCCCG CGTTTCTTCC
      ACCCAGCAAA CAAGTATTTG CGCCCCAAGC CAGGGTCCCG ACCGTGAGAC AGCTATGGGG TGGCTCTGGG GTAACCCCGG TTATGCGGGC GCAAAGAAGG
6901  TTTTCCCCAC CCCACCCCCC AAGTTCGGGT GAAGGCCCAG GGCTCGCAGC CAACGTCGGG GCGGCAGGCC CTGCCATAGC CTCAGGTTAC TCATATATAC
      AAAAGGGGTG GGGTGGGGGG TTCAAGCCCA CTTCCGGGTC CCGAGCGTCG GTTGCAGCCC CGCCGTCCGG GACGGTATCG GAGTCCAATG AGTATATATG
7001  TTTAGATTGA TTTAAAACTT CATTTTTAAT TTAAAAGGAT CTAGGTGAAG ATCCTTTTTG ATAATCTCAT GACCAAAATC CCTTAACGTG AGTTTTCGTT
      AAATCTAACT AAATTTTGAA GTAAAAATTA AATTTTCCTA GATCCACTTC TAGGAAAAAC TATTAGAGTA CTGGTTTTAG GGAATTGCAC TCAAAAGCAA
7101  CCACTGAGCG TCAGACCCCG TAGAAAAGAT CAAAGGATCT TCTTGAGATC CTTTTTTTCT GCGCGTAATC TGCTGCTTGC AAACAAAAAA ACCACCGCTA
      GGTGACTCGC AGTCTGGGGC ATCTTTTCTA GTTTCCTAGA AGAACTCTAG GAAAAAAAGA CGCGCATTAG ACGACGAACG TTTGTTTTTT TGGTGGCGAT
7201  CCAGCGGTGG TTTGTTTGCC GGATCAAGAG CTACCAACTC TTTTTCCGAA GGTAACTGGC TTCAGCAGAG CGCAGATACC AAATACTGTC CTTCTAGTGT
      GGTCGCCACC AAACAAACGG CCTAGTTCTC GATGGTTGAG AAAAAGGCTT CCATTGACCG AAGTCGTCTC GCGTCTATGG TTTATGACAG GAAGATCACA
7301  AGCCGTAGTT AGGCCACCAC TTCAAGAACT CTGTAGCACC GCCTACATAC CTCGCTCTGC TAATCCTGTT ACCAGTGGCT GCTGCCAGTG GCGATAAGTC
      TCGGCATCAA TCCGGTGGTG AAGTTCTTGA GACATCGTGG CGGATGTATG GAGCGAGACG ATTAGGACAA TGGTCACCGA CGACGGTCAC CGCTATTCAG
7401  GTGTCTTACC GGGTTGGACT CAAGACGATA GTTACCGGAT AAGGCGCAGC GGTCGGGCTG AACGGGGGGT TCGTGCACAC AGCCCAGCTT GGAGCGAACG
      CACAGAATGG CCCAACCTGA GTTCTGCTAT CAATGGCCTA TTCCGCGTCG CCAGCCCGAC TTGCCCCCCA AGCACGTGTG TCGGGTCGAA CCTCGCTTGC
7501  ACCTACACCG AACTGAGATA CCTACAGCGT GAGCTATGAG AAAGCGCCAC GCTTCCCGAA GGGAGAAAGG CGGACAGGTA TCCGGTAAGC GGCAGGGTCG
      TGGATGTGGC TTGACTCTAT GGATGTCGCA CTCGATACTC TTTCGCGGTG CGAAGGGCTT CCCTCTTTCC GCCTGTCCAT AGGCCATTCG CCGTCCCAGC
7601  GAACAGGAGA GCGCACGAGG GAGCTTCCAG GGGGAAACGC CTGGTATCTT TATAGTCCTG TCGGGTTTCG CCACCTCTGA CTTGAGCGTC GATTTTTGTG
      CTTGTCCTCT CGCGTGCTCC CTCGAAGGTC CCCCTTTGCG GACCATAGAA ATATCAGGAC AGCCCAAAGC GGTGGAGACT GAACTCGCAG CTAAAAACAC
7701  ATGCTCGTCA GGGGGGCGGA GCCTATGGAA AAACGCCAGC AACGCGGCCT TTTTACGGTT CCTGGCCTTT TGCTGGCCTT TTGCTCACAT GTTCTTTCCT
      TACGAGCAGT CCCCCCGCCT CGGATACCTT TTTGCGGTCG TTGCGCCGGA AAAATGCCAA GGACCGGAAA ACGACCGGAA AACGAGTGTA CAAGAAAGGA
7801  GCGTTATCCC CTGATTCTGT GGATAACCGT ATTACCGCCA TGCATTAGTT ATTAATAGTA ATCAATTACG GGGTCATTAG TTCATAGCCC ATATATGGAG
      CGCAATAGGG GACTAAGACA CCTATTGGCA TAATGGCGGT ACGTAATCAA TAATTATCAT TAGTTAATGC CCCAGTAATC AAGTATCGGG TATATACCTC
7901  TTCCGCGTTA CATAACTTAC GGTAAATGGC CCGCCTGGCT GACCGCCCAA CGACCCCCGC CCATTGACGT CAATAATGAC GTATGTTCCC ATAGTAACGC
      AAGGCGCAAT GTATTGAATG CCATTTACCG GGCGGACCGA CTGGCGGGTT GCTGGGGGCG GGTAACTGCA GTTATTACTG CATACAAGGG TATCATTGCG
8001  CAATAGGGAC TTTCCATTGA CGTCAATGGG TGGAGTATTT ACGGTAAACT GCCCACTTGG CAGTACATCA AGTGTATCAT ATGCCAAGTA CGCCCCCTAT
      GTTATCCCTG AAAGGTAACT GCAGTTACCC ACCTCATAAA TGCCATTTGA CGGGTGAACC GTCATGTAGT TCACATAGTA TACGGTTCAT GCGGGGGATA
8101  TGACGTCAAT GACGGTAAAT GGCCCGCCTG GCATTATGCC CAGTACATGA CCTTATGGGA CTTTCCTACT TGGCAGTACA TCTACGTATT AGTCATCGCT
      ACTGCAGTTA CTGCCATTTA CCGGGCGGAC CGTAATACGG GTCATGTACT GGAATACCCT GAAAGGATGA ACCGTCATGT AGATGCATAA TCAGTAGCGA
8201  ATTACCATGG TGATGCGGTT TTGGCAGTAC ATCAATGGGC GTGGATAGCG GTTTGACTCA CGGGGATTTC CAAGTCTCCA CCCCATTGAC GTCAATGGGA
      TAATGGTACC ACTACGCCAA AACCGTCATG TAGTTACCCG CACCTATCGC CAAACTGAGT GCCCCTAAAG GTTCAGAGGT GGGGTAACTG CAGTTACCCT
8301  GTTTGTTTTG GCACCAAAAT CAACGGGACT TTCCAAAATG TCGTAACAAC TCCGCCCCAT TGACGCAAAT GGGCGGTAGG CGTGTACGGT GGGAGGTCTA
      CAAACAAAAC CGTGGTTTTA GTTGCCCTGA AAGGTTTTAC AGCATTGTTG AGGCGGGGTA ACTGCGTTTA CCCGCCATCC GCACATGCCA CCCTCCAGAT
8401  TATAAGCAGA GCT
      ATATTCGTCT CGA
```

pVHentry-Hisbio1

```
                        Esp3I
                        ~~~~~~~
   1  GGTTTAGTGA ACCGTCAGAT CCGCTAGACG TCTCATATAC CTGACTGGAA TACGACAGCT CCTGCAGCTT CTGGGCGAAG ACCACCGTGG CCCATTGCGT
      CCAAATCACT TGGCAGTCTA GGCGATCTGC AGAGTATATG GACTGACCTT ATGCTGTCGA GGACGTCGAA GACCCGCTTC TGGTGGCACC GGGTAACGCA
 101  ACTTAGCGAT AATCTGGTCC GCTTGGAAGT TAGCACGGCG AGCGCGCTCC AGAGCCAAGT CACGCAGCTT AACAGTACCT ACCGCAGAGC GGTGCATGAA
      TGAATCGCTA TTAGACCAGG CGAACCTTCA ATCGTGCCGC TCGCGCGAGG TCTCGGTTCA GTGCGTCGAA TTGTCATGGA TGGCGTCTCG CCACGTACTT
 201  CAGGCCGATA ACGTTGTCCT TAGCAACCTT GACATTACCC TCACCTTTAT TGGCAGGGAA GACGTGCTTC TGACCAGTAG TGCCCTCACG AGCGGTACCA
      GTCCGGCTAT TGCAACAGGA ATCGTTGGAA CTGTAATGGG AGTGGAAATA ACCGTCCCTT CTGCACGAAG ACTGGTCATC ACGGGAGTGC TCGCCATGGT
 301  GCACCACCAG CGGTGAGGTG CGGAACTTCT ACAACCTCAA AGCCCATAAC GTTGCGGATA GAACCCTTCT CAGGGTCAAT CAGAGCAGCG TAGTTTGCTG
      CGTGGTGGTC GCCACTCCAC GCCTTGAAGA TGTTGGAGTT TCGGGTATTG CAACGCCTAT CTTGGGAAGA GTCCCAGTTA GTCTCGTCGC ATCAAACGAC
 401  CGTTCGGCAT CAGTGCTGCC AGAATCGCAG AGTAGCTATC TGGGTCACAG TAGAACACAC GGTCAGCAGC CGGAACATAG TTCTTGGTCA GAGCCGCACG
      GCAAGCCGTA GTCACGACGG TCTTAGCGTC TCATCGATAG ACCCAGTGTC ATCTTGTGTG CCAGTCGTCG GCCTTGTATC AAGAACCAGT CTCGGCGTGC
 501  AGCCTTAGTC AGAGCCGCAA TAATCTCCTT ACCCAGCGCA ACTTGGTCGG TAAGTGCGGC CTTGTTCTGA GTGGTCTCAA TTACGGTAGC AGTACCTAAG
      TCGGAATCAG TCTCGGCGTT ATTAGAGGAA TGGGTCGCGT TGAACCAGCC ATTCACGCCG GAACAAGACT CACCAGAGTT AATGCCATCG TCATGGATTC
```

APPENDIX 1 -continued

Nucleotide sequences of constructed plasmids(SEQ ID NOs: 53-58, in order of appearance).

```
 601  CCCTCGATGT TCTCATTATA TTTGCTTTCC ACGTTACACA GACCGGCAAT CTCAGCCAGA ACCGCACCAT CCGCAGCCAT CGCCAGAGAT TCACCCAACT
      GGGAGCTACA AGAGTAATAT AAACGAAAGG TGCAATGTGT CTGGCCGTTA GAGTCGGTCT TGGCGTGGTA GGCGTCGGTA GCGGTCTCTA AGTGGGTTGA
 701  GAGAGGTATA CTCAGAGCGA ACGTCGTAGT GGTTCATCGC GTCCTCAATA TCATAAATCA GAACGTCAGC CGTCAGGAGA CCGTCAATGG TGATTACCTT
      CTCTCCATAT GAGTCTCGCT TGCAGCATCA CCAAGTAGCG CAGGAGTTAT AGTATTTAGT CTTGCAGTCG GCAGTCCTCT GGCAGTTACC ACTAATGGAA
 801  CTCGGTGTGT TTGATGTCCT TACGTTTATC GTCGAGGTTC TCGCCCGGAG CCAGATACGC TGCCTGAGTG CGACCCAGAA CAGGGAACTG AGCGGATTTA
      GAGCCACACA AACTACAGGA ATGCAAATAG CAGCTCCAAG AGCGGGCCTC GGTCTATGCG ACGGACTCAC GCTGGGTCTT GTCCCTTGAC TCGCCTAAAT
 901  CCGCTGGAGA TGGAACGTAC CATGTGGCGA GAAGTGGTCA CGGAGGTACG AGCGAACGCA GTCAGGACTT CACCGCCAAA TACCTTCAAG AACAACGCCA
      GGCGACCTCT ACCTTGCATG GTACACCGCT CTTCACCAGT GCCTCCATGC TCGCTTGCGT CAGTCCTGAA GTGGCGGTTT ATGGAAGTTC TTGTTGCGGT
                                                                                                            Esp3I
                                                                                                            ~~~~~
1001  GTTTATCTCC AGCAGCAACT ACACCTTTAC CTTGGTTAGT ACCCATTTGC TGTCCACCAG TCATGCTAGC CATATGTATA TCTCCTTCTT AAAGTCGTCT
      CAAATAGAGG TCGTCGTTGA TGTGGAAATG GAACCAATCA TGGGTAAACG ACAGGTGGTC AGTACGATCG GTATACATAT AGAGGAAGAA TTTCAGCAGA
      Esp3I
      ~
1101  CCAGTGCCTC CACCAAGGGC CCATCGGTCT TCCCCCTGGC GCCCTGCTCC AGGAGCACCT CCGAGAGCAC AGCGGCCCTG GGCTGCCTGG TCAAGGACTA
      GGTCACGGAG GTGGTTCCCG GGTAGCCAGA AGGGGGACCG CGGGACGAGG TCCTCGTGGA GGCTCTCGTG TCGCCGGGAC CCGACGGACC AGTTCCTGAT
1201  CTTCCCCGAA CCGGTGACGG TGTCGTGGAA CTCAGGCGCT CTGACCAGCG GCGTGCACAC CTTCCCAGCT GTCCTACAGT CCTCAGGACT CTACTCCCTC
      GAAGGGGCTT GGCCACTGCC ACAGCACCTT GAGTCCGCGA GACTGGTCGC CGCACGTGTG GAAGGGTCGA CAGGATGTCA GGAGTCCTGA GATGAGGGAG
1301  AGCAGCGTGG TGACCGTGCC CTCCAGCAGC TTGGGCACCC AGACCTACAT CTGCAACGTG AATCACAAGC CCAGCAACAC CAAGGTGGAC AAGAAAGTTG
      TCGTCGCACC ACTGGCACGG GAGGTCGTCG AACCCGTGGG TCTGGATGTA GACGTTGCAC TTAGTGTTCG GGTCGTTGTG GTTCCACCTG TTCTTTCAAC
1401  AGCCCAAATC TTGTGACAAA ACTCACACAT GCCCACCGTG CCCAGCACCT GAACTCCTGG GGGGACCGTC AGTCTTCCTC TTCCCCCCMA AACCCAAGGA
1501  TCGGGTTTAG AACACTGTTT TGAGTGTGTA CGGGTGGCAC GGGTCGTGGA CTTGAGGACC CCCCTGGCAG TCAGAAGGAG AAGGGGGGKT TTGGGTTCCT
      CACCCTCATG ATCTCCCGGA CCCCTGAGGT CACATGCGTG GTGGTGGACG TGAGCCACGA AGACCCTGAG GTCAAGTTCA ACTGGTACGT GGACGGCGTG
1601  GTGGGAGTAC TAGAGGGCCT GGGGACTCCA GTGTACGCAC CACCACCTGC ACTCGGTGCT TCTGGGACTC CAGTTCAAGT TGACCATGCA CCTGCCGCAC
      GAGGTGCATA ATGCCAAGAC AAAGCCGCGG GAGGAGCAGT ACAACAGCAC GTACCGTGTG GTCAGCGTCC TCACCGTCCT GCACCAGGAC TGGCTGAATG
1701  CTCCACGTAT TACGGTTCTG TTTCGGCGCC CTCCTCGTCA TGTTGTCGTG CATGGCACAC CAGTCGCAGG AGTGGCAGGA CGTGGTCCTG ACCGACTTAC
      GCAAGGAGTA CAAGTGCAAG GTCTCCAACA AAGCCCTCCC AGCCCCCATC GAGAAAACCA TCTCCAAAGC CAAAGGGCAG CCCCGAGAAC CACAGGTGTA
1801  CGTTCCTCAT GTTCACGTTC CAGAGGTTGT TTCGGGAGGG TCGGGGGTAG CTCTTTTGGT AGAGGTTTCG GTTTCCCGTC GGGGCTCTTG GTGTCCACAT
      CACCCTGCCC CCATCCCGGG ATGAGCTGAC CAAGAACCAG GTCAGCCTGA CCTGCCTGGT CAAAGGCTTC TACCCCAGCG ACATCGCCGT GGAGTGGGAG
1901  GTGGGACGGG GGTAGGGCCC TACTCGACTG GTTCTTGGTC CAGTCGGACT GGACGGACCA GTTTCCGAAG ATGGGGTCGC TGTAGCGGCA CCTCACCCTC
      AGCAATGGGC AGCCGGAGAA CAACTACAAG ACCACGCCTC CCATGCTGGA CTCCGACGGC TCCTTCTTCC TCTACAGCAA GCTCACCGTG GACAAGAGCA
2001  TCGTTACCCG TCGGCCTCTT GTTGATGTTC TGGTGCGGAG GGTACGACCT GAGGCTGCCG AGGAAGAAGG AGATGTCGTT CGAGTGGCAC CTGTTCTCGT
      GGTGGCAGCA GGGGAACGTC TTCTCATGCT CCGTGATGCA TGAGGCTCTG CACAACCACT ACACGCAGAA GAGCCTCTCC CTGTCTCCGG GTAAAGGGTA
2101  CCACCGTCGT CCCCTTGCAG AAGAGTACGA GGCACTACGT ACTCCGAGAC GTGTTGGTGA TGTGCGTCTT CTCGGAGAGG GACAGAGGCC CATTTCCCAT
      CATGTCCCAT ATGCTCGACA TGGCAAGCAG CCTGAGACAG ATTCTGGACT CCCAGAAAAT GGAGTGGAGG TCCAACGCCG GGGGCAGCGG TAGGGATAAG
2201  GTACAGGGTA TACGAGCTGT ACCGTTCGTC GGACTCTGTC TAAGACCTGA GGGTCTTTTA CCTCACCTCC AGGTTGCGGC CCCCGTCGCC ATCCCTATTC
      TGGTCAGATC TTCGCATGGG CAGCAGCCAT CATCATCATC ATCACAGCAG CGGCATGGCA AGCAGCCTGA GACAGATTCT GGACTCCCAG AAAATGGAGT
      ACCAGTCTAG AAGCGTACCC GTCGTCGGTA GTAGTAGTAG TAGTGTCGTC GCCGTACCGT TCGTCGGACT CTGTCTAAGA CCTGAGGGTC TTTTACCTCA
                                         I-SceI
                                   ~~~~~~~~~~~~~~~~~~~~
2301  GGAGGTCCAA CGCCGGGGGC AGCGGTAGGG ATAACAGGGT AATCCATATG CTCGAGGGGG CCAAGGCCGC GCCGGCCTGC AGGCATGCAA GCTTGGCGTA
      CCTCCAGGTT GCGGCCCCCG TCGCCATCCC TATTGTCCCA TTAGGTATAC GAGCTCCCCC GGTTCCGGCG CGGCCGGACG TCCGTACGTT CGAACCGCAT
2401  ATCATGGTCA TAGCTGTTTC CTGTGTGAAA TTGTTATCCG CTCACAATTC CACACAACAT ACGAGCCGGA AGCATAAAGT GTAAAGCCTG GGGTGCCTAA
      TAGTACCAGT ATCGACAAAG GACACACTTT AACAATAGGC GAGTGTTAAG GTGTGTTGTA TGCTCGGCCT TCGTATTTCA CATTTCGGAC CCCACGGATT
2501  TGAGTGAGCT AACTCACATT AATTGCGTTG CGCTCACTGC CCGCTTTCCA GTCGGGAAAC CTGTCGTGCC AGCGAGCTCG AATTGTTGAC ATTCCCGAAA
      ACTCACTCGA TTGAGTGTAA TTAACGCAAC GCGAGTGACG GGCGAAAGGT CAGCCCTTTG GACAGCACGG TCGCTCGAGC TTAACAACTG TAAGGGCTTT
2601  TCTCTGGATT TAAGGAGATG GCACCCATGG AACAGTTCAT TGCTCAAGTT GATCGCTGCG CTTCCTGCAC TACTGGATGT CTCAAAGGTC TTGCCAATGT
      AGAGACCTAA ATTCCTCTAC CGTGGGTACC TTGTCAAGTA ACGAGTTCAA CTAGCGACGC GAAGGACGTG ATGACCTACA GAGTTTCCAG AACGGTTACA
2701  TAAGTGCTCT GAACTCCTGA AGAAATGGCT GCCTGACAGG TGTGCAAGTT TTGCTGACAA GATTCAAAAA GAAGTTCACA ATATCAAAGG CATGGCCGGC
      ATTCACGAGA CTTGAGGACT TCTTTACCGA CGGACTGTCC ACACGTTCAA AACGACTGTT CTAAGTTTTT CTTCAAGTGT TATAGTTTCC GTACCGGCCG
```

APPENDIX 1 -continued

Nucleotide sequences of constructed plasmids(SEQ ID NOs: 53-58, in order of appearance).

```
2801   GATCGATGAG CGGCCGCAAT TTAATTCCGG TTATTTTCCA CCATATTGCC GTCTTTTGGC AATGTGAGGG CCCGGAAACC TGGCCCTGTC TTCTTGACGA
       CTAGCTACTC GCCGGCGTTA AATTAAGGCC AATAAAAGGT GGTATAACGG CAGAAAACCG TTACACTCCC GGGCCTTTGG ACCGGGACAG AAGAACTGCT
2901   GCATTCCTAG GGGTCTTTCC CCTCTCGCCA AAGGAATGCA AGGTCTGTTG AATGTCGTGA AGGAAGCAGT TCCTCTGGAA GCTTCTTGAA GACAAACAAC
       CGTAAGGATC CCCAGAAAGG GGAGAGCGGT TTCCTTACGT TCCAGACAAC TTACAGCACT TCCTTCGTCA AGGAGACCTT CGAAGAACTT CTGTTTGTTG
3001   GTCTGTAGCG ACCCTTTGCA GGCAGCGGAA CCCCCCACCT GGCGACAGGT GCCTCTGCGG CCAAAAGCCA CGTGTATAAG ATACACCTGC AAAGGCGGCA
       CAGACATCGC TGGGAAACGT CCGTCGCCTT GGGGGGTGGA CCGCTGTCCA CGGAGACGCC GGTTTTCGGT GCACATATTC TATGTGGACG TTTCCGCCGT
3101   CAACCCCAGT GCCACGTTGT GAGTTGGATA GTTGTGGAAA GAGTCAAATG GCTCACCTCA AGCGTATTCA ACAAGGGGCT GAAGGATGCC CAGAAGGTAC
       GTTGGGGTCA CGGTGCAACA CTCAACCTAT CAACACCTTT CTCAGTTTAC CGAGTGGAGT TCGCATAAGT TGTTCCCCGA CTTCCTACGG GTCTTCCATG
3201   CCCATTGTAT GGGATCTGAT CTGGGGCCTC GGTGCACATG CTTTACATGT GTTTAGTCGA GGTTAAAAAA CGTCTAGGCC CCCCGAACCA CGGGGACGTG
       GGGTAACATA CCCTAGACTA GACCCCGGAG CCACGTGTAC GAAATGTACA CAAATCAGCT CCAATTTTTT GCAGATCCGG GGGGCTTGGT GCCCCTGCAC
3301   GTTTTCCTTT GAAAAACACG ATGATAATAT GGCCACCACC CATACCTAGG CTTTTGCAAA GATCGATCAA GAGACAGGAT GAGGATCGTT TCGCATGATT
       CAAAAGGAAA CTTTTTGTGC TACTATTATA CCGGTGGTGG GTATGGATCC GAAAACGTTT CTAGCTAGTT CTCTGTCCTA CTCCTAGCAA AGCGTACTAA
3401   GAACAAGATG GATTGCACGC AGGTTCTCCG GCCGCTTGGG TGGAGAGGCT ATTCGGCTAT GACTGGGCAC AACAGACAAT CGGCTGCTCT GATGCCGCCG
       CTTGTTCTAC CTAACGTGCG TCCAAGAGGC CGGCGAACCC ACCTCTCCGA TAAGCCGATA CTGACCCGTG TTGTCTGTTA GCCGACGAGA CTACGGCGGC
3501   TGTTCCGGCT GTCAGCGCAG GGGCGCCCGG TTCTTTTTGT CAAGACCGAC CTGTCCGGTG CCCTGAATGA ACTGCAAGAC GAGGCAGCGC GGCTATCGTG
       ACAAGGCCGA CAGTCGCGTC CCCGCGGGCC AAGAAAAACA GTTCTGGCTG GACAGGCCAC GGGACTTACT TGACGTTCTG CTCCGTCGCG CCGATAGCAC
3601   GCTGGCCACG ACGGGCGTTC CTTGCGCAGC TGTGCTCGAC GTTGTCACTG AAGCGGGAAG GGACTGGCTG CTATTGGGCG AAGTGCCGGG GCAGGATCTC
       CGACCGGTGC TGCCCGCAAG GAACGCGTCG ACACGAGCTG CAACAGTGAC TTCGCCCTTC CCTGACCGAC GATAACCCGC TTCACGGCCC CGTCCTAGAG
3701   CTGTCATCTC ACCTTGCTCC TGCCGAGAAA GTATCCATCA TGGCTGATGC AATGCGGCGG CTGCATACGC TTGATCCGGC TACCTGCCCA TTCGACCACC
       GACAGTAGAG TGGAACGAGG ACGGCTCTTT CATAGGTAGT ACCGACTACG TTACGCCGCC GACGTATGCG AACTAGGCCG ATGGACGGGT AAGCTGGTGG
3801   AAGCGAAACA TCGCATCGAG CGAGCACGTA CTCGGATGGA AGCCGGTCTT GTCGATCAGG ATGATCTGGA CGAAGAGCAT CAGGGGCTCG CGCCAGCCGA
       TTCGCTTTGT AGCGTAGCTC GCTCGTGCAT GAGCCTACCT TCGGCCAGAA CAGCTAGTCC TACTAGACCT GCTTCTCGTA GTCCCCGAGC GCGGTCGGCT
3901   ACTGTTCGCC AGGCTCAAGG CGAGCATGCC CGACGGCGAG GATCTCGTCG TGACCCATGG CGATGCCTGC TTGCCGAATA TCATGGTGGA AAATGGCCGC
       TGACAAGCGG TCCGAGTTCC GCTCGTACGG GCTGCCGCTC CTAGAGCAGC ACTGGGTACC GCTACGGACG AACGGCTTAT AGTACCACCT TTTACCGGCG
4001   TTTTCTGGAT TCATCGACTG TGGCCGGCTG GGTGTGGCGG ACCGCTATCA GGACATAGCG TTGGCTACCC GTGATATTGC TGAAGAGCTT GGCGGCGAAT
       AAAAGACCTA AGTAGCTGAC ACCGGCCGAC CCACACCGCC TGGCGATAGT CCTGTATCGC AACCGATGGG CACTATAACG ACTTCTCGAA CCGCCGCTTA
4101   GGGCTGACCG CTTCCTCGTG CTTTACGGTA TCGCCGCTCC CGATTCGCAG CGCATCGCCT TCTATCGCCT TCTTGACGAG TTCTTCTGAG CGGGACTCTG
       CCCGACTGGC GAAGGAGCAC GAAATGCCAT AGCGGCGAGG GCTAAGCGTC GCGTAGCGGA AGATAGCGGA AGAACTGCTC AAGAAGACTC GCCCTGAGAC
4201   GGGTTCGGGC CGCACTCGAG CATAAACTTG TTTATTGCAG CTTATAATGG TTACAAATAA AGCAATAGCA TCACAAATTT CACAAATAAA GCATTTTTTT
       CCCAAGCCCG GCGTGAGCTC GTATTTGAAC AAATAACGTC GAATATTACC AATGTTTATT TCGTTATCGT AGTGTTTAAA GTGTTTATTT CGTAAAAAAA
                                                                                  I-SceI
                                                                         ~~~~~~~~~~~~~~~~~~~~
4301   CACTGCATTC TAGTTGTGGT TTGTCCAAAC TCATCAATGT ATCTTAAGTA GGGATAACAG GGTAATTTTG TTAAATCAGC TCATTTTTTA ACCAATAGGA
       GTGACGTAAG ATCAACACCA AACAGGTTTG AGTAGTTACA TAGAATTCAT CCCTATTGTC CCATTAAAAC AATTTAGTCG AGTAAAAAAT TGGTTATCCT
4401   ACGCCATCAA AAATAATTCG CGTCTGGCCT TCCTGTAGCC AGCTTTCATC AACATTAAAT GTGAGCGAGT AACAACCCGT CGGATTCTCC GTGGGAACAA
       TGCGGTAGTT TTTATTAAGC GCAGACCGGA AGGACATCGG TCGAAAGTAG TTGTAATTTA CACTCGCTCA TTGTTGGGCA GCCTAAGAGG CACCCTTGTT
4501   ACGGCGGATT GACCGTAATG GGATAGGTTA CGTTGGTGTA GATGGGCGCA TCGTAACCGT GCATCTGCCA GTTTGAGGGG ACGACGACCG TATCGGCCTC
       TGCCGCCTAA CTGGCATTAC CCTATCCAAT GCAACCACAT CTACCCGCGT AGCATTGGCA CGTAGACGGT CAAACTCCCC TGCTGCTGGC ATAGCCGGAG
4601   AGGAAGATCG CACTCCAGCC AGCTTTCCGG CACCGCTTCT GGTGCCGGAA ACCAGGCAAA GCGCCATTCG CCATTCAGGC TGCGCAACTG TTGGGAAGGG
       TCCTTCTAGC GTGAGGTCGG TCGAAAGGCC GTGGCGAAGA CCACGGCCTT TGGTCCGTTT CGCGGTAAGC GGTAAGTCCG ACGCGTTGAC AACCCTTCCC
4701   CGATCGGTGC GGGCCTCTTC GCTATTACGC CAGCTGGCGA AAGGGGGATG TGCTGCAAGG CGATTAAGTT GGGTAACGCC AGGGTTTTCC CAGTCACGAC
       GCTAGCCACG CCCGGAGAAG CGATAATGCG GTCGACCGCT TTCCCCCTAC ACGACGTTCC GCTAATTCAA CCCATTGCGG TCCCAAAAGG GTCAGTGCTG
4801   GTTGTAAAAC GACGGCCAGT GAATTGCAAT TCGTAATCAT GGTCATAGCT GTTTCCTGTG TGAAATTGTT ATCCGCTCAC AATTCCACAC AACATACGAG
       CAACATTTTG CTGCCGGTCA CTTAACGTTA AGCATTAGTA CCAGTATCGA CAAAGGACAC ACTTTAACAA TAGGCGAGTG TTAAGGTGTG TTGTATGCTC
4901   CCGGAAGCAT AAAGTGTAAA GCCTGGGGTG CCTAATGAGT GAGCTAACTC ACATTAATTG CGTTGCGCTC ACTGCCATTA CCCTGTTATC CCTAGTGAAC
       GGCCTTCGTA TTTCACATTT CGGACCCCAC GGATTACTCA CTCGATTGAG TGTAATTAAC GCAACGCGAG TGACGGTAAT GGGACAATAG GGATCACTTG
5001   CATCACCCTA ATCAAGTTTT TTGGGGTCGA GGTGCCGTAA AGCACTAAAT CGGAACCCTA AAGGGAGCCC CCGATTTAGA GCTTGACGGG GAAAGCCGGC
       GTAGTGGGAT TAGTTCAAAA AACCCCAGCT CCACGGCATT TCGTGATTTA GCCTTGGGAT TTCCCTCGGG GGCTAAATCT CGAACTGCCC CTTTCGGCCG
5101   GAACGTGGCG AGAAAGGAAG GGAAGAAAGC GAAAGGAGCG GGCGCTAGGG CGCTGGCAAG TGTAGCGGTC ACGCTGCGCG TAACCACCAC ACCCGCCGCG
       CTTGCACCGC TCTTTCCTTC CCTTCTTTCG CTTTCCTCGC CCGCGATCCC GCGACCGTTC ACATCGCCAG TGCGACGCGC ATTGGTGGTG TGGGCGGCGC
```

APPENDIX 1 -continued

Nucleotide sequences of constructed plasmids(SEQ ID NOs: 53-58, in order of appearance).

| | |
|---|---|
| 5201 | CTTAATGCGC CGCTACAGGG CGCGTCAGGT GGCACTTTTC GGGGAAATGT GCGCGGAACC CCTATTTGTT TATTTTTCTA AATACATTCA AATATGTATC |
| | GAATTACGCG GCGATGTCCC GCGCAGTCCA CCGTGAAAAG CCCCTTTACA CGCGCCTTGG GGATAAACAA ATAAAAAGAT TTATGTAAGT TTATACATAG |
| 5301 | CGCTCATGAG ACAATAACCC TGATAAATGC TTCAATAATA ACGACCGGTA ATGAAAAAGG AAGAGTATGA GTATTCAACA TTTCCGTGTC GCCCTTATTC |
| | GCGAGTACTC TGTTATTGGG ACTATTTACG AAGTTATTAT TGCTGGCCAT TACTTTTTCC TTCTCATACT CATAAGTTGT AAAGGCACAG CGGGAATAAG |
| 5401 | CCTTTTTTGC GGCATTTTGC CTTCCTGTTT TTGCTCACCC AGAAACGCTG GTGAAAGTAA AAGATGCTGA AGATCAGTTG GGTGCACGAG TGGGTTACAT |
| | GGAAAAAACG CCGTAAAACG GAAGGACAAA AACGAGTGGG TCTTTGCGAC CACTTTCATT TTCTACGACT TCTAGTCAAC CCACGTGCTC ACCCAATGTA |
| 5501 | CGAACTGGAT CTCAACAGCG GTAAGATCCT TGAGAGTTTT CGCCCCGAAG AACGTTTTCC AATGATGAGC ACTTTTAAAG TTCTGCTATG TGGCGCGGTA |
| | GCTTGACCTA GAGTTGTCGC CATTCTAGGA ACTCTCAAAA GCGGGGCTTC TTGCAAAAGG TTACTACTCG TGAAAATTTC AAGACGATAC ACCGCGCCAT |
| 5601 | TTATCCCGTA TTGACGCCGG GCAAGAGCAA CTCGGTCGCC GCATACACTA TTCTCAGAAT GACTTGGTTG AGTCTAGCGT TGATCGGCAC GTAAGAGGTT |
| | AATAGGGCAT AACTGCGGCC CGTTCTCGTT GAGCCAGCGG CGTATGTGAT AAGAGTCTTA CTGAACCAAC TCAGATCGCA ACTAGCCGTG CATTCTCCAA |
| 5701 | CCAACTTTCA CCATAATGAA ATAAGATCAC TACCGGGCGT ATTTTTTGAG TTATCGAGAT TTTCAGGAGC TAAGGAAGCT AAAATGGAGA AAAAAATCAC |
| | GGTTGAAAGT GGTATTACTT TATTCTAGTG ATGGCCCGCA TAAAAAACTC AATAGCTCTA AAAGTCCTCG ATTCCTTCGA TTTTACCTCT TTTTTTAGTG |
| 5801 | TGGATATACC ACCGTTGATA TATCCCAATG GCATCGTAAA GAACATTTTG AGGCATTTCA GTCAGTTGCT CAATGTACCT ATAACCAGAC CGTTCAGCTG |
| | ACCTATATGG TGGCAACTAT ATAGGGTTAC CGTAGCATTT CTTGTAAAAC TCCGTAAAGT CAGTCAACGA GTTACATGGA TATTGGTCTG GCAAGTCGAC |
| 5901 | GATATTACGG CCTTTTTAAA GACCGTAAAG AAAAATAAGC ACAAGTTTTA TCCGGCCTTT ATTCACATTC TTGCCCGCCT GATGAATGCT CATCCGGAAT |
| | CTATAATGCC GGAAAAATTT CTGGCATTTC TTTTTATTCG TGTTCAAAAT AGGCCGGAAA TAAGTGTAAG AACGGGCGGA CTACTTACGA GTAGGCCTTA |
| 6001 | TCCGTATGGC AATGAAAGAC GGTGAGCTGG TGATATGGGA TAGTGTTCAC CCTTGTTACA CCGTTTTCCA TGAGCAAACT GAAACGTTTT CATCGCTCTG |
| | AGGCATACCG TTACTTTCTG CCACTCGACC ACTATACCCT ATCACAAGTG GGAACAATGT GGCAAAAGGT ACTCGTTTGA CTTTGCAAAA GTAGCGAGAC |
| 6101 | GAGTGAATAC CACGACGATT TCCGGCAGTT TCTACACATA TATTCGCAAG ATGTGGCGTG TTACGGTGAA AACCTGGCCT ATTTCCCTAA AGGGTTTATT |
| | CTCACTTATG GTGCTGCTAA AGGCCGTCAA AGATGTGTAT ATAAGCGTTC TACACCGCAC AATGCCACTT TTGGACCGGA TAAAGGGATT TCCCAAATAA |
| 6201 | GAGAATATGT TTTTCGTATC AGCCAATCCC TGGGTGAGTT TCACCAGTTT TGATTTAAAC GTGGCCAATA TGGACAACTT CTTCGCCCCC GTTTTCACCA |
| | CTCTTATACA AAAAGCATAG TCGGTTAGGG ACCCACTCAA AGTGGTCAAA ACTAAATTTG CACCGGTTAT ACCTGTTGAA GAAGCGGGGG CAAAAGTGGT |
| 6301 | TGGGCAAATA TTATACGCAA GGCGACAAGG TGCTGATGCC GCTGGCGATT CAGGTTCATC ATGCCGTCTG TGATGGCTTC CATGTCGGCA GAATGCTTAA |
| | ACCCGTTTAT AATATGCGTT CCGCTGTTCC ACGACTACGG CGACCGCTAA GTCCAAGTAG TACGGCAGAC ACTACCGAAG GTACAGCCGT CTTACGAATT |
| 6401 | TGAATTACAA CAGTACTGCG ATGAGTGGCA GGGCGGGGCG TAATTTTTTT AAGGCAGTTA TTGGTGCCCT TAAACGCCTG GTGCTACGCC TGAATAAGTG |
| | ACTTAATGTT GTCATGACGC TACTCACCGT CCCGCCCCGC ATTAAAAAAA TTCCGTCAAT AACCACGGGA ATTTGCGGAC CACGATGCGG ACTTATTCAC |
| 6501 | ATAATAAGCG GATGAATGGC AGAAATTCGA AATGACCGAC CAAGCGACGC CCAACCTGCC ATCACGAGAT TTCGATTCCA CCGCCGCCTT CTATGAAAGG |
| | TATTATTCGC CTACTTACCG TCTTTAAGCT TTACTGGCTG GTTCGCTGCG GGTTGGACGG TAGTGCTCTA AAGCTAAGGT GGCGGCGGAA GATACTTTCC |
| 6601 | TTGGGCTTCG GAATCGTTTT CCGGGACGCC GGCTGGATGA TCCTCCAGCG CGGGGATCTC ATGCTGGAGT TCTTCGCCCA CCCTAGGGGG AGGCTAACTG |
| | AACCCGAAGC CTTAGCAAAA GGCCCTGCGG CCGACCTACT AGGAGGTCGC GCCCCTAGAG TACGACCTCA AGAAGCGGGT GGGATCCCCC TCCGATTGAC |
| 6701 | AAACACGGAA GGAGACAATA CCGGAAGGAA CCCGCGCTAT GACGGCAATA AAAAGACAGA ATAAAACGCA CGGTGTTGGG TCGTTTGTTC ATAAACGCGG |
| | TTTGTGCCTT CCTCTGTTAT GGCCTTCCTT GGGCGCGATA CTGCCGTTAT TTTTCTGTCT TATTTTGCGT GCCACAACCC AGCAAACAAG TATTTGCGCC |
| 6801 | GGTTCGGTCC CAGGGCTGGC ACTCTGTCGA TACCCCACCG AGACCCCATT GGGGCCAATA CGCCCGCGTT TCTTCCTTTT CCCCACCCCA CCCCCCAAGT |
| | CCAAGCCAGG GTCCCGACCG TGAGACAGCT ATGGGGTGGC TCTGGGGTAA CCCCGGTTAT GCGGGCGCAA AGAAGGAAAA GGGGTGGGGT GGGGGGTTCA |
| 6901 | TCGGGTGAAG GCCCAGGGCT CGCAGCCAAC GTCGGGGCGG CAGGCCCTGC CATAGCCTCA GGTTACTCAT ATATACTTTA GATTGATTTA AAACTTCATT |
| | AGCCCACTTC CGGGTCCCGA GCGTCGGTTG CAGCCCCGCC GTCCGGGACG GTATCGGAGT CCAATGAGTA TATATGAAAT CTAACTAAAT TTTGAAGTAA |
| 7001 | TTTAATTTAA AAGGATCTAG GTGAAGATCC TTTTTGATAA TCTCATGACC AAAATCCCTT AACGTGAGTT TTCGTTCCAC TGAGCGTCAG ACCCCGTAGA |
| | AAATTAAATT TTCCTAGATC CACTTCTAGG AAAAACTATT AGAGTACTGG TTTTAGGGAA TTGCACTCAA AAGCAAGGTG ACTCGCAGTC TGGGGCATCT |
| 7101 | AAAGATCAAA GGATCTTCTT GAGATCCTTT TTTTCTGCGC GTAATCTGCT GCTTGCAAAC AAAAAAACCA CCGCTACCAG CGGTGGTTTG TTTGCCGGAT |
| | TTTCTAGTTT CCTAGAAGAA CTCTAGGAAA AAAAGACGCG CATTAGACGA CGAACGTTTG TTTTTTTGGT GGCGATGGTC GCCACCAAAC AAACGGCCTA |
| 7201 | CAAGAGCTAC CAACTCTTTT TCCGAAGGTA ACTGGCTTCA GCAGAGCGCA GATACCAAAT ACTGTCCTTC TAGTGTAGCC GTAGTTAGGC CACCACTTCA |
| | GTTCTCGATG GTTGAGAAAA AGGCTTCCAT TGACCGAAGT CGTCTCGCGT CTATGGTTTA TGACAGGAAG ATCACATCGG CATCAATCCG GTGGTGAAGT |
| 7301 | AGAACTCTGT AGCACCGCCT ACATACCTCG CTCTGCTAAT CCTGTTACCA GTGGCTGCTG CCAGTGGCGA TAAGTCGTGT CTTACCGGGT TGGACTCAAG |
| | TCTTGAGACA TCGTGGCGGA TGTATGGAGC GAGACGATTA GGACAATGGT CACCGACGAC GGTCACCGCT ATTCAGCACA GAATGGCCCA ACCTGAGTTC |
| 7401 | ACGATAGTTA CCGGATAAGG CGCAGCGGTC GGGCTGAACG GGGGGTTCGT GCACACAGCC CAGCTTGGAG CGAACGACCT ACACCGAACT GAGATACCTA |
| | TGCTATCAAT GGCCTATTCC GCGTCGCCAG CCCGACTTGC CCCCCAAGCA CGTGTGTCGG GTCGAACCTC GCTTGCTGGA TGTGGCTTGA CTCTATGGAT |
| 7501 | CAGCGTGAGC TATGAGAAAG CGCCACGCTT CCCGAAGGGA GAAAGGCGGA CAGGTATCCG GTAAGCGGCA GGGTCGGAAC AGGAGAGCGC ACGAGGGAGC |
| | GTCGCACTCG ATACTCTTTC GCGGTGCGAA GGGCTTCCCT CTTTCCGCCT GTCCATAGGC CATTCGCCGT CCCAGCCTTG TCCTCTCGCG TGCTCCCTCG |
| 7601 | TTCCAGGGGG AAACGCCTGG TATCTTTATA GTCCTGTCGG GTTTCGCCAC CTCTGACTTG AGCGTCGATT TTTGTGATGC TCGTCAGGGG GGCGGAGCCT |
| | AAGGTCCCCC TTTGCGGACC ATAGAAATAT CAGGACAGCC CAAAGCGGTG GAGACTGAAC TCGCAGCTAA AAACACTACG AGCAGTCCCC CCGCCTCGGA |

APPENDIX 1 -continued

Nucleotide sequences of constructed plasmids(SEQ ID NOs: 53-58, in order of appearance).

```
7701  ATGGAAAAAC GCCAGCAACG CGGCCTTTTT ACGGTTCCTG GCCTTTTGCT GGCCTTTTGC TCACATGTTC TTTCCTGCGT TATCCCCTGA TTCTGTGGAT
      TACCTTTTTG CGGTCGTTGC GCCGGAAAAA TGCCAAGGAC CGGAAAACGA CCGGAAAACG AGTGTACAAG AAAGGACGCA ATAGGGGACT AAGACACCTA
7801  AACCGTATTA CCGCCATGCA TTAGTTATTA ATAGTAATCA ATTACGGGGT CATTAGTTCA TAGCCCATAT ATGGAGTTCC GCGTTACATA ACTTACGGTA
      TTGGCATAAT GGCGGTACGT AATCAATAAT TATCATTAGT TAATGCCCCA GTAATCAAGT ATCGGGTATA TACCTCAAGG CGCAATGTAT TGAATGCCAT
7901  AATGGCCCGC CTGGCTGACC GCCCAACGAC CCCCGCCCAT TGACGTCAAT AATGACGTAT GTTCCCATAG TAACGCCAAT AGGGACTTTC CATTGACGTC
      TTACCGGGCG GACCGACTGG CGGGTTGCTG GGGGCGGGTA ACTGCAGTTA TTACTGCATA CAAGGGTATC ATTGCGGTTA TCCCTGAAAG GTAACTGCAG
8001  AATGGGTGGA GTATTTACGG TAAACTGCCC ACTTGGCAGT ACATCAAGTG TATCATATGC CAAGTACGCC CCCTATTGAC GTCAATGACG GTAAATGGCC
      TTACCCACCT CATAAATGCC ATTTGACGGG TGAACCGTCA TGTAGTTCAC ATAGTATACG GTTCATGCGG GGGATAACTG CAGTTACTGC CATTTACCGG
8101  CGCCTGGCAT TATGCCCAGT ACATGACCTT ATGGGACTTT CCTACTTGGC AGTACATCTA CGTATTAGTC ATCGCTATTA CCATGGTGAT GCGGTTTTGG
      GCGGACCGTA ATACGGGTCA TGTACTGGAA TACCCTGAAA GGATGAACCG TCATGTAGAT GCATAATCAG TAGCGATAAT GGTACCACTA CGCCAAAACC
8201  CAGTACATCA ATGGGCGTGG ATAGCGGTTT GACTCACGGG GATTTCCAAG TCTCCACCCC ATTGACGTCA ATGGGAGTTT GTTTTGGCAC CAAAATCAAC
      GTCATGTAGT TACCCGCACC TATCGCCAAA CTGAGTGCCC CTAAAGGTTC AGAGGTGGGG TAACTGCAGT TACCCTCAAA CAAAACCGTG GTTTTAGTTG
8301  GGGACTTTCC AAAATGTCGT AACAACTCCG CCCCATTGAC GCAAATGGGC GGTAGGCGTG TACGGTGGGA GGTCTATATA AGCAGAGCT
      CCCTGAAAGG TTTTACAGCA TTGTTGAGGC GGGGTAACTG CGTTTACCCG CCATCCGCAC ATGCCACCCT CCAGATATAT TCGTCTCGA

pVHentry-CBD1
                                   Esp3I
                                   ~~~~~~~
   1  GGTTTAGTGA ACCGTCAGAT CCGCTAGACG TCTCATATAC CTGACTGGAA TACGACAGCT CCTGCAGCTT CTGGGCGAAG ACCACCGTGG CCCATTGCGT
      CCAAATCACT TGGCAGTCTA GGCGATCTGC AGAGTATATG GACTGACCTT ATGCTGTCGA GGACGTCGAA GACCCGCTTC TGGTGGCACC GGGTAACGCA
 101  ACTTAGCGAT AATCTGGTCC GCTTGGAAGT TAGCACGGCG AGCGCGCTCC AGAGCCAAGT CACGCAGCTT AACAGTACCT ACCGCAGAGC GGTGCATGAA
      TGAATCGCTA TTAGACCAGG CGAACCTTCA ATCGTGCCGC TCGCGCGAGG TCTCGGTTCA GTGCGTCGAA TTGTCATGGA TGGCGTCTCG CCACGTACTT
 201  CAGGCCGATA ACGTTGTCCT TAGCAACCTT GACATTACCC TCACCTTTAT TGGCAGGGAA GACGTGCTTC TGACCAGTAG TGCCCTCACG AGCGGTACCA
      GTCCGGCTAT TGCAACAGGA ATCGTTGGAA CTGTAATGGG AGTGGAAATA ACCGTCCCTT CTGCACGAAG ACTGGTCATC ACGGGAGTGC TCGCCATGGT
 301  GCACCACCAG CGGTGAGGTG CGGAACTTCT ACAACCTCAA AGCCCATAAC GTTGCGGATA GAACCCTTCT CAGGGTCAAT CAGAGCAGCG TAGTTTGCTG
      CGTGGTGGTC GCCACTCCAC GCCTTGAAGA TGTTGGAGTT TCGGGTATTG CAACGCCTAT CTTGGGAAGA GTCCCAGTTA GTCTCGTCGC ATCAAACGAC
 401  CGTTCGGCAT CAGTGCTGCC AGAATCGCAG AGTAGCTATC TGGGTCACAG TAGAACACAC GGTCAGCAGC CGGAACATAG TTCTTGGTCA GAGCCGCACG
      GCAAGCCGTA GTCACGACGG TCTTAGCGTC TCATCGATAG ACCCAGTGTC ATCTTGTGTG CCAGTCGTCG GCCTTGTATC AAGAACCAGT CTCGGCGTGC
 501  AGCCTTAGTC AGAGCCGCAA TAATCTCCTT ACCCAGCGCA ACTTGGTCGG TAAGTGCGGC CTTGTTCTGA GTGGTCTCAA TTACGGTAGC AGTACCTAAG
      TCGGAATCAG TCTCGGCGTT ATTAGAGGAA TGGGTCGCGT TGAACCAGCC ATTCACGCCG GAACAAGACT CACCAGAGTT AATGCCATCG TCATGGATTC
 601  CCCTCGATGT TCTCATTATA TTTGCTTTCC ACGTTACACA GACCGGCAAT CTCAGCCAGA ACCGCACCAT CCGCAGCCAT CGCCAGAGAT TCACCCAACT
      GGGAGCTACA AGAGTAATAT AAACGAAAGG TGCAATGTGT CTGGCCGTTA GAGTCGGTCT TGGCGTGGTA GGCGTCGGTA GCGGTCTCTA AGTGGGTTGA
 701  GAGAGGTATA CTCAGAGCGA ACGTCGTAGT GGTTCATCGC GTCCTCAATA TCATAAATCA GAACGTCAGC CGTCAGGAGA CCGTCAATGG TGATTACCTT
      CTCTCCATAT GAGTCTCGCT TGCAGCATCA CCAAGTAGCG CAGGAGTTAT AGTATTTAGT CTTGCAGTCG GCAGTCCTCT GGCAGTTACC ACTAATGGAA
 801  CTCGGTGTGT TTGATGTCCT TACGTTTATC GTCGAGGTTC TCGCCCGGAG CCAGATACGC TGCCTGAGTG CGACCCAGAA CAGGGAACTG AGCGGATTTA
      GAGCCACACA AACTACAGGA ATGCAAATAG CAGCTCCAAG AGCGGGCCTC GGTCTATGCG ACGGACTCAC GCTGGGTCTT GTCCCTTGAC TCGCCTAAAT
 901  CCGCTGGAGA TGGAACGTAC CATGTGGCGA GAAGTGGTCA CGGAGGTACG AGCGAACGCA GTCAGGACTT CACCGCCAAA TACCTTCAAG AACAACGCCA
      GGCGACCTCT ACCTTGCATG GTACACCGCT CTTCACCAGT GCCTCCATGC TCGCTTGCGT CAGTCCTGAA GTGGCGGTTT ATGGAAGTTC TTGTTGCGGT
                                                                                                           Esp3I
                                                                                                           ~~~~~
1001  GTTTATCTCC AGCAGCAACT ACACCTTTAC CTTGGTTAGT ACCCATTTGC TGTCCACCAG TCATGCTAGC CATATGTATA TCTCCTTCTT AAAGTCGTCT
      CAAATAGAGG TCGTCGTTGA TGTGGAAATG GAACCAATCA TGGGTAAACG ACAGGTGGTC AGTACGATCG GTATACATAT AGAGGAAGAA TTTCAGCAGA
      Esp3I
      ~
1101  CCAGTGCCTC CACCAAGGGC CCATCGGTCT TCCCCCTGGC GCCCTGCTCC AGGAGCACCT CCGAGAGCAC AGCGGCCCTG GGCTGCCTGG TCAAGGACTA
      GGTCACGGAG GTGGTTCCCG GGTAGCCAGA AGGGGGACCG CGGGACGAGG TCCTCGTGGA GGCTCTCGTG TCGCCGGGAC CCGACGGACC AGTTCCTGAT
1201  CTTCCCCGAA CCGGTGACGG TGTCGTGGAA CTCAGGCGCT CTGACCAGCG GCGTGCACAC CTTCCCAGCT GTCCTACAGT CCTCAGGACT CTACTCCCTC
      GAAGGGGCTT GGCCACTGCC ACAGCACCTT GAGTCCGCGA GACTGGTCGC CGCACGTGTG GAAGGGTCGA CAGGATGTCA GGAGTCCTGA GATGAGGGAG
1301  AGCAGCGTGG TGACCGTGCC CTCCAGCAGC TTGGGCACCC AGACCTACAT CTGCAACGTG AATCACAAGC CCAGCAACAC CAAGGTGGAC AAGAAAGTTG
      TCGTCGCACC ACTGGCACGG GAGGTCGTCG AACCCGTGGG TCTGGATGTA GACGTTGCAC TTAGTGTTCG GGTCGTTGTG GTTCCACCTG TTCTTTCAAC
```

APPENDIX 1 -continued

Nucleotide sequences of constructed plasmids(SEQ ID NOs: 53-58, in order of appearance).

```
1401  AGCCCAAATC TTGTGACAAA ACTCACACAT GCCCACCGTG CCCAGCACCT GAACTCCTGG GGGGACCGTC AGTCTTCCTC TTCCCCCCMA AACCCAAGGA
      TCGGGTTTAG AACACTGTTT TGAGTGTGTA CGGGTGGCAC GGGTCGTGGA CTTGAGGACC CCCCTGGCAG TCAGAAGGAG AAGGGGGGKT TTGGGTTCCT
1501  CACCCTCATG ATCTCCCGGA CCCCTGAGGT CACATGCGTG GTGGTGGACG TGAGCCACGA AGACCCTGAG GTCAAGTTCA ACTGGTACGT GGACGGCGTG
      GTGGGAGTAC TAGAGGGCCT GGGGACTCCA GTGTACGCAC CACCACCTGC ACTCGGTGCT TCTGGGACTC CAGTTCAAGT TGACCATGCA CCTGCCGCAC
1601  GAGGTGCATA ATGCCAAGAC AAAGCCGCGG GAGGAGCAGT ACAACAGCAC GTACCGTGTG GTCAGCGTCC TCACCGTCCT GCACCAGGAC TGGCTGAATG
      CTCCACGTAT TACGGTTCTG TTTCGGCGCC CTCCTCGTCA TGTTGTCGTG CATGGCACAC CAGTCGCAGG AGTGGCAGGA CGTGGTCCTG ACCGACTTAC
1701  GCAAGGAGTA CAAGTGCAAG GTCTCCAACA AAGCCCTCCC AGCCCCCATC GAGAAAACCA TCTCCAAAGC CAAAGGGCAG CCCCGAGAAC CACAGGTGTA
      CGTTCCTCAT GTTCACGTTC CAGAGGTTGT TTCGGGAGGG TCGGGGGTAG CTCTTTTGGT AGAGGTTTCG GTTTCCCGTC GGGGCTCTTG GTGTCCACAT
1801  CACCCTGCCC CCATCCCGGG ATGAGCTGAC CAAGAACCAG GTCAGCCTGA CCTGCCTGGT CAAAGGCTTC TACCCCAGCG ACATCGCCGT GGAGTGGGAG
      GTGGGACGGG GGTAGGGCCC TACTCGACTG GTTCTTGGTC CAGTCGGACT GGACGGACCA GTTTCCGAAG ATGGGGTCGC TGTAGCGGCA CCTCACCCTC
1901  AGCAATGGGC AGCCGGAGAA CAACTACAAG ACCACGCCTC CCATGCTGGA CTCCGACGGC TCCTTCTTCC TCTACAGCAA GCTCACCGTG GACAAGAGCA
      TCGTTACCCG TCGGCCTCTT GTTGATGTTC TGGTGCGGAG GGTACGACCT GAGGCTGCCG AGGAAGAAGG AGATGTCGTT CGAGTGGCAC CTGTTCTCGT
2001  GGTGGCAGCA GGGGAACGTC TTCTCATGCT CCGTGATGCA TGAGGCTCTG CACAACCACT ACACGCAGAA GAGCCTCTCC CTGTCTCCGG GTAAAGGGTA
      CCACCGTCGT CCCCTTGCAG AAGAGTACGA GGCACTACGT ACTCCGAGAC GTGTTGGTGA TGTGCGTCTT CTCGGAGAGG GACAGAGGCC CATTTCCCAT
2101  CATGTCCCAT ATGCTCGACA TGGCAAGCAG CCTGAGACAG ATTCTGGACT CCCAGAAAAT GGAGTGGAGG TCCAACGCCG GGGGCAGCGG TAGGGATAAG
      GTACAGGGTA TACGAGCTGT ACCGTTCGTC GGACTCTGTC TAAGACCTGA GGGTCTTTTA CCTCACCTCC AGGTTGCGGC CCCCGTCGCC ATCCCTATTC
2201  TGGTCAGATC TGGTACCGCG GGCGGCGACC AGCAGCATGA GCGTGGAATT TTATAACAGC AACAAAAGCG CGCAGACCAA CAGCATTACC CCGATTATTA
      ACCAGTCTAG ACCATGGCGC CCGCCGCTGG TCGTCGTACT CGCACCTTAA AATATTGTCG TTGTTTTCGC GCGTCTGGTT GTCGTAATGG GGCTAATAAT
2301  AAATTACCAA CACCAGCGAT AGCGATCTGA ACCTGAACGA TGTGAAAGTG CGCTATTATT ATACCAGCGA TGGCACCCAG GGCCAGACCT TTTGGTGCGA
      TTTAATGGTT GTGGTCGCTA TCGCTAGACT TGGACTTGCT ACACTTTCAC GCGATAATAA TATGGTCGCT ACCGTGGGTC CCGGTCTGGA AAACCACGCT
2401  TCATGCGGGC GCGCTGCTGG GCAACAGCTA TGTGGATAAC ACCAGCAAAG TGACCGCGAA CTTTGTGAAA GAAACCGCGA GCCCGACCAG CACCTATGAT
      AGTACGCCCG CGCGACGACC CGTTGTCGAT ACACCTATTG TGGTCGTTTC ACTGGCGCTT GAAACACTTT CTTTGGCGCT CGGGCTGGTC GTGGATACTA
2501  ACCTATGTGG AATTTGGCTT TGCGAGTGGC CGCGCGACCC TGAAAAAAGG CCAGTTTATT ACCATTCAGG GCCGCATTAC CAAAAGCGAT TGGAGCAACT
      TGGATACACC TTAAACCGAA ACGCTCACCG GCGCGCTGGG ACTTTTTTCC GGTCAAATAA TGGTAAGTCC CGGCGTAATG GTTTTCGCTA ACCTCGTTGA
2601  ATACCCAGAC CAACGATTAT AGCTTTGATG CGAGCAGCAG CACCCCGGTG GTGAACCCGA AAGTGACCGG CTATATTGGC GGCGCGAAAG TGCTGGGCAC
      TATGGGTCTG GTTGCTAATA TCGAAACTAC GCTCGTCGTC GTGGGGCCAC CACTTGGGCT TTCACTGGCC GATATAACCG CCGCGCTTTC ACGACCCGTG
2701  CGCGCCGTAA AGCGGCCGCA ATTTAATTCC GGTTATTTTC CACCATATTG CCGTCTTTTG GCAATGTGAG GGCCCGGAAA CCTGGCCCTG TCTTCTTGAC
      GCGCGGCATT TCGCCGGCGT TAAATTAAGG CCAATAAAAG GTGGTATAAC GGCAGAAAAC CGTTACACTC CCGGGCCTTT GGACCGGGAC AGAAGAACTG
2801  GAGCATTCCT AGGGGTCTTT CCCCTCTCGC CAAAGGAATG CAAGGTCTGT TGAATGTCGT GAAGGAAGCA GTTCCTCTGG AAGCTTCTTG AAGACAAACA
      CTCGTAAGGA TCCCCAGAAA GGGGAGAGCG GTTTCCTTAC GTTCCAGACA ACTTACAGCA CTTCCTTCGT CAAGGAGACC TTCGAAGAAC TTCTGTTTGT
2901  ACGTCTGTAG CGACCCTTTG CAGGCAGCGG AACCCCCCAC CTGGCGACAG GTGCCTCTGC GGCCAAAAGC CACGTGTATA AGATACACCT GCAAAGGCGG
      TGCAGACATC GCTGGGAAAC GTCCGTCGCC TTGGGGGGTG GACCGCTGTC CACGGAGACG CCGGTTTTCG GTGCACATAT TCTATGTGGA CGTTTCCGCC
3001  CACAACCCCA GTGCCACGTT GTGAGTTGGA TAGTTGTGGA AAGAGTCAAA TGGCTCACCT CAAGCGTATT CAACAAGGGG CTGAAGGATG CCCAGAAGGT
      GTGTTGGGGT CACGGTGCAA CACTCAACCT ATCAACACCT TTCTCAGTTT ACCGAGTGGA GTTCGCATAA GTTGTTCCCC GACTTCCTAC GGGTCTTCCA
3101  ACCCCATTGT ATGGGATCTG ATCTGGGGCC TCGGTGCACA TGCTTTACAT GTGTTTAGTC GAGGTTAAAA AACGTCTAGG CCCCCCGAAC CACGGGGACG
      TGGGGTAACA TACCCTAGAC TAGACCCCGG AGCCACGTGT ACGAAATGTA CACAAATCAG CTCCAATTTT TTGCAGATCC GGGGGGCTTG GTGCCCCTGC
3201  TGGTTTTCCT TTGAAAAACA CGATGATAAT ATGGCCACCA CCCATACCTA GGCTTTTGCA AAGATCGATC AAGAGACAGG ATGAGGATCG TTTCGCATGA
      ACCAAAAGGA AACTTTTTGT GCTACTATTA TACCGGTGGT GGGTATGGAT CCGAAAACGT TTCTAGCTAG TTCTCTGTCC TACTCCTAGC AAAGCGTACT
3301  TTGAACAAGA TGGATTGCAC GCAGGTTCTC CGGCCGCTTG GGTGGAGAGG CTATTCGGCT ATGACTGGGC ACAACAGACA ATCGGCTGCT CTGATGCCGC
      AACTTGTTCT ACCTAACGTG CGTCCAAGAG GCCGGCGAAC CCACCTCTCC GATAAGCCGA TACTGACCCG TGTTGTCTGT TAGCCGACGA GACTACGGCG
3401  CGTGTTCCGG CTGTCAGCGC AGGGGCGCCC GGTTCTTTTT GTCAAGACCG ACCTGTCCGG TGCCCTGAAT GAACTGCAAG ACGAGGCAGC GCGGCTATCG
      GCACAAGGCC GACAGTCGCG TCCCCGCGGG CCAAGAAAAA CAGTTCTGGC TGGACAGGCC ACGGGACTTA CTTGACGTTC TGCTCCGTCG CGCCGATAGC
3501  TGGCTGGCCA CGACGGGCGT TCCTTGCGCA GCTGTGCTCG ACGTTGTCAC TGAAGCGGGA AGGGACTGGC TGCTATTGGG CGAAGTGCCG GGGCAGGATC
      ACCGACCGGT GCTGCCCGCA AGGAACGCGT CGACACGAGC TGCAACAGTG ACTTCGCCCT TCCCTGACCG ACGATAACCC GCTTCACGGC CCCGTCCTAG
3601  TCCTGTCATC TCACCTTGCT CCTGCCGAGA AAGTATCCAT CATGGCTGAT GCAATGCGGC GGCTGCATAC GCTTGATCCG GCTACCTGCC CATTCGACCA
      AGGACAGTAG AGTGGAACGA GGACGGCTCT TTCATAGGTA GTACCGACTA CGTTACGCCG CCGACGTATG CGAACTAGGC CGATGGACGG GTAAGCTGGT
3701  CCAAGCGAAA CATCGCATCG AGCGAGCACG TACTCGGATG GAAGCCGGTC TTGTCGATCA GGATGATCTG GACGAAGAGC ATCAGGGGCT CGCGCCAGCC
      GGTTCGCTTT GTAGCGTAGC TCGCTCGTGC ATGAGCCTAC CTTCGGCCAG AACAGCTAGT CCTACTAGAC CTGCTTCTCG TAGTCCCCGA GCGCGGTCGG
3801  GAACTGTTCG CCAGGCTCAA GGCGAGCATG CCCGACGGCG AGGATCTCGT CGTGACCCAT GGCGATGCCT GCTTGCCGAA TATCATGGTG GAAAATGGCC
      CTTGACAAGC GGTCCGAGTT CCGCTCGTAC GGGCTGCCGC TCCTAGAGCA GCACTGGGTA CCGCTACGGA CGAACGGCTT ATAGTACCAC CTTTTACCGG
```

APPENDIX 1 -continued

Nucleotide sequences of constructed plasmids(SEQ ID NOs: 53-58, in order of appearance).

```
3901  GCTTTTCTGG ATTCATCGAC TGTGGCCGGC TGGGTGTGGC GGACCGCTAT CAGGACATAG CGTTGGCTAC CCGTGATATT GCTGAAGAGC TTGGCGGCGA
      CGAAAAGACC TAAGTAGCTG ACACCGGCCG ACCCACACCG CCTGGCGATA GTCCTGTATC GCAACCGATG GGCACTATAA CGACTTCTCG AACCGCCGCT
4001  ATGGGCTGAC CGCTTCCTCG TGCTTTACGG TATCGCCGCT CCCGATTCGC AGCGCATCGC CTTCTATCGC CTTCTTGACG AGTTCTTCTG AGCGGGACTC
      TACCCGACTG GCGAAGGAGC ACGAAATGCC ATAGCGGCGA GGGCTAAGCG TCGCGTAGCG GAAGATAGCG GAAGAACTGC TCAAGAAGAC TCGCCCTGAG
4101  TGGGGTTCGG GCCGCACTCG AGCATAAACT TGTTTATTGC AGCTTATAAT GGTTACAAAT AAAGCAATAG CATCACAAAT TTCACAAATA AAGCATTTTT
      ACCCCAAGCC CGGCGTGAGC TCGTATTTGA ACAAATAACG TCGAATATTA CCAATGTTTA TTTCGTTATC GTAGTGTTTA AAGTGTTTAT TTCGTAAAAA
                                                               I-SceI
                                                         ~~~~~~~~~~~~~~~~~~~
4201  TTCACTGCAT TCTAGTTGTG GTTTGTCCAA ACTCATCAAT GTATCTTAAG TAGGGATAAC AGGGTAATTT TGTTAAATCA GCTCATTTTT TAACCAATAG
      AAGTGACGTA AGATCAACAC CAAACAGGTT TGAGTAGTTA CATAGAATTC ATCCCTATTG TCCCATTAAA ACAATTTAGT CGAGTAAAAA ATTGGTTATC
4301  GAACGCCATC AAAAATAATT CGCGTCTGGC CTTCCTGTAG CCAGCTTTCA TCAACATTAA ATGTGAGCGA GTAACAACCC GTCGGATTCT CCGTGGGAAC
      CTTGCGGTAG TTTTTATTAA GCGCAGACCG GAAGGACATC GGTCGAAAGT AGTTGTAATT TACACTCGCT CATTGTTGGG CAGCCTAAGA GGCACCCTTG
4401  AAACGGCGGA TTGACCGTAA TGGGATAGGT TACGTTGGTG TAGATGGGCG CATCGTAACC GTGCATCTGC CAGTTTGAGG GGACGACGAC CGTATCGGCC
      TTTGCCGCCT AACTGGCATT ACCCTATCCA ATGCAACCAC ATCTACCCGC GTAGCATTGG CACGTAGACG GTCAAACTCC CCTGCTGCTG GCATAGCCGG
4501  TCAGGAAGAT CGCACTCCAG CCAGCTTTCC GGCACCGCTT CTGGTGCCGG AAACCAGGCA AAGCGCCATT CGCCATTCAG GCTGCGCAAC TGTTGGGAAG
      AGTCCTTCTA GCGTGAGGTC GGTCGAAAGG CCGTGGCGAA GACCACGGCC TTTGGTCCGT TTCGCGGTAA GCGGTAAGTC CGACGCGTTG ACAACCCTTC
4601  GGCGATCGGT GCGGGCCTCT TCGCTATTAC GCCAGCTGGC GAAAGGGGGA TGTGCTGCAA GGCGATTAAG TTGGGTAACG CCAGGGTTTT CCCAGTCACG
      CCGCTAGCCA CGCCCGGAGA AGCGATAATG CGGTCGACCG CTTTCCCCCT ACACGACGTT CCGCTAATTC AACCCATTGC GGTCCCAAAA GGGTCAGTGC
4701  ACGTTGTAAA ACGACGGCCA GTGAATTGCA ATTCGTAATC ATGGTCATAG CTGTTTCCTG TGTGAAATTG TTATCCGCTC ACAATTCCAC ACAACATACG
      TGCAACATTT TGCTGCCGGT CACTTAACGT TAAGCATTAG TACCAGTATC GACAAAGGAC ACACTTTAAC AATAGGCGAG TGTTAAGGTG TGTTGTATGC
                                                                                                   I-SceI
                                                                                             ~~~~~~~~~~~~~~~~~~~
4801  AGCCGGAAGC ATAAAGTGTA AAGCCTGGGG TGCCTAATGA GTGAGCTAAC TCACATTAAT TGCGTTGCGC TCACTGCCAT TACCCTGTTA TCCCTAGTGA
      TCGGCCTTCG TATTTCACAT TTCGGACCCC ACGGATTACT CACTCGATTG AGTGTAATTA ACGCAACGCG AGTGACGGTA ATGGGACAAT AGGGATCACT
4901  ACCATCACCC TAATCAAGTT TTTTGGGGTC GAGGTGCCGT AAAGCACTAA ATCGGAACCC TAAAGGGAGC CCCCGATTTA GAGCTTGACG GGGAAAGCCG
      TGGTAGTGGG ATTAGTTCAA AAAACCCCAG CTCCACGGCA TTTCGTGATT TAGCCTTGGG ATTTCCCTCG GGGGCTAAAT CTCGAACTGC CCCTTTCGGC
5001  GCGAACGTGG CGAGAAAGGA AGGGAAGAAA GCGAAAGGAG CGGGCGCTAG GGCGCTGGCA AGTGTAGCGG TCACGCTGCG CGTAACCACC ACACCCGCCG
      CGCTTGCACC GCTCTTTCCT TCCCTTCTTT CGCTTTCCTC GCCCGCGATC CCGCGACCGT TCACATCGCC AGTGCGACGC GCATTGGTGG TGTGGGCGGC
5101  CGCTTAATGC GCCGCTACAG GGCGCGTCAG GTGGCACTTT TCGGGGAAAT GTGCGCGGAA CCCCTATTTG TTTATTTTTC TAAATACATT CAAATATGTA
      GCGAATTACG CGGCGATGTC CCGCGCAGTC CACCGTGAAA AGCCCCTTTA CACGCGCCTT GGGGATAAAC AAATAAAAAG ATTTATGTAA GTTTATACAT
5201  TCCGCTCATG AGACAATAAC CCTGATAAAT GCTTCAATAA TAACGACCGG TAATGAAAAA GGAAGAGTAT GAGTATTCAA CATTTCCGTG TCGCCCTTAT
      AGGCGAGTAC TCTGTTATTG GGACTATTTA CGAAGTTATT ATTGCTGGCC ATTACTTTTT CCTTCTCATA CTCATAAGTT GTAAAGGCAC AGCGGGAATA
5301  TCCCTTTTTT GCGGCATTTT GCCTTCCTGT TTTTGCTCAC CCAGAAACGC TGGTGAAAGT AAAAGATGCT GAAGATCAGT TGGGTGCACG AGTGGGTTAC
      AGGGAAAAAA CGCCGTAAAA CGGAAGGACA AAAACGAGTG GGTCTTTGCG ACCACTTTCA TTTTCTACGA CTTCTAGTCA ACCCACGTGC TCACCCAATG
5401  ATCGAACTGG ATCTCAACAG CGGTAAGATC CTTGAGAGTT TTCGCCCCGA AGAACGTTTT CCAATGATGA GCACTTTTAA AGTTCTGCTA TGTGGCGCGG
      TAGCTTGACC TAGAGTTGTC GCCATTCTAG GAACTCTCAA AAGCGGGGCT TCTTGCAAAA GGTTACTACT CGTGAAAATT TCAAGACGAT ACACCGCGCC
5501  TATTATCCCG TATTGACGCC GGGCAAGAGC AACTCGGTCG CCGCATACAC TATTCTCAGA ATGACTTGGT TGAGTCTAGC GTTGATCGGC ACGTAAGAGG
      ATAATAGGGC ATAACTGCGG CCCGTTCTCG TTGAGCCAGC GGCGTATGTG ATAAGAGTCT TACTGAACCA ACTCAGATCG CAACTAGCCG TGCATTCTCC
5601  TTCCAACTTT CACCATAATG AAATAAGATC ACTACCGGGC GTATTTTTTG AGTTATCGAG ATTTTCAGGA GCTAAGGAAG CTAAAATGGA GAAAAAAATC
      AAGGTTGAAA GTGGTATTAC TTTATTCTAG TGATGGCCCG CATAAAAAAC TCAATAGCTC TAAAAGTCCT CGATTCCTTC GATTTTACCT CTTTTTTTAG
5701  ACTGGATATA CCACCGTTGA TATATCCCAA TGGCATCGTA AAGAACATTT TGAGGCATTT CAGTCAGTTG CTCAATGTAC CTATAACCAG ACCGTTCAGC
      TGACCTATAT GGTGGCAACT ATATAGGGTT ACCGTAGCAT TTCTTGTAAA ACTCCGTAAA GTCAGTCAAC GAGTTACATG GATATTGGTC TGGCAAGTCG
5801  TGGATATTAC GGCCTTTTTA AAGACCGTAA AGAAAAATAA GCACAAGTTT TATCCGGCCT TTATTCACAT TCTTGCCCGC CTGATGAATG CTCATCCGGA
      ACCTATAATG CCGGAAAAAT TTCTGGCATT TCTTTTTATT CGTGTTCAAA ATAGGCCGGA AATAAGTGTA AGAACGGGCG GACTACTTAC GAGTAGGCCT
5901  ATTCCGTATG GCAATGAAAG ACGGTGAGCT GGTGATATGG GATAGTGTTC ACCCTTGTTA CACCGTTTTC CATGAGCAAA CTGAAACGTT TTCATCGCTC
      TAAGGCATAC CGTTACTTTC TGCCACTCGA CCACTATACC CTATCACAAG TGGGAACAAT GTGGCAAAAG GTACTCGTTT GACTTTGCAA AAGTAGCGAG
6001  TGGAGTGAAT ACCACGACGA TTTCCGGCAG TTTCTACACA TATATTCGCA AGATGTGGCG TGTTACGGTG AAAACCTGGC CTATTTCCCT AAAGGGTTTA
      ACCTCACTTA TGGTGCTGCT AAAGGCCGTC AAAGATGTGT ATATAAGCGT TCTACACCGC ACAATGCCAC TTTTGGACCG GATAAAGGGA TTTCCCAAAT
6101  TTGAGAATAT GTTTTTCGTA TCAGCCAATC CCTGGGTGAG TTTCACCAGT TTTGATTTAA ACGTGGCCAA TATGGACAAC TTCTTCGCCC CCGTTTTCAC
      AACTCTTATA CAAAAAGCAT AGTCGGTTAG GGACCCACTC AAAGTGGTCA AACTAAATTT TGCACCGGTT ATACCTGTTG AAGAAGCGGG GGCAAAAGTG
```

APPENDIX 1 -continued

Nucleotide sequences of constructed plasmids(SEQ ID NOs: 53-58, in order of appearance).

| | |
|---|---|
| 6201 | CATGGGCAAA TATTATACGC AAGGCGACAA GGTGCTGATG CCGCTGGCGA TTCAGGTTCA TCATGCCGTC TGTGATGGCT TCCATGTCGG CAGAATGCTT |
| | GTACCCGTTT ATAATATGCG TTCCGCTGTT CCACGACTAC GGCGACCGCT AAGTCCAAGT AGTACGGCAG ACACTACCGA AGGTACAGCC GTCTTACGAA |
| 6301 | AATGAATTAC AACAGTACTG CGATGAGTGG CAGGGCGGGG CGTAATTTTT TTAAGGCAGT TATTGGTGCC CTTAAACGCC TGGTGCTACG CCTGAATAAG |
| | TTACTTAATG TTGTCATGAC GCTACTCACC GTCCCGCCCC GCATTAAAAA AATTCCGTCA ATAACCACGG GAATTTGCGG ACCACGATGC GGACTTATTC |
| 6401 | TGATAATAAG CGGATGAATG GCAGAAATTC GAAATGACCG ACCAAGCGAC GCCCAACCTG CCATCACGAG ATTTCGATTC CACCGCCGCC TTCTATGAAA |
| | ACTATTATTC GCCTACTTAC CGTCTTTAAG CTTTACTGGC TGGTTCGCTG CGGGTTGGAC GGTAGTGCTC TAAAGCTAAG GTGGCGGCGG AAGATACTTT |
| 6501 | GGTTGGGCTT CGGAATCGTT TTCCGGGACG CCGGCTGGAT GATCCTCCAG CGCGGGGATC TCATGCTGGA GTTCTTCGCC CACCCTAGGG GGAGGCTAAC |
| | CCAACCCGAA GCCTTAGCAA AAGGCCCTGC GGCCGACCTA CTAGGAGGTC GCGCCCCTAG AGTACGACCT CAAGAAGCGG GTGGGATCCC CCTCCGATTG |
| 6601 | TGAAACACGG AAGGAGACAA TACCGGAAGG AACCCGCGCT ATGACGGCAA TAAAAAGACA GAATAAAACG CACGGTGTTG GGTCGTTTGT TCATAAACGC |
| | ACTTTGTGCC TTCCTCTGTT ATGGCCTTCC TTGGGCGCGA TACTGCCGTT ATTTTTCTGT CTTATTTTGC GTGCCACAAC CCAGCAAACA AGTATTTGCG |
| 6701 | GGGGTTCGGT CCCAGGGCTG GCACTCTGTC GATACCCCAC CGAGACCCCA TTGGGGCCAA TACGCCCGCG TTTCTTCCTT TTCCCCACCC CACCCCCCAA |
| | CCCCAAGCCA GGGTCCCGAC CGTGAGACAG CTATGGGGTG GCTCTGGGGT AACCCCGGTT ATGCGGGCGC AAAGAAGGAA AAGGGGTGGG GTGGGGGGTT |
| 6801 | GTTCGGGTGA AGGCCCAGGG CTCGCAGCCA ACGTCGGGGC GGCAGGCCCT GCCATAGCCT CAGGTTACTC ATATATACTT TAGATTGATT TAAAACTTCA |
| | CAAGCCCACT TCCGGGTCCC GAGCGTCGGT TGCAGCCCCG CCGTCCGGGA CGGTATCGGA GTCCAATGAG TATATATGAA ATCTAACTAA ATTTTGAAGT |
| 6901 | TTTTTAATTT AAAAGGATCT AGGTGAAGAT CCTTTTTGAT AATCTCATGA CCAAAATCCC TTAACGTGAG TTTTCGTTCC ACTGAGCGTC AGACCCCGTA |
| | AAAAATTAAA TTTTCCTAGA TCCACTTCTA GGAAAAACTA TTAGAGTACT GGTTTTAGGG AATTGCACTC AAAAGCAAGG TGACTCGCAG TCTGGGGCAT |
| 7001 | GAAAAGATCA AAGGATCTTC TTGAGATCCT TTTTTTCTGC GCGTAATCTG CTGCTTGCAA ACAAAAAAAC CACCGCTACC AGCGGTGGTT TGTTTGCCGG |
| | CTTTTCTAGT TTCCTAGAAG AACTCTAGGA AAAAAAGACG CGCATTAGAC GACGAACGTT TGTTTTTTTG GTGGCGATGG TCGCCACCAA ACAAACGGCC |
| 7201 | ATCAAGAGCT ACCAACTCTT TTTCCGAAGG TAACTGGCTT CAGCAGAGCG CAGATACCAA ATACTGTCCT TCTAGTGTAG CCGTAGTTAG GCCACCACTT |
| | TAGTTCTCGA TGGTTGAGAA AAAGGCTTCC ATTGACCGAA GTCGTCTCGC GTCTATGGTT TATGACAGGA AGATCACATC GGCATCAATC CGGTGGTGAA |
| 7301 | CAAGAACTCT GTAGCACCGC CTACATACCT CGCTCTGCTA ATCCTGTTAC CAGTGGCTGC TGCCAGTGGC GATAAGTCGT GTCTTACCGG GTTGGACTCA |
| | GTTCTTGAGA CATCGTGGCG GATGTATGGA GCGAGACGAT TAGGACAATG GTCACCGACG ACGGTCACCG CTATTCAGCA CAGAATGGCC CAACCTGAGT |
| 7401 | AGACGATAGT TACCGGATAA GGCGCAGCGG TCGGGCTGAA CGGGGGGTTC GTGCACACAG CCCAGCTTGG AGCGAACGAC CTACACCGAA CTGAGATACC |
| | TCTGCTATCA ATGGCCTATT CCGCGTCGCC AGCCCGACTT GCCCCCCAAG CACGTGTGTC GGGTCGAACC TCGCTTGCTG GATGTGGCTT GACTCTATGG |
| 7501 | TACAGCGTGA GCTATGAGAA AGCGCCACGC TTCCCGAAGG GAGAAAGGCG GACAGGTATC CGGTAAGCGG CAGGGTCGGA ACAGGAGAGC GCACGAGGGA |
| | ATGTCGCACT CGATACTCTT TCGCGGTGCG AAGGGCTTCC CTCTTTCCGC CTGTCCATAG GCCATTCGCC GTCCCAGCCT TGTCCTCTCG CGTGCTCCCT |
| 7601 | GCTTCCAGGG GGAAACGCCT GGTATCTTTA TAGTCCTGTC GGGTTTCGCC ACCTCTGACT TGAGCGTCGA TTTTTGTGAT GCTCGTCAGG GGGGCGGAGC |
| | CGAAGGTCCC CCTTTGCGGA CCATAGAAAT ATCAGGACAG CCCAAAGCGG TGGAGACTGA ACTCGCAGCT AAAAACACTA CGAGCAGTCC CCCCGCCTCG |
| 7801 | CTATGGAAAA ACGCCAGCAA CGCGGCCTTT TTACGGTTCC TGGCCTTTTG CTGGCCTTTT GCTCACATGT TCTTTCCTGC GTTATCCCCT GATTCTGTGG |
| | GATACCTTTT TGCGGTCGTT GCGCCGGAAA AATGCCAAGG ACCGGAAAAC GACCGGAAAA CGAGTGTACA AGAAAGGACG CAATAGGGGA CTAAGACACC |
| 7901 | ATAACCGTAT TACCGCCATG CATTAGTTAT TAATAGTAAT CAATTACGGG GTCATTAGTT CATAGCCCAT ATATGGAGTT CCGCGTTACA TAACTTACGG |
| | TATTGGCATA ATGGCGGTAC GTAATCAATA ATTATCATTA GTTAATGCCC CAGTAATCAA GTATCGGGTA TATACCTCAA GGCGCAATGT ATTGAATGCC |
| 8001 | TAAATGGCCC GCCTGGCTGA CCGCCCAACG ACCCCCGCCC ATTGACGTCA ATAATGACGT ATGTTCCCAT AGTAACGCCA ATAGGGACTT TCCATTGACG |
| | ATTTACCGGG CGGACCGACT GGCGGGTTGC TGGGGGCGGG TAACTGCAGT TATTACTGCA TACAAGGGTA TCATTGCGGT TATCCCTGAA AGGTAACTGC |
| 8101 | TCAATGGGTG GAGTATTTAC GGTAAACTGC CCACTTGGCA GTACATCAAG TGTATCATAT GCCAAGTACG CCCCCTATTG ACGTCAATGA CGGTAAATGG |
| | AGTTACCCAC CTCATAAATG CCATTTGACG GGTGAACCGT CATGTAGTTC ACATAGTATA CGGTTCATGC GGGGGATAAC TGCAGTTACT GCCATTTACC |
| 8201 | CCCGCCTGGC ATTATGCCCA GTACATGACC TTATGGGACT TTCCTACTTG GCAGTACATC TACGTATTAG TCATCGCTAT TACCATGGTG ATGCGGTTTT |
| | GGGCGGACCG TAATACGGGT CATGTACTGG AATACCCTGA AAGGATGAAC CGTCATGTAG ATGCATAATC AGTAGCGATA ATGGTACCAC TACGCCAAAA |
| 8301 | GGCAGTACAT CAATGGGCGT GGATAGCGGT TTGACTCACG GGGATTTCCA AGTCTCCACC CCATTGACGT CAATGGGAGT TTGTTTTGGC ACCAAAATCA |
| | CCGTCATGTA GTTACCCGCA CCTATCGCCA AACTGAGTGC CCCTAAAGGT TCAGAGGTGG GGTAACTGCA GTTACCCTCA AACAAAACCG TGGTTTTAGT |
| 8401 | ACGGGACTTT CCAAAATGTC GTAACAACTC CGCCCCATTG ACGCAAATGG GCGGTAGGCG TGTACGGTGG GAGGTCTATA TAAGCAGAGC T |
| | TGCCCTGAAA GGTTTTACAG CATTGTTGAG GCGGGGTAAC TGCGTTTACC CGCCATCCGC ACATGCCACC CTCCAGATAT ATTCGTCTCG A |

APPENDIX 2

Sequences of cloned light chains (SEQ ID NOs: 59-75, in order of appearance).

```
               1                                                                    70
   16    (1) --MDTPAQLLFLLLLWLPDTTGEIVLTQSPATLSLSPGERATLSCRAS-----QSVSSYLAWYQQKPGQA
    6    (1) --METPAQLLFLLLLWLPDTTGEIVLTQSPATLSLSPGERATLSCRAS-----QSVSSYLAWYQQKPGQA
   22    (1) --METPAQLLFLLLLWLPDTTGEIVLTQSPATLSLSPGERATLSCRAS-----QSVGSSLAWYQQKPGQP
    1    (1) MDMRVPAQLLGLLMLWVSGGSGDIVMTQSPLSLPVTPGEPASISCRSSQSLLHSNGYNYLDWYLQKPGQS
   21    (1) MDMRVPAQLLGLLMLWVSGSSGDIVMTQSPLSLPVTPGEPASISCRSSQSLLHSNGYNYLDWYLQKPGQS
   24    (1) ----------------------------------------------------------------------
   33    (1) MDMRVPAQLLGLLLLWLPGAKCDIQMTQSPSTLSASVGDRVTITCRASQSIS-----SWLAWYQQKPGKA
33-35    (1) MDMRVPAQLLGLLLLWLPGAKCDIQMTQSPSTLSASVGDRVTITCRASQSIS-----SWLAWYQQKPGKA
   41    (1) MDMRVPAQLLGLLLLWLPGAKCDIQMTQSPSTLSASVGDRVTITCRASQSIS-----SWLAWYQQKPGKA
    7    (1) MDMRVPAQLLGLLLLWLPGARCAIRMTQSPSSFSASTGDRVTITCRASQGIS-----TYLAWYQQKPGKA
  7-7    (1) MDMRVPAQLLGLLLLWLRGARCDIQMTQSPSSLSASVGDRVTITCRAGQSIS-----SYLNWYQQKPGKA
41-40    (1) MDMRVPAQLLGLLLLCFPDARCDIQMTQSPSSLSASVGDRVTITCRASQDIG-----NSLTWFQQEPGKA
    8    (1) --METPAQLLFLLLLWLPDTTGEIVLTQSPGTLSLSPGERATLSCRAGQ----SIRSDYLAWYQQKPGQA
    4    (1) --METPAQLLFLLLLWLPDTTGEIVLTQSPGTLSLSPGERATLSCRAS-----SVSSSYLAWYQQKPGQA
    9    (1) --METPAQLLFLLLLWLPDTTGEIVLTQSPGTLSLSPGERATLSCRASQ----SVSSSYLAWYQQKPGQA
   31    (1) --METPAQLLFLLLLWLPDTTGEIVLTQSPGTLSLSPGERATLSCRASQ----SVSSSYLAWYQQKPGQA
   17    (1) MDMRVPAQLLGLLLLWFPGSRCDIQMTQSPSSVSASVGDRVTITCRASQGIS-----SWLAWYQQKPGKA

               71                                                                  140
   16   (64) PRLLTYDASNRATGIPARFSGSGSGTDFTLTISSLEPEDFAVYYCQQRSNWQR-TFGGGTKVEIKRTVAA
    6   (64) PRLLIYDASNRATGIPARFSGSGSGTDFTLTISSLEPEDFAVYYCQQRSNWPALTFGGGTKVEIKRTVAA
   22   (64) PRLLLYETSKRATGIPARFRGSGSGTDFTLTINSLEPDDFAVYYCQERHNFNWRTFGPGTKVEIKRTVAA
    1   (71) PQLLIYLGSNRASGVPDRFSGSGSGTDFTLKISRVEAEDVGVYYCMQALQTPPFTFGGGTKVDIKRTVAA
   21   (71) PQLLIYLGSNRASGVPDRFSGSGSGTDFTLKISRVEAEDVGVYYCMQALQTP-HTFGQGTKLEIKRTVAA
   24    (1) -------------------------------MDMRVPAQLLGLLLLWLPG----------------TVAA
   33   (66) PKLLIYKASSLESGVPSRFSGSGSGTEFTLTISSLQPDDFATYYCQQYNSYP-YTFGQGTKLEIKRTVAA
33-35   (66) PKLLIYKASSLESGVPSRFSGSGSGTEFTLTISSLQPDDFATYYCQQYNSYP-YTFGQGTKLEIKRTVAA
   41   (66) PKLLIYKASSLESGVPSRFSGSGSGTEFTLTISSLQPDDFATYYCQQYNSYP-YTFGQGTKLEIKRTVAA
    7   (66) PNFLIFAASTLQSGVPSRFSGSGSGTDFTLNISSLQSEDFATYYCQQYYTYP-PTFGQGTKLEIKRTVAA
  7-7   (66) PKLLIYAASSLQSGVPSRFSGSGSGTDLTLTISSLQPEDFATYYCQQSYSTP-PTFGQGTKVEIKRTVAA
41-40   (66) PKSLIYDASSLQTGAPSKFSGSGSGTDFTLTISSLQPEDFATYFCQQYKNYP-YTFGPGTKVDITRTVAA
    8   (65) PRLLMYGESRRPSGIPDRFSGSGSGTDFTLTISRLGPEDFAVYYCHQYGS-STRTFGQGTKVEVKRTVAA
    4   (64) PKLLIYGASSRATGIPDKFSGSGSGTDFTLTISRLEPEDFAVYYCQQYG--SSLTFGGGTKVEIKRTVAA
    9   (65) PKLLIYGASSRATGIPDRFSGSGSGTDFTLTISRLEPEDFAVYYCQQYGS-SPYTFGQGTKLEIKRTVAA
   31   (65) PKLLIYGASSRATGIPDRFSGSGSGTDFTLTISRLEPEDFAVYYCQQYGSSLTWTFGQGTKVEIKRTVAA
   17   (66) PKLLIYAASSLQSGVPSRFSGSGSGTDFTLTISSLQPEDFATYYCQQANSFP-FTFGPGTKVDIKRTVAA

               141                                                                 210
   16  (133) PSVFIFPPSDEQLKSGTASVVCLLNNFYPREAKVQWKVDNALQSGNSQESVTEQDSKDSTYSLSSTLTLS
    6  (134) PSVFIFPPSDEQLKSGTASVVCLLNNFYPREAKVQWKVDNALQSGNSQESVTEQDSKDSTYSLSSTLTLG
   22  (134) PSVFIFPPSDEQLKSGTASVVCLLNNFYPREAKVQWKVDNALQSGNSQESVTEQDSKDSTYSLSSTLTLS
    1  (141) PSVFIFPPSDEQLKSGTASVVCLLNNFYPREAKVQWKVDNALQSGNSQESVTEQDSKDSTYSLSSTLTLS
   21  (140) PSVFIFPPSDEQLKSGTASVVCLLNNFYPREAKVQWKVDNALQSGNSQESVTEQDSKDSTYSLSSTLTLS
   24   (24) PSVFIFPPSDEQLKSGTASVVCLLNNFYPREAKVQWKVDNALQSGNSQESVTEQDSKDSTYSLSSTLTLS
   33  (135) PSVFIFPPSDEQLKSGTASVVCLLNNFYPREAKVQWKVDNALQSGNSQESVTEQDSKDSTYSLSSTLTLS
33-35  (135) PSVFIFPPSDEQLKSGTASVVCLLNNFYPREAKVQWKVDNALQSGNSQESVTEQDSKDSTYSLSSILTLS
   41  (135) PSVFIFPPSDEQLKSGTASVVCLLNNFYPREAKVQWKVDNALQSGNSQESVTEQDSKDSTYSLSSTLTLS
    7  (135) PSVFIFPPSDEQLKSGTASVVCLLNNFYPREAKVQWRVDNALQSGNSQESVTEQDSKDSTYSLSSTLTPS
  7-7  (135) PSVFIFPPSDEQLKSGTASVVCLLNNFYPREAKVQWKVDNALQSGNSQESVTEQDSKDSTYSLSSTLTLS
41-40  (135) PSVFIFPPSDEQLKSGTASVVCLLNNFYPREAKVQWKVDNALQSGNSQESVTEQDSKDSTYSLSSTLTLS
    8  (134) PSVFIFPPSDEQLKSGTASVVCLLNNFYPREAKVQWKVDNALQSGNSQESVTEQDSKDSTYSLSSTLTLS
    4  (132) PSVFIFPPSDEQLKSGTASVVCLLNNFYPREAKVQWKVDNALQSGNS-----------------------
    9  (134) PSVFIFTPSDEQLKSGTASVVCLLNNFYPREAKVQWKVDNALQSGNSQESVTEQDSKDSTYSLSSTLTLS
   31  (135) PSVFIFPPSDEQLKSGTASVVCLLNNFYPREAKVQWKVDNALQSGNSQESVTEQDSKDSTYSLSSTLTLS
   17  (135) PSVFIFPPSDEQLKSGTASVVCLLNNFYPREAKVQWKVDNALQSGNSQESVAEQDSKDSTYSLSG

               211                                              261
   16  (203) KADYEKHKVYAC---------------------------------------
    6  (204) KADYEKHKVYACEVTHQGLSSPVTKSFNRGEC-------------------
   22  (204) KADYEKHKVYACEVTHQGLSSPVTKSFNRGSVRPLRDARDPHQSMLFSVCP
    1  (211) KADYEKHKVYACEVTHQGLSSPVTKSFNRGEC-------------------
   21  (210) KADYEKHKVYACEVTHQGLSSPVTKSFNRGEC-------------------
   24   (94) KADYEKHKVYACEVTHQGLSSPVTKSFNRGEC-------------------
   33  (205) KADYEKHKVYACEVTHQGLSSPVTKSFNRGEC-------------------
33-35  (205) KADYEKHKVYACEVTHQGLSSPDTKSFNRGEC-------------------
   41  (205) KADYEKHKVYACEVTHQGLSSPVTKSSTGESVRPLRDARDPHQSMLFSVCP
    7  (205) KADYEKHKVYACEVTHQGLSSPVTKSFNRGEC-------------------
  7-7  (205) KADYEKHKVYACEVTHQGLSSPVTKSFNRGEC-------------------
41-40  (205) KADYEKHKVYACEVTHQGLSSPVTKSFNRGEC-------------------
    8  (204) KADYEKHKVYACEVTHQGLSSPVTKSFNRGEC-------------------
    4  (179) ---------------------------------------------------
    9  (204) KADYEKHKVYACEVTHQGLSSPVTKSFNRGEC-------------------
   31  (205) KADYEKHKVYACEVTHQGLSSPVTKSFNRGEC-------------------
   17  (205) KADYEKHKVYACEVTHQGLSSPVTKSFKGESVRPLRDARDPHQSMLFSVCP
```

APPENDIX 3

Alignment of sequences of cloned variable domains of heavy chains(SEQ ID NOs: 76-87, in order of appearance).

```
               1                                                                   70
14     (1) MEFGLSWVFLVALLRGVQCQVQLVESGGGVVQPGMSLRLSCEASGFN--FNMYGLHWARQAPGKGLEWVA
15     (1) MEFGLSWVFLIAILEGVQCEVQLVESGGGLVQPGGSLRLSCAASGFS--FSNYEMNWVRQAPGKGLEWVS
 1     (1) MDILCSTLLLLTIPSWVLSQITLKESGPTLVKPTQTLTLTCTFSGFSLSTSGVGVGWIRQPPGKALEWLA
21     (1) MEFGLSWVFLVAILEGVQCEVQLVESGGGLVQPGGSLRLSCAASGFT--FSCYWMSWVRQAPGKGLEWVA
33     (1) MEFGLSWVFLVVILQGVQCEVQLVESGGDLVQPGGSLRLSCTTSGFT--FSDHHMDWVRQAPGKGLEWVG
41     (1) MDWTWRFLFVVAAATGVQSQVQLVQSGAEVKKPGSSVKVSCKASGGT--FSSYAISWVRQAPGQGLEWMG
 6     (1) MGSTAILALLLAVLQGVCAEVQLVQSGAEVKKPGESLKISCKGPGYS--FTSYWIGWVRQTPGKGLEWMG
 7     (1) MKLLWFLLLLVAAPRWVLSQVQLQESGPGLVKPSETLSLTCSVSGG--SVSSYYWSWIRQPPGKGLEWIG
 8     (1) MGSTAILALLLAVLQGVCAEVQLVQSGAEVKEPGESLRVSCKAYGYT--FTSYWITWVRQMPGRGLEYMG
 9     (1) MEFGLSWVFLVAIIKGVQCQVQLVESGGGLVKPGGSLRLSCAASGFT--FSDYYMSWIRQAPGKGLEWVS
32     (1) MEFGLSWLFLVAILKGVQCEVQLLESGGGLVQPGGSLRLSCAASGFT--FSSYAMSWVRQAPGKGLEWVS
31     (1) MEFGLSWVFLVALLRGVQCQVQLVESGGGVVQPGRSLRLSCAASGFT--FSSYGMHWVRQAPGKGLEWVA

               71                                                                 140
14    (69) VITFDGG--NKLYADSVRGRFSISRDNSKNTVYLQMNSLRTDDTAVYYCARDWSGGIRLGELSAHFDYWG
15    (69) YISPSGDP--TYYADSVKGRFTISRDNAKNSLYLQMNSLRVEDTAVYYCARDPPECCTG-AICVHFDYWG
 1    (71) LIYWDDD---KRYSPSLKSRLTITKDTSKNQVVLTMTNMDPVDTATYYCA-HR---------YYYFDYWG
21    (69) NIKQDGS--EKYYVDSVKGRFTISRDNAKNSLYLQMNSLRAGDTAAYYCARMSGSGYD--SEYYGMDVWG
33    (69) RARGRASRYTAQYAASVEGRFSVSRDESKASFYLHMRSLKTEDAATYYCVRG----------YHGFDVWG
41    (69) GIIPIFG--TANYAQKFQGRVTITADESTSTAYMELSSLRSEDTAVYYCARGYP-------AAGHMDVWG
 6    (69) IIYPGDS--DTRYSPSFQGQVTISADKSISTAYLQWSSLKASDTAMYYCARLYCSSTSCYTGGYYFDYWG
 7    (69) YFHYSGS---TNYNPSLRSRVSISVDTSKNQFSLKLSSVTAADTAVYYCARDR---------VGAIPYWG
 8    (69) RISPGDS--YTEYSPSFQGHVTISTDKSINTAYLQWSSLKASDTAVYFCARMGAWEVP--------DFWG
 9    (69) YISSSSS--YTNYADSVKGRFTISRDNAKNSLYLQMNSLRAEDTAVYYCARVFG---DT-AMGPAFDYWG
32    (69) AISGSGG--STYYADSVKGRFTISRDNSKNTLYLQMNSLRAEDTAVYYCAKTPTAR----VVVPPFDYWG
31    (69) VIWYDGS--NKYYADSVKGRFTISRDNSKNTLYLQMNSLRAEDTAVYYCAREYYYEG----GSHAFDIWG

               141                                                                210
14   (137) QGTLVTVSSVSANTRRSTLEDPRVPAPAASSGLTTFGSRWRSLLQPPPRAHRSSPWRPAPGAPPRAQRPW
15   (136) QGTLVTVSSVSANTRRSTLEDPRVPAPAASSGLTTFGSRWRSLLQPPPRAHRSSPWRPAPGAPPRAQRPW
 1   (128) QGTVVTVSSVSANTRRSTLEDPRVPAPAASSGLTTFGSRWRSLLQPPPRAHRSSPWRPAPGAPPRAQRPW
21   (135) QGTLVTVSSVSAN---------------------------------------------------------
33   (129) QGTLVTVSSVSAN---------------------------------------------------------
41   (130) QGTLVTVSSVSAN---------------------------------------------------------
 6   (137) QGTLVTVSSVSANTRRSTLEDPRVPAPAASSGLTTFGSRWRSLLQPPPRAHRSSPWRPAPGAPPRAQRPW
 7   (127) QGTLVTVSSVSANTRRSTLEDPRVPAPAASSGLTTFGSRWRSLLQPPPRAHRSSPWRPAPGAPPRAQRPW
 8   (129) QGTLVTVSSVSANTRRSTLEDPRVPAPAASSGLTTFGSRWRSLLQPPPRAHRSSPWRPAPGAPPRAQRPW
 9   (133) QGTLVTVSSVSANTRRSTLEDPRVPAPAASSGLTTFGSRWRSLLQPPPRAHRSSPWRPAPGAPPRAQRPW
32   (133) QGTLVTVSSVSANTRRSTLEDPRVPAPAASSGLTTFGSRWRSLLQPPPRAHRSSPWRPAPGAPPRAQRPW
31   (133) QGTLVTVSSVSANTRRSTLEDPRVPAPAASSGLTTFGSRWRSLLQPPPRAHRSSPWRPAPGAPPRAQRPW

               211     221
14   (207) AAWSRTTSPNR
15   (206) AAWSRTTSPNR
 1   (198) AAWSRTTSPNR
21   (148) -----------
33   (142) -----------
41   (143) -----------
 6   (207) AAWSRTTSPNR
 7   (197) AAWSRTTSPNR
 8   (199) AAWSRTTSPNR
 9   (203) AAWSRTTSPNR
32   (203) AAWSRTTSPNR
31   (203) AAWSRTTSPNR
```

APPENDIX 4

Sequences of plasmids encoding spAG-MLuc and spAG-ΔN-MLuc hybrids(SEQ ID NOs: 88-90, in order of appearance).

pETspAG-ΔN-MLuc1
1 GGAAAAATGC CTGGCAAAAA ACTGCCACTG GCAGTTATCA TGGAAATGGA AGCCAATGCT TTCAAAGCTG GCTGCACCAG GGGATGCCTT ATCTGTCTTT
CCTTTTTACG GACCGTTTTT TGACGGTGAC CGTCAATAGT ACCTTTACCT TCGGTTACGA AAGTTTCGAC CGACGTGGTC CCCTACGGAA TAGACAGAAA
101 CAAAAATTAA GTGTACAGCC AAAATGAAGG TATACATTCC AGGAAGGTGT CACGATTATG GTGGTGACAA GAAAACTGGA CAGGCAGGAA TTGTTGGTGC
GTTTTTAATT CACATGTCGG TTTTACTTCC ATATGTAAGG TCCTTCCACA GTGCTAATAC CACCACTGTT CTTTTGACCT GTCCGTCCTT AACAACCACG
201 AATTGTTGAC ATTCCCGAAA TCTCTGGATT TAAGGAGATG GCACCCATGG AACAGTTCAT TGCTCAAGTT GATCGCTGCG CTTCCTGCAC TACTGGATGT
TTAACAACTG TAAGGGCTTT AGAGACCTAA ATTCCTCTAC CGTGGGTACC TTGTCAAGTA ACGAGTTCAA CTAGCGACGC GAAGGACGTG ATGACCTACA
301 CTCAAAGGTC TTGCCAATGT TAAGTGCTCT GAACTCCTGA AGAAATGGCT GCCTGACAGG TGTGCAAGTT TTGCTGACAA GATTCAAAAA GAAGTTCACA
GAGTTTCCAG AACGGTTACA ATTCACGAGA CTTGAGGACT TCTTTACCGA CGGACTGTCC ACACGTTCAA AACGACTGTT CTAAGTTTTT CTTCAAGTGT
401 ATATCAAAGG CATGGCCGTA CAGCTGCAGG TCGAGCACCA CCACCACCAC CACTGAGATC CGGCTGCTAA CAAAGCCCGA AAGGAAGCTG AGTTGGCTGC
TATAGTTTCC GTACCGGCAT GTCGACGTCC AGCTCGTGGT GGTGGTGGTG GTGACTCTAG GCCGACGATT GTTTCGGGCT TTCCTTCGAC TCAACCGACG
501 TGCCACCGCT GAGCAATAAC TAGCATAACC CCTTGGGGCC TCTAAACGGG TCTTGAGGGG TTTTTTGCTG AAAGGAGGAA CTATATCCGG ATTGGCGAAT
ACGGTGGCGA CTCGTTATTG ATCGTATTGG GGAACCCCGG AGATTTGCCC AGAACTCCCC AAAAAACGAC TTTCCTCCTT GATATAGGCC TAACCGCTTA
601 GGGACGCGCC CTGTAGCGGC GCATTAAGCG CGGCGGGTGT GGTGGTTACG CGCAGCGTGA CCGCTACACT TGCCAGCGCC CTAGCGCCCG CTCCTTTCGC
CCCTGCGCGG GACATCGCCG CGTAATTCGC GCCGCCCACA CCACCAATGC GCGTCGCACT GGCGATGTGA ACGGTCGCGG GATCGCGGGC GAGGAAAGCG
701 TTTCTTCCCT TCCTTTCTCG CCACGTTCGC CGGCTTTCCC CGTCAAGCTC TAAATCGGGG GCTCCCTTTA GGGTTCCGAT TTAGTGCTTT ACGGCACCTC
AAAGAAGGGA AGGAAAGAGC GGTGCAAGCG GCCGAAAGGG GCAGTTCGAG ATTTAGCCCC CGAGGGAAAT CCCAAGGCTA AATCACGAAA TGCCGTGGAG
801 GACCCCAAAA AACTTGATTA GGGTGATGGT TCACGTAGTG GGCCATCGCC CTGATAGACG GTTTTTCGCC CTTTGACGTT GGAGTCCACG TTCTTTAATA
CTGGGGTTTT TTGAACTAAT CCCACTACCA AGTGCATCAC CCGGTAGCGG GACTATCTGC CAAAAAGCGG GAAACTGCAA CCTCAGGTGC AAGAAATTAT
901 GTGGACTCTT GTTCCAAACT GGAACAACAC TCAACCCTAT CTCGGTCTAT TCTTTTGATT TATAAGGGAT TTTGCCGATT TCGGCCTATT GGTTAAAAAA
CACCTGAGAA CAAGGTTTGA CCTTGTTGTG AGTTGGGATA GAGCCAGATA AGAAAACTAA ATATTCCCTA AAACGGCTAA AGCCGGATAA CCAATTTTTT
1001 TGAGCTGATT TAACAAAAAT TTAACGCGAA TTTTAACAAA ATATTAACGT TTACAATTTC AGGTGGCACT TTTCGGGGAA ATGTGCGCGG AACCCCTATT
ACTCGACTAA ATTGTTTTTA AATTGCGCTT AAAATTGTTT TATAATTGCA AATGTTAAAG TCCACCGTGA AAAGCCCCTT TACACGCGCC TTGGGGATAA
1101 TGTTTATTTT TCTAAATACA TTCAAATATG TATCCGCTCA TGAATTAATT CTTAGAAAAA CTCATCGAGC ATCAAATGAA ACTGCAATTT ATTCATATCA
ACAAATAAAA AGATTTATGT AAGTTTATAC ATAGGCGAGT ACTTAATTAA GAATCTTTTT GAGTAGCTCG TAGTTTACTT TGACGTTAAA TAAGTATAGT
1201 GGATTATCAA TACCATATTT TTGAAAAAGC CGTTTCTGTA ATGAAGGAGA AAACTCACCG AGGCAGTTCC ATAGGATGGC AAGATCCTGG TATCGGTCTG
CCTAATAGTT ATGGTATAAA AACTTTTTCG GCAAAGACAT TACTTCCTCT TTTGAGTGGC TCCGTCAAGG TATCCTACCG TTCTAGGACC ATAGCCAGAC
1301 CGATTCCGAC TCGTCCAACA TCAATACAAC CTATTAATTT CCCCTCGTCA AAAATAAGGT TATCAAGTGA GAAATCACCA TGAGTGACGA CTGAATCCGG
GCTAAGGCTG AGCAGGTTGT AGTTATGTTG GATAATTAAA GGGGAGCAGT TTTTATTCCA ATAGTTCACT CTTTAGTGGT ACTCACTGCT GACTTAGGCC
1401 TGAGAATGGC AAAAGTTTAT GCATTTCTTT CCAGACTTGT TCAACAGGCC AGCCATTACG CTCGTCATCA AAATCACTCG CATCAACCAA ACCGTTATTC
ACTCTTACCG TTTTCAAATA CGTAAAGAAA GGTCTGAACA AGTTGTCCGG TCGGTAATGC GAGCAGTAGT TTTAGTGAGC GTAGTTGGTT TGGCAATAAG
1501 ATTCGTGATT GCGCCTGAGC GAGACGAAAT ACGCGATCGC TGTTAAAAGG ACAATTACAA ACAGGAATCG AATGCAACCG GCGCAGGAAC ACTGCCAGCG
TAAGCACTAA CGCGGACTCG CTCTGCTTTA TGCGCTAGCG ACAATTTTCC TGTTAATGTT TGTCCTTAGC TTACGTTGGC CGCGTCCTTG TGACGGTCGC
1601 CATCAACAAT ATTTTCACCT GAATCAGGAT ATTCTTCTAA TACCTGGAAT GCTGTTTTCC CGGGGATCGC AGTGGTGAGT AACCATGCAT CATCAGGAGT
GTAGTTGTTA TAAAAGTGGA CTTAGTCCTA TAAGAAGATT ATGGACCTTA CGACAAAAGG GCCCCTAGCG TCACCACTCA TTGGTACGTA GTAGTCCTCA
1701 ACGGATAAAA TGCTTGATGG TCGGAAGAGG CATAAATTCC GTCAGCCAGT TTAGTCTGAC CATCTCATCT GTAACATCAT TGGCAACGCT ACCTTTGCCA
TGCCTATTTT ACGAACTACC AGCCTTCTCC GTATTTAAGG CAGTCGGTCA AATCAGACTG GTAGAGTAGA CATTGTAGTA ACCGTTGCGA TGGAAACGGT
1801 TGTTTCAGAA ACAACTCTGG CGCATCGGGC TTCCCATACA ATCGATAGAT TGTCGCACCT GATTGCCCGA CATTATCGCG AGCCCATTTA TACCCATATA
ACAAAGTCTT TGTTGAGACC GCGTAGCCCG AAGGGTATGT TAGCTATCTA ACAGCGTGGA CTAACGGGCT GTAATAGCGC TCGGGTAAAT ATGGGTATAT
1901 AATCAGCATC CATGTTGGAA TTTAATCGCG GCCTAGAGCA AGACGTTTCC CGTTGAATAT GGCTCATAAC ACCCCTTGTA TTACTGTTTA TGTAAGCAGA
TTAGTCGTAG GTACAACCTT AAATTAGCGC CGGATCTCGT TCTGCAAAGG GCAACTTATA CCGAGTATTG TGGGGAACAT AATGACAAAT ACATTCGTCT
2001 CAGTTTTATT GTTCATGACC AAAATCCCTT AACGTGAGTT TTCGTTCCAC TGAGCGTCAG ACCCCGTAGA AAAGATCAAA GGATCTTCTT GAGATCCTTT
GTCAAAATAA CAAGTACTGG TTTTAGGGAA TTGCACTCAA AAGCAAGGTG ACTCGCAGTC TGGGGCATCT TTTCTAGTTT CCTAGAAGAA CTCTAGGAAA
2101 TTTTCTGCGC GTAATCTGCT GCTTGCAAAC AAAAAAACCA CCGCTACCAG CGGTGGTTTG TTTGCCGGAT CAAGAGCTAC CAACTCTTTT TCCGAAGGTA
AAAAGACGCG CATTAGACGA CGAACGTTTG TTTTTTTGGT GGCGATGGTC GCCACCAAAC AAACGGCCTA GTTCTCGATG GTTGAGAAAA AGGCTTCCAT
2201 ACTGGCTTCA GCAGAGCGCA GATACCAAAT ACTGTCCTTC TAGTGTAGCC GTAGTTAGGC CACCACTTCA AGAACTCTGT AGCACCGCCT ACATACCTCG
TGACCGAAGT CGTCTCGCGT CTATGGTTTA TGACAGGAAG ATCACATCGG CATCAATCCG GTGGTGAAGT TCTTGAGACA TCGTGGCGGA TGTATGGAGC
2301 CTCTGCTAAT CCTGTTACCA GTGGCTGCTG CCAGTGGCGA TAAGTCGTGT CTTACCGGGT TGGACTCAAG ACGATAGTTA CCGGATAAGG CGCAGCGGTC
GAGACGATTA GGACAATGGT CACCGACGAC GGTCACCGCT ATTCAGCACA GAATGGCCCA ACCTGAGTTC TGCTATCAAT GGCCTATTCC GCGTCGCCAG

APPENDIX 4-continued

Sequences of plasmids encoding spAG-MLuc and spAG-ΔN-MLuc hybrids(SEQ ID NOs: 88-90, in order of appearance).

| | |
|---|---|
| 2401 | GGGCTGAACG GGGGGTTCGT GCACACAGCC CAGCTTGGAG CGAACGACCT ACACCGAACT GAGATACCTA CAGCGTGAGC TATGAGAAAG CGCCACGCTT |
| | CCCGACTTGC CCCCCAAGCA CGTGTGTCGG GTCGAACCTC GCTTGCTGGA TGTGGCTTGA CTCTATGGAT GTCGCACTCG ATACTCTTTC GCGGTGCGAA |
| 2501 | CCCGAAGGGA GAAAGGCGGA CAGGTATCCG GTAAGCGGCA GGGTCGGAAC AGGAGAGCGC ACGAGGGAGC TTCCAGGGGG AAACGCCTGG TATCTTTATA |
| | GGGCTTCCCT CTTTCCGCCT GTCCATAGGC CATTCGCCGT CCCAGCCTTG TCCTCTCGCG TGCTCCCTCG AAGGTCCCCC TTTGCGGACC ATAGAAATAT |
| 2601 | GTCCTGTCGG GTTTCGCCAC CTCTGACTTG AGCGTCGATT TTTGTGATGC TCGTCAGGGG GGCGGAGCCT ATGGAAAAAC GCCAGCAACG CGGCCTTTTT |
| | CAGGACAGCC CAAAGCGGTG GAGACTGAAC TCGCAGCTAA AAACACTACG AGCAGTCCCC CCGCCTCGGA TACCTTTTTG CGGTCGTTGC GCCGGAAAAA |
| 2701 | ACGGTTCCTG GCCTTTTGCT GGCCTTTTGC TCACATGTTC TTTCCTGCGT TATCCCCTGA TTCTGTGGAT AACCGTATTA CCGCCTTTGA GTGAGCTGAT |
| | TGCCAAGGAC CGGAAAACGA CCGGAAAACG AGTGTACAAG AAAGGACGCA ATAGGGGACT AAGACACCTA TTGGCATAAT GGCGGAAACT CACTCGACTA |
| 2801 | ACCGCTCGCC GCAGCCGAAC GACCGAGCGC AGCGAGTCAG TGAGCGAGGA AGCGGAAGAG CGCCTGATGC GGTATTTTCT CCTTACGCAT CTGTGCGGTA |
| | TGGCGAGCGG CGTCGGCTTG CTGGCTCGCG TCGCTCAGTC ACTCGCTCCT TCGCCTTCTC GCGGACTACG CCATAAAAGA GGAATGCGTA GACACGCCAT |
| 2901 | TTTCACACCG CATATATGGT GCACTCTCAG TACAATCTGC TCTGATGCCG CATAGTTAAG CCAGTATACA CTCCGCTATC GCTACGTGAC TGGGTCATGG |
| | AAAGTGTGGC GTATATACCA CGTGAGAGTC ATGTTAGACG AGACTACGGC GTATCAATTC GGTCATATGT GAGGCGATAG CGATGCACTG ACCCAGTACC |
| 3001 | CTGCGCCCCG ACACCCGCCA ACACCCGCTG ACGCGCCCTG ACGGGCTTGT CTGCTCCCGG CATCCGCTTA CAGACAAGCT GTGACCGTCT CCGGGAGCTG |
| | GACGCGGGGC TGTGGGCGGT TGTGGGCGAC TGCGCGGGAC TGCCCGAACA GACGAGGGCC GTAGGCGAAT GTCTGTTCGA CACTGGCAGA GGCCCTCGAC |
| 3101 | CATGTGTCAG AGGTTTTCAC CGTCATCACC GAAACGCGCG AGGCAGCTGC GGTAAAGCTC ATCAGCGTGG TCGTGAAGCG ATTCACAGAT GTCTGCCTGT |
| | GTACACAGTC TCCAAAAGTG GCAGTAGTGG CTTTGCGCGC TCCGTCGACG CCATTTCGAG TAGTCGCACC AGCACTTCGC TAAGTGTCTA CAGACGGACA |
| 3201 | TCATCCGCGT CCAGCTCGTT GAGTTTCTCC AGAAGCGTTA ATGTCTGGCT TCTGATAAAG CGGGCCATGT TAAGGGCGGT TTTTTCCTGT TTGGTCACTG |
| | AGTAGGCGCA GGTCGAGCAA CTCAAAGAGG TCTTCGCAAT TACAGACCGA AGACTATTTC GCCCGGTACA ATTCCCGCCA AAAAAGGACA AACCAGTGAC |
| 3301 | ATGCCTCCGT GTAAGGGGGA TTTCTGTTCA TGGGGGTAAT GATACCGATG AAACGAGAGA GGATGCTCAC GATACGGGTT ACTGATGATG AACATGCCCG |
| | TACGGAGGCA CATTCCCCCT AAAGACAAGT ACCCCCATTA CTATGGCTAC TTTGCTCTCT CCTACGAGTG CTATGCCCAA TGACTACTAC TTGTACGGGC |
| 3401 | GTTACTGGAA CGTTGTGAGG GTAAACAACT GGCGGTATGG ATGCGGCGGG ACCAGAGAAA AATCACTCAG GGTCAATGCC AGCGCTTCGT TAATACAGAT |
| | CAATGACCTT GCAACACTCC CATTTGTTGA CCGCCATACC TACGCCGCCC TGGTCTCTTT TTAGTGAGTC CCAGTTACGG TCGCGAAGCA ATTATGTCTA |
| 3501 | GTAGGTGTTC CACAGGGTAG CCAGCAGCAT CCTGCGATGC AGATCCGGAA CATAATGGTG CAGGGCGCTG ACTTCCGCGT TTCCAGACTT TACGAAACAC |
| | CATCCACAAG GTGTCCCATC GGTCGTCGTA GGACGCTACG TCTAGGCCTT GTATTACCAC GTCCCGCGAC TGAAGGCGCA AAGGTCTGAA ATGCTTTGTG |
| 3601 | GGAAACCGAA GACCATTCAT GTTGTTGCTC AGGTCGCAGA CGTTTTGCAG CAGCAGTCGC TTCACGTTCG CTCGCGTATC GGTGATTCAT TCTGCTAACC |
| | CCTTTGGCTT CTGGTAAGTA CAACAACGAG TCCAGCGTCT GCAAAACGTC GTCGTCAGCG AAGTGCAAGC GAGCGCATAG CCACTAAGTA AGACGATTGG |
| 3701 | AGTAAGGCAA CCCCGCCAGC CTAGCCGGGT CCTCAACGAC AGGAGCACGA TCATGCGCAC CCGTGGGGCC GCCATGCCGG CGATAATGGC CTGCTTCTCG |
| | TCATTCCGTT GGGGCGGTCG GATCGGCCCA GGAGTTGCTG TCCTCGTGCT AGTACGCGTG GGCACCCCGG CGGTACGGCC GCTATTACCG GACGAAGAGC |
| 3801 | CCGAAACGTT TGGTGGCGGG ACCAGTGACG AAGGCTTGAG CGAGGGCGTG CAAGATTCCG AATACCGCAA GCGACAGGCC GATCATCGTC GCGCTCCAGC |
| | GGCTTTGCAA ACCACCGCCC TGGTCACTGC TTCCGAACTC GCTCCCGCAC GTTCTAAGGC TTATGGCGTT CGCTGTCCGG CTAGTAGCAG CGCGAGGTCG |
| 3901 | GAAAGCGGTC CTCGCCGAAA ATGACCCAGA GCGCTGCCGG CACCTGTCCT ACGAGTTGCA TGATAAAGAA GACAGTCATA AGTGCGGCGA CGATAGTCAT |
| | CTTTCGCCAG GAGCGGCTTT TACTGGGTCT CGCGACGGCC GTGGACAGGA TGCTCAACGT ACTATTTCTT CTGTCAGTAT TCACGCCGCT GCTATCAGTA |
| 4001 | GCCCCGCGCC CACCGGAAGG AGCTGACTGG GTTGAAGGCT CTCAAGGGCA TCGGTCGAGA TCCCGGTGCC TAATGAGTGA GCTAACTTAC ATTAATTGCG |
| | CGGGGCGCGG GTGGCCTTCC TCGACTGACC CAACTTCCGA GAGTTCCCGT AGCCAGCTCT AGGGCCACGG ATTACTCACT CGATTGAATG TAATTAACGC |
| 4101 | TTGCGCTCAC TGCCCGCTTT CCAGTCGGGA AACCTGTCGT GCCAGCTGCA TTAATGAATC GGCCAACGCG CGGGGAGAGG CGGTTTGCGT ATTGGGCGCC |
| | AACGCGAGTG ACGGGCGAAA GGTCAGCCCT TTGGACAGCA CGGTCGACGT AATTACTTAG CCGGTTGCGC GCCCCTCTCC GCCAAACGCA TAACCCGCGG |
| 4201 | AGGGTGGTTT TTCTTTTCAC CAGTGAGACG GGCAACAGCT GATTGCCCTT CACCGCCTGG CCCTGAGAGA GTTGCAGCAA GCGGTCCACG CTGGTTTGCC |
| | TCCCACCAAA AAGAAAAGTG GTCACTCTGC CCGTTGTCGA CTAACGGGAA GTGGCGGACC GGGACTCTCT CAACGTCGTT CGCCAGGTGC GACCAAACGG |
| 4301 | CCAGCAGGCG AAAATCCTGT TTGATGGTGG TTAACGGCGG GATATAACAT GAGCTGTCTT CGGTATCGTC GTATCCCACT ACCGAGATAT CCGCACCAAC |
| | GGTCGTCCGC TTTTAGGACA AACTACCACC AATTGCCGCC CTATATTGTA CTCGACAGAA GCCATAGCAG CATAGGGTGA TGGCTCTATA GGCGTGGTTG |
| 4401 | GCGCAGCCCG GACTCGGTAA TGGCGCGCAT TGCGCCCAGC GCCATCTGAT CGTTGGCAAC CAGCATCGCA GTGGGAACGA TGCCCTCATT CAGCATTTGC |
| | CGCGTCGGGC CTGAGCCATT ACCGCGCGTA ACGCGGGTCG CGGTAGACTA GCAACCGTTG GTCGTAGCGT CACCCTTGCT ACGGGAGTAA GTCGTAAACG |
| 4501 | ATGGTTTGTT GAAAACCGGA CATGGCACTC CAGTCGCCTT CCCGTTCCGC TATCGGCTGA ATTTGATTGC GAGTGAGATA TTTATGCCAG CCAGCCAGAC |
| | TACCAAACAA CTTTTGGCCT GTACCGTGAG GTCAGCGGAA GGGCAAGGCG ATAGCCGACT TAAACTAACG CTCACTCTAT AAATACGGTC GGTCGGTCTG |
| 4601 | GCAGACGCGC CGAGACAGAA CTTAATGGGC CCGCTAACAG CGCGATTTGC TGGTGACCCA ATGCGACCAG ATGCTCCACG CCCAGTCGCG TACCGTCTTC |
| | CGTCTGCGCG GCTCTGTCTT GAATTACCCG GGCGATTGTC GCGCTAAACG ACCACTGGGT TACGCTGGTC TACGAGGTGC GGGTCAGCGC ATGGCAGAAG |
| 4701 | ATGGGAGAAA ATAATACTGT TGATGGGTGT CTGGTCAGAG ACATCAAGAA ATAACGCCGG AACATTAGTG CAGGCAGCTT CCACAGCAAT GGCATCCTGG |
| | TACCCTCTTT TATTATGACA ACTACCCACA GACCAGTCTC TGTAGTTCTT TATTGCGGCC TTGTAATCAC GTCCGTCGAA GGTGTCGTTA CCGTAGGACC |
| 4801 | TCATCCAGCG GATAGTTAAT GATCAGCCCA CTGACGCGTT GCGCGAGAAG ATTGTGCACC GCCGCTTTAC AGGCTTCGAC GCCGCTTCGT TCTACCATCG |
| | AGTAGGTCGC CTATCAATTA CTAGTCGGGT GACTGCGCAA CGCGCTCTTC TAACACGTGG CGGCGAAATG TCCGAAGCTG CGGCGAAGCA AGATGGTAGC |

APPENDIX 4-continued

Sequences of plasmids encoding spAG-MLuc and spAG-ΔN-MLuc hybrids(SEQ ID NOs: 88-90, in order of appearance).

4901 ACACCACCAC GCTGGCACCC AGTTGATCGG CGCGAGATTT AATCGCCGCG ACAATTTGCG ACGGCGCGTG CAGGGCCAGA CTGGAGGTGG CAACGCCAAT
TGTGGTGGTG CGACCGTGGG TCAACTAGCC GCGCTCTAAA TTAGCGGCGC TGTTAAACGC TGCCGCGCAC GTCCCGGTCT GACCTCCACC GTTGCGGTTA
5001 CAGCAACGAC TGTTTGCCCG CCAGTTGTTG TGCCACGCGG TTGGGAATGT AATTCAGCTC CGCCATCGCC GCTTCCACTT TTTCCCGCGT TTTCGCAGAA
GTCGTTGCTG ACAAACGGGC GGTCAACAAC ACGGTGCGCC AACCCTTACA TTAAGTCGAG GCGGTAGCGG CGAAGGTGAA AAAGGGCGCA AAAGCGTCTT
5101 ACGTGGCTGG CCTGGTTCAC CACGCGGGAA ACGGTCTGAT AAGAGACACC GGCATACTCT GCGACATCGT ATAACGTTAC TGGTTTCACA TTCACCACCC
TGCACCGACC GGACCAAGTG GTGCGCCCTT TGCCAGACTA TTCTCTGTGG CCGTATGAGA CGCTGTAGCA TATTGCAATG ACCAAAGTGT AAGTGGTGGG
5201 TGAATTGACT CTCTTCCGGG CGCTATCATG CCATACCGCG AAAGGTTTTG CGCCATTCGA TGGTGTCCGG GATCTCGACG CTCTCCCTTA TGCGACTCCT
ACTTAACTGA GAGAAGGCCC GCGATAGTAC GGTATGGCGC TTTCCAAAAC GCGGTAAGCT ACCACAGGCC CTAGAGCTGC GAGAGGGAAT ACGCTGAGGA
5301 GCATTAGGAA GCAGCCCAGT AGTAGGTTGA GGCCGTTGAG CACCGCCGCC GCAAGGAATG GTGCATGCAA GGAGATGGCG CCCAACAGTC CCCCGGCCAC
CGTAATCCTT CGTCGGGTCA TCATCCAACT CCGGCAACTC GTGGCGGCGG CGTTCCTTAC CACGTACGTT CCTCTACCGC GGGTTGTCAG GGGGCCGGTG
5401 GGGGCCTGCC ACCATACCCA CGCCGAAACA AGCGCTCATG AGCCCGAAGT GGCGAGCCCG ATCTTCCCCA TCGGTGATGT CGGCGATATA GGCGCCAGCA
CCCCGGACGG TGGTATGGGT GCGGCTTTGT TCGCGAGTAC TCGGGCTTCA CCGCTCGGGC TAGAAGGGGT AGCCACTACA GCCGCTATAT CCGCGGTCGT
5501 ACCGCACCTG TGGCGCCGGT GATGCCGGCC ACGATGCGTC CGGCGTAGAG GATCGAGATC TCGATCCCGC GAAATTAATA CGACTCACTA TAGGGGAATT
TGGCGTGGAC ACCGCGGCCA CTACGGCCGG TGCTACGCAG GCCGCATCTC CTAGCTCTAG AGCTAGGGCG CTTTAATTAT GCTGAGTGAT ATCCCCTTAA
5601 GTGAGCGGAT AACAATTCCC CTCTAGAAAT AATTTTGTTT AACTTTAAGA AGGAGATATA CCATGGGCAG CAGCCATCAT CATCATCATC ACAGCAGCGG
CACTCGCCTA TTGTTAAGGG GAGATCTTTA TTAAAACAAA TTGAAATTCT TCCTCTATAT GGTACCCGTC GTCGGTAGTA GTAGTAGTAG TGTCGTCGCC
5701 CCTGGTGCCG CGCGGCAGCC ATAGGTCGAC TCTAGAGGAT CCAAGCCAAA GCACTAACGT TTTAGGTGAA GCTAAAAAAT TAAACGAATC TCAAGCACCG
GGACCACGGC GCGCCGTCGG TATCCAGCTG AGATCTCCTA GGTTCGGTTT CGTGATTGCA AAATCCACTT CGATTTTTTA ATTTGCTTAG AGTTCGTGGC
5801 AAAGCTGACA ACAATTTCAA CAAAGAACAA CAAAATGCTT TCTATGAAAT CTTGAACATG CCTAACTTGA ACGAAGAACA ACGCAATGGT TTCATCCAAA
TTTCGACTGT TGTTAAAGTT GTTTCTTGTT GTTTTACGAA AGATACTTTA GAACTTGTAC GGATTGAACT TGCTTCTTGT TGCGTTACCA AAGTAGGTTT
5901 GCTTAAAAGA TGACCCAAGT CAAAGTGCTA ACCTTTTAGC AGAAGCTAAA AAGTTAAATG AATCTCAAGC ACCGAAAGCT GATAACAAAT TCAACAAAGA
CGAATTTTCT ACTGGGTTCA GTTTCACGAT TGGAAAATCG TCTTCGATTT TTCAATTTAC TTAGAGTTCG TGGCTTTCGA CTATTGTTTA AGTTGTTTCT
6001 ACAACAAAAT GCTTTCTATG AAATCTTACA TTTACCTAAC TTAAATGAAG AACAACGCAA TGGTTTCATC CAAAGCTTAA AAGATGACCC AAGCCAAAGC
TGTTGTTTTA CGAAAGATAC TTTAGAATGT AAATGGATTG AATTTACTTC TTGTTGCGTT ACCAAAGTAG GTTTCGAATT TTCTACTGGG TTCGGTTTCG
6101 GCTAACCTTT TAGCAGAAGC TAAAAAGCTA AATGATGCAC AAGCACCAAA AGCTGACAAC AAATTCAACA AAGAACAACA AAATGCTTTC TATGAAATTT
CGATTGGAAA ATCGTCTTCG ATTTTTCGAT TTACTACGTG TTCGTGGTTT TCGACTGTTG TTTAAGTTGT TTCTTGTTGT TTTACGAAAG ATACTTTAAA
6201 TACATTTACC TAACTTAACT GAAGAACAAC GTAACGGCTT CATCCAAAGC CTTAAAGACG ATCCCCGGTC GACTCTAGCG GCAGCTTCCG GTGCTAGCAC
ATGTAAATGG ATTGAATTGA CTTCTTGTTG CATTGCCGAA GTAGGTTTCG GAATTTCTGC TAGGGGCCAG CTGAGATCGC CGTCGAAGGC CACGATCGTG
6301 TGACACTTAC AAATTAATCC TTAATGGTAA AACATTGAAA GGCGAAACAA CTACTGAAGC TGTTGATGCT GCTACTGCAG AAAAAGTCTT CAAACAATAC
ACTGTGAATG TTTAATTAGG AATTACCATT TTGTAACTTT CCGCTTTGTT GATGACTTCG ACAACTACGA CGATGACGTC TTTTTCAGAA GTTTGTTATG
6401 GCTAACGACA ACGGTGTTGA CGGTGAATGG ACTTACGACG ATGCGACTAA GACCTTTACA GTTACTGAAA AACCAGAAGT GATCGATGCG TCTGAATTAA
CGATTGCTGT TGCCACAACT GCCACTTACC TGAATGCTGC TACGCTGATT CTGGAAATGT CAATGACTTT TTGGTCTTCA CTAGCTACGC AGACTTAATT
6501 CACCAGCCGT GACAACTTAC AAACTTGTTA TTAATGGTAA AACATTGAAA GGCGAAACAA CTACTAAAGC AGTAGACGCA GAAACTGCAG AAAAAGCCTT
GTGGTCGGCA CTGTTGAATG TTTGAACAAT AATTACCATT TTGTAACTTT CCGCTTTGTT GATGATTTCG TCATCTGCGT CTTTGACGTC TTTTTCGGAA
6601 CAAACAATAC GCTAACGACA ACGGTGTTGA TGGTGTTTGG ACTTATGATG ATGCGACTAA GACCTTTACG GTAACTGAAA TGGTTACAGA GGTACCAGAT
GTTTGTTATG CGATTGCTGT TGCCACAACT ACCACAAACC TGAATACTAC TACGCTGATT CTGGAAATGC CATTGACTTT ACCAATGTCT CCATGGTCTA
6701 CTTAGCAACT TTGTTGCAAC TGAAACCGAT GCTAACCGC
GAATCGTTGA AACAACGTTG ACTTTGGCTA CGATTGGCG pS14L-spAG-MLuc16

1 AGCGCCCAAT ACGCAAACCG CCTCTCCCCG CGCGTTGGCC GATTCATTAA TGCAGCTGGC ACGACAGGTT TCCCGACTGG AAAGCGGGCA GTGAGCGCAA
TCGCGGGTTA TGCGTTTGGC GGAGAGGGGC GCGCAACCGG CTAAGTAATT ACGTCGACCG TGCTGTCCAA AGGGCTGACC TTTCGCCCGT CACTCGCGTT
101 CGCAATTAAT GTGAGTTAGC TCACTCATTA GGCACCCCAG GCTTTACACT TTATGCTTCC GGCTCGTATG TTGTGTGGAA TTGTGAGCGG ATAACAATTT
GCGTTAATTA CACTCAATCG AGTGAGTAAT CCGTGGGGTC CGAAATGTGA AATACGAAGG CCGAGCATAC AACACACCTT AACACTCGCC TATTGTTAAA
201 CACACAGGAA ACAGCTATGA CCATGATTAC GCCAAGCTTT AGGGATAACA GGGTAATCGC CATGCATTAG TTATTAATAG TAATCAATTA CGGGGTCATT
GTGTGTCCTT TGTCGATACT GGTACTAATG CGGTTCGAAA TCCCTATTGT CCCATTAGCG GTACGTAATC AATAATTATC ATTAGTTAAT GCCCCAGTAA
301 AGTTCATAGC CCATATATGG AGTTCCGCGT TACATAACTT ACGGTAAATG GCCCGCCTGG CTGACCGCCC AACGACCCCC GCCCATTGAC GTCAATAATG
TCAAGTATCG GGTATATACC TCAAGGCGCA ATGTATTGAA TGCCATTTAC CGGGCGGACC GACTGGCGGG TTGCTGGGGG CGGGTAACTG CAGTTATTAC
401 ACGTATGTTC CCATAGTAAC GCCAATAGGG ACTTTCCATT GACGTCAATG GGTGGAGTAT TTACGGTAAA CTGCCCACTT GGCAGTACAT CAAGTGTATC
TGCATACAAG GGTATCATTG CGGTTATCCC TGAAAGGTAA CTGCAGTTAC CCACCTCATA AATGCCATTT GACGGGTGAA CCGTCATGTA GTTCACATAG

APPENDIX 4-continued

Sequences of plasmids encoding spAG-MLuc and spAG-ΔN-MLuc hybrids(SEQ ID NOs: 88-90, in order of appearance).

```
501   ATATGCCAAG TACGCCCCCT ATTGACGTCA ATGACGGTAA ATGGCCCGCC TGGCATTATG CCCAGTACAT GACCTTATGG GACTTTCCTA CTTGGCAGTA
      TATACGGTTC ATGCGGGGGA TAACTGCAGT TACTGCCATT TACCGGGCGG ACCGTAATAC GGGTCATGTA CTGGAATACC CTGAAAGGAT GAACCGTCAT
601   CATCTACGTA TTAGTCATCG CTATTACCAT GGTGATGCGG TTTTGGCAGT ACATCAATGG GCGTGGATAG CGGTTTGACT CACGGGGATT TCCAAGTCTC
      GTAGATGCAT AATCAGTAGC GATAATGGTA CCACTACGCC AAAACCGTCA TGTAGTTACC CGCACCTATC GCCAAACTGA GTGCCCCTAA AGGTTCAGAG
701   CACCCCATTG ACGTCAATGG GAGTTTGTTT TGGCACCAAA ATCAACGGGA CTTTCCAAAA TGTCGTAACA ACTCCGCCCC ATTGACGCAA ATGGGCGGTA
      GTGGGGTAAC TGCAGTTACC CTCAAACAAA ACCGTGGTTT TAGTTGCCCT GAAAGGTTTT ACAGCATTGT TGAGGCGGGG TAACTGCGTT TACCCGCCAT
801   GGCGTGTACG GTGGGAGGTC TATATAAGCA GAGCTGGTTT AGTGAACCGT CAGATCCGCT AGACGTCTCA TTTAGGCATG GAAACCCCAG CGCAGCTTCT
      CCGCACATGC CACCCTCCAG ATATATTCGT CTCGACCAAA TCACTTGGCA GTCTAGGCGA TCTGCAGAGT AAATCCGTAC CTTTGGGGTC GCGTCGAAGA
901   CTTCCTCCTG CTACTCTGGA TCCCAGACAC CATTGAAGAA ATAGTGATGA CGCAGTCTCC AGCCACCCTG TCTGTGTCTC CAGGGGAAAG AGTCACCCTC
      GAAGGAGGAC GATGAGACCT AGGGTCTGTG GTAACTTCTT TATCACTACT GCGTCAGAGG TCGGTGGGAC AGACACAGAG GTCCCCTTTC TCAGTGGGAG
1001  TCCAGCAGCC ATCATCATCA TCATCACAGC AGCGGCCTGG TGCCGCGCGG CAGCCATAGG TCGACTCTAG AGGATCCAAG CCAAAGCACT AACGTTTTAG
      AGGTCGTCGG TAGTAGTAGT AGTAGTGTCG TCGCCGGACC ACGGCGCGCC GTCGGTATCC AGCTGAGATC TCCTAGGTTC GGTTTCGTGA TTGCAAAATC
1101  GTGAAGCTAA AAAATTAAAC GAATCTCAAG CACCGAAAGC TGACAACAAT TTCAACAAAG AACAACAAAA TGCTTTCTAT GAAATCTTGA ACATGCCTAA
      CACTTCGATT TTTTAATTTG CTTAGAGTTC GTGGCTTTCG ACTGTTGTTA AAGTTGTTTC TTGTTGTTTT ACGAAAGATA CTTTAGAACT TGTACGGATT
1201  CTTGAACGAA GAACAACGCA ATGGTTTCAT CCAAAGCTTA AAAGATGACC CAAGTCAAAG TGCTAACCTT TTAGCAGAAG CTAAAAAGTT AAATGAATCT
      GAACTTGCTT CTTGTTGCGT TACCAAAGTA GGTTTCGAAT TTTCTACTGG GTTCAGTTTC ACGATTGGAA AATCGTCTTC GATTTTTCAA TTTACTTAGA
1301  CAAGCACCGA AAGCTGATAA CAAATTCAAC AAAGAACAAC AAAATGCTTT CTATGAAATC TTACATTTAC CTAACTTAAA TGAAGAACAA CGCAATGGTT
      GTTCGTGGCT TTCGACTATT GTTTAAGTTG TTTCTTGTTG TTTTACGAAA GATACTTTAG AATGTAAATG GATTGAATTT ACTTCTTGTT GCGTTACCAA
1401  TCATCCAAAG CTTAAAAGAT GACCCAAGCC AAAGCGCTAA CCTTTTAGCA GAAGCTAAAA AGCTAAATGA TGCACAAGCA CCAAAAGCTG ACAACAAATT
      AGTAGGTTTC GAATTTTCTA CTGGGTTCGG TTATGCGATT GGAAAATCGT CTTCGATTTT TCGATTTACT ACGTGTTCGT GGTTTTCGAC TGTTGTTTAA
1501  CAACAAAGAA CAACAAAATG CTTTCTATGA AATTTTACAT TTACCTAACT TAACTGAAGA ACAACGTAAC GGCTTCATCC AAAGCCTTAA AGACGATCCC
      GTTGTTTCTT GTTGTTTTAC GAAAGATACT TTAAAATGTA AATGGATTGA ATTGACTTCT TGTTGCATTG CCGAAGTAGG TTTCGGAATT TCTGCTAGGG
1601  CGGTCGACTC TAGCGGCAGC TTCCGGTGCT AGCACTGACA CTTACAAATT AATCCTTAAT GGTAAAACAT TGAAAGGCGA AACAACTACT GAAGCTGTTG
      GCCAGCTGAG ATCGCCGTCG AAGGCCACGA TCGTGACTGT GAATGTTTAA TTAGGAATTA CCATTTTGTA ACTTTCCGCT TTGTTGATGA CTTCGACAAC
1701  ATGCTGCTAC TGCAGAAAAA GTCTTCAAAC AATACGCTAA CGACAACGGT GTTGACGGTG AATGGACTTA CGACGATGCG ACTAAGACCT TTACAGTTAC
      TACGACGATG ACGTCTTTTT CAGAAGTTTG TTATGCGATT GCTGTTGCCA CAACTGCCAC TTACCTGAAT GCTGCTACGC TGATTCTGGA AATGTCAATG
1801  TGAAAAACCA GAAGTGATCG ATGCGTCTGA ATTAACACCA GCCGTGACAA CTTACAAACT TGTTATTAAT GGTAAAACAT TGAAAGGCGA AACAACTACT
      ACTTTTTGGT CTTCACTAGC TACGCAGACT TAATTGTGGT CGGCACTGTT GAATGTTTGA ACAATAATTA CCATTTTGTA ACTTTCCGCT TTGTTGATGA
1901  AAAGCAGTAG ACGCAGAAAC TGCAGAAAAA GCCTTCAAAC AATACGCTAA CGACAACGGT GTTGATGGTG TTTGGACTTA TGATGATGCG ACTAAGACCT
      TTTCGTCATC TGCGTCTTTG ACGTCTTTTT CGGAAGTTTG TTATGCGATT GCTGTTGCCA CAACTACCAC AAACCTGAAT ACTACTACGC TGATTCTGGA
2001  TTACGGTAAC TGAAATGGTT ACAGAGGTAC CGCGGGCCCG GGATCCACCG GCTAGCGGGA ATTCCAAATC AACTGAGTTC GATCCTAACA TTGACATTGT
      AATGCCATTG ACTTTACCAA TGTCTCCATG GCGCCCGGGC CCTAGGTGGC CGATCGCCCT TAAGGTTTAG TTGACTCAAG CTAGGATTGT AACTGTAACA
2101  TGGTTTAGAA GGAAAATTTG GTATTACAAA CCTAGAGACG GATTTATTCA CAATCTGGGA GACAATGGAG GTCATGATCA AAGCAGATAT TGCAGATACT
      ACCAAATCTT CCTTTTAAAC CATAATGTTT GGATCTCTGC CTAAATAAGT GTTAGACCCT CTGTTACCTC CAGTACTAGT TTCGTCTATA ACGTCTATGA
2201  GATAGAGCCA GCAACTTTGT TGCAACTGAA ACCGATGCTA ACCGCGGAAA AATGCCTGGC AAAAAACTGC CACTGGCAGT TATCATGGAA ATGGAAGCCA
      CTATCTCGGT CGTTGAAACA ACGTTGACTT TGGCTACGAT TGGCGCCTTT TTACGGACCG TTTTTTGACG GTGACCGTCA ATAGTACCTT TACCTTCGGT
2301  ATGCTTTCAA AGCTGGCTGC ACCAGGGGAT GCCTTATCTG TCTTTCAAAA ATTAAGTGTA CAGCCAAAAT GAAGGTATAC ATTCCAGGAA GGTGTCACGA
      TACGAAAGTT TCGACCGACG TGGTCCCCTA CGGAATAGAC AGAAAGTTTT TAATTCACAT GTCGGTTTTA CTTCCATATG TAAGGTCCTT CCACAGTGCT
2401  TTATGGTGGT GACAAGAAAA CTGGACAGGC AGGAATTGTT GGTGCAATTG TTGACATTCC CGAAATCTCT GGATTTAAGG AGATGGCACC CATGGAACAG
      AATACCACCA CTGTTCTTTT GACCTGTCCG TCCTTAACAA CCACGTTAAC AACTGTAAGG GCTTTAGAGA CCTAAATTCC TCTACCGTGG GTACCTTGTC
2501  TTCATTGCTC AAGTTGATCG CTGCGCTTCC TGCACTACTG GATGTCTCAA AGGTCTTGCC AATGTTAAGT GCTCTGAACT CCTGAAGAAA TGGCTGCCTG
      AAGTAACGAG TTCAACTAGC GACGCGAAGG ACGTGATGAC CTACAGAGTT TCCAGAACGG TTACAATTCA CGAGACTTGA GGACTTCTTT ACCGACGGAC
2601  ACAGGTGTGC AAGTTTTGCT GACAAGATTC AAAAAGAAGT TCACAATATC AAAGGCATGG CCGGCGATCG ATGAGCGGCC GCAATTTAAT TCCGGTTATT
      TGTCCACACG TTCAAAACGA CTGTTCTAAG TTTTTCTTCA AGTGTTATAG TTTCCGTACC GGCCGCTAGC TACTCGCCGG CGTTAAATTA AGGCCAATAA
2701  TTCCACCATA TTGCCGTCTT TTGGCAATGT GAGGGCCCGG AAACCTGGCC CTGTCTTCTT GACGAGCATT CCTAGGGGTC TTTCCCCTCT CGCCAAAGGA
      AAGGTGGTAT AACGGCAGAA AACCGTTACA CTCCCGGGCC TTTGGACCGG GACAGAAGAA CTGCTCGTAA GGATCCCCAG AAAGGGGAGA GCGGTTTCCT
2801  ATGCAAGGTC TGTTGAATGT CGTGAAGGAA GCAGTTCCTC TGGAAGCTTC TTGAAGACAA ACAACGTCTG TAGCGACCCT TTGCAGGCAG CGGAACCCCC
      TACGTTCCAG ACAACTTACA GCACTTCCTT CGTCAAGGAG ACCTTCGAAG AACTTCTGTT TGTTGCAGAC ATCGCTGGGA AACGTCCGTC GCCTTGGGGG
2901  CACCTGGCGA CAGGTGCCTC TGCGGCCAAA AGCCACGTGT ATAAGATACA CCTGCAAAGG CGGCACAACC CCAGTGCCAC GTTGTGAGTT GGATAGTTGT
      GTGGACCGCT GTCCACGGAG ACGCCGGTTT TCGGTGCACA TATTCTATGT GGACGTTTCC GCCGTGTTGG GGTCACGGTG CAACACTCAA CCTATCAACA
```

APPENDIX 4-continued

Sequences of plasmids encoding spAG-MLuc and spAG-ΔN-MLuc hybrids(SEQ ID NOs: 88-90, in order of appearance).

3001 GGAAAGAGTC AAATGGCTCA CCTCAAGCGT ATTCAACAAG GGGCTGAAGG ATGCCCAGAA GGTACCCCAT TGTATGGGAT CTGATCTGGG GCCTCGGTGC
CCTTTCTCAG TTTACCGAGT GGAGTTCGCA TAAGTTGTTC CCCGACTTCC TACGGGTCTT CCATGGGGTA ACATACCCTA GACTAGACCC CGGAGCCACG
3101 ACATGCTTTA CATGTGTTTA GTCGAGGTTA AAAAACGTCT AGGCCCCCCG AACCACGGGG ACGTGGTTTT CCTTTGAAAA ACACGATGAT AATATGGCCA
TGTACGAAAT GTACACAAAT CAGCTCCAAT TTTTTGCAGA TCCGGGGGGC TTGGTGCCCC TGCACCAAAA GGAAACTTTT TGTGCTACTA TTATACCGGT
3201 CCACCCATAC CTAGGCTTTT GCAAAGATCG ATCAGATCCC GGGGGGCAAT GAGATATGAA AAAGCCTGAA CTCACCGCGA CGTCTGTCGA GAAGTTTCTG
GGTGGGTATG GATCCGAAAA CGTTTCTAGC TAGTCTAGGG CCCCCCGTTA CTCTATACTT TTTCGGACTT GAGTGGCGCT GCAGACAGCT CTTCAAAGAC
3301 ATCGAAAAGT TCGACAGCGT CTCCGACCTG ATGCAGCTCT CGGAGGGCGA AGAATCTCGT GCTTTCAGCT TCGATGTAGG AGGGCGTGGA TATGTCCTGC
TAGCTTTTCA AGCTGTCGCA GAGGCTGGAC TACGTCGAGA GCCTCCCGCT TCTTAGAGCA CGAAAGTCGA AGCTACATCC TCCCGCACCT ATACAGGACG
3401 GGGTAAATAG CTGCGCCGAT GGTTTCTACA AAGATCGTTA TGTTTATCGG CACTTTGCAT CGGCCGCGCT CCCGATTCCG GAAGTGCTTG ACATTGGGGA
CCCATTTATC GACGCGGCTA CCAAAGATGT TTCTAGCAAT ACAAATAGCC GTGAAACGTA GCCGGCGCGA GGGCTAAGGC CTTCACGAAC TGTAACCCCT
3501 ATTCAGCGAG AGCCTGACCT ATTGCATCTC CCGCCGTGCA CAGGGTGTCA CGTTGCAAGA CCTGCCTGAA ACCGAACTGC CCGCTGTTCT GCAGCCGGTC
TAAGTCGCTC TCGGACTGGA TAACGTAGAG GGCGGCACGT GTCCCACAGT GCAACGTTCT GGACGGACTT TGGCTTGACG GGCGACAAGA CGTCGGCCAG
3601 GCGGAGGCCA TGGATGCGAT CGCTGCGGCC GATCTTAGCC AGACGAGCGG GTTCGGCCCA TTCGGACCGC AAGGAATCGG TCAATACACT ACATGGCGTG
CGCCTCCGGT ACCTACGCTA GCGACGCCGG CTAGAATCGG TCTGCTCGCC CAAGCCGGGT AAGCCTGGCG TTCCTTAGCC AGTTATGTGA TGTACCGCAC
3701 ATTTCATATG CGCGATTGCT GATCCCCATG TGTATCACTG GCAAACTGTG ATGGACGACA CCGTCAGTGC GTCCGTCGCG CAGGCTCTCG ATGAGCTGAT
TAAAGTATAC GCGCTAACGA CTAGGGGTAC ACATAGTGAC CGTTTGACAC TACCTGCTGT GGCAGTCACG CAGGCAGCGC GTCCGAGAGC TACTCGACTA
3801 GCTTTGGGCC GAGGACTGCC CCGAAGTCCG GCACCTCGTG CACGCGGATT TCGGCTCCAA CAATGTCCTG ACGGACAATG GCCGCATAAC AGCGGTCATT
CGAAACCCGG CTCCTGACGG GGCTTCAGGC CGTGGAGCAC GTGCGCCTAA AGCCGAGGTT GTTACAGGAC TGCCTGTTAC CGGCGTATTG TCGCCAGTAA
3901 GACTGGAGCG AGGCGATGTT CGGGGATTCC CAATACGAGG TCGCCAACAT CTTCTTCTGG AGGCCGTGGT TGGCTTGTAT GGAGCAGCAG ACGCGCTACT
CTGACCTCGC TCCGCTACAA GCCCCTAAGG GTTATGCTCC AGCGGTTGTA GAAGAAGACC TCCGGCACCA ACCGAACATA CCTCGTCGTC TGCGCGATGA
4001 TCGAGCGGAG GCATCCGGAG CTTGCAGGAT CGCCGCGGCT CCGGGCGTAT ATGCTCCGCA TTGGTCTTGA CCAACTCTAT CAGAGCTTGG TTGACGGCAA
AGCTCGCCTC CGTAGGCCTC GAACGTCCTA GCGGCGCCGA GGCCCGCATA TACGAGGCGT AACCAGAACT GGTTGAGATA GTCTCGAACC AACTGCCGTT
4101 TTTCGATGAT GCAGCTTGGG CGCAGGGTCG ATGCGACGCA ATCGTCCGAT CCGGAGCCGG GACTGTCGGG CGTACACAAA TCGCCCGCAG AAGCGCGGCC
AAAGCTACTA CGTCGAACCC GCGTCCCAGC TACGCTGCGT TAGCAGGCTA GGCCTCGGCC CTGACAGCCC GCATGTGTTT AGCGGGCGTC TTCGCGCCGG
4201 GTCTGGACCG ATGGCTGTGT AGAAGTACTC GCCGATAGTG GAAACCGACG CCCCAGCACT CGTCCGGATC GGGAGATGGG GGAGGCTAAC TGAAACACGG
CAGACCTGGC TACCGACACA TCTTCATGAG CGGCTATCAC CTTTGGCTGC GGGGTCGTGA GCAGGCCTAG CCCTCTACCC CCTCCGATTG ACTTTGTGCC
4301 AAGGAGACAA TACCGGAAGG AACCTCGACG TTAACTTGTT TATTGCAGCT TATAATGGTT ACAAATAAAG CAATAGCATC ACAAATTTCA CAAATAAAGC
TTCCTCTGTT ATGGCCTTCC TTGGAGCTGC AATTGAACAA ATAACGTCGA ATATTACCAA TGTTTATTTC GTTATCGTAG TGTTTAAAGT GTTTATTTCG
4401 ATTTATTACC CTGTTATCCC TAGAATTCAC TGGCCGTCGT TTTACAACGT CGTGACTGGG AAAACCCTGG CGTTACCCAA CTTAATCGCC TTGCAGCACA
TAAATAATGG GACAATAGGG ATCTTAAGTG ACCGGCAGCA AAATGTTGCA GCACTGACCC TTTTGGGACC GCAATGGGTT GAATTAGCGG AACGTCGTGT
4501 TCCCCCTTTC GCCAGCTGGC GTAATAGCGA AGAGGCCCGC ACCGATCGCC CTTCCCAACA GTTGCGCAGC CTGAATGGCG AATGGCGCCT GATGCGGTAT
AGGGGGAAAG CGGTCGACCG CATTATCGCT TCTCCGGGCG TGGCTAGCGG GAAGGGTTGT CAACGCGTCG GACTTACCGC TTACCGCGGA CTACGCCATA
4601 TTTCTCCTTA CGCATCTGTG CGGTATTTCA CACCGCATAC GTCAAAGCAA CCATAGTACG CGCCCTGTAG CGGCGCATTA AGCGCGGCGG GTGTGGTGGT
AAAGAGGAAT GCGTAGACAC GCCATAAAGT GTGGCGTATG CAGTTTCGTT GGTATCATGC GCGGGACATC GCCGCGTAAT TCGCGCCGCC CACACCACCA
4701 TACGCGCAGC GTGACCGCTA CACTTGCCAG CGCCCTAGCG CCCGCTCCTT TCGCTTTCTT CCCTTCCTTT CTCGCCACGT TCGCCGGCTT TCCCCGTCAA
ATGCGCGTCG CACTGGCGAT GTGAACGGTC GCGGGATCGC GGGCGAGGAA AGCGAAAGAA GGGAAGGAAA GAGCGGTGCA AGCGGCCGAA AGGGGCAGTT
4801 GCTCTAAATC GGGGGCTCCC TTTAGGGTTC CGATTTAGTG CTTTACGGCA CCTCGACCCC AAAAAACTTG ATTTGGGTGA TGGTTCACGT AGTGGGCCAT
CGAGATTTAG CCCCCGAGGG AAATCCCAAG GCTAAATCAC GAAATGCCGT GGAGCTGGGG TTTTTTGAAC TAAACCCACT ACCAAGTGCA TCACCCGGTA
4901 CGCCCTGATA GACGGTTTTT CGCCCTTTGA CGTTGGAGTC CACGTTCTTT AATAGTGGAC TCTTGTTCCA AACTGGAACA ACACTCAACC CTATCTCGGG
GCGGGACTAT CTGCCAAAAA GCGGGAAACT GCAACCTCAG GTGCAAGAAA TTATCACCTG AGAACAAGGT TTGACCTTGT TGTGAGTTGG GATAGAGCCC
5001 CTATTCTTTT GATTTATAAG GGATTTTGCC GATTTCGGCC TATTGGTTAA AAAATGAGCT GATTTAACAA AAATTTAACG CGAATTTTAA CAAAATATTA
GATAAGAAAA CTAAATATTC CCTAAAACGG CTAAAGCCGG ATAACCAATT TTTTACTCGA CTAAATTGTT TTTAAATTGC GCTTAAAATT GTTTTATAAT
5101 ACGTTTACAA TTTTATGGTG CACTCTCAGT ACAATCTGCT CTGATGCCGC ATAGTTAAGC CAGCCCCGAC ACCCGCCAAC ACCCGCTGAC GCGCCCTGAC
TGCAAATGTT AAAATACCAC GTGAGAGTCA TGTTAGACGA GACTACGGCG TATCAATTCG GTCGGGGCTG TGGGCGGTTG TGGGCGACTG CGCGGGACTG
5201 GGGCTTGTCT GCTCCCGGCA TCCGCTTACA GACAAGCTGT GACCGTCTAG ACGAAAGGGC CTCGTGATAC GCCTATTTTT ATAGGTTAAT GTCATGATAA
CCCGAACAGA CGAGGGCCGT AGGCGAATGT CTGTTCGACA CTGGCAGATC TGCTTTCCCG GAGCACTATG CGGATAAAAA TATCCAATTA CAGTACTATT
5301 TAATGGTTTC TTAGACGTCA GGTGGCACTT TTCGGGGAAA TGTGCGCGGA ACCCCTATTT GTTTATTTTT CTAAATACAT TCAAATATGT ATCCGCTCAT
ATTACCAAAG AATCTGCAGT CCACCGTGAA AAGCCCCTTT ACACGCGCCT TGGGGATAAA CAAATAAAAA GATTTATGTA AGTTTATACA TAGGCGAGTA
5401 GAGACAATAA CCCTGATAAA TGCTTCAATA ATATTGAAAA AGGAAGAGTA TGAGTATTCA ACATTTCCGT GTCGCCCTTA TTCCCTTTTT TGCGGCATTT
CTCTGTTATT GGGACTATTT ACGAAGTTAT TATAACTTTT TCCTTCTCAT ACTCATAAGT TGTAAAGGCA CAGCGGGAAT AAGGGAAAAA ACGCCGTAAA

APPENDIX 4-continued

Sequences of plasmids encoding spAG-MLuc and spAG-ΔN-MLuc hybrids(SEQ ID NOs: 88-90, in order of appearance).

```
5501   TGCCTTCCTG TTTTTGCTCA CCCAGAAACG CTGGTGAAAG TAAAAGATGC TGAAGATCAG TTGGGTGCAC GAGTGGGTTA CATCGAACTG GATCTCAACA
       ACGGAAGGAC AAAAACGAGT GGGTCTTTGC GACCACTTTC ATTTTCTACG ACTTCTAGTC AACCCACGTG CTCACCCAAT GTAGCTTGAC CTAGAGTTGT
5601   GCGGTAAGAT CCTTGAGAGT TTTCGCCCCG AAGAACGTTT TCCAATGATG AGCACTTTTA AAGTTCTGCT ATGTGGCGCG GTATTATCCC GTATTGACGC
       CGCCATTCTA GGAACTCTCA AAAGCGGGGC TTCTTGCAAA AGGTTACTAC TCGTGAAAAT TTCAAGACGA TACACCGCGC CATAATAGGG CATAACTGCG
5701   CGGGCAAGAG CAACTCGGTC GCCGCATACA CTATTCTCAG AATGACTTGG TTGAGTACTC ACCAGTCACA GAAAAGCATC TTACGGATGG CATGACAGTA
       GCCCGTTCTC GTTGAGCCAG CGGCGTATGT GATAAGAGTC TTACTGAACC AACTCATGAG TGGTCAGTGT CTTTTCGTAG AATGCCTACC GTACTGTCAT
5801   AGAGAATTAT GCAGTGCTGC CATAACCATG AGTGATAACA CTGCGGCCAA CTTACTTCTG ACAACGATCG GAGGACCGAA GGAGCTAACC GCTTTTTTGC
       TCTCTTAATA CGTCACGACG GTATTGGTAC TCACTATTGT GACGCCGGTT GAATGAAGAC TGTTGCTAGC CTCCTGGCTT CCTCGATTGG CGAAAAAACG
5901   ACAACATGGG GGATCATGTA ACTCGCCTTG ATCGTTGGGA ACCGGAGCTG AATGAAGCCA TACCAAACGA CGAGCGTGAC ACCACGATGC CTGTAGCAAT
       TGTTGTACCC CCTAGTACAT TGAGCGGAAC TAGCAACCCT TGGCCTCGAC TTACTTCGGT ATGGTTTGCT GCTCGCACTG TGGTGCTACG GACATCGTTA
6001   GGCAACAACG TTGCGCAAAC TATTAACTGG CGAACTACTT ACTCTAGCTT CCCGGCAACA ATTAATAGAC TGGATGGAGG CGGATAAAGT TGCAGGACCA
       CCGTTGTTGC AACGCGTTTG ATAATTGACC GCTTGATGAA TGAGATCGAA GGGCCGTTGT TAATTATCTG ACCTACCTCC GCCTATTTCA ACGTCCTGGT
6101   CTTCTGCGCT CGGCCCTTCC GGCTGGCTGG TTTATTGCTG ATAAATCTGG AGCCGGTGAG CGTGGGTCTC GCGGTATCAT TGCAGCACTG GGGCCAGATG
       GAAGACGCGA GCCGGGAAGG CCGACCGACC AAATAACGAC TATTTAGACC TCGGCCACTC GCACCCAGAG CGCCATAGTA ACGTCGTGAC CCCGGTCTAC
6201   GTAAGCCCTC CCGTATCGTA GTTATCTACA CGACGGGGAG TCAGGCAACT ATGGATGAAC GAAATAGACA GATCGCTGAG ATAGGTGCCT CACTGATTAA
       CATTCGGGAG GGCATAGCAT CAATAGATGT GCTGCCCCTC AGTCCGTTGA TACCTACTTG CTTTATCTGT CTAGCGACTC TATCCACGGA GTGACTAATT
6301   GCATTGGTAA CTGTCAGACC AAGTTTACTC ATATATACTT TAGATTGATT TAAAACTTCA TTTTTAATTT AAAAGGATCT AGGTGAAGAT CCTTTTTGAT
       CGTAACCATT GACAGTCTGG TTCAAATGAG TATATATGAA ATCTAACTAA ATTTTGAAGT AAAAATTAAA TTTTCCTAGA TCCACTTCTA GGAAAAACTA
6401   AATCTCATGA CCAAAATCCC TTAACGTGAG TTTTCGTTCC ACTGAGCGTC AGACCCCGTA GAAAAGATCA AAGGATCTTC TTGAGATCCT TTTTTTCTGC
       TTAGAGTACT GGTTTTAGGG AATTGCACTC AAAAGCAAGG TGACTCGCAG TCTGGGGCAT CTTTTCTAGT TTCCTAGAAG AACTCTAGGA AAAAAAGACG
6501   GCGTAATCTG CTGCTTGCAA ACAAAAAAAC CACCGCTACC AGCGGTGGTT TGTTTGCCGG ATCAAGAGCT ACCAACTCTT TTTCCGAAGG TAACTGGCTT
       CGCATTAGAC GACGAACGTT TGTTTTTTTG GTGGCGATGG TCGCCACCAA ACAAACGGCC TAGTTCTCGA TGGTTGAGAA AAAGGCTTCC ATTGACCGAA
6601   CAGCAGAGCG CAGATACCAA ATACTGTCCT TCTAGTGTAG CCGTAGTTAG GCCACCACTT CAAGAACTCT GTAGCACCGC CTACATACCT CGCTCTGCTA
       GTCGTCTCGC GTCTATGGTT TATGACAGGA AGATCACATC GGCATCAATC CGGTGGTGAA GTTCTTGAGA CATCGTGGCG GATGTATGGA GCGAGACGAT
6701   ATCCTGTTAC CAGTGGCTGC TGCCAGTGGC GATAAGTCGT GTCTTACCGG GTTGGACTCA AGACGATAGT TACCGGATAA GGCGCAGCGG TCGGGCTGAA
       TAGGACAATG GTCACCGACG ACGGTCACCG CTATTCAGCA CAGAATGGCC CAACCTGAGT TCTGCTATCA ATGGCCTATT CCGCGTCGCC AGCCCGACTT
6801   CGGGGGGTTC GTGCACACAG CCCAGCTTGG AGCGAACGAC CTACACCGAA CTGAGATACC TACAGCGTGA GCTATGAGAA AGCGCCACGC TTCCCGAAGG
       GCCCCCCAAG CACGTGTGTC GGGTCGAACC TCGCTTGCTG GATGTGGCTT GACTCTATGG ATGTCGCACT CGATACTCTT TCGCGGTGCG AAGGGCTTCC
6901   GAGAAAGGCG GACAGGTATC CGGTAAGCGG CAGGGTCGGA ACAGGAGAGC GCACGAGGGA GCTTCCAGGG GGAAACGCCT GGTATCTTTA TAGTCCTGTC
       CTCTTTCCGC CTGTCCATAG GCCATTCGCC GTCCCAGCCT TGTCCTCTCG CGTGCTCCCT CGAAGGTCCC CCTTTGCGGA CCATAGAAAT ATCAGGACAG
7001   GGGTTTCGCC ACCTCTGACT TGAGCGTCGA TTTTTGTGAT GCTCGTCAGG GGGGCGGAGC CTATGGAAAA ACGCCAGCAA CGCGGCCTTT TTACGGTTCC
       CCCAAAGCGG TGGAGACTGA ACTCGCAGCT AAAAACACTA CGAGCAGTCC CCCCGCCTCG GATACCTTTT TGCGGTCGTT GCGCCGGAAA AATGCCAAGG
7101   TGGCCTTTTG CTGGCCTTTT GCTCACATGT TCTTTCCTGC GTTATCCCCT GATTCTGTGG ATAACCGTAT TACCGCCTTT GAGTGAGCTG ATACCGCTCG
       ACCGGAAAAC GACCGGAAAA CGAGTGTACA AGAAAGGACG CAATAGGGGA CTAAGACACC TATTGGCATA ATGGCGGAAA CTCACTCGAC TATGGCGAGC
7201   CCGCAGCCGA ACGACCGAGC GCAGCGAGTC AGTGAGCGAG GAAGCGGAAG
       GGCGTCGGCT TGCTGGCTCG CGTCGCTCAG TCACTCGCTC CTTCGCCTTC
```

pS14L-spAG-ΔN-MLuc15

```
1      AGCGCCCAAT ACGCAAACCG CCTCTCCCCG CGCGTTGGCC GATTCATTAA TGCAGCTGGC ACGACAGGTT TCCCGACTGG AAAGCGGGCA GTGAGCGCAA
       TCGCGGGTTA TGCGTTTGGC GGAGAGGGGC GCGCAACCGG CTAAGTAATT ACGTCGACCG TGCTGTCCAA AGGGCTGACC TTTCGCCCGT CACTCGCGTT
101    CGCAATTAAT GTGAGTTAGC TCACTCATTA GGCACCCCAG GCTTTACACT TTATGCTTCC GGCTCGTATG TTGTGTGGAA TTGTGAGCGG ATAACAATTT
       GCGTTAATTA CACTCAATCG AGTGAGTAAT CCGTGGGGTC CGAAATGTGA AATACGAAGG CCGAGCATAC AACACACCTT AACACTCGCC TATTGTTAAA
201    CACACAGGAA ACAGCTATGA CCATGATTAC GCCAAGCTTT AGGGATAACA GGGTAATCGC CATGCATTAG TTATTAATAG TAATCAATTA CGGGGTCATT
       GTGTGTCCTT TGTCGATACT GGTACTAATG CGGTTCGAAA TCCCTATTGT CCCATTAGCG GTACGTAATC AATAATTATC ATTAGTTAAT GCCCCAGTAA
301    AGTTCATAGC CCATATATGG AGTTCCGCGT TACATAACTT ACGGTAAATG GCCCGCCTGG CTGACCGCCC AACGACCCCC GCCCATTGAC GTCAATAATG
       TCAAGTATCG GGTATATACC TCAAGGCGCA ATGTATTGAA TGCCATTTAC CGGGCGGACC GACTGGCGGG TTGCTGGGGG CGGGTAACTG CAGTTATTAC
401    ACGTATGTTC CCATAGTAAC GCCAATAGGG ACTTTCCATT GACGTCAATG GGTGGAGTAT TTACGGTAAA CTGCCCACTT GGCAGTACAT CAAGTGTATC
       TGCATACAAG GGTATCATTG CGGTTATCCC TGAAAGGTAA CTGCAGTTAC CCACCTCATA AATGCCATTT GACGGGTGAA CCGTCATGTA GTTCACATAG
501    ATATGCCAAG TACGCCCCCT ATTGACGTCA ATGACGGTAA ATGGCCCGCC TGGCATTATG CCCAGTACAT GACCTTATGG GACTTTCCTA CTTGGCAGTA
       TATACGGTTC ATGCGGGGGA TAACTGCAGT TACTGCCATT TACCGGGCGG ACCGTAATAC GGGTCATGTA CTGGAATACC CTGAAAGGAT GAACCGTCAT
```

APPENDIX 4-continued

Sequences of plasmids encoding spAG-MLuc and spAG-ΔN-MLuc hybrids(SEQ ID NOs: 88-90, in order of appearance).

```
 601  CATCTACGTA TTAGTCATCG CTATTACCAT GGTGATGCGG TTTTGGCAGT ACATCAATGG GCGTGGATAG CGGTTTGACT CACGGGGATT TCCAAGTCTC
      GTAGATGCAT AATCAGTAGC GATAATGGTA CCACTACGCC AAAACCGTCA TGTAGTTACC CGCACCTATC GCCAAACTGA GTGCCCCTAA AGGTTCAGAG
 701  CACCCCATTG ACGTCAATGG GAGTTTGTTT TGGCACCAAA ATCAACGGGA CTTTCCAAAA TGTCGTAACA ACTCCGCCCC ATTGACGCAA ATGGGCGGTA
      GTGGGGTAAC TGCAGTTACC CTCAAACAAA ACCGTGGTTT TAGTTGCCCT GAAAGGTTTT ACAGCATTGT TGAGGCGGGG TAACTGCGTT TACCCGCCAT
 801  GGCGTGTACG GTGGGAGGTC TATATAAGCA GAGCTGGTTT AGTGAACCGT CAGATCCGCT AGACGTCTCA TTTAGGCATG GAAACCCCAG CGCAGCTTCT
      CCGCACATGC CACCCTCCAG ATATATTCGT CTCGACCAAA TCACTTGGCA GTCTAGGCGA TCTGCAGAGT AAATCCGTAC CTTTGGGGTC GCGTCGAAGA
 901  CTTCCTCCTG CTACTCTGGA TCCCAGACAC CATTGAAGAA ATAGTGATGA CGCAGTCTCC AGCCACCCTG TCTGTGTCTC CAGGGGAAAG AGTCACCCTC
      GAAGGAGGAC GATGAGACCT AGGGTCTGTG GTAACTTCTT TATCACTACT GCGTCAGAGG TCGGTGGGAC AGACACAGAG GTCCCCTTTC TCAGTGGGAG
1001  TCCAGCAGCC ATCATCATCA TCATCACAGC AGCGGCCTGG TGCCGCGCGG CAGCCATAGG TCGACTCTAG AGGATCCAAG CCAAAGCACT AACGTTTTAG
      AGGTCGTCGG TAGTAGTAGT AGTAGTGTCG TCGCCGGACC ACGGCGCGCC GTCGGTATCC AGCTGAGATC TCCTAGGTTC GGTTTCGTGA TTGCAAAATC
1101  GTGAAGCTAA AAAATTAAAC GAATCTCAAG CACCGAAAGC TGACAACAAT TTCAACAAAG AACAACAAAA TGCTTTCTAT GAAATCTTGA ACATGCCTAA
      CACTTCGATT TTTTAATTTG CTTAGAGTTC GTGGCTTTCG ACTGTTGTTA AAGTTGTTTC TTGTTGTTTT ACGAAAGATA CTTTAGAACT TGTACGGATT
1201  CTTGAACGAA GAACAACGCA ATGGTTTCAT CCAAAGCTTA AAAGATGACC CAAGTCAAAG TGCTAACCTT TTAGCAGAAG CTAAAAAGTT AAATGAATCT
      GAACTTGCTT CTTGTTGCGT TACCAAAGTA GGTTTCGAAT TTTCTACTGG GTTCAGTTTC ACGATTGGAA AATCGTCTTC GATTTTTCAA TTTACTTAGA
1301  CAAGCACCGA AAGCTGATAA CAAATTCAAC AAAGAACAAC AAAATGCTTT CTATGAAATC TTACATTTAC CTAACTTAAA TGAAGAACAA CGCAATGGTT
      GTTCGTGGCT TTCGACTATT GTTTAAGTTG TTTCTTGTTG TTTTACGAAA GATACTTTAG AATGTAAATG GATTGAATTT ACTTCTTGTT GCGTTACCAA
1401  TCATCCAAAG CTTAAAAGAT GACCCAAGCC AAAGCGCTAA CCTTTTAGCA GAAGCTAAAA AGCTAAATGA TGCACAAGCA CCAAAAGCTG ACAACAAATT
      AGTAGGTTTC GAATTTTCTA CTGGGTTCGG TTTCGCGATT GGAAAATCGT CTTCGATTTT TCGATTTACT ACGTGTTCGT GGTTTTCGAC TGTTGTTTAA
1501  CAACAAAGAA CAACAAAATG CTTTCTATGA AATTTTACAT TTACCTAACT TAACTGAAGA ACAACGTAAC GGCTTCATCC AAAGCCTTAA AGACGATCCC
      GTTGTTTCTT GTTGTTTTAC GAAAGATACT TTAAAATGTA AATGGATTGA ATTGACTTCT TGTTGCATTG CCGAAGTAGG TTTCGGAATT TCTGCTAGGG
1601  CGGTCGACTC TAGCGGCAGC TTCCGGTGCT AGCACTGACA CTTACAAATT AATCCTTAAT GGTAAAACAT TGAAAGGCGA AACAACTACT GAAGCTGTTG
      GCCAGCTGAG ATCGCCGTCG AAGGCCACGA TCGTGACTGT GAATGTTTAA TTAGGAATTA CCATTTTGTA ACTTTCCGCT TTGTTGATGA CTTCGACAAC
1701  ATGCTGCTAC TGCAGAAAAA GTCTTCAAAC AATACGCTAA CGACAACGGT GTTGACGGTG AATGGACTTA CGACGATGCG ACTAAGACCT TTACAGTTAC
      TACGACGATG ACGTCTTTTT CAGAAGTTTG TTATGCGATT GCTGTTGCCA CAACTGCCAC TTACCTGAAT GCTGCTACGC TGATTCTGGA AATGTCAATG
1801  TGAAAAACCA GAAGTGATCG ATGCGTCTGA ATTAACACCA GCCGTGACAA CTTACAAACT TGTTATTAAT GGTAAAACAT TGAAAGGCGA AACAACTACT
      ACTTTTTGGT CTTCACTAGC TACGCAGACT TAATTGTGGT CGGCACTGTT GAATGTTTGA ACAATAATTA CCATTTTGTA ACTTTCCGCT TTGTTGATGA
1901  AAAGCAGTAG ACGCAGAAAC TGCAGAAAAA GCCTTCAAAC AATACGCTAA CGACAACGGT GTTGATGGTG TTTGGACTTA TGATGATGCG ACTAAGACCT
      TTTCGTCATC TGCGTCTTTG ACGTCTTTTT CGGAAGTTTG TTATGCGATT GCTGTTGCCA CAACTACCAC AAACCTGAAT ACTACTACGC TGATTCTGGA
2001  TTACGGTAAC TGAAATGGTT ACAGAGGTAC CAGATCTTAG CAACTTTGTT GCAACTGAAA CCGATGCTAA CCGCGGAAAA ATGCCTGGCA AAAAACTGCC
      AATGCCATTG ACTTTACCAA TGTCTCCATG GTCTAGAATC GTTGAAACAA CGTTGACTTT GGCTACGATT GGCGCCTTTT TACGGACCGT TTTTTGACGG
2101  ACTGGCAGTT ATCATGGAAA TGGAAGCCAA TGCTTTCAAA GCTGGCTGCA CCAGGGGATG CCTTATCTGT CTTTCAAAAA TTAAGTGTAC AGCCAAAATG
      TGACCGTCAA TAGTACCTTT ACCTTCGGTT ACGAAAGTTT CGACCGACGT GGTCCCCTAC GGAATAGACA GAAAGTTTTT AATTCACATG TCGGTTTTAC
2201  AAGGTATACA TTCCAGGAAG GTGTCACGAT TATGGTGGTG ACAAGAAAAC TGGACAGGCA GGAATTGTTG GTGCAATTGT TGACATTCCC GAAATCTCTG
      TTCCATATGT AAGGTCCTTC CACAGTGCTA ATACCACCAC TGTTCTTTTG ACCTGTCCGT CCTTAACAAC CACGTTAACA ACTGTAAGGG CTTTAGAGAC
2301  GATTTAAGGA GATGGCACCC ATGGAACAGT TCATTGCTCA AGTTGATCGC TGCGCTTCCT GCACTACTGG ATGTCTCAAA GGTCTTGCCA ATGTTAAGTG
      CTAAATTCCT CTACCGTGGG TACCTTGTCA AGTAACGAGT TCAACTAGCG ACGCGAAGGA CGTGATGACC TACAGAGTTT CCAGAACGGT TACAATTCAC
2401  CTCTGAACTC CTGAAGAAAT GGCTGCCTGA CAGGTGTGCA AGTTTTGCTG ACAAGATTCA AAAAGAAGTT CACAATATCA AAGGCATGGC CGGCGATCGA
      GAGACTTGAG GACTTCTTTA CCGACGGACT GTCCACACGT TCAAAACGAC TGTTCTAAGT TTTTCTTCAA GTGTTATAGT TTCCGTACCG GCCGCTAGCT
2501  TGAGCGGCCG CAATTTAATT CCGGTTATTT TCCACCATAT TGCCGTCTTT TGGCAATGTG AGGGCCCGGA AACCTGGCCC TGTCTTCTTG ACGAGCATTC
      ACTCGCCGGC GTTAAATTAA GGCCAATAAA AGGTGGTATA ACGGCAGAAA ACCGTTACAC TCCCGGGCCT TTGGACCGGG ACAGAAGAAC TGCTCGTAAG
2601  CTAGGGGTCT TTCCCCTCTC GCCAAAGGAA TGCAAGGTCT GTTGAATGTC GTGAAGGAAG CAGTTCCTCT GGAAGCTTCT TGAAGACAAA CAACGTCTGT
      GATCCCCAGA AAGGGGAGAG CGGTTTCCTT ACGTTCCAGA CAACTTACAG CACTTCCTTC GTCAAGGAGA CCTTCGAAGA ACTTCTGTTT GTTGCAGACA
 201  AGCGACCCTT TGCAGGCAGC GGAACCCCCC ACCTGGCGAC AGGTGCCTCT GCGGCCAAAA GCCACGTGTA TAAGATACAC CTGCAAAGGC GGCACAACCC
      TCGCTGGGAA ACGTCCGTCG CCTTGGGGGG TGGACCGCTG TCCACGGAGA CGCCGGTTTT CGGTGCACAT ATTCTATGTG GACGTTTCCG CCGTGTTGGG
2801  CAGTGCCACG TTGTGAGTTG GATAGTTGTG GAAAGAGTCA AATGGCTCAC CTCAAGCGTA TTCAACAAGG GGCTGAAGGA TGCCCAGAAG GTACCCCATT
      GTCACGGTGC AACACTCAAC CTATCAACAC CTTTCTCAGT TTACCGAGTG GAGTTCGCAT AAGTTGTTCC CCGACTTCCT ACGGGTCTTC CATGGGGTAA
2901  GTATGGGATC TGATCTGGGG CCTCGGTGCA CATGCTTTAC ATGTGTTTAG TCGAGGTTAA AAAACGTCTA GGCCCCCCGA ACCACGGGGA CGTGGTTTTC
      CATACCCTAG ACTAGACCCC GGAGCCACGT GTACGAAATG TACACAAATC AGCTCCAATT TTTTGCAGAT CCGGGGGGCT TGGTGCCCCT GCACCAAAAG
3001  CTTTGAAAAA CACGATGATA ATATGGCCAC CACCCATACC TAGGCTTTTG CAAAGATCGA TCAGATCCCG GGGGGCAATG AGATATGAAA AAGCCTGAAC
      GAAACTTTTT GTGCTACTAT TATACCGGTG GTGGGTATGG ATCCGAAAAC GTTTCTAGCT AGTCTAGGGC CCCCCGTTAC TCTATACTTT TTCGGACTTG
```

APPENDIX 4-continued

Sequences of plasmids encoding spAG-MLuc and spAG-ΔN-MLuc hybrids(SEQ ID NOs: 88-90, in order of appearance).

```
3101  TCACCGCGAC GTCTGTCGAG AAGTTTCTGA TCGAAAAGTT CGACAGCGTC TCCGACCTGA TGCAGCTCTC GGAGGGCGAA GAATCTCGTG CTTTCAGCTT
      AGTGGCGCTG CAGACAGCTC TTCAAAGACT AGCTTTTCAA GCTGTCGCAG AGGCTGGACT ACGTCGAGAG CCTCCCGCTT CTTAGAGCAC GAAAGTCGAA
3201  CGATGTAGGA GGGCGTGGAT ATGTCCTGCG GGTAAATAGC TGCGCCGATG GTTTCTACAA AGATCGTTAT GTTTATCGGC ACTTTGCATC GGCCGCGCTC
      GCTACATCCT CCCGCACCTA TACAGGACGC CCATTTATCG ACGCGGCTAC CAAAGATGTT TCTAGCAATA CAAATAGCCG TGAAACGTAG CCGGCGCGAG
3301  CCGATTCCGG AAGTGCTTGA CATTGGGGAA TTCAGCGAGA GCCTGACCTA TTGCATCTCC CGCCGTGCAC AGGGTGTCAC GTTGCAAGAC CTGCCTGAAA
      GGCTAAGGCC TTCACGAACT GTAACCCCTT AAGTCGCTCT CGGACTGGAT AACGTAGAGG GCGGCACGTG TCCCACAGTG CAACGTTCTG GACGGACTTT
3401  CCGAACTGCC CGCTGTTCTG CAGCCGGTCG CGGAGGCCAT GGATGCGATC GCTGCGGCCG ATCTTAGCCA GACGAGCGGG TTCGGCCCAT TCGGACCGCA
      GGCTTGACGG GCGACAAGAC GTCGGCCAGC GCCTCCGGTA CCTACGCTAG CGACGCCGGC TAGAATCGGT CTGCTCGCCC AAGCCGGGTA AGCCTGGCGT
3501  AGGAATCGGT CAATACACTA CATGGCGTGA TTTCATATGC GCGATTGCTG ATCCCCATGT GTATCACTGG CAAACTGTGA TGGACGACAC CGTCAGTGCG
      TCCTTAGCCA GTTATGTGAT GTACCGCACT AAAGTATACG CGCTAACGAC TAGGGGTACA CATAGTGACC GTTTGACACT ACCTGCTGTG GCAGTCACGC
3601  TCCGTCGCGC AGGCTCTCGA TGAGCTGATG CTTTGGGCCG AGGACTGCCC CGAAGTCCGG CACCTCGTGC ACGCGGATTT CGGCTCCAAC AATGTCCTGA
      AGGCAGCGCG TCCGAGAGCT ACTCGACTAC GAAACCCGGC TCCTGACGGG GCTTCAGGCC GTGGAGCACG TGCGCCTAAA GCCGAGGTTG TTACAGGACT
3701  CGGACAATGG CCGCATAACA GCGGTCATTG ACTGGAGCGA GGCGATGTTC GGGGATTCCC AATACGAGGT CGCCAACATC TGATTCTGGA GGCCGTGGTT
      GCCTGTTACC GGCGTATTGT CGCCAGTAAC TGACCTCGCT CCGCTACAAG CCCCTAAGGG TTATGCTCCA GCGGTTGTAG AAGAAGACCT CCGGCACCAA
3801  GGCTTGTATG GAGCAGCAGA CGCGCTACTT CGAGCGGAGG CATCCGGAGC TTGCAGGATC GCCGCGGCTC CGGGCGTATA TGCTCCGCAT TGGTCTTGAC
      CCGAACATAC CTCGTCGTCT GCGCGATGAA GCTCGCCTCC GTAGGCCTCG AACGTCCTAG CGGCGCCGAG GCCCGCATAT ACGAGGCGTA ACCAGAACTG
3901  CAACTCTATC AGAGCTTGGT TGACGGCAAT TTCGATGATG CAGCTTGGGC GCAGGGTCGA TGCGACGCAA TCGTCCGATC CGGAGCCGGG ACTGTCGGGC
      GTTGAGATAG TCTCGAACCA ACTGCCGTTA AAGCTACTAC GTCGAACCCG CGTCCCAGCT ACGCTGCGTT AGCAGGCTAG GCCTCGGCCC TGACAGCCCG
4001  GTACACAAAT CGCCCGCAGA AGCGCGGCCG TCTGGACCGA TGGCTGTGTA GAAGTACTCG CCGATAGTGG AAACCGACGC CCCAGCACTC GTCCGGATCG
      CATGTGTTTA GCGGGCGTCT TCGCGCCGGC AGACCTGGCT ACCGACACAT CTTCATGAGC GGCTATCACC TTTGGCTGCG GGGTCGTGAG CAGGCCTAGC
4101  GGAGATGGGG GAGGCTAACT GAAACACGGA AGGAGACAAT ACCGGAAGGA ACCTCGACGT TAACTTGTTT ATTGCAGCTT ATAATGGTTA CAAATAAAGC
      CCTCTACCCC CTCCGATTGA CTTTGTGCCT TCCTCTGTTA TGGCCTTCCT TGGAGCTGCA ATTGAACAAA TAACGTCGAA TATTACCAAT GTTTATTTCG
4201  AATAGCATCA CAAATTTCAC AAATAAAGCA TTTATTACCC TGTTATCCCT AGAATTCACT GGCCGTCGTT TTACAACGTC GTGACTGGGA AAACCCTGGC
      TTATCGTAGT GTTTAAAGTG TTTATTTCGT AAATAATGGG ACAATAGGGA TCTTAAGTGA CCGGCAGCAA AATGTTGCAG CACTGACCCT TTTGGGACCG
4301  GTTACCCAAC TTAATCGCCT TGCAGCACAT CCCCCTTTCG CCAGCTGGCG TAATAGCGAA GAGGCCCGCA CCGATCGCCC TTCCCAACAG TTGCGCAGCC
      CAATGGGTTG AATTAGCGGA ACGTCGTGTA GGGGGAAAGC GGTCGACCGC ATTATCGCTT CTCCGGGCGT GGCTAGCGGG AAGGGTTGTC AACGCGTCGG
4401  TGAATGGCGA ATGGCGCCTG ATGCGGTATT TTCTCCTTAC GCATCTGTGC GGTATTTCAC ACCGCATACG TCAAAGCAAC CATAGTACGC GCCCTGTAGC
      ACTTACCGCT TACCGCGGAC TACGCCATAA AAGAGGAATG CGTAGACACG CCATAAAGTG TGGCGTATGC AGTTTCGTTG GTATCATGCG CGGGACATCG
4501  GGCGCATTAA GCGCGGCGGG TGTGGTGGTT ACGCGCAGCG TGACCGCTAC ACTTGCCAGC GCCCTAGCGC CCGCTCCTTT CGCTTTCTTC CCTTCCTTTC
      CCGCGTAATT CGCGCCGCCC ACACCACCAA TGCGCGTCGC ACTGGCGATG TGAACGGTCG CGGGATCGCG GGCGAGGAAA GCGAAAGAAG GGAAGGAAAG
4601  TCGCCACGTT CGCCGGCTTT CCCCGTCAAG CTCTAAATCG GGGGCTCCCT TTAGGGTTCC GATTTAGTGC TTTACGGCAC CTCGACCCCA AAAAACTTGA
      AGCGGTGCAA GCGGCCGAAA GGGGCAGTTC GAGATTTAGC CCCCGAGGGA AATCCCAAGG CTAAATCACG AAATGCCGTG GAGCTGGGGT TTTTTGAACT
4701  TTTGGGTGAT GGTTCACGTA GTGGGCCATC GCCCTGATAG ACGGTTTTTC GCCCTTTGAC GTTGGAGTCC ACGTTCTTTA ATAGTGGACT CTTGTTCCAA
      AAACCCACTA CCAAGTGCAT CACCCGGTAG CGGGACTATC TGCCAAAAAG CGGGAAACTG CAACCTCAGG TGCAAGAAAT TATCACCTGA GAACAAGGTT
4801  ACTGGAACAA CACTCAACCC TATCTCGGGC TATTCTTTTG ATTTATAAGG GATTTTGCCG ATTTCGGCCT ATTGGTTAAA AAATGAGCTG ATTTAACAAA
      TGACCTTGTT GTGAGTTGGG ATAGAGCCCG ATAAGAAAAC TAAATATTCC CTAAAACGGC TAAAGCCGGA TAACCAATTT TTTACTCGAC TAAATTGTTT
4901  AATTTAACGC GAATTTTAAC AAAATATTAA CGTTTACAAT TTTATGGTGC ACTCTCAGTA CAATCTGCTC TGATGCCGCA TAGTTAAGCC AGCCCCGACA
      TTAAATTGCG CTTAAAATTG TTTTATAATT GCAAATGTTA AAATACCACG TGAGAGTCAT GTTAGACGAG ACTACGGCGT ATCAATTCGG TCGGGGCTGT
5001  CCCGCCAACA CCCGCTGACG CGCCCTGACG GGCTTGTCTG CTCCCGGCAT CCGCTTACAG ACAAGCTGTG ACCGTCTAGA CGAAAGGGCC TCGTGATACG
      GGGCGGTTGT GGGCGACTGC GCGGGACTGC CCGAACAGAC GAGGGCCGTA GGCGAATGTC TGTTCGACAC TGGCAGATCT GCTTTCCCGG AGCACTATGC
5101  CCATTTTGTA TAGGTTAATG TCATGATAAT AATGGTTTCT TAGACGTCAG GTGGCACTTT TCGGGGAAAT GTGCGCGGAA CCCCTATTTG TTTATTTTTC
      GGATAAAAAT ATCCAATTAC AGTACTATTA TTACCAAAGA ATCTGCAGTC CACCGTGAAA AGCCCCTTTA CACGCGCCTT GGGGATAAAC AAATAAAAAG
5201  TAAATACATT CAAATATGTA TCCGCTCATG AGACAATAAC CCTGATAAAT GCTTCAATAA TATTGAAAAA GGAAGAGTAT GAGTATTCAA CATTTCCGTG
      ATTTATGTAA GTTTATACAT AGGCGAGTAC TCTGTTATTG GGACTATTTA CGAAGTTATT ATAACTTTTT CCTTCTCATA CTCATAAGTT GTAAAGGCAC
5301  TCGCCCTTAT TCCCTTTTTT GCGGCATTTT GCCTTCCTGT TTTTGCTCAC CCAGAAACGC TGGTGAAAGT AAAAGATGCT GAAGATCAGT TGGGTGCACG
      AGCGGGAATA AGGGAAAAAA CGCCGTAAAA CGGAAGGACA AAAACGAGTG GGTCTTTGCG ACCACTTTCA TTTTCTACGA CTTCTAGTCA ACCCACGTGC
5401  AGTGGGTTAC ATCGAACTGG ATCTCAACAG CGGTAAGATC CTTGAGAGTT TTCGCCCCGA AGAACGTTTT CCAATGATGA GCACTTTTAA AGTTCTGCTA
      TCACCCAATG TAGCTTGACC TAGAGTTGTC GCCATTCTAG GAACTCTCAA AAGCGGGGCT TCTTGCAAAA GGTTACTACT CGTGAAAATT TCAAGACGAT
5501  TGTGGCGCGG TATTATCCCG TATTGACGCC GGGCAAGAGC AACTCGGTCG CCGCATACAC TATTCTCAGA ATGACTTGGT TGAGTACTCA CCAGTCACAG
      ACACCGCGCC ATAATAGGGC ATAACTGCGG CCCGTTCTCG TTGAGCCAGC GGCGTATGTG ATAAGAGTCT TACTGAACCA ACTCATGAGT GGTCAGTGTC
```

APPENDIX 4-continued

| Sequences of plasmids encoding spAG-MLuc and spAG-ΔN-MLuc hybrids(SEQ ID NOs: 88-90, in order of appearance). | |
|---|---|
| 5601 | AAAAGCATCT TACGGATGGC ATGACAGTAA GAGAATTATG CAGTGCTGCC ATAACCATGA GTGATAACAC TGCGGCCAAC TTACTTCTGA CAACGATCGG |
| | TTTTCGTAGA ATGCCTACCG TACTGTCATT CTCTTAATAC GTCACGACGG TATTGGTACT CACTATTGTG ACGCCGGTTG AATGAAGACT GTTGCTAGCC |
| 5701 | AGGACCGAAG GAGCTAACCG CTTTTTTGCA CAACATGGGG GATCATGTAA CTCGCCTTGA TCGTTGGGAA CCGGAGCTGA ATGAAGCCAT ACCAAACGAC |
| | TCCTGGCTTC CTCGATTGGC GAAAAAACGT GTTGTACCCC CTAGTACATT GAGCGGAACT AGCAACCCTT GGCCTCGACT TACTTCGGTA TGGTTTGCTG |
| 5801 | GAGCGTGACA CCACGATGCC TGTAGCAATG GCAACAACGT TGCGCAAACT ATTAACTGGC GAACTACTTA CTCTAGCTTC CCGGCAACAA TTAATAGACT |
| | CTCGCACTGT GGTGCTACGG ACATCGTTAC CGTTGTTGCA ACGCGTTTGA TAATTGACCG CTTGATGAAT GAGATCGAAG GGCCGTTGTT AATTATCTGA |
| 5901 | GGATGGAGGC GGATAAAGTT GCAGGACCAC TTCTGCGCTC GGCCCTTCCG GCTGGCTGGT TTATTGCTGA TAAATCTGGA GCCGGTGAGC GTGGGTCTCG |
| | CCTACCTCCG CCTATTTCAA CGTCCTGGTG AAGACGCGAG CCGGGAAGGC CGACCGACCA AATAACGACT ATTTAGACCT CGGCCACTCG CACCCAGAGC |
| 6001 | CGGTATCATT GCAGCACTGG GGCCAGATGG TAAGCCCTCC CGTATCGTAG TTATCTACAC GACGGGGAGT CAGGCAACTA TGGATGAACG AAATAGACAG |
| | GCCATAGTAA CGTCGTGACC CCGGTCTACC ATTCGGGAGG GCATAGCATC AATAGATGTG CTGCCCCTCA GTCCGTTGAT ACCTACTTGC TTTATCTGTC |
| 6101 | ATCGCTGAGA TAGGTGCCTC ACTGATTAAG CATTGGTAAC TGTCAGACCA AGTTTACTCA TATATACTTT AGATTGATTT AAAACTTCAT TTTTAATTTA |
| | TAGCGACTCT ATCCACGGAG TGACTAATTC GTAACCATTG ACAGTCTGGT TCAAATGAGT ATATATGAAA TCTAACTAAA TTTTGAAGTA AAAATTAAAT |
| 6201 | AAAGGATCTA GGTGAAGATC CTTTTTGATA ATCTCATGAC CAAAATCCCT TAACGTGAGT TTTCGTTCCA CTGAGCGTCA GACCCCGTAG AAAAGATCAA |
| | TTTCCTAGAT CCACTTCTAG GAAAAACTAT TAGAGTACTG GTTTTAGGGA ATTGCACTCA AAAGCAAGGT GACTCGCAGT CTGGGGCATC TTTTCTAGTT |
| 6301 | AGGATCTTCT TGAGATCCTT TTTTTCTGCG CGTAATCTGC TGCTTGCAAA CAAAAAAACC ACCGCTACCA GCGGTGGTTT GTTTGCCGGA TCAAGAGCTA |
| | TCCTAGAAGA ACTCTAGGAA AAAAAGACGC GCATTAGACG ACGAACGTTT GTTTTTTTGG TGGCGATGGT CGCCACCAAA CAAACGGCCT AGTTCTCGAT |
| 6401 | CCAACTCTTT TTCCGAAGGT AACTGGCTTC AGCAGAGCGC AGATACCAAA TACTGTCCTT CTAGTGTAGC CGTAGTTAGG CCACCACTTC AAGAACTCTG |
| | GGTTGAGAAA AAGGCTTCCA TTGACCGAAG TCGTCTCGCG TCTATGGTTT ATGACAGGAA GATCACATCG GCATCAATCC GGTGGTGAAG TTCTTGAGAC |
| 6501 | TAGCACCGCC TACATACCTC GCTCTGCTAA TCCTGTTACC AGTGGCTGCT GCCAGTGGCG ATAAGTCGTG TCTTACCGGG TTGGACTCAA GACGATAGTT |
| | ATCGTGGCGG ATGTATGGAG CGAGACGATT AGGACAATGG TCACCGACGA CGGTCACCGC TATTCAGCAC AGAATGGCCC AACCTGAGTT CTGCTATCAA |
| 6601 | ACCGGATAAG GCGCAGCGGT CGGGCTGAAC GGGGGGTTCG TGCACACAGC CCAGCTTGGA GCGAACGACC TACACCGAAC TGAGATACCT ACAGCGTGAG |
| | TGGCCTATTC CGCGTCGCCA GCCCGACTTG CCCCCCAAGC ACGTGTGTCG GGTCGAACCT CGCTTGCTGG ATGTGGCTTG ACTCTATGGA TGTCGCACTC |
| 6701 | CTATGAGAAA GCGCCACGCT TCCCGAAGGG AGAAAGGCGG ACAGGTATCC GGTAAGCGGC AGGGTCGGAA CAGGAGAGCG CACGAGGGAG CTTCCAGGGG |
| | GATACTCTTT CGCGGTGCGA AGGGCTTCCC TCTTTCCGCC TGTCCATAGG CCATTCGCCG TCCCAGCCTT GTCCTCTCGC GTGCTCCCTC GAAGGTCCCC |
| 6801 | GAAACGCCTG GTATCTTTAT AGTCCTGTCG GGTTTCGCCA CCTCTGACTT GAGCGTCGAT TTTTGTGATG CTCGTCAGGG GGGCGGAGCC TATGGAAAAA |
| | CTTTGCGGAC CATAGAAATA TCAGGACAGC CCAAAGCGGT GGAGACTGAA CTCGCAGCTA AAAACACTAC GAGCAGTCCC CCCGCCTCGG ATACCTTTTT |
| 6901 | CGCCAGCAAC GCGGCCTTTT TACGGTTCCT GGCCTTTTGC TGGCCTTTTG CTCACATGTT CTTTCCTGCG TTATCCCCTG ATTCTGTGGA TAACCGTATT |
| | GCGGTCGTTG CGCCGGAAAA ATGCCAAGGA CCGGAAAACG ACCGGAAAAC GAGTGTACAA GAAAGGACGC AATAGGGGAC TAAGACACCT ATTGGCATAA |
| 7001 | ACCGCCTTTG AGTGAGCTGA TACCGCTCGC CGCAGCCGAA CGACCGAGCG CAGCGAGTCA GTGAGCGAGG AAGCGGAAG |
| | TGGCGGAAAC TCACTCGACT ATGGCGAGCG GCGTCGGCTT GCTGGCTCGC GTCGCTCAGT CACTCGCTCC TTCGCCTTC |

APPENDIX 5

Sequence of the plasmid encoding bioSNAP25-ΔN-MLuc hybrid(SEQ ID NO: 91).

```
pS14LbioSNAP25-ΔN-MLuc-CITE-Hyg1
   1   AGCGCCCAAT ACGCAAACCG CCTCTCCCCG CGCGTTGGCC GATTCATTAA TGCAGCTGGC ACGACAGGTT TCCCGACTGG AAAGCGGGCA GTGAGCGCAA
       TCGCGGGTTA TGCGTTTGGC GGAGAGGGGC GCGCAACCGG CTAAGTAATT ACGTCGACCG TGCTGTCCAA AGGGCTGACC TTTCGCCCGT CACTCGCGTT

 101   CCCAATTAAT GTGAGTTAGC TCACTCATTA GGCACCCCAG GCTTTACACT TTATGCTTCC GGCTCGTATG TTGTGTGGAA TTGTGAGCGG ATAACAATTT
       GCGTTAATTA CACTCAATCG AGTGAGTAAT CCGTGGGGTC CGAAATGTGA AATACGAAGG CCGAGCATAC AACACACCTT AACACTCGCC TATTGTTAAA

 201   CACACAGGAA ACAGCTATGA CCATGATTAC GCCAAGCTTT AGGGATAACA GGGTAATCGC CATGCATTAG TTATTAATAG TAATCAATTA CGGGGTCATT
       GTGTGTCCTT TGTCGATACT GGTACTAATG CGGTTCGAAA TCCCTATTGT CCCATTAGCG GTACGTAATC AATAATTATC ATTAGTTAAT GCCCCAGTAA

 301   AGTTCATAGC CCATATATGG AGTTCCGCGT TACATAACTT ACGGTAAATG GCCCGCCTGG CTGACCGCCC AACGACCCCC GCCCATTGAC GTCAATAATG
       TCAAGTATCG GGTATATACC TCAAGGCGCA ATGTATTGAA TGCCATTTAC CGGGCGGACC GACTGGCGGG TTGCTGGGGG CGGGTAACTG CAGTTATTAC

 401   ACGTATGTTC CCATAGTAAC GCCAATAGGG ACTTTCCATT GACGTCAATG GGTGGAGTAT TTACGGTAAA CTGCCCACTT GGCAGTACAT CAAGTGTATC
       TGCATACAAG GGTATCATTG CGGTTATCCC TGAAAGGTAA CTGCAGTTAC CCACCTCATA AATGCCATTT GACGGGTGAA CCGTCATGTA GTTCACATAG

 501   ATATGCCAAG TACGCCCCCT ATTGACGTCA ATGACGGTAA ATGGCCCGCC TGGCATTATG CCCAGTACAT GACCTTATGG GACTTTCCTA CTTGGCAGTA
       TATACGGTTC ATGCGGGGGA TAACTGCAGT TACTGCCATT TACCGGGCGG ACCGTAATAC GGGTCATGTA CTGGAATACC CTGAAAGGAT GAACCGTCAT

 601   CATCTACGTA TTAGTCATCG CTATTACCAT GGTGATGCGG TTTTGGCAGT ACATCAATGG GCGTGGATAG CGGTTTGACT CACGGGGATT TCCAAGTCTC
       GTAGATGCAT AATCAGTAGC GATAATGGTA CCACTACGCC AAAACCGTCA TGTAGTTACC CGCACCTATC GCCAAACTGA GTGCCCCTAA AGGTTCAGAG

 701   CACCCCATTG ACGTCAATGG GAGTTTGTTT TGGCACCAAA ATCAACGGGA CTTTCCAAAA TGTCGTAACA ACTCCGCCCC ATTGACGCAA ATGGGCGGTA
       GTGGGGTAAC TGCAGTTACC CTCAAACAAA ACCGTGGTTT TAGTTGCCCT GAAAGGTTTT ACAGCATTGT TGAGGCGGGG TAACTGCGTT TACCCGCCAT

 801   GGCGTGTACG GTGGGAGGTC TATATAAGCA GAGCTGGTTT AGTGAACCGT CAGATCCGCT AGACGTCTCA TTTAGGCATG GAAACCCCAG CGCAGCTTCT
       CCGCACATGC CACCCTCCAG ATATATTCGT CTCGACCAAA TCACTTGGCA GTCTAGGCGA TCTGCAGAGT AAATCCGTAC CTTTGGGGTC GCGTCGAAGA

 901   CTTCCTCCTG CTACTCTGGA TCCCAGACAC CATTGAAGAA ATAGTGATGA CGCAGTCTCC AGCCACCCTG TCTGTGTCTC CAGGGGAAAG AGTCACCCTC
       GAAGGAGGAC GATGAGACCT AGGGTCTGTG GTAACTTCTT TATCACTACT GCGTCAGAGG TCGGTGGGAC AGACACAGAG GTCCCCTTTC TCAGTGGGAG

1001   TCCTCAGGCG GCGCAAGCAG CCTGAGACAG ATTCTGGACT CCCAGAAAAT GGAGTGGAGG TCCAACGCCG GGGGCAGCGG TAGGGATAAC AGGGTAATCG
       AGGAGTCCGC CGCGTTCGTC GGACTCTGTC TAAGACCTGA GGGTCTTTTA CCTCACCTCC AGGTTGCGGC CCCCGTCGCC ATCCCTATTG TCCCATTAGC

1101   CCGAGGACGC AGACATGCGT AATGAACTGG AGGAGATGCA GAGGAGGGCT GACCAGCTGG CTGATGAGTC CCTGGAAAGC ACCCGTCGCA TGCTGCAGCT
       GGCTCCTGCG TCTGTACGCA TTACTTGACC TCCTCTACGT CTCCTCCCGA CTGGTCGACC GACTACTCAG GGACCTTTCG TGGGCAGCGT ACGACGTCGA

1201   GGTCGAAGAG AGTAAAGATG CTGGCATCAG GACTTTGGTT ATGTTGGATG AGCAAGGCGA ACAACTGGAA CGCATTGAGG AAGGGATGGA CCAAATCAAT
       CCAGCTTCTC TCATTTCTAC GACCGTAGTC CTGAAACCAA TACAACCTAC TCGTTCCGCT TGTTGACCTT GCGTAACTCC TTCCCTACCT GGTTTAGTTA

1301   AAGGATATGA AAGAAGCAGA AAAGAATTTG ACGGACCTAG GAAAATTCTG CGGGCTTTGT GTGTGTCCCT GTAACAAGCT TAAATCCAGT GATGCTTACA
       TTCCTATACT TTCTTCGTCT TTTCTTAAAC TGCCTGGATC CTTTTAAGAC GCCCGAAACA CACACAGGGA CATTGTTCGA ATTTAGGTCA CTACGAATGT

1401   AAAAAGCCTG GGGCAATAAT CAGGATGGAG TAGTGGCCAG CCAGCCTGCC CGTGTGGTGG ATGAACGGGA GCAGATGGCC ATCAGTGGTG GCTTCATCCG
       TTTTTCGGAC CCCGTTATTA GTCCTACCTC ATCACCGGTC GGTCGGACGG GCACACCACC TACTTGCCCT CGTCTACCGG TAGTCACCAC CGAAGTAGGC

1501   CAGGGTAACA AACGATGCCC GGGAAAATGA AATGGATGAA AACCTAGAGC AGGTGAGCGG CATCATCGGA AACCTCCGTC ATATGGCCCT AGACATGGGC
       GTCCCATTGT TTGCTACGGG CCCTTTTACT TTACCTACTT TTGGATCTCG TCCACTCGCC GTAGTAGCCT TTGGAGGCAG TATACCGGGA TCTGTACCCG
```

APPENDIX 5-continued

Sequence of the plasmid encoding bioSNAP25-AN-MLuc hybrid(SEQ ID NO: 91).

```
1601  AATGAGATTG ACACCCAGAA TCGCCAGATT GACAGGATCA TGGAGAAGGC TGACTCCAAC AAAACCAGAA TTGATGAAGC CAACCAACGT GCAACAAAGA
      TTACTCTAAC TGTGGGTCTT AGCGGTCTAA CTGTCCTAGT ACCTCTTCCG ACTGAGGTTG TTTTGGTCTT AACTACTTCG GTTGGTTGCA CGTTGTTTCT

1701  TGCTGGGAAG TGGGGAGATC TCCGCGGCCC GGGATCCACC GGCTAGCGGG AATTCCAAAT CAACTGAGTT CGATCCTAAC ATTGACATTG TTGGTTTAGA
      ACGACCCTTC ACCCCTCTAG AGGCGCCGGG CCCTAGGTGG CCGATCGCCC TTAAGGTTTA GTTGACTCAA GCTAGGATTG TAACTGTAAC AACCAAATCT

1801  AGGAAAATTT GGTATTACAA ACCTAGAGAC GGATTTATTC ACAATCTGGG AGACAATGGA GGTCATGATC AAAGCAGATA TTGCAGATAC TGATAGAGCC
      TCCTTTTAAA CCATAATGTT TGGATCTCTG CCTAAATAAG TGTTAGACCC TCTGTTACCT CCAGTACTAG TTTCGTCTAT AACGTCTATG ACTATCTCGG

1901  AGCAACTTTG TTGCAACTGA AACCGATGCT AACCGCGGAA AAATGCCTGG CAAAAAACTG CCACTGGCAG TTATCATGGA AATGGAAGCC AATGCTTTCA
      TCGTTGAAAC AACGTTGACT TTGGCTACGA TTGGCGCCTT TTTACGGACC GTTTTTTGAC GGTGACCGTC AATAGTACCT TTACCTTCGG TTACGAAAGT

2001  AAGCTGGCTG CACCAGGGGA TGCCTTATCT GTCTTTCAAA AATTAAGTGT ACAGCCAAAA TGAAGGTATA CATTCCAGGA AGGTGTCACG ATTATGGTGG
      TTCGACCGAC GTGGTCCCCT ACGGAATAGA CAGAAAGTTT TTAATTCACA TGTCGGTTTT ACTTCCATAT GTAAGGTCCT TCCACAGTGC TAATACCACC

2101  TGACAAGAAA ACTGGACAGG CAGGAATTGT TGGTGCAATT GTTGACATTC CCGAAATCTC TGGATTTAAG GAGATGGCAC CCATGGAACA GTTCATTGCT
      ACTGTTCTTT TGACCTGTCC GTCCTTAACA ACCACGTTAA CAACTGTAAG GGCTTTAGAG ACCTAAATTC CTCTACCGTG GGTACCTTGT CAAGTAACGA

2201  CAAGTTGATC GCTGCGCTTC CTGCACTACT GGATGTCTCA AAGGTCTTGC CAATGTTAAG TGCTCTGAAC TCCTGAAGAA ATGGCTGCCT GACAGGTGTG
      GTTCAACTAG CGACGCGAAG GACGTGATGA CCTACAGAGT TTCCAGAACG GTTACAATTC ACGAGACTTG AGGACTTCTT TACCGACGGA CTGTCCACAC

2301  CAAGTTTTGC TGACAAGATT CAAAAAGAAG TTCACAATAT CAAAGGCATG GCCGGCGATC GATGAGCGGC CGCAATTTAA TTCCGGTTAT TTTCCACCAT
      GTTCAAAACG ACTGTTCTAA GTTTTTCTTC AAGTGTTATA GTTTCCGTAC CGGCCGCTAG CTACTCGCCG GCGTTAAATT AAGGCCAATA AAAGGTGGTA

2401  ATTGCCGTCT TTTGGCAATG TGAGGGCCCG GAAACCTGGC CCTGTCTTCT TGACGAGCAT TCCTAGGGGT CTTTCCCCTC TCGCCAAAGG AATGCAAGGT
      TAACGGCAGA AAACCGTTAC ACTCCCGGGC CTTTGGACCG GGACAGAAGA ACTGCTCGTA AGGATCCCCA GAAAGGGGAG AGCGGTTTCC TTACGTTCCA

2501  CTGTTGAATG TCGTGAAGGA AGCAGTTCCT CTGGAAGCTT CTTGAAGACA AACAACGTCT GTAGCGACCC TTTGCAGGCA GCGGAACCCC CCACCTGGCG
      GACAACTTAC AGCACTTCCT TCGTCAAGGA GACCTTCGAA GAACTTCTGT TTGTTGCAGA CATCGCTGGG AAACGTCCGT CGCCTTGGGG GGTGGACCGC

2601  ACAGGTGCCT CTGCGGCCAA AAGCCACGTG TATAAGATAC ACCTGCAAAG GCGGCACAAC CCCAGTGCCA CGTTGTGAGT TGGATAGTTG TGGAAAGAGT
      TGTCCACGGA GACGCCGGTT TTCGGTGCAC ATATTCTATG TGGACGTTTC CGCCGTGTTG GGGTCACGGT GCAACACTCA ACCTATCAAC ACCTTTCTCA

2701  CAAATGGCTC ACCTCAAGCG TATTCAACAA GGGGCTGAAG GATGCCCAGA AGGTACCCCA TTGTATGGGA TCTGATCTGG GGCCTCGGTG CACATGCTTT
      GTTTACCGAG TGGAGTTCGC ATAAGTTGTT CCCCGACTTC CTACGGGTCT TCCATGGGGT AACATACCCT AGACTAGACC CCGGAGCCAC GTGTACGAAA

2801  ACATGTGTTT AGTCGAGGTT AAAAAACGTC TAGGCCCCCC GAACCACGGG GACGTGGTTT TCCTTTGAAA AACACGATGA TAATATGGCC ACCACCCATA
      TGTACACAAA TCAGCTCCAA TTTTTTGCAG ATCCGGGGGG CTTGGTGCCC CTGCACCAAA AGGAAACTTT TTGTGCTACT ATTATACCGG TGGTGGGTAT

2901  CCTAGGCTTT TGCAAAGATC GATCAGATCC CGGGGGGCAA TGAGATATGA AAAAGCCTGA ACTCACCGCG ACGTCTGTCG AGAAGTTTCT GATCGAAAAG
      GGATCCGAAA ACGTTTCTAG CTAGTCTAGG GCCCCCCGTT ACTCTATACT TTTTCGGACT TGAGTGGCGC TGCAGACAGC TCTTCAAAGA CTAGCTTTTC

3001  TTCGACAGCG TCTCCGACCT GATGCAGCTC TCGGAGGGCG AAGAATCTCG TGCTTTCAGC TTCGATGTAG GAGGGCGTGG ATATGTCCTG CGGGTAAATA
      AAGCTGTCGC AGAGGCTGGA CTACGTCGAG AGCCTCCCGC TTCTTAGAGC ACGAAAGTCG AAGCTACATC CTCCCGCACC TATACAGGAC GCCCATTTAT

3101  GCTGCGCCGA TGGTTTCTAC AAAGATCGTT ATGTTTATCG GCACTTTGCA TCGGCCGCGC TCCCGATTCC GGAAGTGCTT GACATTGGGG AATTCAGCGA
      CGACGCGGCT ACCAAAGATG TTTCTAGCAA TACAAATAGC CGTGAAACGT AGCCGGCGCG AGGGCTAAGG CCTTCACGAA CTGTAACCCC TTAAGTCGCT
3201  GAGCCTGACC TATTGCATCT CCCGCCGTGC ACAGGGTGTC ACGTTGCAAG ACCTGCCTGA AACCGAACTG CCCGCTGTTC TGCAGCCGGT CGCGGAGGCC

      CTCGGACTGG ATAACGTAGA GGGCGGCACG TGTCCCACAG TGCAACGTTC TGGACGGACT TTGGCTTGAC GGGCGACAAG ACGTCGGCCA GCGCCTCCGG
```

APPENDIX 5-continued

Sequence of the plasmid encoding bioSNAP25-AN-MLuc hybrid(SEQ ID NO: 91).

3301 ATGGATGCGA TCGCTGCGGC CGATCTTAGC CAGACGAGCG GGTTCGGCCC ATTCGGACCG CAAGGAATCG GTCAATACAC TACATGGCGT GATTTCATAT

TACCTACGCT AGCGACGCCG GCTAGAATCG GTCTGCTCGC CCAAGCCGGG TAAGCCTGGC GTTCCTTAGC CAGTTATGTG ATGTACCGCA CTAAAGTATA

3401 GCGCGATTGC TGATCCCCAT GTGTATCACT GGCAAACTGT GATGGACGAC ACCGTCAGTG CGTCCGTCGC GCAGGCTCTC GATGAGCTGA TGCTTTGGGC
CGCGCTAACG ACTAGGGGTA CACATAGTGA CCGTTTGACA CTACCTGCTG TGGCAGTCAC GCAGGCAGCG CGTCCGAGAG CTACTCGACT ACGAAACCCG

3501 CGAGGACTGC CCCGAAGTCC GGCACCTCGT GCACGCGGAT TTCGGCTCCA ACAATGTCCT GACGGACAAT GGCCGCATAA CAGCGGTCAT TGACTGGAGC
GCTCCTGACG GGGCTTCAGG CCGTGGAGCA CGTGCGCCTA AAGCCGAGGT TGTTACAGGA CTGCCTGTTA CCGGCGTATT GTCGCCAGTA ACTGACCTCG
3601 GAGGCGATGT TCGGGGATTC CCAATACGAG GTCGCCAACA TCTTCTTCTG GAGGCCGTGG TTGGCTTGTA TGGAGCAGCA GACGCGCTAC TTCGAGCGGA

CTCCGCTACA AGCCCCTAAG GGTTATGCTC CAGCGGTTGT AGAAGAAGAC CTCCGGCACC AACCGAACAT ACCTCGTCGT CTGCGCGATG AAGCTCGCCT

3701 GGCATCCGGA GCTTGCAGGA TCGCCGCGGC TCCGGGCGTA TATGCTCCGC ATTGGTCTTG ACCAACTCTA TCAGAGCTTG GTTGACGGCA ATTTCGATGA
CCGTAGGCCT CGAACGTCCT AGCGGCGCCG AGGCCCGCAT ATACGAGGCG TAACCAGAAC TGGTTGAGAT AGTCTCGAAC CAACTGCCGT TAAAGCTACT

3801 TGCAGCTTGG GCGCAGGGTC GATGCGACGC AATCGTCCGA TCCGGAGCCG GGACTGTCGG GCGTACACAA ATCGCCCGCA GAAGCGCGGC CGTCTGGACC
ACGTCGAACC CGCGTCCCAG CTACGCTGCG TTAGCAGGCT AGGCCTCGGC CCTGACAGCC CGCATGTGTT TAGCGGGCGT CTTCGCGCCG GCAGACCTGG

3901 GATGGCTGTG TAGAAGTACT CGCCGATAGT GGAAACCGAC GCCCCAGCAC TCGTCCGGAT CGGGAGATGG GGGAGGCTAA CTGAAACACG GAAGGAGACA
CTACCGACAC ATCTTCATGA GCGGCTATCA CCTTTGGCTG CGGGGTCGTG AGCAGGCCTA GCCCTCTACC CCCTCCGATT GACTTTGTGC CTTCCTCTGT

4001 ATACCGGAAG GAACCTCGAC GTTAACTTGT TTATTGCAGC TTATAATGGT TACAAATAAA GCAATAGCAT CACAAATTTC ACAAATAAAG CATTTATTAC
TATGGCCTTC CTTGGAGCTG CAATTGAACA AATAACGTCG AATATTACCA ATGTTTATTT CGTTATCGTA GTGTTTAAAG TGTTTATTTC GTAAATAATG

4101 CCTGTTATCC CTAGAATTCA CTGGCCGTCG TTTTACAACG TCGTGACTGG GAAAACCCTG GCGTTACCCA ACTTAATCGC CTTGCAGCAC ATCCCCCTTT
GGACAATAGG GATCTTAAGT GACCGGCAGC AAAATGTTGC AGCACTGACC CTTTTGGGAC CGCAATGGGT TGAATTAGCG GAACGTCGTG TAGGGGGAAA

4201 CGCCAGCTGG CGTAATAGCG AAGAGGCCCG CACCGATCGC CCTTCCCAAC AGTTGCGCAG CCTGAATGGC GAATGGCGCC TGATGCGGTA TTTTCTCCTT
GCGGTCGACC GCATTATCGC TTCTCCGGGC GTGGCTAGCG GGAAGGGTTG TCAACGCGTC GGACTTACCG CTTACCGCGG ACTACGCCAT AAAAGAGGAA

4301 ACGCATCTGT GCGGTATTTC ACACCGCATA CGTCAAAGCA ACCATAGTAC GCGCCCTGTA GCGGCGCATT AAGCGCGGCG GGTGTGGTGG TTACGCGCAG
TGCGTAGACA CGCCATAAAG TGTGGCGTAT GCAGTTTCGT TGGTATCATG CGCGGGACAT CGCCGCGTAA TTGCGCCGC CCACACCACC AATGCGCGTC

4401 CGTGACCGCT ACACTTGCCA GCGCCCTAGC GCCCGCTCCT TTCGCTTTCT TCCCTTCCTT TCTCGCCACG TTCGCCGGCT TTCCCCGTCA AGCTCTAAAT
GCACTGGCGA TGTGAACGGT CGCGGGATCG CGGGCGAGGA AAGCGAAAGA AGGGAAGGAA AGAGCGGTGC AAGCGGCCGA AAGGGGCAGT TCGAGATTTA

4501 CGGGGGCTCC CTTTAGGGTT CCGATTTAGT GCTTTACGGC ACCTCGACCC CAAAAAACTT GATTTGGGTG ATGGTTCACG TAGTGGGCCA TCGCCCTGAT
GCCCCCGAGG GAAATCCCAA GGCTAAATCA CGAAATGCCG TGGAGCTGGG GTTTTTTGAA CTAAACCCAC TACCAAGTGC ATCACCCGGT AGCGGGACTA

4601 AGACGGTTTT TCGCCCTTTG ACGTTGGAGT CCACGTTCTT TAATAGTGGA CTCTTGTTCC AAACTGGAAC AACACTCAAC CCTATCTCGG GCTATTCTTT
TCTGCCAAAA AGCGGGAAAC TGCAACCTCA GGTGCAAGAA ATTATCACCT GAGAACAAGG TTTGACCTTG TTGTGAGTTG GGATAGAGCC CGATAAGAAA

4701 TGATTTATAA GGGATTTTGC CGATTTCGGC CTATTGGTTA AAAAATGAGC TGATTTAACA AAAATTTAAC GCGAATTTTA ACAAAATATT AACGTTTACA
ACTAAATATT CCCTAAAACG GCTAAAGCCG GATAACCAAT TTTTTACTCG ACTAAATTGT TTTTAAATTG CGCTTAAAAT TGTTTTATAA TTGCAAATGT

4801 ATTTTATGGT GCACTCTCAG TACAATCTGC TCTGATGCCG CATAGTTAAG CCAGCCCCGA CACCCGCCAA CACCCGCTGA CGCGCCCTGA CGGGCTTGTC
TAAAATACCA CGTGAGAGTC ATGTTAGACG AGACTACGGC GTATCAATTC GGTCGGGGCT GTGGGCGGTT GTGGGCGACT GCGCGGGACT GCCCGAACAG

4901 TGCTCCCGGC ATCCGCTTAC AGACAAGCTG TGACCGTCTA GACGAAAGGG CCTCGTGATA CGCCTATTTT TATAGGTTAA TGTCATGATA ATAATGGTTT
ACGAGGGCCG TAGGCGAATG TCTGTTCGAC ACTGGCAGAT CTGCTTTCCC GGAGCACTAT GCGGATAAAA ATATCCAATT ACAGTACTAT TATTACCAAA

APPENDIX 5-continued

Sequence of the plasmid encoding bioSNAP25-AN-MLuc hybrid(SEQ ID NO: 91).

```
5001  CTTAGACGTC AGGTGGCACT TTTCGGGGAA ATGTGCGCGG AACCCCTATT TGTTTATTTT TCTAAATACA TTCAAATATG TATCCGCTCA TGAGACAATA
      GAATCTGCAG TCCACCGTGA AAAGCCCCTT TACACGCGCC TTGGGGATAA ACAAATAAAA AGATTTATGT AAGTTTATAC ATAGGCGAGT ACTCTGTTAT

5101  ACCCTGATAA ATGCTTCAAT AATATTGAAA AAGGAAGAGT ATGAGTATTC AACATTTCCG TGTCGCCCTT ATTCCCTTTT TTGCGGCATT TTGCCTTCCT
      TGGGACTATT TACGAAGTTA TTATAACTTT TTCCTTCTCA TACTCATAAG TTGTAAAGGC ACAGCGGGAA TAAGGGAAAA AACGCCGTAA AACGGAAGGA

5201  GTTTTTGCTC ACCCAGAAAC GCTGGTGAAA GTAAAAGATG CTGAAGATCA GTTGGGTGCA CGAGTGGGTT ACATCGAACT GGATCTCAAC AGCGGTAAGA
      CAAAAACGAG TGGGTCTTTG CGACCACTTT CATTTTCTAC GACTTCTAGT CAACCCACGT GCTCACCCAA TGTAGCTTGA CCTAGAGTTG TCGCCATTCT

5301  TCCTTGAGAG TTTTCGCCCC GAAGAACGTT TTCCAATGAT GAGCACTTTT AAAGTTCTGC TATGTGGCGC GGTATTATCC CGTATTGACG CCGGGCAAGA
      AGGAACTCTC AAAAGCGGGG CTTCTTGCAA AAGGTTACTA CTCGTGAAAA TTTCAAGACG ATACACCGCG CCATAATAGG GCATAACTGC GGCCCGTTCT

5401  GCAACTCGGT CGCCGCATAC ACTATTCTCA GAATGACTTG GTTGAGTACT CACCAGTCAC AGAAAAGCAT CTTACGGATG GCATGACAGT AAGAGAATTA
      CGTTGAGCCA GCGGCGTATG TGATAAGAGT CTTACTGAAC CAACTCATGA GTGGTCAGTG TCTTTTCGTA GAATGCCTAC CGTACTGTCA TTCTCTTAAT

5501  TGCAGTGCTG CCATAACCAT GAGTGATAAC ACTGCGGCCA ACTTACTTCT GACAACGATC GGAGGACCGA AGGAGCTAAC CGCTTTTTTG CACAACATGG
      ACGTCACGAC GGTATTGGTA CTCACTATTG TGACGCCGGT TGAATGAAGA CTGTTGCTAG CCTCCTGGCT TCCTCGATTG GCGAAAAAAC GTGTTGTACC

5601  GGGATCATGT AACTCGCCTT GATCGTTGGG AACCGGAGCT GAATGAAGCC ATACCAAACG ACGAGCGTGA CACCACGATG CCTGTAGCAA TGGCAACAAC
      CCCTAGTACA TTGAGCGGAA CTAGCAACCC TTGGCCTCGA CTTACTTCGG TATGGTTTGC TGCTCGCACT GTGGTGCTAC GGACATCGTT ACCGTTGTTG

5701  GTTGCGCAAA CTATTAACTG GCGAACTACT TACTCTAGCT TCCCGGCAAC AATTAATAGA CTGGATGGAG GCGGATAAAG TTGCAGGACC ACTTCTGCGC
      CAACGCGTTT GATAATTGAC CGCTTGATGA ATGAGATCGA AGGGCCGTTG TTAATTATCT GACCTACCTC CGCCTATTTC AACGTCCTGG TGAAGACGCG

5801  TCGGCCCTTC CGGCTGGCTG GTTTATTGCT GATAAATCTG GAGCCGGTGA GCGTGGGTCT CGCGGTATCA TTGCAGCACT GGGGCCAGAT GGTAAGCCCT
      AGCCGGGAAG GCCGACCGAC CAAATAACGA CTATTTAGAC CTCGGCCACT CGCACCCAGA GCGCCATAGT AACGTCGTGA CCCCGGTCTA CCATTCGGGA

5901  CCCGTATCGT AGTTATCTAC ACGACGGGGA GTCAGGCAAC TATGGATGAA CGAAATAGAC AGATCGCTGA GATAGGTGCC TCACTGATTA AGCATTGGTA
      GGGCATAGCA TCAATAGATG TGCTGCCCCT CAGTCCGTTG ATACCTACTT GCTTTATCTG TCTAGCGACT CTATCCACGG AGTGACTAAT TCGTAACCAT

6001  ACTGTCAGAC CAAGTTTACT CATATATACT TTAGATTGAT TTAAAACTTC ATTTTTAATT TAAAAGGATC TAGGTGAAGA TCCTTTTTGA TAATCTCATG
      TGACAGTCTG GTTCAAATGA GTATATATGA AATCTAACTA AATTTTGAAG TAAAAATTAA ATTTTCCTAG ATCCACTTCT AGGAAAAACT ATTAGAGTAC

6101  ACCAAAATCC CTTAACGTGA GTTTTCGTTC CACTGAGCGT CAGACCCCGT AGAAAAGATC AAAGGATCTT CTTGAGATCC TTTTTTTCTG CGCGTAATCT
      TGGTTTTAGG GAATTGCACT CAAAAGCAAG GTGACTCGCA GTCTGGGGCA TCTTTTCTAG TTTCCTAGAA GAACTCTAGG AAAAAAAGAC GCGCATTAGA

6201  GCTGCTTGCA AACAAAAAAA CCACCGCTAC CAGCGGTGGT TTGTTTGCCG GATCAAGAGC TACCAACTCT TTTTCCGAAG GTAACTGGCT TCAGCAGAGC
      CGACGAACGT TTGTTTTTTT GGTGGCGATG GTCGCCACCA AACAAACGGC CTAGTTCTCG ATGGTTGAGA AAAAGGCTTC CATTGACCGA AGTCGTCTCG

6301  GCAGATACCA AATACTGTCC TTCTAGTGTA GCCGTAGTTA GGCCACCACT TCAAGAACTC TGTAGCACCG CCTACATACC TCGCTCTGCT AATCCTGTTA
      CGTCTATGGT TTATGACAGG AAGATCACAT CGGCATCAAT CCGGTGGTGA AGTTCTTGAG ACATCGTGGC GGATGTATGG AGCGAGACGA TTAGGACAAT

6401  CCAGTGGCTG CTGCCAGTGG CGATAAGTCG TGTCTTACCG GGTTGGACTC AAGACGATAG TTACCGGATA AGGCGCAGCG GTCGGGCTGA ACGGGGGGTT
      GGTCACCGAC GACGGTCACC GCTATTCAGC ACAGAATGGC CCAACCTGAG TTCTGCTATC AATGGCCTAT TCCGCGTCGC CAGCCCGACT TGCCCCCCAA

6501  CGTGCACACA GCCCAGCTTG GAGCGAACGA CCTACACCGA ACTGAGATAC CTACAGCGTG AGCTATGAGA AAGCGCCACG CTTCCCGAAG GGAGAAAGGC
      GCACGTGTGT CGGGTCGAAC CTCGCTTGCT GGATGTGGCT TGACTCTATG GATGTCGCAC TCGATACTCT TTCGCGGTGC GAAGGGCTTC CCTCTTTCCG

6601  GGACAGGTAT CCGGTAAGCG GCAGGGTCGG AACAGGAGAG CGCACGAGGG AGCTTCCAGG GGGAAACGCC TGGTATCTTT ATAGTCCTGT CGGGTTTCGC
      CCTGTCCATA GGCCATTCGC CGTCCCAGCC TTGTCCTCTC GCGTGCTCCC TCGAAGGTCC CCCTTTGCGG ACCATAGAAA TATCAGGACA GCCCAAAGCG
```

APPENDIX 5-continued

Sequence of the plasmid encoding bioSNAP25-AN-MLuc hybrid(SEQ ID NO: 91).

```
6701   CACCTCTGAC TTGAGCGTCG ATTTTTGTGA TGCTCGTCAG GGGGGCGGAG CCTATGGAAA AACGCCAGCA ACGCGGCCTT TTTACGGTTC CTGGCCTTTT
       GTGGAGACTG AACTCGCAGC TAAAAACACT ACGAGCAGTC CCCCCGCCTC GGATACCTTT TTGCGGTCGT TGCGCCGGAA AAATGCCAAG GACCGGAAAA

6801   GCTGGCCTTT TGCTCACATG TTCTTTCCTG CGTTATCCCC TGATTCTGTG GATAACCGTA TTACCGCCTT TGAGTGAGCT GATACCGCTC GCCGCAGCCG
       CGACCGGAAA ACGAGTGTAC AAGAAAGGAC GCAATAGGGG ACTAAGACAC CTATTGGCAT AATGGCGGAA ACTCACTCGA CTATGGCGAG CGGCGTCGGC

6901   AACGACCGAG CGCAGCGAGT CAGTGAGCGA GGAAGCGGAA G
       TTGCTGGCTC GCGTCGCTCA GTCACTCGCT CCTTCGCCTT C
```

What is claimed is:

1. A method for producing a chimeric immunoglobulin-G (IgG) antibody that specifically binds an antigen of interest comprising:

a) isolating nucleic acid sequences encoding IgG heavy and light chain variable regions from a single immune cell producing an IgG that specifically binds the antigen of interest;

b) cloning the light chain variable region nucleic acid sequences of part a) into the expression vector pVLentry-Hyg10, and cloning the heavy chain variable region nucleic acid sequences of part a) into an expression vector selected from the group consisting of pVHentry-Cm5, pVHentry-GFP1, pVHentry-MLuc7, pVHentry-Hisbio1, and pVHentry-CBD1; wherein the light chain variable region nucleic acid sequences are operably linked to nucleic acid sequences encoding a light chain constant region, and wherein the heavy chain variable region nucleic acid sequences are operably linked to nucleic acid sequences encoding a heavy chain constant region;

c) combining the vectors used for part b) into a single vector comprising nucleic acid sequences encoding the IgG heavy and light chain variable regions;

d) introducing the expression vector of part c) into a host cell;

e) establishing one or more stable cell lines from the host cell of part d); and f) isolating the IgG produced by the one or more stable cell lines of part e).

2. The method of claim 1, wherein the antigen of interest is derived from a pathogen.

3. The method of claim 1, wherein the antigen of interest is a *Clostridium botulinum* neurotoxin.

4. The method of claim 1, wherein the one or more stable cell lines of part e) is established through expression of antibiotic resistance genes present in the expression vectors of part b) or part c).

5. The method of claim 4, wherein the level of expression of the antibiotic resistance genes by the one or more stable cell lines correlates to the level of IgG production by the cell lines.

6. The method of claim 1, wherein parts a) and b) comprise the steps of:

i) reverse-transcription of mRNA released from the immune cell upon exposure to perfingolysin O;

ii) simultaneous amplification of cDNAs produced in part i) encoding the IgG heavy chain variable region (VH) and the IgG light chain variable region (VL);

iii) separate re-amplification of the VH and VL sequences of part ii), and iv) insertion of the re-amplified sequences of part iii) into the expression vectors of part b).

7. The method of claim 6, wherein the reverse transcription is performed using a primer selected from the group consisting of IgG-CHH, Cm1, and Clv-3.

8. The method of claim 6, wherein the simultaneous amplification is performed using primers selected from the group consisting of pVk-1, pVk-2, pVk-3, pVk-4, hIgGk-3, IgGH-1, IgGH-2, IgGH-3, IgGH-4, IgGH-5, IgG-CHH, M1, M2, M3, M4, Cm1, V11-5T7, V12-5T7, V13-5T7, V14-5T7, V15-5T7, and C1-3.

9. The method of claim 6, wherein the re-amplification is performed using primers selected from the group consisting of Vk-1/2-5T7, Vk-3-5T7, Vk-4-5T7, hIgGk-3, IgG-CH, Vh-1-3T7, Vh-1-3T75, Vh-1-5T7, Vh-2-5T7, Vh-3-5T7, Vh-4-5T7, Vh-5-5T7, Vh-6-5T7, Vh-7-5T7, Vh-8-5T7, Vh-1-3T75, Vm-1-5T7, Vm-2-5T7, Vm-3-5T7, Vh-1-3T75, V11-5T7, V12-5T7, V13-5T7, V14-5T7, V15-5T7, and hIgGl-3.

10. The method of claim 1, wherein the host cell is selected from the group consisting of a Chinese hamster ovary(CHO) cell, a human embryonic kidney (HEK), a mouse NS1/1-Ag 4-1 cell, a NSO/u cell, an X63/Ag 8.653 cell, an SP2/0 Ag14 cell, a rat Y3 (210.RCY3.Ag 1.2.3) cell, a YB213.0Ag3 (Y0) cell, and any other mammalian secondary cell line capable of producing immunoglobulins.

11. A method for producing a chimeric immunoglobulin-G (IgG) antibody that specifically binds an antigen of interest comprising:

a) isolating nucleic acid sequences encoding IgG heavy and light chain variable regions from a single immune cell producing an IgG that specifically binds the antigen of interest;

b) cloning the light chain variable region nucleic acid sequences of part a) into the expression vector pVLentry-Hyg10, and cloning the heavy chain variable region nucleic acid sequences of part a) into an expression vector selected from the group consisting of pVHentry-Cm5, pVHentry-GFP1, pVHentry-MLuc7, pVHentry-Hisbio1, and pVHentry-CBD1; wherein the light chain variable region nucleic acid sequences are operably linked to nucleic acid sequences encoding a light chain constant region, and wherein the heavy chain variable region nucleic acid sequences are operably linked to nucleic acid sequences encoding a heavy chain constant region;

c) introducing the expression vectors of part b) into a host cell;

d) establishing one or more stable cell lines from the host cell of part c); and e) isolating the IgG produced by the one or more stable cell lines of part d).

12. The method of claim 11, wherein the antigen of interest is derived from a pathogen.

13. The method of claim 11, wherein the antigen of interest is a *Clostridium botulinum* neurotoxin.

14. The method of claim 11, wherein the one or more stable cell lines of part d) is established through expression of antibiotic resistance genes present in the expression vectors of part b).

15. The method of claim 14, wherein the level of expression of the antibiotic resistance genes by the one or more stable cell lines correlates to the level of IgG production by the cell lines.

16. The method of claim 11, wherein parts a) and b) comprise the steps of:

i) reverse-transcription of mRNA released from the immune cell upon exposure to perfingolysin O;

ii) simultaneous amplification of cDNAs produced in part i) encoding the IgG heavy chain variable region (VH) and the IgG light chain variable region (VL);

iii) separate re-amplification of the VH and VL sequences of part ii), and iv) insertion of the re-amplified sequences of part iii) into the expression vectors of part b).

17. The method of claim 16, wherein the reverse transcription is performed using a primer selected from the group consisting of IgG-CHH, Cm1, and Clv-3.

18. The method of claim 16, wherein the simultaneous amplification is performed using primers selected from the group consisting of pVk-1, pVk-2, pVk-3, pVk-4, hIgGk-3, IgGH-1, IgGH-2, IgGH-3, IgGH-4, IgGH-5, IgG-CHH, M1, M2, M3, M4, Cm1, V11-5T7, V12-5T7, V13-5T7, V14-5T7, V15-5T7, and C1-3.

19. The method of claim 16, wherein the re-amplification is performed using primers selected from the group consisting of Vk-1/2-5T7, Vk-3-5T7, Vk-4-5T7, hIgGk-3, IgG-CH, Vh-1-3T7, Vh-1-3T75, Vh-1-5T7, Vh-2-5T7, Vh-3-5T7, Vh-4-5T7, Vh-5-5T7, Vh-6-5T7, Vh-7-5T7, Vh-8-5T7, Vh-1-3T75, Vm-1-5T7, Vm-2-5T7, Vm-3-5T7, Vh-1-3T75, V11-5T7, V12-5T7, V13-5T7, V14-5T7, V15-5T7, and hIgGl-3.

20. The method of claim 11, wherein the host cell is selected from the group consisting of a Chinese hamster ovary(CHO) cell, a human embryonic kidney (HEK), a mouse NS1/1-Ag 4-1 cell, a NSO/u cell, an X63/Ag 8.653 cell, an SP2/0 Ag14 cell, a rat Y3 (210.RCY3.Ag 1.2.3) cell, a YB213.0Ag3 (Y0) cell, and any other mammalian secondary cell line capable of producing immunoglobulins.

* * * * *